(12) United States Patent
Johns

(10) Patent No.: US 9,910,054 B2
(45) Date of Patent: Mar. 6, 2018

(54) SYSTEM AND METHOD FOR PROCESSING SAMPLES

(71) Applicant: Beckman Coulter, Inc., Brea, CA (US)

(72) Inventor: Charles W. Johns, Brownsburg, IN (US)

(73) Assignee: Beckman Coulter, Inc., Brea, CA (US)

( * ) Notice: Subject to any disclaimer, the term of this patent is extended or adjusted under 35 U.S.C. 154(b) by 644 days.

(21) Appl. No.: 14/356,347

(22) PCT Filed: Nov. 7, 2012

(86) PCT No.: PCT/US2012/063931
§ 371 (c)(1),
(2) Date: May 5, 2014

(87) PCT Pub. No.: WO2013/070756
PCT Pub. Date: May 16, 2013

(65) Prior Publication Data
US 2014/0305227 A1    Oct. 16, 2014

Related U.S. Application Data

(60) Provisional application No. 61/680,066, filed on Aug. 6, 2012, provisional application No. 61/616,994, filed
(Continued)

(51) Int. Cl.
*G01N 35/00* (2006.01)
*B65G 47/28* (2006.01)
(Continued)

(52) U.S. Cl.
CPC ....... *G01N 35/0099* (2013.01); *B01D 21/262* (2013.01); *B04B 7/02* (2013.01);
(Continued)

(58) Field of Classification Search
CPC ..... G01N 35/0099; G01N 2035/00752; G01N 2035/0441; G01N 2035/0465;
(Continued)

(56) References Cited

U.S. PATENT DOCUMENTS 3,158,765 A  11/1964 Prolgreen
4,052,161 A  10/1977 Atwood et al.
(Continued)

FOREIGN PATENT DOCUMENTS

CA    1 282 692 A1   4/1991
CN    1127887 A      7/1996
(Continued)

OTHER PUBLICATIONS

International Search Report and Written Opinion dated Aug. 9, 2012 for PCT Patent Application No. PCT/US2012/037585, 10 pages.
(Continued)

*Primary Examiner* — David A Rogers
(74) *Attorney, Agent, or Firm* — Kilpatrick Townsend & Stockton LLP

(57) ABSTRACT

An analytical laboratory system and method for processing samples is disclosed. The system includes a manager unit, as well as an aliquotter unit and a centrifuge unit.

12 Claims, 93 Drawing Sheets

Related U.S. Application Data on Mar. 28, 2012, provisional application No. 61/556,667, filed on Nov. 7, 2011.

(51) Int. Cl.

| | | |
|---|---|---|
| *B01D 21/26* | (2006.01) | |
| *B04B 7/08* | (2006.01) | |
| *B04B 15/00* | (2006.01) | |
| *B25J 11/00* | (2006.01) | |
| *B04B 9/14* | (2006.01) | |
| *G01N 35/04* | (2006.01) | |
| *G01B 11/02* | (2006.01) | |
| *G01B 11/08* | (2006.01) | |
| *G01B 11/10* | (2006.01) | |
| *G01M 1/14* | (2006.01) | |
| *G01N 21/27* | (2006.01) | |
| *B04B 7/02* | (2006.01) | |
| *B04B 13/00* | (2006.01) | |
| *B65D 51/24* | (2006.01) | |
| *G01L 19/08* | (2006.01) | |
| *G01B 11/24* | (2006.01) | |
| *G01F 23/00* | (2006.01) | |
| *B04B 11/04* | (2006.01) | |
| *G01N 35/10* | (2006.01) | |
| *B01L 3/00* | (2006.01) | |

(52) U.S. Cl.
CPC ............... *B04B 7/08* (2013.01); *B04B 9/14* (2013.01); *B04B 9/146* (2013.01); *B04B 11/04* (2013.01); *B04B 13/00* (2013.01); *B04B 15/00* (2013.01); *B25J 11/00* (2013.01); *B65D 51/24* (2013.01); *B65G 47/28* (2013.01); *G01B 11/02* (2013.01); *G01B 11/08* (2013.01); *G01B 11/10* (2013.01); *G01B 11/24* (2013.01); *G01F 23/00* (2013.01); *G01L 19/08* (2013.01); *G01M 1/14* (2013.01); *G01N 21/27* (2013.01); *G01N 35/00584* (2013.01); *G01N 35/00732* (2013.01); *G01N 35/04* (2013.01); *G01N 35/10* (2013.01); *G01N 35/1009* (2013.01); *B01L 3/5021* (2013.01); *B04B 2009/143* (2013.01); *B04B 2011/046* (2013.01); *B04B 2013/006* (2013.01); *G01N 2035/00495* (2013.01); *G01N 2035/0405* (2013.01); *G01N 2035/0462* (2013.01); *G01N 2035/0491* (2013.01); *G01N 2035/1025* (2013.01); *G01N 2035/1032* (2013.01); *Y10T 29/49826* (2015.01)

(58) Field of Classification Search
CPC ......... G01N 2035/1025; G01N 35/025; G01N 2035/0453; G01N 2035/1076; G01N 21/253; G01N 2035/00831; G01N 2035/0406; G01N 2035/041; Y10T 436/11; Y10T 436/114165; Y10T 436/113332; Y10T 436/119163; Y10T 436/111666
See application file for complete search history.

(56) References Cited

U.S. PATENT DOCUMENTS

| | | |
|---|---|---|
| 4,101,070 A | 7/1978 | Hoare et al. |
| 4,119,381 A | 10/1978 | Muka et al. |
| 4,250,266 A | 2/1981 | Wade |
| 4,401,189 A | 8/1983 | Majewski |
| 4,486,539 A | 12/1984 | Ranki et al. |
| 4,501,495 A | 2/1985 | Faulkner et al. |
| 4,530,056 A | 7/1985 | MacKinnon et al. |
| 4,593,238 A | 6/1986 | Yamamoto |
| 4,593,239 A | 6/1986 | Yamamoto |
| 4,673,657 A | 6/1987 | Christian |
| 4,674,640 A | 6/1987 | Asa et al. |
| 4,676,952 A | 6/1987 | Edelmann et al. |
| 4,683,195 A | 7/1987 | Mullis et al. |
| 4,683,202 A | 7/1987 | Mullis |
| 4,751,177 A | 6/1988 | Stabinsky |
| 4,780,817 A | 10/1988 | Lofgren |
| 4,800,159 A | 1/1989 | Mullis et al. |
| 4,851,330 A | 7/1989 | Kohne |
| 4,865,986 A | 9/1989 | Coy et al. |
| 4,943,415 A | 7/1990 | Przybylowicz et al. |
| 4,947,094 A | 8/1990 | Dyer et al. |
| 4,950,613 A | 8/1990 | Arnold, Jr. et al. |
| 5,055,393 A | 10/1991 | Kwoh et al. |
| 5,055,408 A | 10/1991 | Higo et al. |
| 5,075,853 A | 12/1991 | Luke, Jr. |
| 5,118,191 A | 6/1992 | Hopkins |
| 5,147,529 A | 9/1992 | Lee et al. |
| 5,154,888 A | 10/1992 | Zander et al. |
| 5,158,895 A | 10/1992 | Ashihara et al. |
| 5,168,766 A | 12/1992 | Henschke et al. |
| 5,179,329 A | 1/1993 | Nishikawa et al. |
| 5,185,439 A | 2/1993 | Arnold, Jr. et al. |
| 5,186,827 A | 2/1993 | Liberti et al. |
| 5,190,136 A | 3/1993 | Greckseh et al. |
| 5,196,168 A | 3/1993 | Muszak et al. |
| 5,205,393 A | 4/1993 | Malow et al. |
| 5,229,297 A | 7/1993 | Schinpelsky et al. |
| 5,234,665 A | 8/1993 | Ohta et al. |
| 5,244,055 A | 9/1993 | Shimizu |
| 5,283,174 A | 2/1994 | Arnold et al. |
| 5,283,739 A | 2/1994 | Summerville et al. |
| 5,288,463 A | 2/1994 | Chemelli |
| 5,314,825 A * | 5/1994 | Weyrauch ........ G01N 35/00663 356/246 |
| 5,330,916 A | 7/1994 | Williams et al. |
| 5,350,564 A | 9/1994 | Mazza et al. |
| 5,351,801 A | 10/1994 | Markin et al. |
| 5,358,691 A * | 10/1994 | Clark ................. B01L 3/08 422/63 |
| 5,362,291 A | 11/1994 | Williamson, IV |
| 5,366,896 A | 11/1994 | Ooura et al. |
| 5,374,395 A | 12/1994 | Robinson et al. |
| 5,375,898 A | 12/1994 | Ohmori et al. |
| 5,376,313 A * | 12/1994 | Kanewske, III ......... B01L 3/08 264/1.1 |
| 5,380,487 A | 1/1995 | Choperena et al. |
| 5,388,682 A | 2/1995 | Dudley |
| 5,389,339 A | 2/1995 | Petschek et al. |
| 5,397,709 A | 3/1995 | Berndt |
| 5,399,491 A | 3/1995 | Kacian et al. |
| 5,403,711 A | 4/1995 | Walder et al. |
| 5,415,839 A | 5/1995 | Zuan et al. |
| 5,422,271 A | 6/1995 | Chen et al. |
| 5,427,930 A | 6/1995 | Birkenmeyer et al. |
| 5,437,990 A | 8/1995 | Burg et al. |
| 5,443,791 A | 8/1995 | Cathcart et al. |
| 5,447,687 A | 9/1995 | Lewis et al. |
| 5,449,602 A | 9/1995 | Royer et al. |
| 5,462,881 A | 10/1995 | Perlman |
| 5,466,574 A | 11/1995 | Liberti et al. |
| 5,480,784 A | 1/1996 | Kacian et al. |
| 5,482,834 A | 1/1996 | Gillespie |
| 5,504,345 A | 4/1996 | Bartunek et al. |
| 5,514,550 A | 5/1996 | Findlay et al. |
| 5,525,300 A | 6/1996 | Danssaert et al. |
| 5,527,673 A | 6/1996 | Reinhartz et al. |
| 5,536,649 A | 7/1996 | Fraiser et al. |
| 5,538,849 A | 7/1996 | Uematsu et al. |
| 5,554,516 A | 9/1996 | Kacian et al. |
| 5,563,037 A | 10/1996 | Sutherland et al. |
| 5,578,270 A | 11/1996 | Reichler et al. |
| 5,582,796 A | 12/1996 | Carey et al. |
| 5,585,242 A | 12/1996 | Bourma et al. |
| 5,585,481 A | 12/1996 | Arnold, Jr. et al. |
| 5,587,128 A | 12/1996 | Wilding et al. |

(56) References Cited

U.S. PATENT DOCUMENTS

| | | |
|---|---|---|
| 5,589,333 A | 12/1996 | Bagasra et al. |
| 5,602,042 A | 2/1997 | Farber |
| 5,604,130 A | 2/1997 | Warner et al. |
| 5,612,200 A | 3/1997 | Dattagupta et al. |
| 5,612,525 A | 3/1997 | Apter et al. |
| 5,623,415 A | 4/1997 | O'Bryan et al. |
| 5,628,962 A | 5/1997 | Kanbara et al. |
| 5,637,275 A | 6/1997 | Carey et al. |
| 5,639,599 A | 6/1997 | Ryder et al. |
| 5,639,604 A | 6/1997 | Arnold et al. |
| 5,641,658 A | 6/1997 | Adams et al. |
| 5,652,489 A | 7/1997 | Kawakami |
| 5,653,940 A | 8/1997 | Carey et al. |
| 5,656,493 A | 8/1997 | Mullis et al. |
| 5,665,554 A | 9/1997 | Reeve et al. |
| 5,679,553 A | 10/1997 | Van Gemen et al. |
| 5,686,272 A | 11/1997 | Marshall et al. |
| 5,702,950 A | 12/1997 | Tajima |
| 5,705,062 A | 1/1998 | Knobel |
| 5,714,380 A | 2/1998 | Neri et al. |
| 5,720,923 A | 2/1998 | Haff et al. |
| 5,723,591 A | 3/1998 | Livak et al. |
| 5,730,938 A | 3/1998 | Carbonari et al. |
| 5,735,587 A | 4/1998 | Malin et al. |
| 5,741,708 A | 4/1998 | Carey et al. |
| 5,746,978 A | 5/1998 | Bienhaus et al. |
| 5,750,338 A | 5/1998 | Collins et al. |
| 5,773,268 A | 6/1998 | Korenberg et al. |
| 5,779,981 A | 7/1998 | Danssaert et al. |
| 5,786,182 A | 7/1998 | Catanzariti et al. |
| 5,795,547 A | 8/1998 | Moser et al. |
| 5,798,263 A | 8/1998 | Wood et al. |
| 5,814,008 A | 9/1998 | Chen et al. |
| 5,814,276 A | 9/1998 | Riggs |
| 5,814,961 A | 9/1998 | Imahashi |
| 5,827,653 A | 10/1998 | Sammes et al. |
| 5,846,489 A | 12/1998 | Bienhaus et al. |
| 5,846,491 A | 12/1998 | Choperena et al. |
| 5,846,726 A | 12/1998 | Nadeau et al. |
| 5,857,955 A | 1/1999 | Phillips et al. |
| 5,866,336 A | 2/1999 | Nazarenko et al. |
| 5,881,781 A | 3/1999 | Bishop |
| 5,882,903 A | 3/1999 | Andrevski et al. |
| 5,895,631 A | 4/1999 | Tajima et al. |
| 5,897,090 A | 4/1999 | Smith et al. |
| 5,897,783 A | 4/1999 | Howe et al. |
| 5,914,230 A | 6/1999 | Liu et al. |
| 5,919,622 A | 7/1999 | Macho et al. |
| 5,922,591 A | 7/1999 | Anderson et al. |
| 5,925,517 A | 7/1999 | Tyagi et al. |
| 5,928,907 A | 7/1999 | Woudenberg |
| 5,948,673 A | 9/1999 | Cottingham et al. |
| 5,966,309 A | 10/1999 | O'Bryan et al. |
| 5,994,056 A | 11/1999 | Higuchi et al. |
| 6,011,508 A | 1/2000 | Perreault et al. |
| 6,033,574 A | 3/2000 | Siddiqi |
| 6,033,880 A | 3/2000 | Haff et al. |
| 6,043,880 A | 3/2000 | Andrews et al. |
| 6,049,745 A | 4/2000 | Douglas et al. |
| 6,056,106 A | 5/2000 | van Dyke, Jr. et al. |
| 6,060,022 A | 5/2000 | Pang et al. |
| 6,063,340 A | 5/2000 | Lewis et al. |
| 6,068,978 A | 5/2000 | Zaun et al. |
| 6,071,395 A | 6/2000 | Lange |
| 6,100,079 A | 8/2000 | Tajima |
| 6,110,676 A | 8/2000 | Coull et al. |
| 6,110,678 A | 8/2000 | Weisburg et al. |
| 6,117,398 A | 9/2000 | Bienhaus et al. |
| 6,129,428 A | 10/2000 | Helwig et al. |
| 6,150,097 A | 11/2000 | Tyagi et al. |
| 6,165,778 A | 12/2000 | Kedar |
| 6,171,780 B1 | 1/2001 | Pham et al. |
| 6,212,448 B1 | 4/2001 | Xydis |
| 6,277,332 B1 | 8/2001 | Sucholeiki |
| 6,300,068 B1 | 10/2001 | Burg et al. |
| 6,300,138 B1 | 10/2001 | Gleason et al. |
| 6,306,658 B1 | 10/2001 | Turner et al. |
| 6,333,008 B1 | 12/2001 | Leistner et al. |
| 6,335,166 B1 | 1/2002 | Ammann et al. |
| 6,353,774 B1 | 3/2002 | Goldenberg et al. |
| 6,368,872 B1 | 4/2002 | Juranas |
| 6,370,452 B1 | 4/2002 | Pfister |
| 6,374,989 B1 | 4/2002 | van Dyke, Jr. et al. |
| 6,377,888 B1 | 4/2002 | Olch |
| 6,429,016 B1 | 8/2002 | McNeil |
| 6,436,349 B1 | 8/2002 | Carey et al. |
| 6,444,171 B1 | 9/2002 | Sakazume et al. |
| RE37,891 E | 10/2002 | Collins et al. |
| 6,458,324 B1 | 10/2002 | Schinzel |
| 6,520,313 B1 | 2/2003 | Kaarakainen et al. |
| 6,548,026 B1 | 4/2003 | Dales et al. |
| 6,586,234 B1 | 7/2003 | Burg et al. |
| 6,586,255 B1 | 7/2003 | Tanaka et al. |
| 6,597,450 B1 | 7/2003 | Andrews et al. |
| 6,599,476 B1 | 7/2003 | Watson et al. |
| 6,605,213 B1 | 8/2003 | Ammann et al. |
| 6,629,028 B2 | 9/2003 | Paromtchik et al. |
| 6,633,785 B1 | 10/2003 | Kasahara et al. |
| 6,692,708 B2 | 2/2004 | Chandler, Jr. |
| 6,764,649 B2 | 7/2004 | Ammann |
| 6,770,883 B2 | 8/2004 | Mc Neal et al. |
| 6,818,183 B2 | 11/2004 | Hajduk et al. |
| 6,890,742 B2 | 5/2005 | Ammann et al. |
| 6,919,058 B2 | 7/2005 | Andersson et al. |
| 6,919,175 B1 | 7/2005 | Beinhaus et al. |
| 6,941,200 B2 | 9/2005 | Sonoyama et al. |
| 6,993,176 B2 | 1/2006 | Yamagishi et al. |
| 7,028,831 B2 | 1/2006 | Veiner |
| 6,999,847 B2 | 2/2006 | Barry et al. |
| 7,033,820 B2 | 4/2006 | Ammann et al. |
| 7,045,358 B2 | 5/2006 | Chandler, Jr. |
| 7,071,006 B2 | 7/2006 | Tajima et al. |
| 7,078,698 B2 | 7/2006 | Itoh |
| 7,118,892 B2 | 10/2006 | Ammann et al. |
| 7,135,145 B2 | 11/2006 | Ammann et al. |
| 7,174,836 B2 | 2/2007 | Marino et al. |
| 7,237,749 B2 | 9/2007 | Wittwer et al. |
| 7,264,111 B2 | 9/2007 | Veiner |
| 7,264,432 B2 * | 9/2007 | Wiggli ............. G01N 35/00732 269/73 |
| 7,267,795 B2 | 9/2007 | Ammann et al. |
| 7,269,480 B2 | 9/2007 | Hashimoto et al. |
| 7,288,229 B2 | 10/2007 | Turner et al. |
| 7,362,258 B2 | 4/2008 | Kawabe et al. |
| 7,419,830 B2 | 9/2008 | Canos et al. |
| 7,463,948 B2 | 12/2008 | Orita |
| 7,473,897 B2 | 1/2009 | Braendle et al. |
| 7,482,143 B2 | 1/2009 | Ammann et al. |
| 7,499,581 B2 | 3/2009 | Tribble et al. |
| 7,524,652 B2 | 4/2009 | Ammann et al. |
| 7,560,255 B2 | 7/2009 | Ammann et al. |
| 7,560,256 B2 | 7/2009 | Ammann et al. |
| 7,688,448 B2 | 3/2010 | Bamberg et al. |
| 7,771,659 B2 | 8/2010 | Ziegler |
| 7,985,375 B2 * | 7/2011 | Edens ................ G01N 35/0099 422/50 |
| 8,012,768 B2 * | 9/2011 | Jafari ..................... G01N 1/38 422/501 |
| 8,074,578 B2 | 12/2011 | Thornton |
| 8,192,992 B2 | 6/2012 | Ammann et al. |
| 9,335,336 B2 * | 5/2016 | Silbert ................ G01F 23/265 |
| 2002/0025064 A1 | 2/2002 | Itoh |
| 2002/0028489 A1 | 3/2002 | Ammann et al. |
| 2002/0031768 A1 | 3/2002 | McMillan et al. |
| 2002/0077239 A1 | 6/2002 | Evans, III et al. |
| 2002/0086417 A1 | 7/2002 | Chen |
| 2002/0098117 A1 | 7/2002 | Ammann et al. |
| 2002/0123156 A1 | 9/2002 | Tajima |
| 2002/0137194 A1 | 9/2002 | Ammann et al. |
| 2002/0137197 A1 | 9/2002 | Ammann et al. |
| 2002/0146347 A1 | 10/2002 | McNeil |
| 2002/0147515 A1 | 10/2002 | Fava et al. |
| 2003/0026736 A1 | 2/2003 | Hajduk et al. |
| 2003/0027206 A1 | 2/2003 | Ammann et al. |

(56) References Cited

U.S. PATENT DOCUMENTS

| | | |
|---|---|---|
| 2003/0054542 A1 | 3/2003 | Burns et al. |
| 2003/0129614 A1 | 7/2003 | Parameswaran et al. |
| 2003/0190755 A1 | 10/2003 | Turner et al. |
| 2003/0213313 A1 | 11/2003 | Katagi |
| 2003/0223916 A1 | 12/2003 | Testrut et al. |
| 2004/0029260 A1 | 2/2004 | Hansen et al. |
| 2004/0076983 A1 | 4/2004 | Karlsen |
| 2004/0087426 A1 | 5/2004 | Lattanzi |
| 2004/0115796 A1 | 6/2004 | Burns |
| 2004/0158355 A1 | 8/2004 | Holmqvist et al. |
| 2004/0184959 A1 | 9/2004 | Itoh |
| 2004/0206419 A1 | 10/2004 | Ganz et al. |
| 2004/0213651 A1 | 10/2004 | Malin |
| 2005/0130198 A1 | 6/2005 | Ammann et al. |
| 2005/0158212 A1 | 7/2005 | Yavilevich |
| 2005/0163354 A1 | 7/2005 | Ziegler |
| 2005/0207937 A1 | 9/2005 | Itoh |
| 2005/0220670 A1 | 10/2005 | Palmieri et al. |
| 2005/0233370 A1 | 10/2005 | Ammann et al. |
| 2005/0239127 A1 | 10/2005 | Ammann et al. |
| 2005/0266489 A1 | 12/2005 | Ammann et al. |
| 2005/0271555 A1 | 12/2005 | Itoh |
| 2006/0003373 A1 | 1/2006 | Ammann et al. |
| 2006/0014295 A1 | 1/2006 | Ziegler |
| 2006/0020370 A1 | 1/2006 | Abramson |
| 2006/0148063 A1 | 7/2006 | Fauzzi et al. |
| 2006/0228268 A1 | 10/2006 | Heimberg et al. |
| 2007/0044676 A1 | 3/2007 | Clark et al. |
| 2007/0059209 A1* | 3/2007 | Pang .................. G01N 35/0099 422/72 |
| 2007/0100498 A1 | 5/2007 | Matsumoto et al. |
| 2007/0110634 A1 | 5/2007 | Heimberg et al. |
| 2007/0134131 A1 | 6/2007 | Watson et al. |
| 2007/0179690 A1 | 8/2007 | Stewart |
| 2007/0184548 A1 | 8/2007 | Tan et al. |
| 2007/0193859 A1 | 8/2007 | Kyutoku et al. |
| 2007/0196237 A1 | 8/2007 | Neuzil et al. |
| 2007/0208440 A1 | 9/2007 | Bliss et al. |
| 2007/0225901 A1 | 9/2007 | Yamaguchi |
| 2007/0225906 A1 | 9/2007 | Ikeda |
| 2008/0014181 A1 | 1/2008 | Ariff et al. |
| 2008/0015470 A1 | 1/2008 | Sarstedt |
| 2008/0056958 A1 | 3/2008 | Vijay et al. |
| 2008/0069730 A1 | 3/2008 | Itoh |
| 2008/0138249 A1 | 6/2008 | Itoh |
| 2008/0167817 A1 | 7/2008 | Hessler et al. |
| 2008/0241837 A1 | 10/2008 | Ammann et al. |
| 2008/0255683 A1 | 10/2008 | Takahashi et al. |
| 2008/0268528 A1 | 10/2008 | Ammann et al. |
| 2008/0274511 A1 | 11/2008 | Tan et al. |
| 2008/0297769 A1 | 12/2008 | Bamberg et al. |
| 2009/0029352 A1 | 1/2009 | Ammann et al. |
| 2009/0029871 A1 | 1/2009 | Ammann et al. |
| 2009/0029877 A1 | 1/2009 | Ammann et al. |
| 2009/0030551 A1 | 1/2009 | Hein et al. |
| 2009/0035185 A1 | 2/2009 | Tsujimura et al. |
| 2009/0042281 A1 | 2/2009 | Chang et al. |
| 2009/0047179 A1 | 2/2009 | Ping et al. |
| 2009/0117620 A1 | 5/2009 | Fritchie et al. |
| 2009/0318276 A1 | 12/2009 | Miller |
| 2009/0324032 A1 | 12/2009 | Chen |
| 2010/0018330 A1 | 1/2010 | Marty et al. |
| 2010/0049358 A1* | 2/2010 | Koch .................. G01N 35/0099 700/214 |
| 2010/0115887 A1 | 5/2010 | Schroeder et al. |
| 2010/0129789 A1 | 5/2010 | Self et al. |
| 2010/0141756 A1 | 6/2010 | Grote et al. |
| 2010/0261595 A1 | 10/2010 | Schaefer et al. |
| 2010/0291619 A1 | 11/2010 | Robinson et al. |
| 2011/0065193 A1 | 3/2011 | Kitagawa et al. |
| 2011/0173927 A1* | 7/2011 | Yamada .................. G01N 35/04 53/236 |
| 2011/0226584 A1 | 9/2011 | Ek |
| 2012/0129673 A1 | 5/2012 | Fukugaki et al. |
| 2013/0123089 A1 | 5/2013 | Johns et al. |
| 2013/0125675 A1 | 5/2013 | Mueller et al. |
| 2013/0126302 A1 | 5/2013 | Johns et al. |
| 2013/0128035 A1 | 5/2013 | Johns et al. |
| 2013/0129166 A1 | 5/2013 | Mueller et al. |

FOREIGN PATENT DOCUMENTS

| | | |
|---|---|---|
| CN | 1164894 A | 11/1997 |
| CN | 1212019 A | 3/1999 |
| CN | 1212021 A | 3/1999 |
| CN | 1245218 A | 2/2000 |
| CN | 1281462 A | 1/2001 |
| CN | 1974781 A | 6/2007 |
| CN | 101379403 A | 3/2009 |
| DE | 35 10 797 C2 | 1/1988 |
| DE | 696 33 532 T2 | 2/2006 |
| EP | 0 324 616 A2 | 7/1989 |
| EP | 0 328 829 A2 | 8/1989 |
| EP | 0 410 645 A2 | 1/1991 |
| EP | 0 479 448 A2 | 4/1992 |
| EP | 0 502 589 A2 | 9/1992 |
| EP | 0 502 638 A2 | 9/1992 |
| EP | 0 542 422 A1 | 5/1993 |
| EP | 0 574 267 A2 | 12/1993 |
| EP | 0 574 267 A3 | 12/1993 |
| EP | 0 622 457 A1 | 2/1994 |
| EP | 0 600 130 A2 | 6/1994 |
| EP | 0 687 501 B1 | 12/1995 |
| EP | 0 656 864 B1 | 3/1996 |
| EP | 0 727 665 A2 | 8/1996 |
| EP | 0 763 739 A1 | 3/1997 |
| EP | 0 819 941 A2 | 1/1998 |
| EP | 0 875 584 A2 | 4/1998 |
| EP | 0 843 176 A1 | 5/1998 |
| EP | 0 680 883 B1 | 12/1998 |
| EP | 0 889 328 A | 7/1999 |
| EP | 0 953 838 A1 | 11/1999 |
| EP | 0 640 828 B1 | 5/2000 |
| EP | 1 069 942 B1 | 1/2001 |
| EP | 1 075 328 B1 | 2/2001 |
| EP | 0 875 584 A3 | 5/2001 |
| EP | 0 752 971 B1 | 6/2001 |
| EP | 1 205 756 A2 | 5/2002 |
| EP | 1 248 170 B1 | 10/2002 |
| EP | 1 273 919 A1 | 1/2003 |
| EP | 0 687 502 B1 | 3/2003 |
| EP | 1 288 758 B1 | 3/2003 |
| EP | 1 326 077 B1 | 9/2004 |
| EP | 1 557 961 A1 | 7/2005 |
| EP | 1 712 971 A2 | 10/2006 |
| EP | 1 712 971 A3 | 10/2006 |
| EP | 1 398 729 B1 | 10/2007 |
| EP | 1 024 355 B1 | 3/2008 |
| EP | 0 885 958 B1 | 6/2008 |
| EP | 1 138 784 B1 | 10/2008 |
| EP | 1 623 764 B1 | 2/2009 |
| EP | 1 614 470 B1 | 3/2009 |
| EP | 1 721 671 B1 | 10/2009 |
| EP | 1 731 222 B1 | 3/2010 |
| EP | 2 295 144 A | 3/2011 |
| EP | 2 316 570 A2 | 5/2011 |
| EP | 2 316 571 A2 | 5/2011 |
| EP | 2 316 572 A2 | 5/2011 |
| EP | 2 148 205 B1 | 1/2013 |
| GB | 2 101 514 A | 1/1983 |
| GB | 2 203 243 A | 10/1988 |
| JP | 62-148858 A | 7/1987 |
| JP | 01-211500 A1 | 8/1989 |
| JP | 02-025754 A2 | 1/1990 |
| JP | 05-184397 A | 7/1993 |
| JP | 05-219933 A | 8/1993 |
| JP | 05-281239 A | 10/1993 |
| JP | 05-081715 U | 11/1993 |
| JP | 06-011512 A | 1/1994 |
| JP | 06-197797 A | 7/1994 |
| JP | 06-327476 A | 11/1994 |
| JP | 07-049346 A | 2/1995 |
| JP | 07-75544 A | 3/1995 |
| JP | 07-191042 A | 7/1995 |

(56) References Cited

FOREIGN PATENT DOCUMENTS

| | | |
|---|---|---|
| JP | 07-213586 A | 8/1995 |
| JP | 07-107999 B2 | 11/1995 |
| JP | 07-301637 A | 11/1995 |
| JP | 07-333230 A | 12/1995 |
| JP | 08-9957 A | 1/1996 |
| JP | 08-62224 A | 3/1996 |
| JP | 08-211071 A | 8/1996 |
| JP | 08-285857 A | 11/1996 |
| JP | 08-286749 A | 11/1996 |
| JP | 08-320274 A | 12/1996 |
| JP | 09-021805 A | 1/1997 |
| JP | 09-080056 A | 3/1997 |
| JP | 09-089902 A | 4/1997 |
| JP | 09-89907 A | 4/1997 |
| JP | 09-121899 A | 5/1997 |
| JP | 09-329602 A | 12/1997 |
| JP | 10-062426 A | 3/1998 |
| JP | 11-503315 A | 3/1999 |
| JP | 2000-500331 A | 1/2000 |
| JP | 2000-046842 A | 2/2000 |
| JP | 3007571 B2 | 2/2000 |
| JP | 2001-503730 A | 3/2001 |
| JP | 2001-124786 A | 5/2001 |
| JP | 2002-296286 A | 10/2002 |
| JP | 2003-083991 A | 3/2003 |
| JP | 2006-317330 A | 11/2006 |
| JP | 2009-150859 A | 7/2007 |
| JP | 2007-249632 A | 9/2007 |
| JP | 2008-032652 A | 2/2008 |
| JP | 2008-032652 A2 | 2/2008 |
| JP | 4511034 A | 5/2010 |
| JP | 2011-503544 A | 1/2011 |
| JP | 4662580 A | 3/2011 |
| WO | 88/01302 A1 | 2/1988 |
| WO | 88/10315 A1 | 12/1988 |
| WO | 89/02476 A1 | 3/1989 |
| WO | 90/06042 A2 | 6/1990 |
| WO | 90/08840 A1 | 8/1990 |
| WO | 91/15768 A1 | 10/1991 |
| WO | 91/16675 A1 | 10/1991 |
| WO | 93/07292 A1 | 4/1993 |
| WO | 93/25912 A2 | 12/1993 |
| WO | 93/25912 A3 | 12/1993 |
| WO | 93/25913 A1 | 12/1993 |
| WO | 95/08774 A2 | 3/1995 |
| WO | 95/11454 A1 | 4/1995 |
| WO | 95/21382 A2 | 8/1995 |
| WO | 95/30139 A1 | 11/1995 |
| WO | 95/35390 A1 | 12/1995 |
| WO | 96/29602 A1 | 9/1996 |
| WO | 96/31781 A1 | 10/1996 |
| WO | 96/40990 A1 | 12/1996 |
| WO | 97/03348 A1 | 1/1997 |
| WO | 97/05492 A1 | 2/1997 |
| WO | 97/16561 A1 | 5/1997 |
| WO | 97/22882 A1 | 6/1997 |
| WO | 97/31105 A1 | 8/1997 |
| WO | 97/34908 A1 | 9/1997 |
| WO | 97/46707 A2 | 12/1997 |
| WO | 98/18008 A1 | 4/1998 |
| WO | 99/25476 A2 | 5/1999 |
| WO | 99/28724 A1 | 6/1999 |
| WO | 99/57561 A2 | 11/1999 |
| WO | 00/08472 A2 | 2/2000 |
| WO | 00/08472 A3 | 2/2000 |
| WO | 00/15481 A1 | 3/2000 |
| WO | 00/38046 A1 | 6/2000 |
| WO | 00/67547 A2 | 11/2000 |
| WO | 01/44510 A2 | 6/2001 |
| WO | 03/046412 A1 | 6/2003 |
| WO | 03/097808 A2 | 11/2003 |
| WO | 2004/013640 A1 | 2/2004 |
| WO | 2006/021052 A1 | 3/2006 |
| WO | 2006/068470 A1 | 6/2006 |
| WO | 2007/094744 A1 | 8/2007 |
| WO | 2008/030914 A2 | 3/2008 |
| WO | 2008/043393 A1 | 4/2008 |
| WO | 2008/057375 A2 | 5/2008 |
| WO | 2008/067847 A1 | 6/2008 |
| WO | 2009/068555 A1 | 6/2009 |
| WO | 2009/097263 A1 | 8/2009 |
| WO | 2009/150632 A2 | 12/2009 |
| WO | 2009/150632 A3 | 12/2009 |
| WO | 2010/017528 A2 | 2/2010 |
| WO | 2010/080340 A1 | 7/2010 |
| WO | 2010/081606 A1 | 7/2010 |
| WO | 2011/013701 A1 | 2/2011 |
| WO | 2011/028166 A1 | 3/2011 |
| WO | 2011/039932 A1 | 4/2011 |
| WO | 2011/093442 A1 | 4/2011 |
| WO | 2012/090795 A1 | 7/2012 |
| WO | 2012/158541 A1 | 11/2012 |

OTHER PUBLICATIONS

Abe et al., "Quantitation of Hepatitis B Virus Genomic DNA by Real-Time Detection PCR," J. Clin. Microbiol., 1999, 37(9):2899-2903, American Society for Microbiology, Washington D.C., USA.

ABI PRISM® 373 DNA Sequencer With XL Upgrade—User's Manual, Mar. 2001, TOC-iii-TOC-v & 6-11-6-16, Applied Biosystems, USA.

Abravaya, "Strategies to Avoid Amplicon Contamination," in Nucleic Acid Amplification Technologies: Application to Disease Diagnosis, 1997, pp. 125-133, Eaton Pub. Co., Natick, USA.

Akane, "Identification of the heme compound copurified with deoxyribonucleic acid (DNA) from bloodstains, a major inhibitor of polymerase chain reaction (PCR) amplification", J. Forensic Sci., 1994, 39:362-72, Blackwell Pub., USA.

Akduman et al., "Evaluation of a Strand Displacement Amplification Assay (BD ProbeTec-SDA) for Detection of Neisseria gonorrhoeae in Urine Specimens," J. Clin. Microbiol., 2002, 40(1):281-282, American Society for Microbiology, Washington D.C., USA.

Amplification Technical Bulletin, "Comparison of TMA with PCR and LCR Amplification Methods," undated, Gen-Probe Incorporated, San Diego, USA, 1 page.

Analog Device; "±5 g to ±5 g, Low Noise, Low Power, Single/Dual Axis / MEMS® Accelerometers,"; http://hibp.ecse.rpi.edu/~connor.education/EISpecs/ADXL150_250_0.pdf;; Jan. 1, 1998; pp. 1-15.

Anderson et al., "Microfluidic Biochemical Analysis System," Transducers, International Conference on Solib-Slate Sensors and Actuators, Jun. 16-19, 1997, p. 477-480, IEEE Electron Devices Society, Piscataway, USA.

Armstrong et al., 1996, "Automated high throughput RT-PCR," Laboratory Robotics and Automation 8:311-315, VCH Publishers, USA.

Astle, "Standards in Robotics and Instrucmentation," Society Updates, Working Group Updates, and Conference Highlights, J. Biomol. Screen., 1996, 1(4):161-172, Sage Publications, USA.

Bailey et al., "Robotic Nucleic Acid Isolation Using a Magnetic Bead Resin and an Automated Liquid Handler for Biological Agent Simulants,", JALA, Dec. 2003, 8:113-120.

Bassam. "Nucleic Acid Sequence Detection Systems: Revolutionary Automation for Monitoring and Reporting PCR Products" Australasian Biotechnology, 1996, 6:285-294, Australian Biotechnology Association, Australia.

Belgrader et al., "Automated DNA Purification and Amplification from Blood-Stained Cards Using a Robotic Workstation," Short Technical Reports, Biotechniques, 1995, 19(9):426-432, Informa Healthcare USA, Inc., UK.

Belgrader et al., "Automated Polymerase Chain Reaction Product Sample Preparation for Capillary Electrophoresis Analysis," J. Chromatogr. B Biomed. Appl., 1996, 683:109-114, Elsevier Science, Amsterdam, Netherlands.

Belgrader et al., "Automated Sample Processing Using Robotics for Genetic Typing of Short Tandem Repeat Polymorphisms by Capillary Electrophoresis," Laboratory Robotics and Automation, 1997, 9:3-7, Wiley & Sons Inc., USA.

(56) References Cited

OTHER PUBLICATIONS

Borst et al., "False-Positive Results and Contamination in Nucleic Acid Amplification Assays: Suggestions for a Prevent and Destroy Strategy," Eur. J. Clin. Microbiol. Infect Dis., 2004, 23:289-299, Springer-Verlag, Berlin, Germany.
Boyd et al., "Robotics and the changing face of the clinical laboratory," Clin. Chem., 1996, 42(12):1901-1910, Washington DC American Association for Clinical Chemistry, USA.
Brochure, "Amplified Mycobacteria Direct Tests," undated, Gen-Probe Incorporated, San Diego, USA, 6 pages.
Brochure, "Introducing the Amplified Mycobacterium Tuberculosis Direct (MTD) Test from Gen-Probe," Oct. 1996, Gen-Probe Incorporated, San Diego, USA, 2 pages.
Brochure, "The Future of Amplification Technology has Arrived," Oct. 1995, Gen-Probe Incorporated, San Diego, USA, 4 pages.
Buhlmann et al., "An Open Software Environment to Optimize the Productivity of Robotized Laboratories," J. Chromatogra. Sci., 1994, 32:243-248, Preston Technical Abstracts, Niles, USA.
Bush et al., "Detection of human immunodeficiency virus type 1 RNA in plasma samples from high-risk pediatric patients by using the self-sustained sequence replication reaction," J. Clin. Microbiol., 1992, 30(2):281-286, American Society for Microbiology, Washington D.C., USA.
Butler et al., "Forensic DNA typing by capillary electrophoresis using the ABI Prism 310 and 3100 genetic analyzers for STR analysis," Electrophoresis, 2004, 25:1397-1412, Wiley-VCH Verlag GmbH & Co. KGaA, Germany.
Caprari, G. et al.; "The autonomous Micro Robot "Alice": a platform for scientific and commercial applications"; *Proceedings of the 1998 International Symposium on Micromechatronics and Human Science*, Nagoya, Japan; Nov. 25-28, 1998; pp. 1-5.
Carlson et al., "Laboratory Detection of Chlamydia trachomatis, Neisseria gonorrhoeae, and Other Sexually-Transmitted Agents," 97th General Meeting of the American Society for Microbiology, C-308, May 4-8, 1997, Miami Beach, USA.
Carrino et al., "Nucleic Acid Amplification Methods," J. Micorbiol. Methods, 1995, 23:3-20.
Check, "Real-time PCR for the rest of us," CAP Today, Jun. 2006, College of American Pathologists, Skokie, IL, USA, 6 pages.
Chemistry Guide, "Automated DNA Sequencing," PE Applied Biosystems, 1998, pp. I-4-I-6, The Perkin-Elmer Corporation.
Cimino et al., "Post-PCR sterilization: a method to control carry-over contamination for the polymerase chain reaction," Nucleic Acids Res., 1991, 19(1):99-107, Oxford University Press, Oxford, United Kingdom.
Clewley, "Automation of the Polymerase Chain Reaction Part 2. Extraction—the Foundation for Success," Communicable Disease and Public Health, Jun. 1999, 2(2):147-148, Public Health Laboratory Service in association with the Scottish Centre for Infection and Environmental Health, London, United Kingdom.
Corkan et al., "Experiment Manager Software for an Automated Chemistry Workstation, Including a Scheduler for Parallel Experimentation," Chemometrics and Intelligent Laboratory Systems: Laboratory Information Management, 1992, 17:47-74, Elsevier Science Publishers, Amsterdam, Netherlands.
Corrected Request for Inter Partes Reexamination of U.S. Pat. No. 7,482,143, filed on Sep. 14, 2012, 121 pages.
Crotchfelt et al., "Detection of Chlamydia trachomatis by the Gen-Probe Amplified *Chlamydia trachomatis* Assay (AMP CT) in Urine Specimens from Men and Women and Endocervical Specimens from Women," J. Clin. Microbiol., Feb. 1998, 36(2):391-394, American Society for Microbiology, Washington D.C., USA.
Davis et al., "Amplification of DNA Using the Polymerase Chain Reaction," in Basic Methods in Molecular Biology, 2nd ed., 1994, p. 121, Appleton & Lange, Norwalk, USA.
Diamandis, "Automation of molecular diagnostics," Clinical Chemistry, 1996, 42:7-8, American Association for Clinical Chemistry, USA.
DiDomenico et al., "COBAS AMPLICOR™: fully automated RNA and DNA amplification and detection system for routine diagnostic PCR," Clin. Chem., 1996, 42(12):1915-1923, Washington DC American Association for Clinical Chemistry, USA.
Dieffenbach et al., "Setting Up a PCR Laboratory," Genome Rsearch, PCR Methods and Applications, 1993, 3:s2-s7, Cold Spring Harbor Laboratory, Cold Spring Harbor, USA.
Dragon, "Handling Reagents in the PCR Laboratory," Genome Research, PCR Methods and Applications, 1993, 3:s8-s9, Cold Spring Harbor Laboratory, Cold Spring Harbor, USA.
DYNAL®, Technical Handbook. Molecular Biology, First Edition. "Dynabeads® biomagnetic separation system," 1992, 4 pages, Dynal AS, Norway.
Erlich, "PCR Technology," in Encyclopedia of Molecular Biology and Molecular Medicine: Mass Spectrometry High Speed DNA Fragment Sizing to Plasma Lipoproteins, vol. 4, 1996, p. 337, VCH Verlagsgesellschaft mbH, Weinheim, Germany.
Espy et al., "Dependence of polymerase chain reaction product inactivation protocols on amplicon length and sequence composition," J. Clin. Microbiol., 1993, 31(9):2361-2365, American Society for Microbiology, Washington D.C., USA.
Farrell, Jr., "RT PCR" in RNA Method: A Laboratory Guide for Isolation and Characterization, 1998, 2nd ed., Chapter 15, pp. 296-307, Academic Press, San Diego, California, USA.
Feinberg, "A Technique for Radiolabeling DNA Restriction Endonuclease Fragments to High Specific Activity", Analytical Biochemistry, 1983, 132:6-13, Academic Press, USA.
Findlay et al., "Automated Closed-Vessel System for in Vitro Diagnostics Based on Polymerase Chain Reaction," Clin. Chem., 1993, 39(9):1927-1933, American Association for Clinical Chemistry, Washington, D.C., USA.
Fiore et al., "The Abbott IMx automated benchtop immunochemistry analyzer system," Clin. Chem., 1988, 34 (9):1726-32, American Association for Clinical Chemistry, Washington D.C., USA.
FLEXLINK®; "TX45E puck handling (mx. 250g),"; located at http://www.flexlink.com/en/offering/conveyor-systems/pallet-and-puck-handling/x45e.jsp; last visited on Jul. 20, 2013; 2 pages.
Friendenberg et al., "Developing a fully automated instrument for molecular diagnostic assays," IVD Technology, 2005, 11(6), 6 pages, A Canon Communications, Los Angeles, USA.
Furrows et al., "'Good laboratory practice' in diagnostic laboratories using nucleic acid amplification methods," Clin. Microbiol. Infect., 2001, 7(5):227-229, Blackwell Science, Oxford, United Kingdom.
Gelmini et al., "Quantitative polymerase chain reaction-based homogeneous assay with fluorogenic probes to measure c-erbB-2 oncogene amplification," Clin. Chem., 1997, 43(5):752-758, American Association for Clinical Chemistry, Washington D.C., USA.
Gerber et al., "Differential Transcriptional Regulation of the Two Vascular Endothelial Growth Factor Receptor Genes," J. Biol. Chem., 1997, 272(38):23659-23667, The American Society for Biochemistry and Molecular Biology, Baltimore, USA.
Gibson et al., "A homogenous method for genotyping with fluorescence polarization," Clin. Chem., 1997, 43(8):1336-1341, American Association for Clinical Chemistry, Washington D.C., USA.
Gibson et al., "A novel method for real time quantitative RT-PCR," Genome Methods, 1996, 6:995-1001, Cold Spring Harbor Laboratory Press, Cold Spring Harbor, USA.
Giesendorf et al., "Molecular beacons: a new approach for semiautomated mutation analysis," Clin. Chem., 1998, 44(3):482-486, American Association for Clinical Chemistry, Washington D.C., USA.
Gilgen et al., "Hydroxyquinoline overcomes PCR inhibition by UV-damaged mineral oil," Nucleic Acids Res., 1995, 23(19):4001-4002, Oxford University Press, Oxford, United Kingdom.
Ginocchio, "Life Beyond PCR: Alternative Target Amplification Technologies for the Diagnosis of Infectious Diseases, Part II," Clinical Microbiology Newsletter, 2004, 26(17):129-136, Elsevier Science, New York, USA.
Godfrey-Faussett, "Molecular Diagnosis of Tuberculosis: The Need for New Diagnostic Tools," Thorax, 1995, 50(7):709-711, British Medical Association, London, United Kingdom.

(56) References Cited

OTHER PUBLICATIONS

Greenstein, "Preparing and Using M13-Derived Vectors," Current Protocols in Molecular Biology, published 1990, §1.151 and 1.15.4, J. Wiley and Sons, USA.
Haas, "Clinical Instrumentation (General Chemistry and Immunoassay Analyzers)," Anal. Chem., 1993, 65(12):444R-449R, American Chemical Society, Washington D.C., USA.
Haglund et al., "Polymerase Chain Reaction," in Forensic Taphonomy: the Postmortem Fate of Human Remains, 1997, p. 114-115, CRC Press LLC, Boca Raton, USA.
Hartley et al., "Dealing with Contamination: Enzymatic Control of Carryover Contamination in PCR," Genome Research, PCR Methods and Applications, 1993, 3:s10-s14, Cold Spring Harbor Laboratory, Cold Spring Harbor, USA.
Hawker, "Laboratory Automation: Total and Subtotal," Clin. Lab. Med., 2007, 27:749-770, Elsevier Health Sciences Division, Philadelphia, USA.
Hawkes et al., "Asymptomatic carriage of *Haemophilus ducreyi* confirmed by the polymerase chain reaction," J. Genitourin. Med., 1995, 71:224-227.
Hawkins et al., "A Magnetic Attraction to High-Throughput Genomics," Science, 1997, 276:1887 & 1889 (p. 1888 omitted—advertisement only), Washington, DC: American Association for the Advancement of Science, USA.
Hedrum et al., "Immunomagnetic Recovery of *Chlamydia trachomatis* from Urine with Subsequent Colorimetric DNA Detection," PCR Methods Appl., 1992, 2:167-171, Cold Spring Harbor Laboratory Press, Cold Spring Harbor, USA.
Heid et al., "Real Time Quantitative PCR," Genome Research, 1996, 6:986-994, Cold Spring Harbor Laboratory Press, Cold Spring Harbor, USA.
Hellyer et al., "Letter to the Editor: Specificity of IS6110-Based Amplification Assays for *Mycobacterium tuberculosis* Complex," J. Clin. Microbiol., 1997, 35(3):799-801, American Society for Microbiology, Washington D.C., USA.
Herring et al., "ELISA Automation: A Biomek 1000 to Biomek 2000 Comparison of Clinical ELISAs", Application Information, 1995, Beckman Industries, Inc., USA.
Herrmann et al., "General Aspects of Sample Preparation," in Ancient DNA: Recovery and Analysis of Genetic Material from Paleontological, Archaeological, Museum, Medical, and Forensic Specimens, 1994, pp. 63-64, Springer-Verlag, New York City, USA.
Hicks et al., "Beckman/Sagian "Core" Molecular Biology System,", T-1845A, Beckman Instruments, Inc., 1997, 4 pages.
Higuchi et al., "Simultaneous Amplification and Detection of Specific DNA Sequences," Bio/Technology, 1992, 10:413-417, Nature Publishing Company, New York, USA.
Hildebrandt et al,, Development of an Automated Sample Preparation Method for HCV, J. Microbiol. Methods, 1997, 30:235-253, Abstract 17, 1 page, Elsevier Biomedical, Amsterdam, Netherlands.
Hill, "Gen-Probe Transcription-Mediated Amplification: System Principles," Jan. 1996, Gen-Probe Incorporated, San Diego, USA, 4 pages.
Hill, "How Full Automation of Molecular Diagnostic Testing Can Increase Accuracy, Lab Efficiency, Cost Savings," Issue Stories, Jul. 2004, 3 pages, Clinical Lab Products, Los Angeles, USA.
Hill, "Molecular diagnostic testing for infectious diseases using TMA technology," Expert Rev. Mol. Diagn., 2001, 1 (4):445-455, Future Drugs Ltd., London, United Kingdom.
Hill, "Molecular Diagnostic Tests for Sexually Transmitted Infections in Women," in Infectious Diseases in Obstetrics and Gynecology, 2008, 6th ed., pp. 612-623, Informa plc, St. Helier, Jersey.
Hill, "Molecular Diagnostics for Infectious Diseases," J. Clin. Ligand Assay, 1996, 19(1):43-52, Clinical Ligand Assay Society, Wayne, Michigan, USA.
Hoad et al., "Virus Genome Detection by the PCR," in Practical Molecular Virology: Viral Vectors for Gene Expression, 1991, pp. 75-76, Humana Press, Totowa, USA.
Holland et al., "Detection of specific polymerase chain reaction product by utilizing the 5'→ 3' exonuclease activity of Thermus aquaticus DNA polymerase," Biochemistry, 1991, 88:7276-7280, Proc. Natl. Acad. Sci. USA, Washington D.C., USA.
International Search Report and Written Opinion dated Feb. 15, 2013 for PCT Application No. PCT/US2012/063923, 12 pages.
International Search Report and Written Opinion dated Feb. 15, 2013 for PCT Application No. PCT/US2012/063914, 9 pages.
International Search Report and Written Opinion dated Jun. 12, 2013 for PCT Patent Application No. PCT/US2012/063888, 18 pages.
International Search Report and Written Opinion dated Mar. 19, 2013 for PCT Application No. PCT/US2012/063929, 13 pages.
International Search Report and Written Opinion dated Dec. 7, 2012 for PCT Patent Application No. PCT/US2011/045107, 18 pages.
International Search Report and Written Opinion dated Oct. 4, 2013 for PCT Patent Application No. PCT/US2012/063931, 24 pages.
International Search Report and Written Opinion dated Sep. 30, 2013 for PCT Patent Application No. PCT/US2012/063930, 37 pages.
Invitation to Pay Additional Fees dated Mar. 1, 2013 for PCT Patent Application No. PCT/US2012/063918, 6 pages.
Invitation to Pay Additional Fees dated Mar. 19, 2013 for PCT Patent Application No. PCT/US2012/063930, 8 pages.
Invitation to Pay Additional Fees dated Mar. 25, 2013 for PCT Patent Application No. PCT/US2012/063931, 8 pages.
Invitation to Pay Additional Fees dated Mar. 6, 2013 for PCT Patent Application No. PCT/US2012/063888, 6 pages.
Invitrogen; Manual, "Dynabeads® DNA Direct™ Blood" Cat. No. 631.02 "For the isolation of PCR-ready genomic DNA from blood" Rev. o. 006, Invitrogen *Dynal® Invitrogen Bead Separations*, 2007.
Jaklevic, "Automation of High-Throughput PCR Assays," Laboratory Robotics and Automation, 8(5):277-286, John Wiley & Sons Inc., USA.
Jaton et al., "Development of polymerase chain reaction assays for detection of Listeria monocytogenes in clinical cerebrospinal fluid samples," J. Clin. Microbiol., 1992, 30(8):1931-1936, American Society for Microbiology, Washington D.C., USA.
Jungkind et al., "Evaluation of Automated COBAS Amplicor PCR System for Detection of Several Infectious Agents and Its Impact on Laboratory Management," J. Clin. Microbiol., 1996, 34(11):2778-2783, American Society for Microbiology, Washington, D.C., USA.
Kalinina et al., "Nanoliter scale PCR with TaqMan detection," Nucleic Acids Res., 1997, 25(10):1999-2004, Oxford University Press, Oxford, United Kingdom.
Kapperud et al., "Detection of Pathogenic Yersinia enterocolitica in Foods and Water by Immunomagnetic Separation, Nested Polymerase Chain Reactions, and Colorimetric Detection of Amplified DNA," Appl. Environ. Microbiol., 1993, 59(9):2938-2944, American Society for Microbiology, Washington, D.C., USA.
Kendrew et al., "Polymerase Chain Reaction," in The Encyclopedia of Molecular Biology, 1994, pp. 864-865, Blackwell Science Ltd., Cambridge, USA.
Khalil "Automation and Use of Robotics in Nucleic Acid Amplification Assays," in Nucleic Acid Amplification Technologies: Application to Disease Diagnosis, 1997, p. 151-164, Eaton Pub. Co., Natick, USA.
Kolk et al., "Development of Individual and Multiplex Assays for the Detection of HIV and HCV," 13th Annual Clinical Virology Symposium and Annual Meeting of the Pan American Society for Clinical Virology, M7, Apr. 27-30, 1997, Clearwater Beach, USA.
Kolmodin et al., "Basic Principles and Routine Practice," in PCR Cloning Protocols From Molecular Cloning to Genetic Engineering, 1997, pp. 3-5, Humana Press, Totowa, USA.
Kost, G. J., *Handbook of Clinical Automation, Robotics, and Optimization*; Chapters 1, 10, and 12-14; 1996 by John Wiley & Sons, Inc.; 189 pages total.
Kretz et al., "Cycle sequencing," PCR Methods and Applications, 1994, 3:S107-S112, Cold Spring Harbor Laboratory, Cold Spring Harbor Press, USA.
Krieg, "Quantification of RNA by Competitive RT PCR," in a Laboratory Guide to RNA, 1996, p. 210, Wiliey-Liss, New York City, USA.
Kwok et al., "Avoiding False Positive with PCR," Nature, 1989, 339:237-238, Nature Publishing Group, Basingstoke, USA.

(56) References Cited

OTHER PUBLICATIONS

Landry, "False-Positive Polymerase Chain Reaction Results in the Diagnosis of Herpes Simplex Encephalitis," J. Infect. Dis., 1995, 172(6):1641-1642, University of Chicago Press, Chicago, USA.

Lay et al., "Real-time fluorescence genotyping of factor V Leiden during rapid-cycle PCR," Clin. Chem., 1997, 43(12):2262-2267, American Association for Clinical Chemistry, Washington D.C., USA.

Lee et al., "Direct Identification of *Vibrio vulmificus* in Clinical Specimens by Nested PCR," J. Clin. Microbial., 1998, 36 (10):2887-2892, American Society for Microbiology, Washington D.C., USA.

Lee et al., "Nucleic Acid Amplification Technologies: Application to Disease Diagnosis," BioTechniques Books, 1997, pp. 1-286, Eaton Publishing, Massachusetts, USA.

Leone et al., "Molecular beacon probes combined with amplification by NASBA enable homogeneous, real-time detection of RNA," Nucleic Acids Res., 1998, 26(9): 2150-2155, Oxford University Press, Oxford, United Kingdom.

Lisby, "Application of Nucleic Acid Amplification in Clinical Microbiology," in Methods in Molecular Biology: PCR in Bioanalysis, 1998, pp. 1-29, Humana Press, Totowa, USA.

Livak et al., "Oligonucleotides with Fluorescent Dyes at Opposite Ends Provide a Quenched Probe System Useful for Detecting PCR Product and Nucleic Acid Hybridization," PCR Methods and Applications, 1995, 4:357-362, Cold Spring Harbor Laboratory Press, Cold Spring Harbor, New York, USA.

Lo et al., "Quantitative Analysis of Fetal DNA in Maternal Plasma ad Serum: Implications for Noninvasive Prenatal Diagnosis," 1998, Am. J. Hum. Genet., 62:768-775, American Society of Human Genetics, Baltimore, USA.

Lo, "Setting Up a PCR Laboratory," in Methods in Molecular Medicine: Clinical Applications of PCR, 1998, pp. 12-17, Humana Press, Totowa, USA.

Longo, "Use of uracil DNA glycosylase to control carry-over contamination in polymerase chain reactions" Gene, 1990, 93: 125-128, Elsevier/North-Holland, Amsterdam.

Mabilat et al., "Routine Identification of *Mycobacterium tuberculosis* Complex Isolates by Automated Hybridization," J. Clin. Microbiol., 1994, 32(11):2702-2705, American Society for Microbiology, Washington, D.C., USA.

Magnemotion; "MagneMover™ LITE,"; located at http://www.magnemotion.com/industrial-automation/magmoverlite.cfm; last visited on Jul. 20, 2013; 3 pages.

Mangiapan, "Sequence capture-PCR improves detection of mycobacterial DNA in clinical specimens" J Clin Microbiol., 1996, 34: 1209-1215, American Society for Microbiology, USA.

Martin et al., "PCR and Its Modifications for the Detection of Infectious Disease," Nucleic Acid Amplification Technologies: Application to Disease Diagnosis, 1997, p. 79-100, Eaton Pub. Co., Massachusetts, USA.

McCreedy et al., "Laboratory Design and Work Flow," Diagnostic Molecular Microbiology Principles and Applications, 1993, p. 149-159, Mayo Foundation, Rochester, USA.

Meng et al., "Turbo PCR—An Integrated Robotic System for Continuously Setting Up and Running Multiple PCR Reactions," DOE Human Genome Program Contractor-Grantee Workshop IV, Nov. 13-17, 1994, Santa Fe, New Mexico, 1 page.

Mercier et al., "Direct PCR from whole blood, without DNA extraction," Nucleic Acids Res., 1990, 18(19):5908, Oxford University Press, Oxford, United Kingdom.

Merel et al., "Completely Automated Extraction of DNA from Whole Blood," Clin. Chem., 1996, 42(8):1285-1286, American Association for Clinical Chemistry, USA.

Merel et al., "Perspectives on Molecular Diagnostics Automation," JALA, 2005, 10:342-350, Association for Laboratory Automation, Charlottesville, USA.

Meyers, "PCR Technology," Molecular Biology and Biotechnology: A Comprehensive Desk Reference, 1995, pp. 642-646, VCH Publishers Inc., New York City, USA.

Mischiati et al., "Use of an Automated Laboratory Workstation for Isloation of Genomic DNA Suitable for PCR and Allele-Specific Hybridization," BioTechniques, 1993, 15(1):146-151, Eaton Pub. Co., Natick, USA.

Mondada, Francesco et al.; "The e-Puck, a Robot Designed for Education in Engineering", *Proceedings of the 9th Conference on Autonomous Robot Systems and Competitions*, Castelo Branco, Portugal; May 7, 2009; vol. 1; Issue 1; pp. 59-65.

Mullis, "Eine Nachtfahrt und die Polymerase-Kettenreaktion," Spektrum der Wissenschaft, 1950, pp. 60-67, Germany.

Muramatsu et al., "Molecular Cell Biology Dictionary," 1997, Tokyo Kagaku Dojin Publisher, Tokyo, Japan, English Translation, 10 pages.

Nace, "Automation in Molecular Diagnostics: A Pleasant Surprise," Advance for Medical Laboratory Professionals, 2006, 14(11):64, Merion Publications, King of Prussia, PA, USA.

Nazarenko et al., "A closed tube format for amplification and detection of DNA based on energy transfer," Nucleic Acids Res., 1997, 25(12):2516-2521, Oxford University Press, Oxford, United Kingdom.

Neumaier et al., "Fundamentals of Quality Assessment of Molecular Amplification Methods in Clinical Diagnostics," Clin. Chem., 1998, 44(1):12-26, American Society for Clinical Chemistry, Washington D.C., USA.

Newton et al., "Instrumentation, Reagents and Consumables," PCR, 1996, 2nd ed., Chpt. 2, pp. 9-28, Bios Scientific, UK.

Nickerson et al., "Automated DNA Diagnostics Using an ELISA-based Oligonucleotide Ligation Assay," Proc. Natl. Acad. Sci. USA, 1990, 87:8923-8927, National Academy of Sciences, Washington, D.C., USA.

Niederhauser et al., "Direct Detection of *Listeria monocytogenes* Using Paramagnetic Bead DNA Extraction and Enzymatic DNA Amplificaiton,", Molecular and Cellular Probes, 1994, 8:223-228.

Noordhoek et al., "Reliability of Nucleic Acid Amplification for Detection of *Mycobacterium tuberculosis*: an International Collaborative Quality Control Study Among 30 Laboratories," J. Clin. Microbiol., 1996, 34(10):2522-2524, American Society for Microbiology, Washington D.C., USA.

Obata et al., "Development of a Novel Method for Operating Magnetic Particles, Magtration Technology, and Its Use for Automating Nucleic Acid Purification," J. Biosci. Bioeng., 2001, 91(5):500-503, Elsevier Science, Amsterdam, Netherlands.

Oehlenschlager et al., "Detection of HIV-1 RNA by nucleic acid sequence-based amplification combined with fluorescence correlation spectroscopy," Biochemistry, 1996, 93:12811-12816, Proc. Natl. Acad. Sci. USA, Washington D.C., USA.

Olive, "Q-Beta Replicase Assays for the Clinical Detection of Infectious Agents," in Nucleic Acid Amplification Technologies: Application to Disease Diagnosis, 1997, p. 110, Eaton Pub. Co., Natick, USA.

Olsvik et al., "Magnetic Separation Techniques in Diagnostic Microbiology," Clin. Microbiol. Rev., 1994, 7(1):43-54, American Society for Microbiology, Washington, D.C., USA.

Oste, "Polymerase Chain Reaction," Product Application FOCUS, BioTechniques, 1988, 6(2):162-167, Informa Healthcare USA, Inc., UK.

Package Insert, "APTIMA® Assay for *Neisseria gonorrhoeae*," IN0148-01-REG, Rev. 1, Nov. 2004, Gen-Probe Incorporated, San Diego, USA, 20 pages.

Package Insert, "APTIMA® HCV RNA Qualitative Assay," 500237 Rev. B, Jul. 2006, Gen-Probe Incorporated, San Diego, USA, 18 pages.

Package Insert, "Gen-Probe® Amplified Mycobacterium Tuberculosis Direct Test," IN0006 Rev. A, Feb. 24, 1994, Gen-Probe Incorporated, San Diego, USA, 14 pages.

Package Insert, "Gen-Probe® Amplified™ Chlamydia Trachomatis Assay," IN0012 Rev. A, Jan. 6, 1997, Gen-Probe Incorporated, San Diego, USA, 17 pages.

Package Insert, "Gen-Probe® Amplified™ Chlamydia Trachomatis Swab Specimen Preparation Kit," In0016 Rev. A, Jan. 6, 1997, Gen-Probe Incorporated, San Diego, USA, 3 pages.

(56) References Cited

OTHER PUBLICATIONS

Package Insert, "Gen-Probe® Amplified™ Chlamydia Trachomatis Urine Specimen Preparation Kit," IN0017 Rev. A, Nov. 11, 1996, Gen-Probe Incorporated, San Diego, USA, 3 pages.

Package Insert, "Gen-Probe® Aptima® Combo 2 Assay," IN0037 Rev. A, Jun. 6, 2001, Gen-Probe Incorporated, San Diego, USA, 28 pages.

Package Insert, "Gen-Probe® Aptima Combo 2® Assay," 501011 Rev. A, Jan. 2007, Gen-Probe Incorporated, San Diego, USA, 44 pages.

Package Insert, "Gen-Probe® Aptima® Assay for *Chlamydia trachomatis*," IN0147-01, Rev. B, Apr. 2005, Gen-Probe Incorporated, San Diego, USA, 24 pages.

Package Insert, "Procleix® HIV-1/HCV Assay," IN0076-01-FDA, Rev. 3, Jun. 2004, Gen-Probe Incorporated, San Diego, USA, 28 pages.

Package Insert, "Procleix® HIV-1/HCV Assay," IN0076-02-FDA, Rev. 1, Jan. 2005, Gen-Probe Incorporated, San Diego, USA., 32 pages.

Package Insert, "Procleix® Ultrio™ Assay," IN0167EN, Rev. 1, Aug. 2004, Gen-Probe Incorporated, San Diego, USA, 44 pages.

Package Insert, "Procleix® WNV Assay," IN0155, Rev. 1, Apr. 2004, Gen-Probe Incorporated, San Diego, USA, 15 pages.

Paillard et al., "Direct nucleic acid diagnostic tests for bacterial infectious diseases: Streptococcal pharyngitis, pulmonary tuberculosis, vaginitis, chlamydial and gonococcal infections," MLO, Jan. 2004, pp. 10-15, Medical Laboratory Observer, NP Communications, LLC, Monroe Township, USA.

Panaccio et al., "PCR based diagnosis in the presence of 8% (v/v) blood," Nucleic Acids Res., 1991, 19(5):1151, Oxford University Press, Oxford, United Kingdom.

Patel et al., "Death from Inappropriate Therapy for Lyme Disease," Clin. Infect. Dis., 2000, 31:1107-1109, The University of Chicago Press, Chicago, USA.

Patterson et al., "Random and continuous-access immunoassays with chemiluminescent detection by Access automated analyzer," Clin. Chem., 1994, 40(11):2042-2045, American Association for Clinical Chemistry, Washington D.C., USA.

Pauwels et al., "Automated techniques in biotechnology," Current Opinion in Biotechnology, 1995, 6:111-117, Current Biology Ltd., London, United Kingdom.

Pawlotsky, "Measuring Hepatitis C Viremia in Clinical Samples: Can We Trust the Assays?" J. Hepatol., 1997, 26(1):1-4, Viral Hepatitis Foundation Bangladesh, Dhaka, Bangladesh.

Persing, "Diagnostic molecular microbiology. Current challenges and future directions," Diagn. Microbiol. Infect. Dis., 1993, 16(2):159-163, Elsevier Biomedical, New York, USA.

Petrik et al., "Human Hepatic Glyceraldehyde-3-phosphate dehydrogenase Binds to the poly(U) tract of the 3' Non-Coding Region of Hepatitis C Virus Genomic RNA," J. General Virology, 1999, 80:3109-3113.

Request for Inter Partes Reexamination of U.S. Pat. No. 7,524,652, filed on Sep. 15, 2012, 134 pages.

Riggio et al., "Identification by PCR of Helicobacter pylori in subgingival plaque of adult periodontitis patients," J. Med. Microbiol., 1999, 48:317-322, The Pathological Society of Great Britain and Ireland.

Rosenblum et al., "New dye-labeled terminators for improved DNA sequencing patterns," Nucleic Acids Res., 1997, 25(22):4500-4504, Oxford University Press, UK.

Rudi et al., "Rapid, Universal Method to Isolate PCR-Ready DNA Using Magnetic Beads," BioTechniques, 1997, 22(3):506-511, Informa Healthcare USA, Inc., UK.

Rudi, et al., "Detection of Toxin-Producing Cyanobacteria by Use of Paramagnetic Beads for Cell Concentration and DNA Purification," 1998, Appl. Environ. Microbiol., 64(1):34-37, Am. Society of Microbiol., USA.

Schepetiuk et al., "Detection of *Chlamydia trachomatis* in Urine Samples by Nucleic Acid Tests: Comparison with Culture and Enzyme Immunoassay of Genital Swab Specimens," J. Clin Micorbiol., Dec. 1997, 35(12):3355-3357.

Skeggs, "An automatic method for colorimetric analysis," Am. J. Clin. Pathol., 1957, 28:311-322, American Society of Clinical Pathologists, Chicago, USA.

Smith et al., "Abbott AxSYM random and continuous access immunoassay system for improved workflow in the clinical laboratory," Clin. Chem., 1993, 39(10):2063-2069, American Association for Clinical Chemistry, Washington D. C., USA.

Smith et al., "Detection of *Mycobacterium tuberculosis* Directly from Sputum by Using a Prototype Automated Q-Beta Replicase Assay," J. Clin. Microbiol., 1997, 35(6):1477-1483, American Society for Microbiology, Washington, D.C., USA.

Smith et al., "Performance of an Automated Q-Beta Replicase Amplification Assay for *Mycobacterium tuberculosis* in a Clinical Trial," J. Clin. Microbiol., 1997, 35(6):1484-1491, Am. Society for Microbiology, USA.

Stanley et al., "A Survey of More Than 90 Commercially Available Luminometers and Imaging Devices for Low-Light Measurements of Chemiluminescence and Bioluminescence, Including Instruments for Manual, Automatic and Specialized Operation, for HPLC, LC, GLC and Microtitre Plates. Part 2: Photographs," J. Biolumin. Chemilumin., 1992, 7:157-169, John Wiley & Sons, Ltd., Chichester, Sussex, England.

Stanley, "Commercially Available Luminometers and Imaging Devices for Low-Light Level Measurements and Kits and Reagents Utilizing Bioluminescence or Chemiluminescence: Survey Update 3," J. Biolumin. Chemilumin., 1994, 9:123-125, John Wiley & Sons, Ltd., UK.

Stone et al., "Detection of rRNA from four respiratory pathogens using an automated Qβ replicase assay," Mol. Cell. Probes, 1996, 10:359-370, Academic Press Limited, San Diego, California, USA.

Suryanarayana et al., "Plasma SIV RNA Viral Load Determination by Real-Time Quantification of Product Generation in Reverse Transcriptase-Polymerase Chain Reaction," AIDS Res. Hum. Retroviruses, 1998, 14(2):183-189, Mary Ann Liebert, Inc., USA.

Sutton et al., "Hands Free Polymerase Chain Reaction," International Symposium on Laboratory Automation and Robotics, Oct. 17-20, 1993, p. 326-336, Boston, USA.

Sutton et al., "PCR Has Outgrown Appropriate Automated Instrumentation but Help is on the Way," Today's Chemist at Work, 1995, p. 42-48, American Chemical Society, Washington, D.C., USA.

TAOS Inc. "TCS230 Programmable Color to Light-to-Frequency Converter," www.http?pdfl.alldatasheet.com/datasheet-pdf/view/96470/ETC/TCS230.html; Jan. 31, 2003, pp. 1-8.

Techne PHC-3 Thermal Cycler—Techni, Jun. 2009, Pegasus Scientific Inc., USA.

Tjian, "Purification and comparative properties of the delta and sigma subunits of RNA polymerase from Bacillus subtilis" Eur. J. Biochem., 1977, 74:149, Blackwell Science Ltd. on behalf of the Federation of European Biochemical Societies, UK.

Tyagi et al., "Extremely sensitive, background-free gene detection using binary proves and QB Replicase," Biochemistry, 1996, 93:5395-5400, Proc. Natl. Acad. Sci. USA, Washington D.C., USA.

Tyagi et al., "Molecular Beacons: Probes that Fluoresce upon Hybridization," Nature Biotechnology, 1996, 14:303-308, Nature Publishing Company, New York, USA.

Uckun et al., "Clinical Significance of MLL-AF4 Fusion Transcript Expression in the Absence of a Cytogenetically Detectable t(4;11)(q21;q23) Chromosomal Translocation," Blood, 1998, 92(3):810-821, American Society of Hematology, Washington D.C., USA.

Van Gemen, B. at al.; "The One-tube Quantitative HIV-1 RNA NASBA: Precision, Accuract and Application,"; 1995; *PCR Methods Appl.*; vol. 4; pp. 177-184.

Victor et al., "Laboratory Experience and Guidelines for Avoiding False Positive Polymerase Chain Reaction Results," Eur. J. Clin. Chem. Clin. Biochem., 1993, 31(8):531-535, Walter de Gruyter & Co., Berlin, Germany.

Voss et al., "Direct genomic fluorescent on-line sequencing and analysis using in vitro amplification of DNA," Nucl. Acids Res., 1989, 17(7):2517-2527, IRL Press, USA.

(56) References Cited

OTHER PUBLICATIONS

Walker et al., "Detection of *Mycobacterium tuberculosis* DNA with thermophilic strand displacement amplification and fluorescence polarization," Clin. Chem., 1996, 42(10):1604-1608, American Association for Clinical Chemistry, Washington D.C., USA.

Walker et al., "Strand displacement amplification (SDA) and transient-state fluorescence polarization detection of *Mycobacterium tuberculosis* DNA," Clin. Chem., 1996, 42(1):9-13, American Association for Clinical Chemistry, Washington D.C., USA.

Walter et al., "Fluorescence correlation analysis of probe diffusion simplifies quantitative pathogen detection by PCR," Proc. Natl. Acad. Sci. USA, 1996, 93:12805-12810, National Academy of Sciences, Washington D.C., USA.

Whelan et al., "The Role of Nucleic Acid Amplification and Detection in the Clinical Microbiology Laboratory," Annu. Rev. Microbiol., 1996, 50:349-373, Annual Reviews, Palo Alto, USA.

Wilke et al., "Automation of Polymerase Chain Reaction Tests Reduction of Human Errors Leading to Contamination," Diagn. Microbiol. Infect. Dis., 1995, 21:181-185, Elsevier Sciences, New York City, USA.

Wilke et al., "Automation of Polymerase Chain Reaction Tests to Achieve Acceptable Contamination Rates," Clin. Chem., 1995, 41(4):622-623, American Association for Clinical Chemistry, Washington, D.C., USA.

Wittwer et al., "The LightCycler: a microvolume multisample fluorimeter with rapid temperature control," BioTechniques, 1997, 22:176-181, Informa Healthcare USA, Inc., London, United Kingdom.

Yourno et al., "A method for nested PCR with single closed reaction tubes," PCR Methods Appl., 1992, 2(1):60-65, Cold Spring Harbor Laboratory Press, Cold Spring Harbor, New York, USA.

GenProbe; "Test Procedure Guide. Amplified *Mycobacterium tuberculosis* Direct (MTD) Test,"; 2000, 1 page.

International Search Report and Written Opinion dated Nov. 6, 2013 for PCT Patent Application No. PCT/US2012/063918, 22 pages.

ABI Product Catalogue, 1993-1994, "DNA Sequencing Reagents," p. 146, Applied Biosystems, USA.

Anonymous, "GeneAmp optical reaction plate," Nature, 1998, 391(8):210, Nature Publishing Group, USA.

Asper et al., "Laboratory Mechanization and Automation," in Laboratory Organization Automation, 1991, pp. 271-275, Walter deGruyter, USA.

Bieche et al., "Novel Approach to Quantitative Polymerase Chain Reaction Using Real-Time Detection: Application to the Detection of Gene Amplification in Breast Cancer," Int. J. Cancer, 1998, 78:661-666, Wiley-Liss, Inc., USA.

Billyard, et al., "Early detection of HIV-1 RNA from sero-conversion panels using Gen-Probe's transcription-mediated amplification," The San Diego Conference Nucleic Acid Technology: The Cutting Edge of Discovery, Nov. 6-8, 1997, Clin. Chem., 1997, 43(11):2221, Am. Assoc. For Clin. Chem., USA.

Burg et al., "Real-time fluorescence detection of RNA amplified by Q beta replicase," Anal. Biochem., 1995, 230(2):263-272, Academic Press, Orlando, Florida, USA.

Chemistry Guide, "ABI Prism DNA Sequencing," 1995, pp. 1-3-1-6, The Perkin-Elmer Corporation, USA.

Civitello et al., "A simple protocol for the automation of DNA cycle sequencing reactions and polymerase chain reactions," DNA Sequence—J. DNA Sequencing and Mapping, 1992, 3:17-23, Harwood Academic Publishers GmbH, UK.

Dangler, ed., Nucleic Acid Analysis: Principles and BioApplications, 1996, pp. 1-3, 19, 68-75, 106-109, 116, 117, 144, 145, 157, 162 & 163, Wiley-Liss, Inc., USA.

Educational Guide, "New Directions in Molecular Diagnostic Testing," pp. 1-12, Rev. A, 2000, Gen-Probe Incorporated, San Diego, USA.

Felder, "Automation of Preanalytical Processing and Mobile Robotics," in Handbook of Clinical Automation, Robotics, and Optimization, 1996, pp. 252-256, John Wiley & Sons, Inc., USA.

Hawkins et al., "Thermal Cycle DNA Sequence Setup Using a Modified Lab Workstation," LRA, 1995, 7:117-122, VCH Publishers, New York City, USA.

Higuchi et al., "Kinetic PCR Analysis: Real-time Monitoring of DNA Amplification Reactions," Bio/Technology, 1993, 11(9):1026-30, Nature Publishing Group, New York, USA.

Hill et al., "The Polymerase Chain Reaction in Molecular and Micro-biology," Biotechnol. Genet. Eng. Rev., 1992, 10:343-377, Taylor & Francis, UK.

Holmberg et al., "Automatic Preparation of DNA Templates for Sequencing on the ABI Catalyst Robotic Workstation," Automated DNA Sequencing and Analysis, 1994, Academic Press Inc., San Diego, USA.

Hunkapiller, "Advances in DNA sequencing technology," Curr. Opin. Genet. Dev., 1991, 1:88-92, Elsevier, UK.

Jakobsen et al., "Direct mRNA Isolation Using Magnetic Oligo (dT) Beads: A Protocol for All Types of Cell Cultures, Animal and Plant Tissues," in Advances in Biomagnetic Separation, 1994, pp. 61-71, Eaton Publishing, USA.

Kasper, "Automated Instrumentation (Generic)," in Clinical Laboratory Instrumentation and Automation: Principles, Applications, and Selection, 1994, pp. 184-205, W.B. Saunders Company, USA.

Kaufman et al., "Direct Sequencing by PCR," in Handbook of Molecular and Cellular Methods in Biology and Medicine, 1995, pp. 233-235, CRC Press, USA.

Krieg, ed., "Quantitation of RNA Transcripts Using RT-PCR," in a Laboratory Guide to RNA: Isolation, Analysis, and Synthesis, 1996, pp. 176-190, John Wiley & Sons, Inc., USA.

Little et al., "Recent Advances in Robotic Automation of Microplate Assays," Lab. Info. Mgmt., 1994, 26:89-99, Elsevier Science, Amsterdam, Netherlands.

Lundeberg et al., "Solid-Phase Technology: Magnetic Beads to Improve Nucleic Acid Detection and Analysis," Biotechnol. Annu. Rev., 1995, 1:373-401, Elsevier Science, Amsterdam, Netherlands.

Mahan et al., "An Automated System for Infectious Disease Diagnosis with Q-Beta Replicase Amplification," in New Horizons in Gene Amplification Technologies: Proceedings of a CHI Meeting, 1994, Cambridge, USA, 25 pages.

McDonough et al., High Throughput Assay for the Simultaneous or Separate Detection of Human Immunodeficiency Virus (HIV) and Hepatitis Type C Virus (HCV), Infusionsther. Transfusionsmed, 1998, 25:164-169, Karger GmbH, Germany.

Mertes et al., Automatische genetische Analytik, 1997, forward and pp. 68, 69, 73 & 74, Wiley-VCH, Germany; German Language Reference.

Mizutani et al., "Magnetic Separation in Molecular Studies of Human Leukemia," in Advances in Biomagnetic Separation, 1994, p. 127-133, Eaton Publishing, USA.

Olsvik et al., "Magnetic Separation in Laboratory Diagnosis of Infectious Diseases," in Advances in Biomagnetic Separation, 1994, pp. 149-158, Eaton Publishing, USA.

Olympus Corporation, "Olympus News Release: Automated Chemistry Analyser AU1000," 1997, http://www.olympus-global.com/en/news/1997a/nr970421au1000e.jsp, downloaded Jun. 17, 2013, USA, 3 pages.

Overbergh et al., "Quantification of Murine Cytokine mRNAs Using Real Time Quantitative Reverse Transcriptase PCR," Cytokine, 1999, 11(4):305-312, Academic Press, USA.

Petrik et al., "High throughput PCR detection of HCV based on semiautomated multisample RNA capture," J. Virol. Methods, 1997, 64:147-159, Elsevier/North-Holland Biomedical Press, Amsterdam, Netherlands.

Piatek et al., "Molecular beacon sequence analysis for detecting drug resistance in *Mycobacterium tuberculosis*," Nature Biotechnology, 1998, 16:359-363, Nature America Publishing, New York, USA.

Shah et al., "Novel, Ultrasensitive, Q-Beta Replicase-Amplified Hybridization Assay for Detection of Chlamydia trachomatis," J. Clin. Microbiol., 1994, 32(11):2718-2724, American Society for Microbiology, USA.

Slatko, "Thermal Cycle Dideoxy DNA Sequencing," in Protocols for Gene Analysis (Methods in Molecular Biology), 1994, vol. 31, pp. 35-45, Humana Press Inc., USA.

(56) References Cited

OTHER PUBLICATIONS

Sloan et al., "Screening Yeast Artificial Chromosome Libraries with Robot-Aided Automation," GATA, 1993, 10(6):128-143, Elsevier Science Publishing Co., Inc., USA.
Truchaud et al., "Liquid-Phase Reactions Started by Rehydrating Lyophilized Reagents in a Centrifugal Analyzer," Clin. Chem., 1985, 31(9):1506-1508, Am. Assoc. for Clin. Chem., USA.
Tyagi et al., "Multicolor molecular beacons for allele discrimination," Nat. Biotechnol., 1998, 16:49-53, Nature Publishing Group, USA.
Vonderschmitt, ed., "Robots in the Clinical Laboratory," in Laboratory Automation Organization, 1991, pp. 576-577, Walter deGruyter, USA.
Ward, ed., "Improving Laboratory Efficiency Through Workflow Analysis", in Clinical Laboratory Instrumentation and Automation: Principles, Applications, and Selection, 1994, pp. 453 & 457, W.B. Saunders Company, USA.
Webster's New World Dictionary, Third college Edition, 1988: Definition of Incubate, Incubator.
Yohda et al., "Development of a Novel Laboratory Automation System for Molecular Biology," Kaguku-Koguku Symposium, 1998, p. 17-20.
Muller et al., "Evaluation des klinish-chemischen Analysensystems Technicon DAX 72," Lab. Med., 1992, 16:210-218, Am. Soc. for Clinical Pathology, USA, with English Summary.

\* cited by examiner

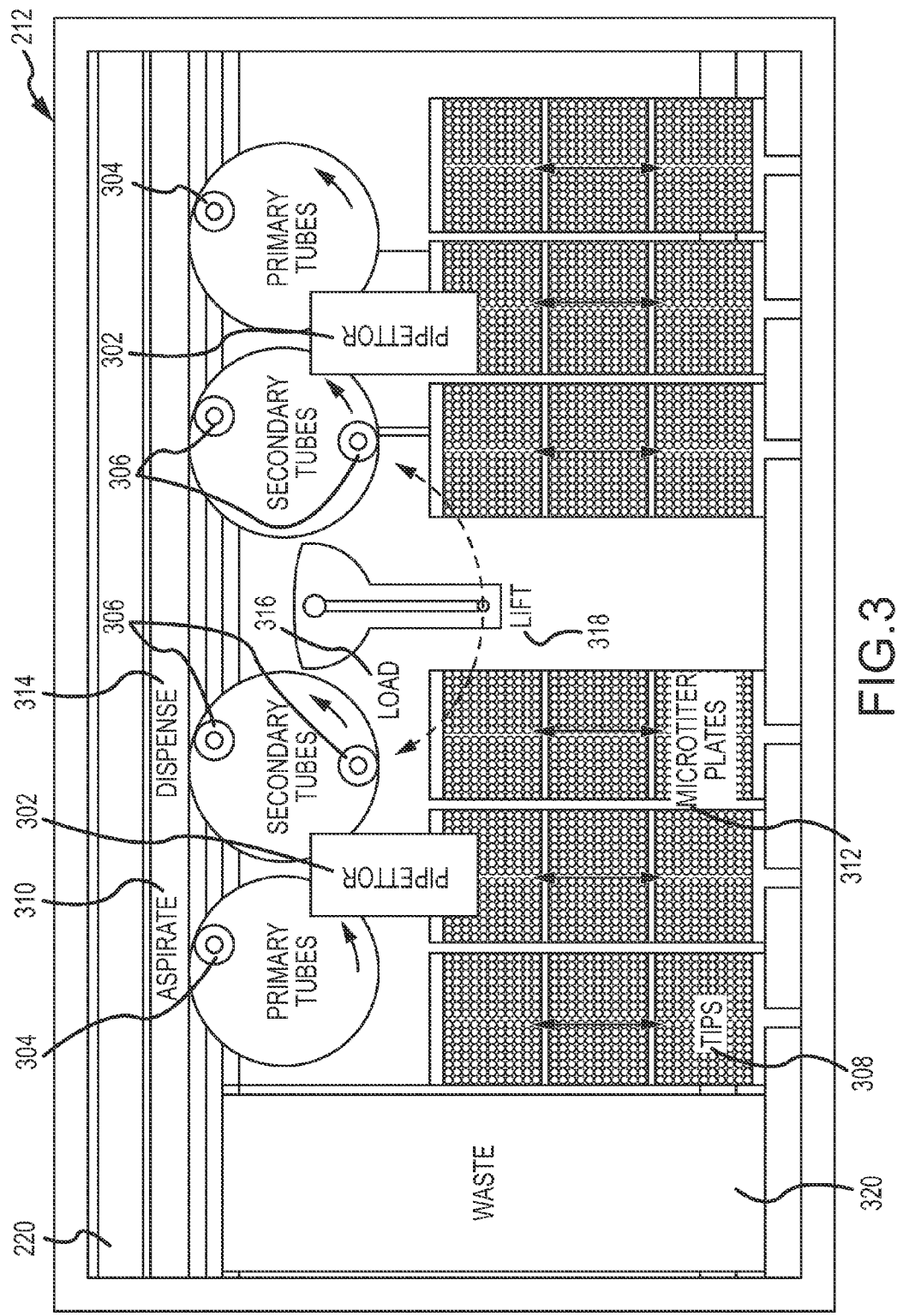

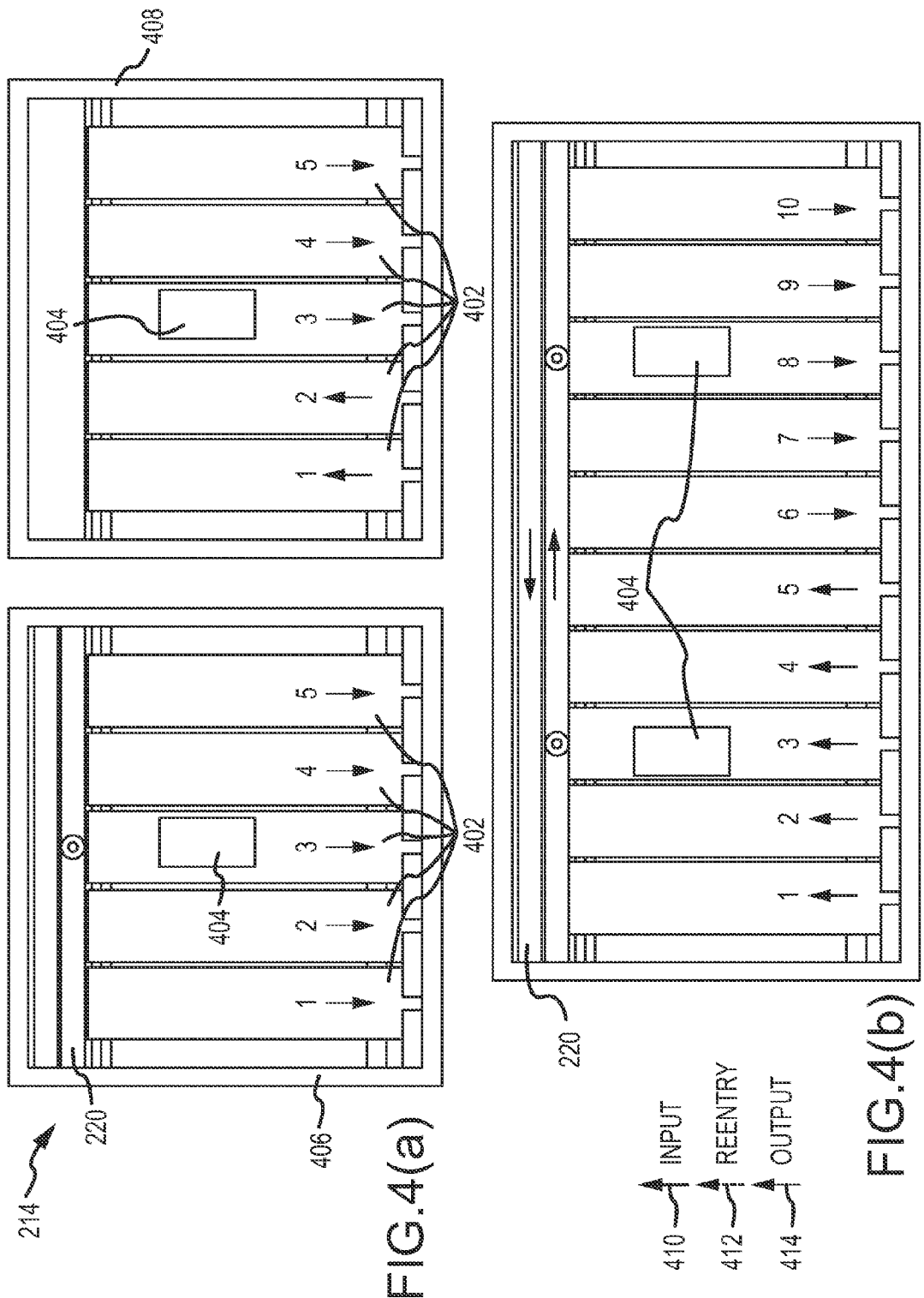

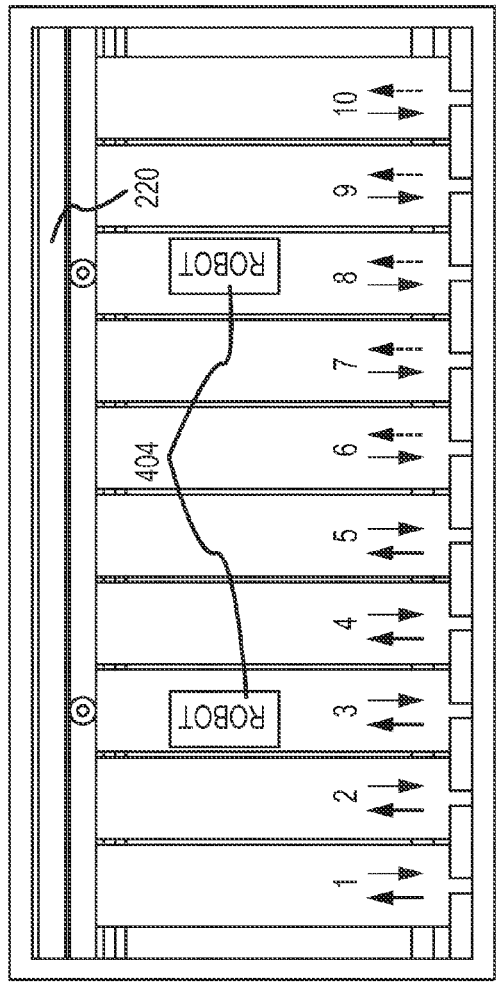
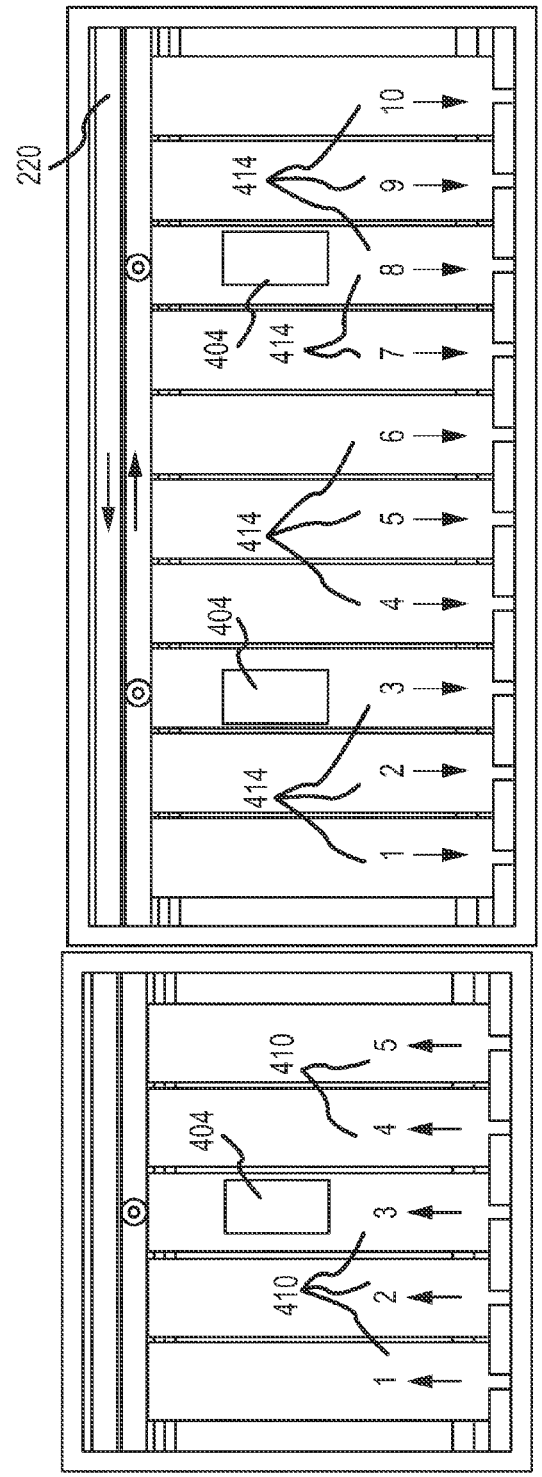
FIG.4(c)
FIG.4(d)

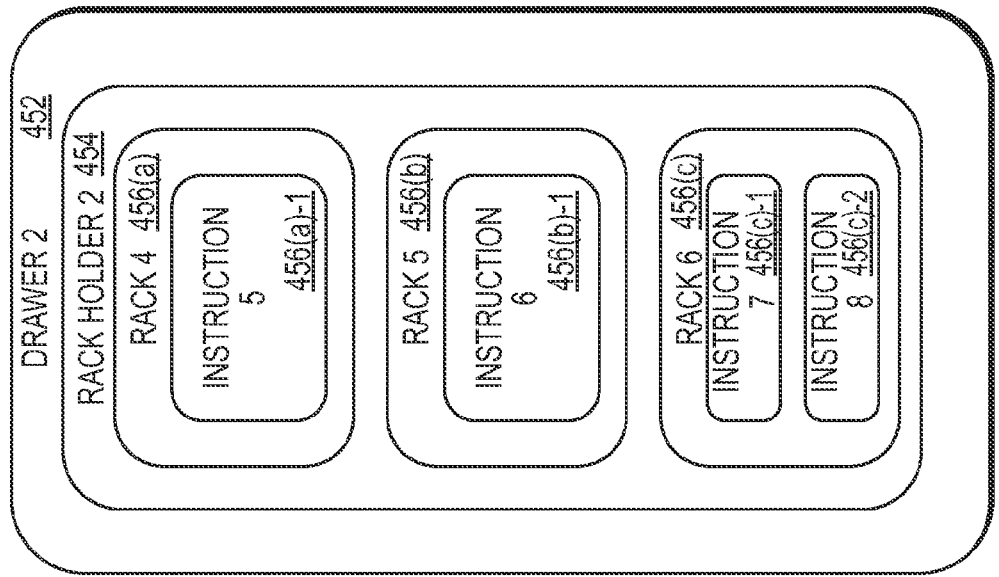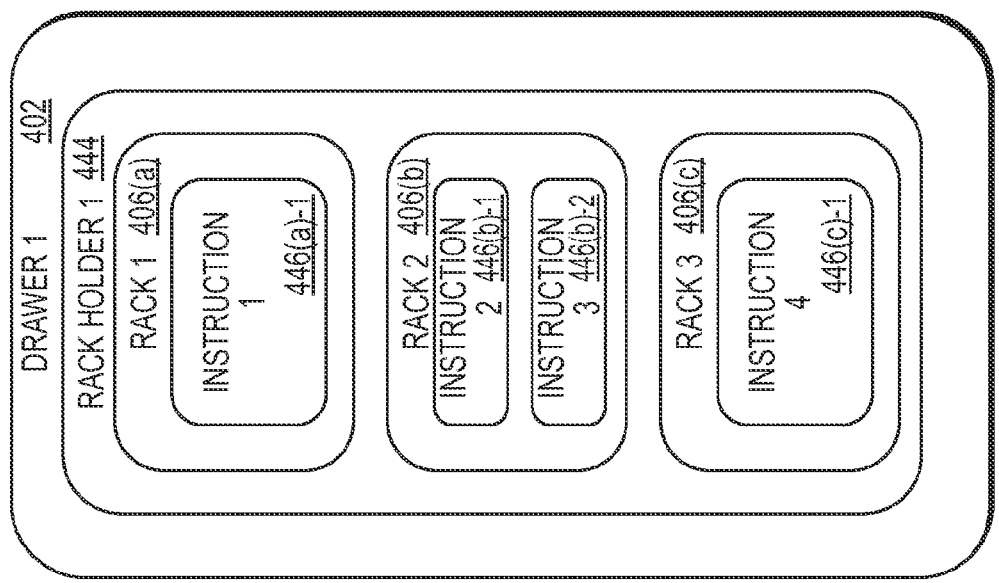
FIG. 4(f)

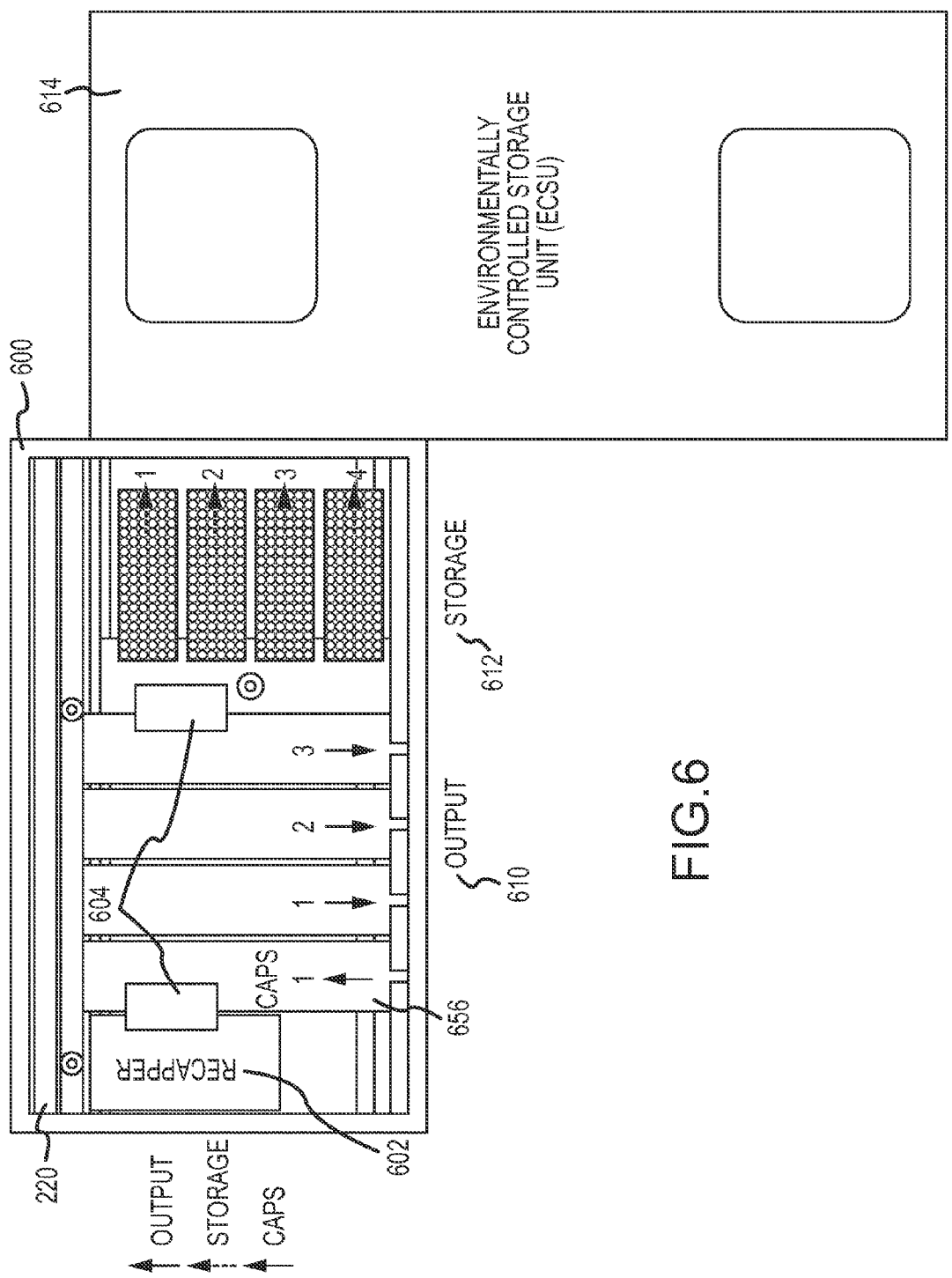

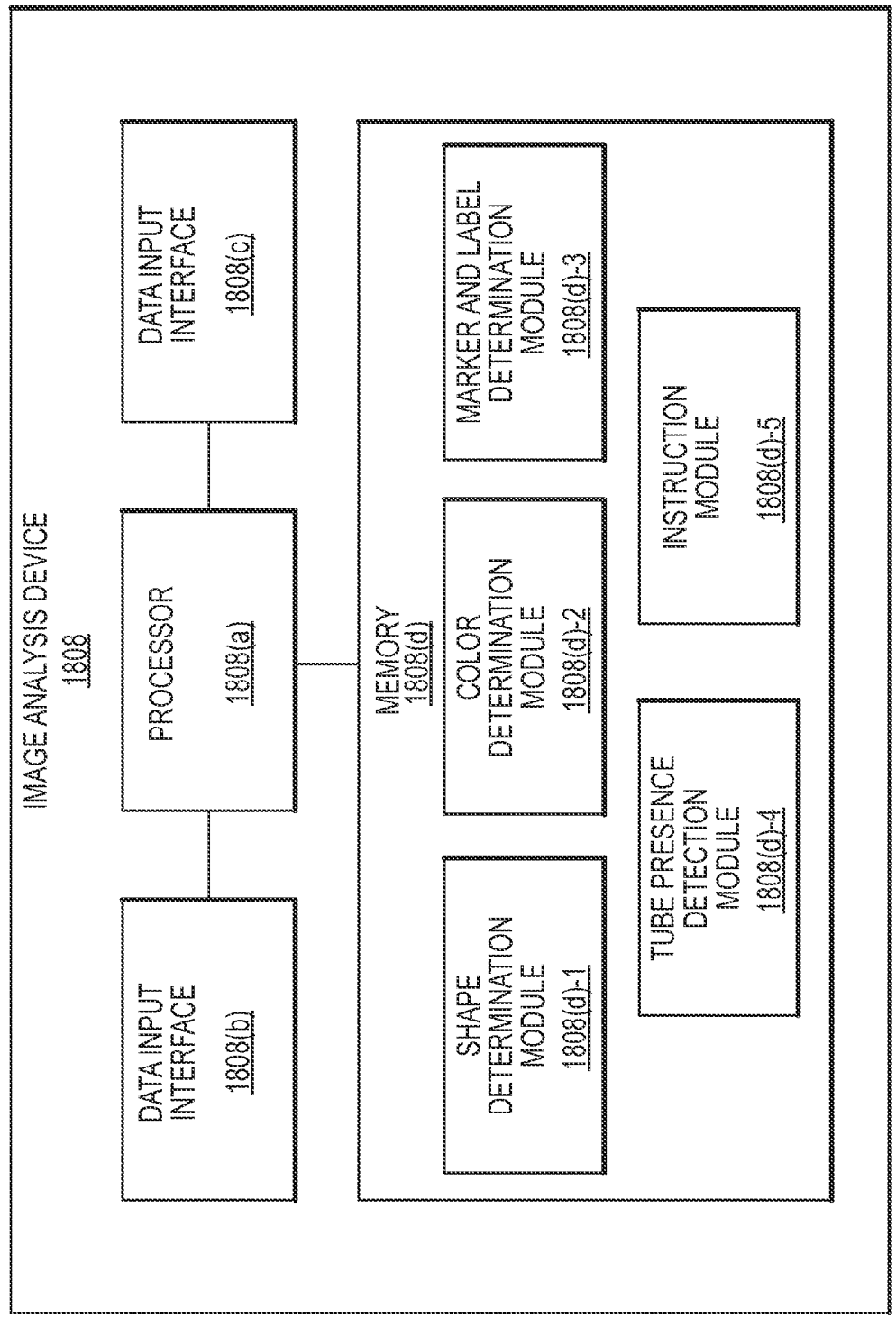

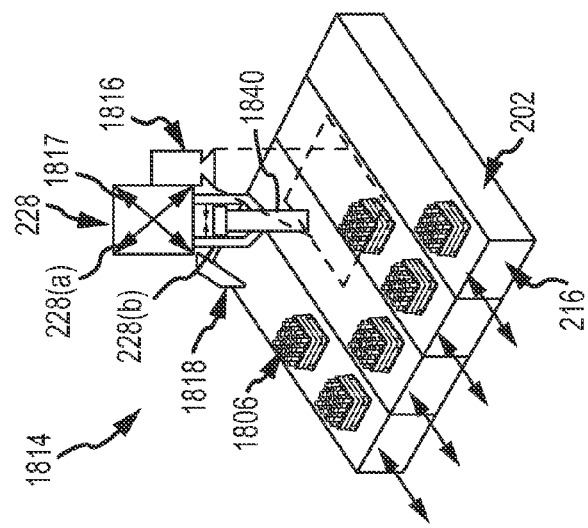
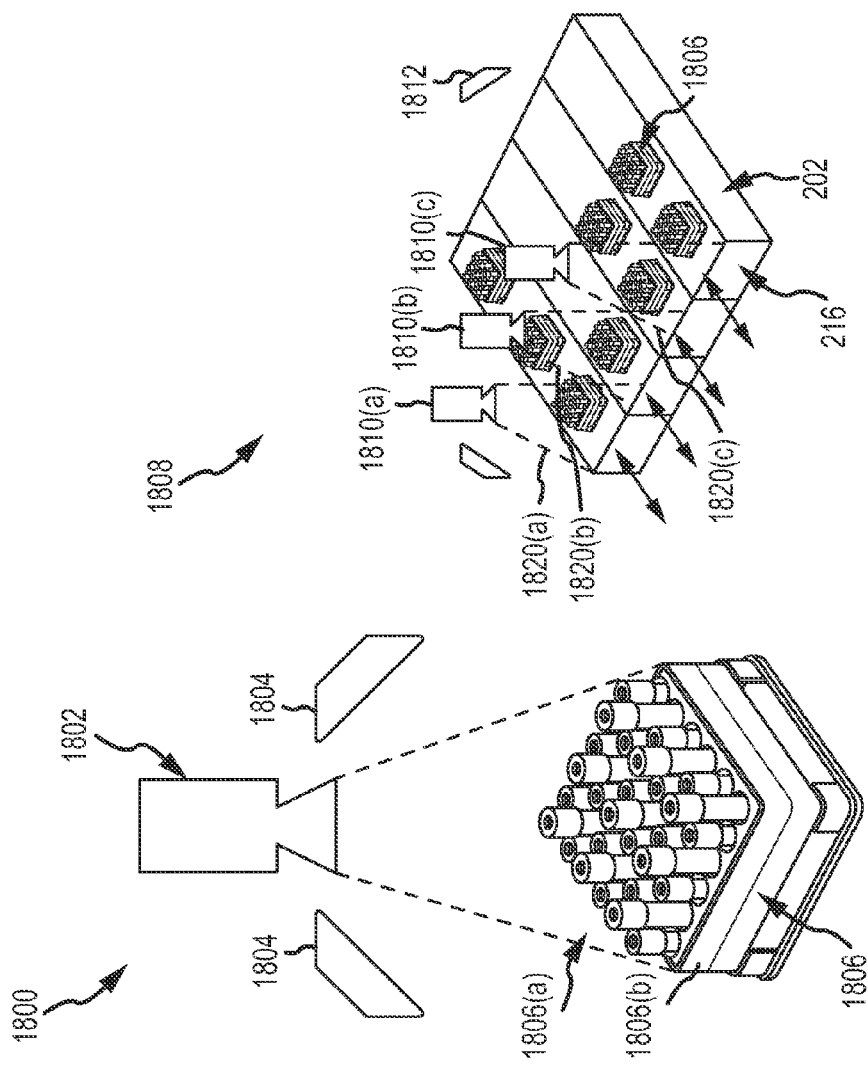
FIG.28(c)
FIG.28(b)
FIG.28(a)

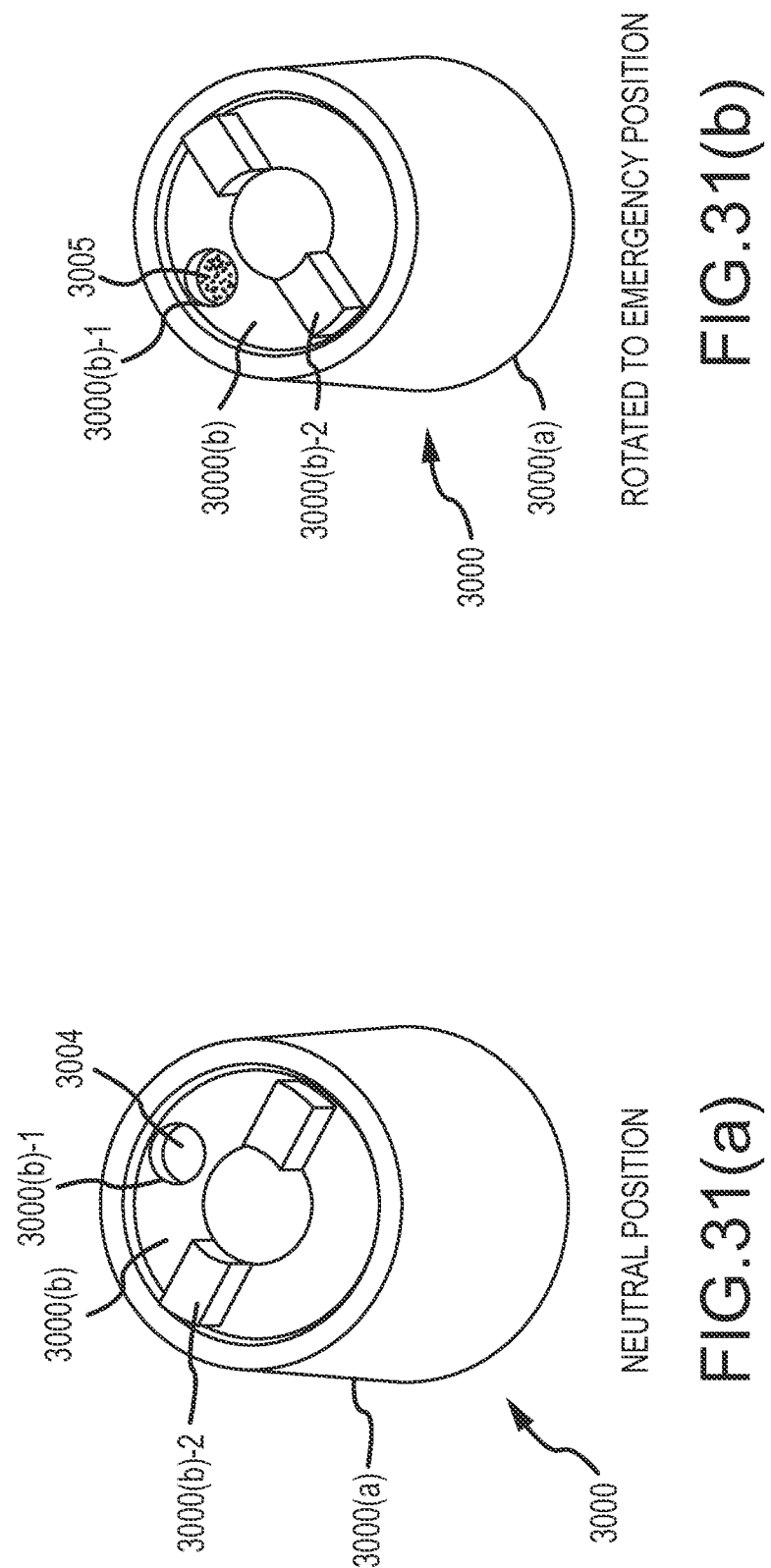

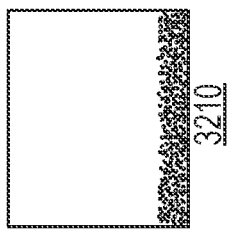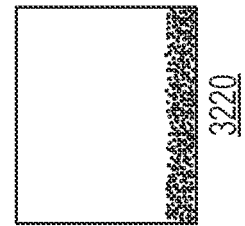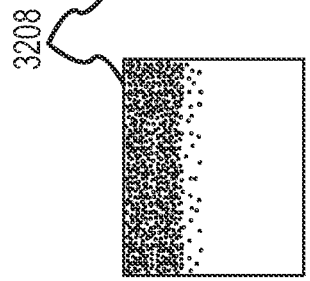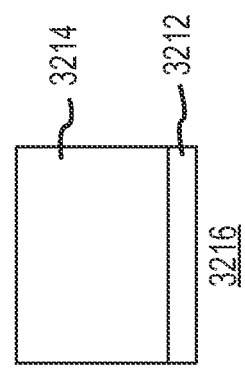
FIG.32(a)
FIG.32(b)

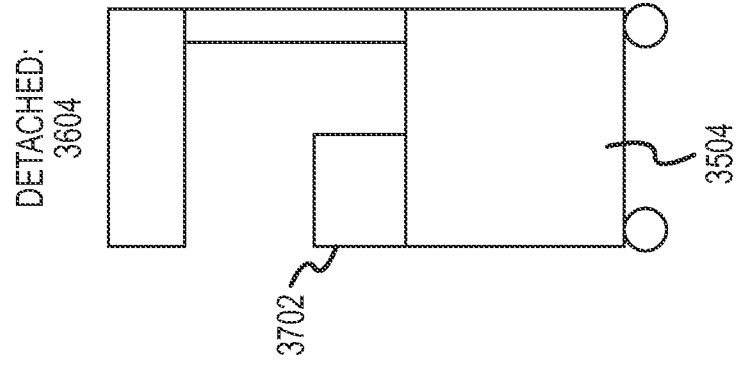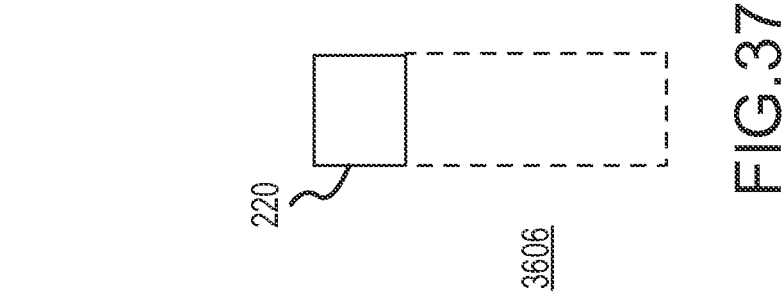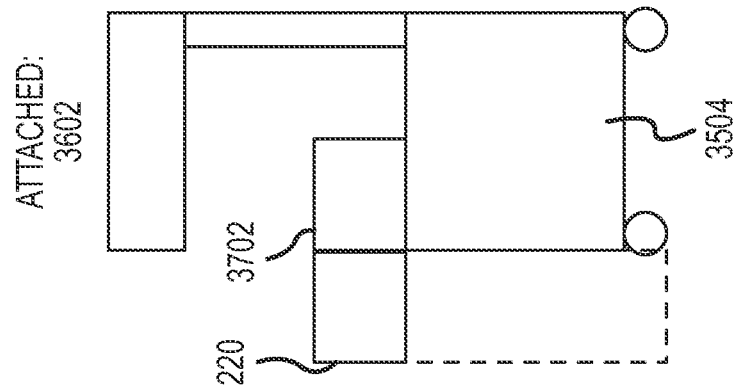
FIG. 37

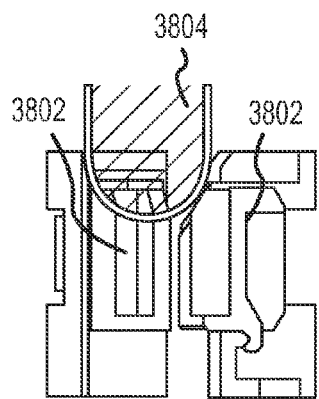 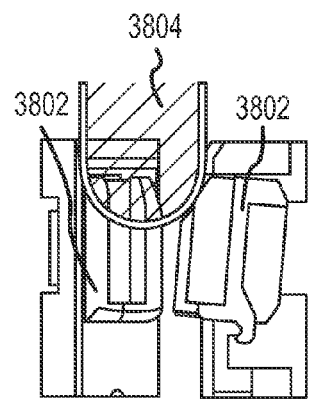 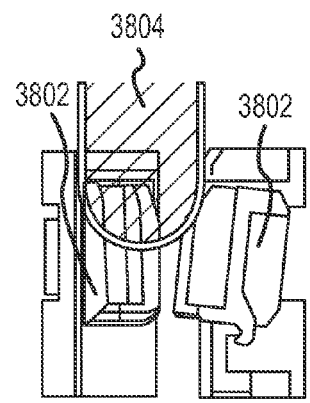
FIG.38(a)　　　FIG.38(b)　　　FIG.38(c)
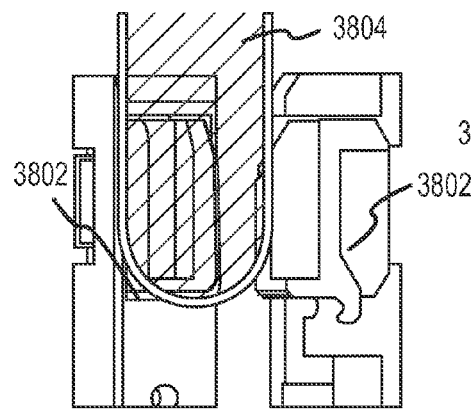 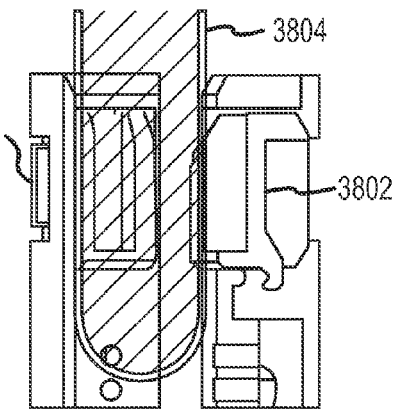
FIG.38(d)　　　FIG.38(e)

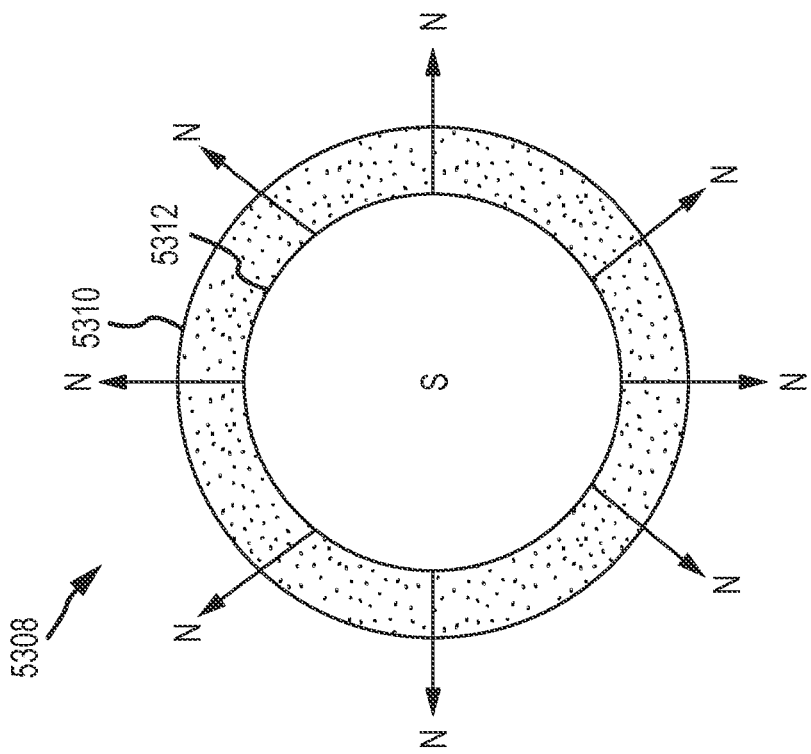
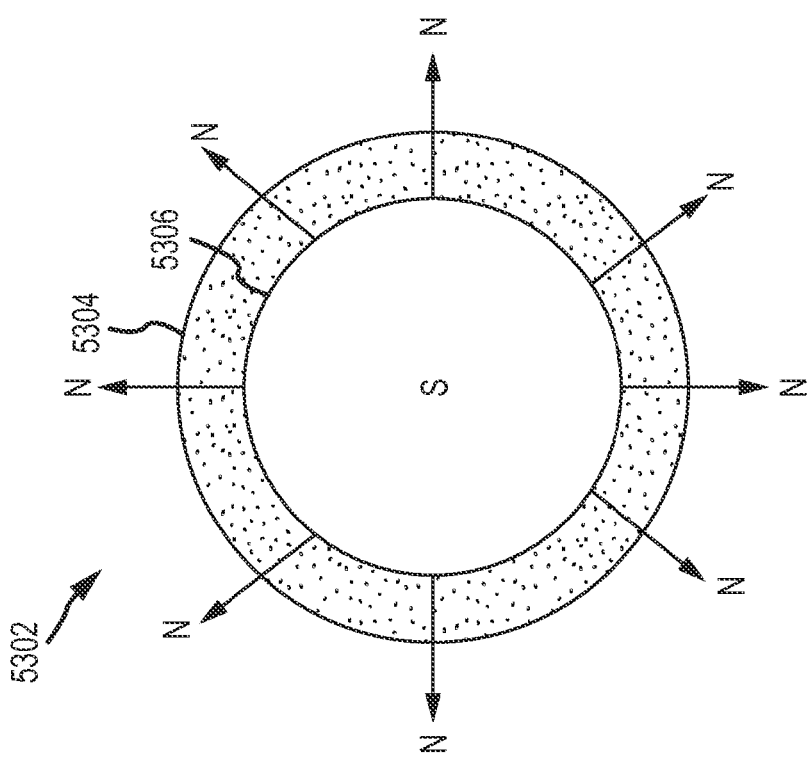
FIG. 53

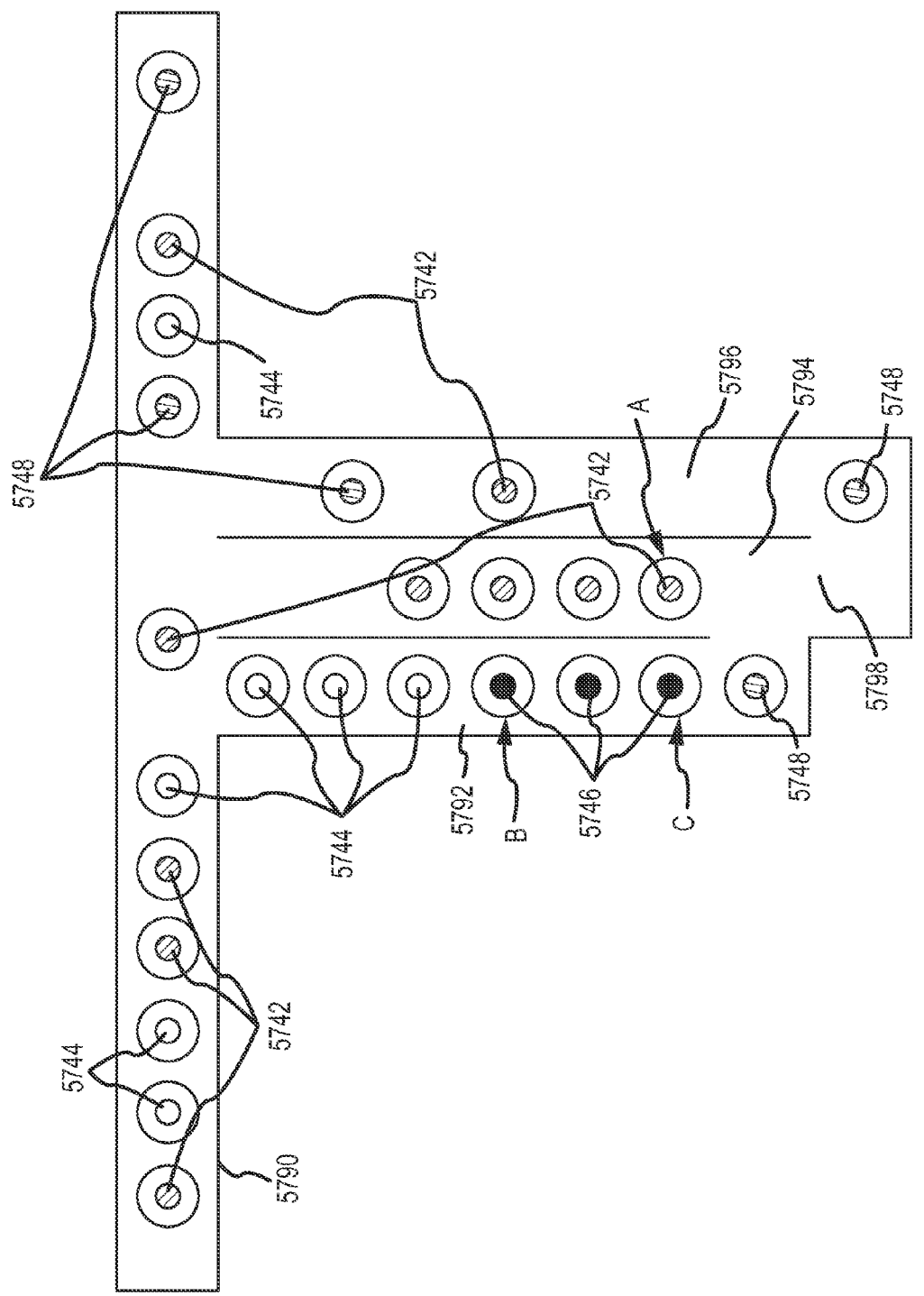

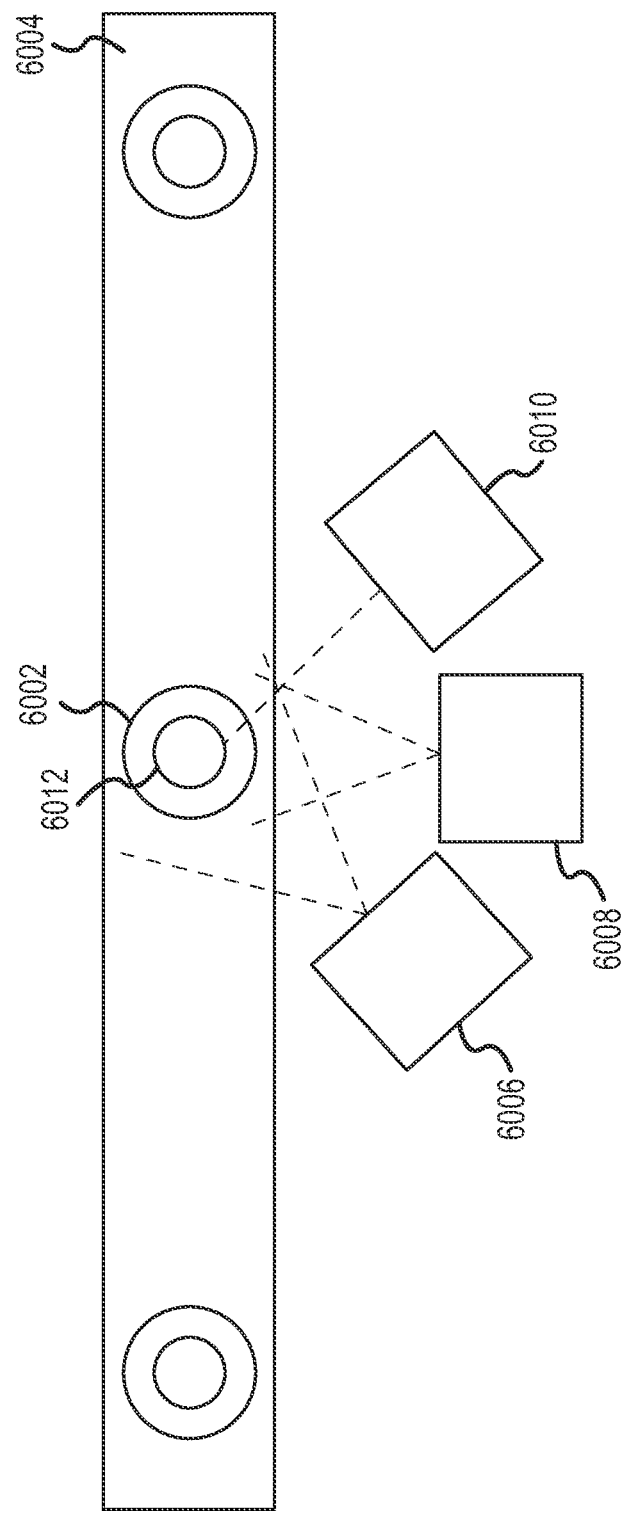

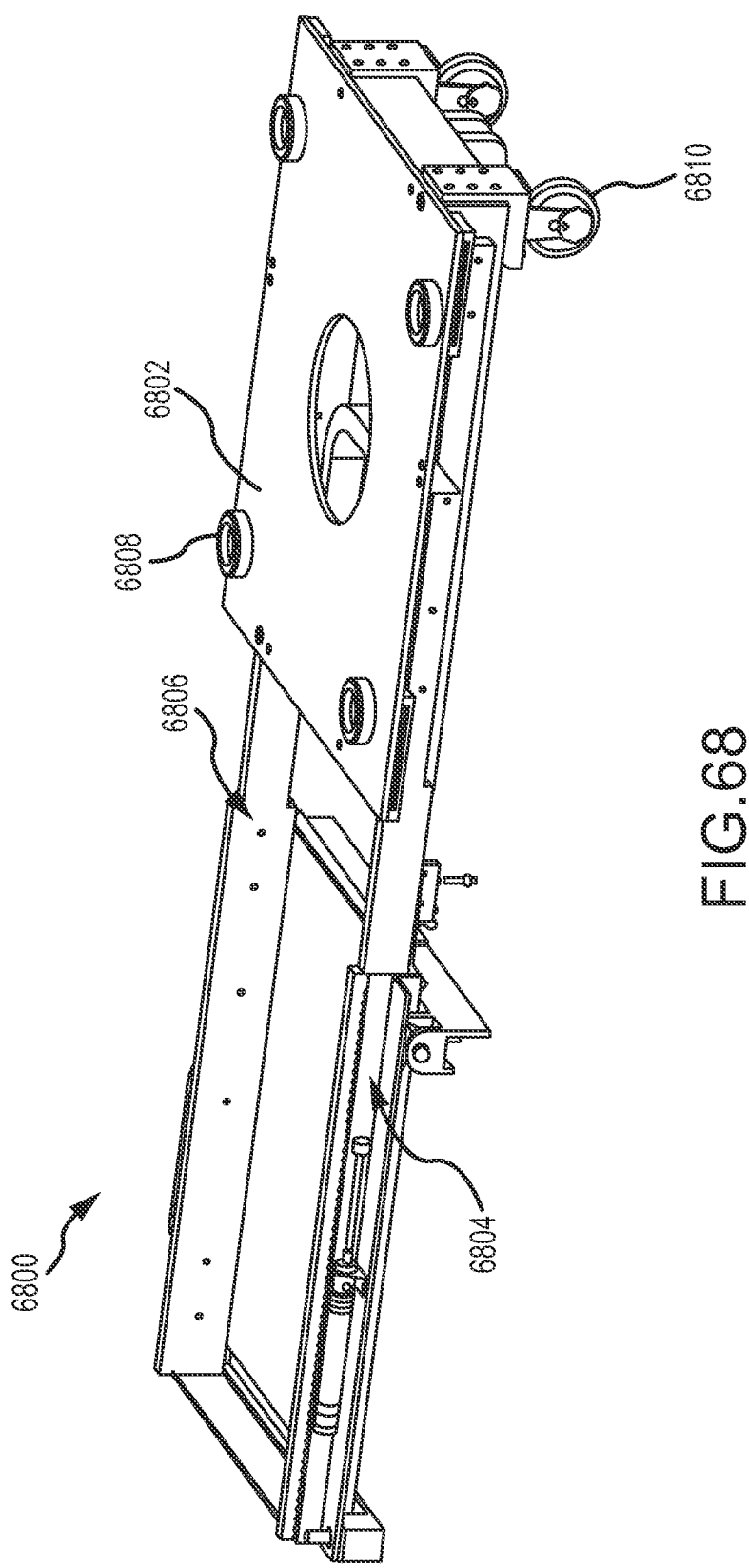

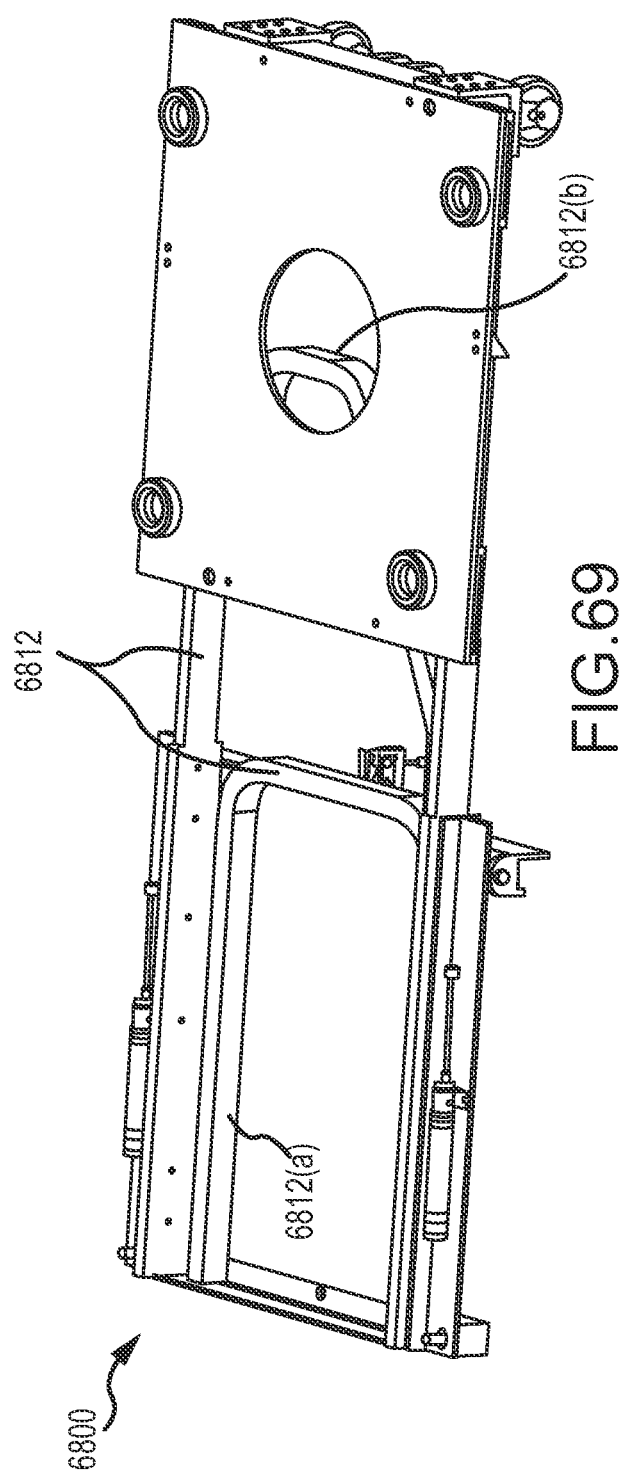

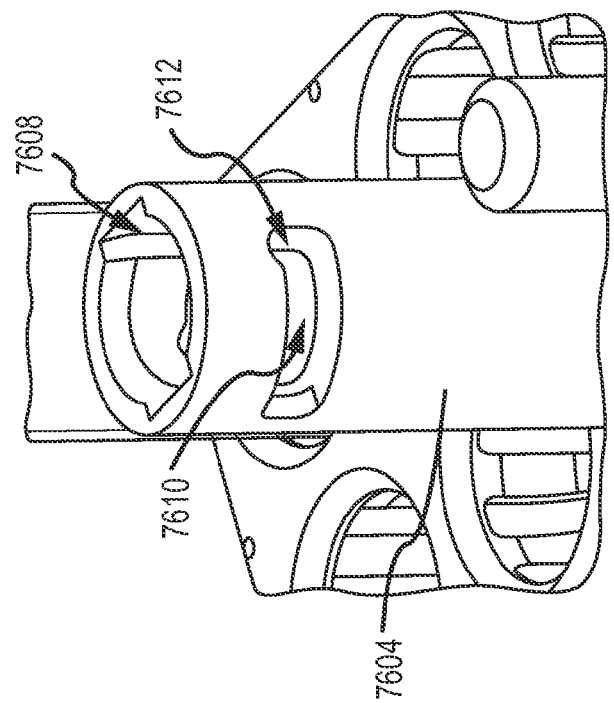
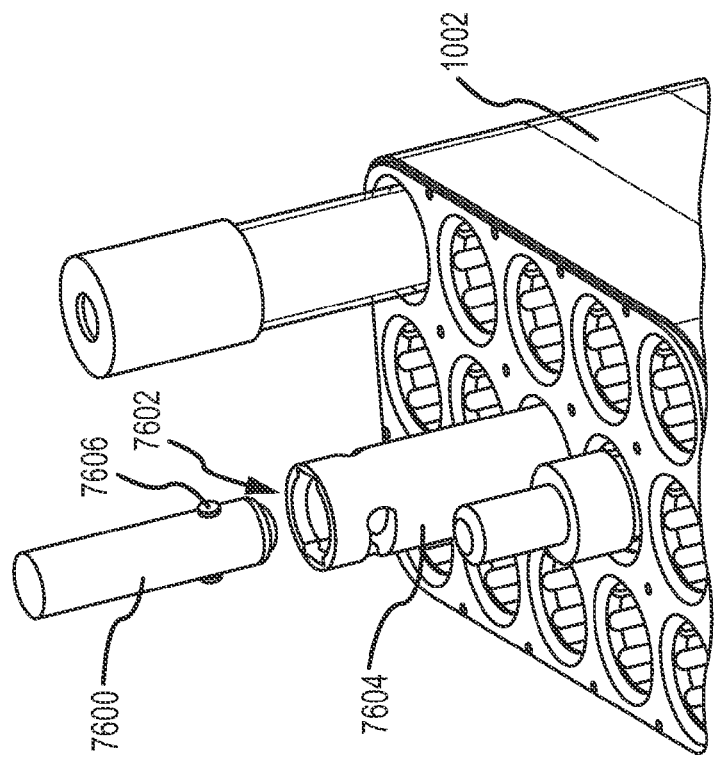
FIG. 76(b)
FIG. 76(a)

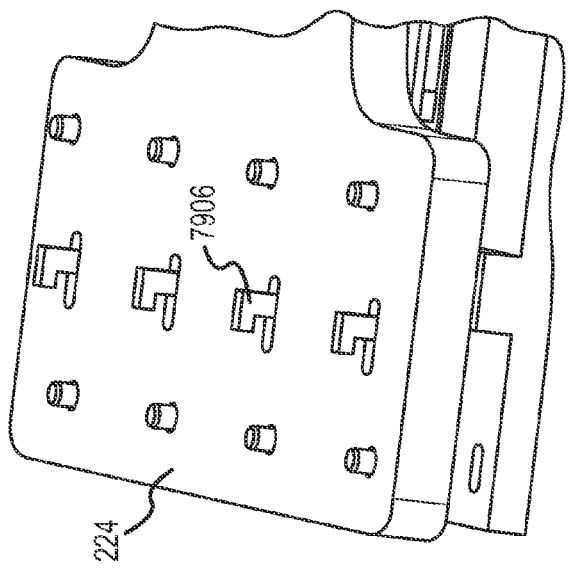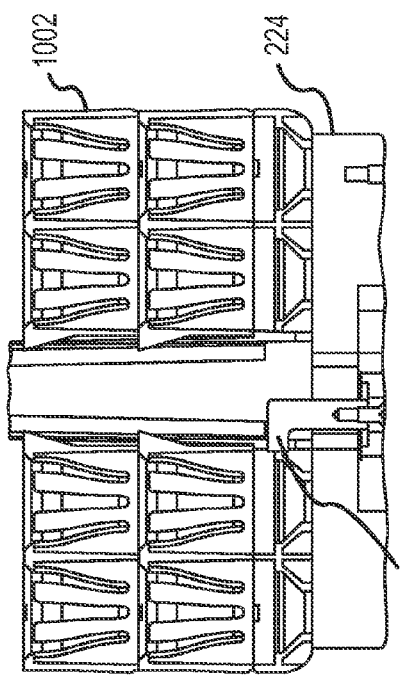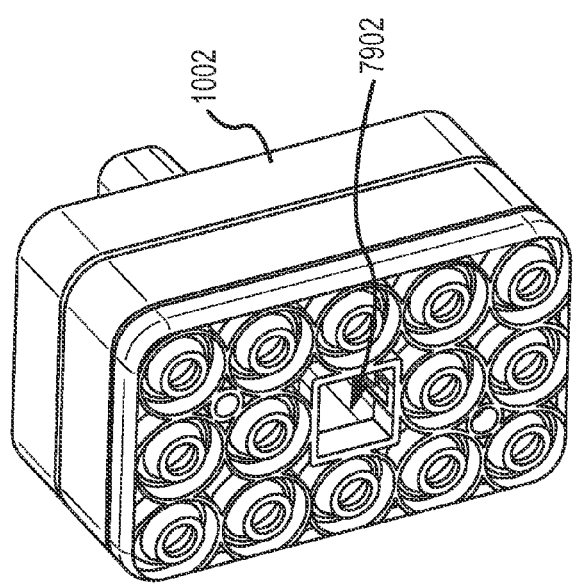

SYSTEM AND METHOD FOR PROCESSING SAMPLES

CROSS-REFERENCES TO RELATED APPLICATIONS

This application is a US National Stage Entry under §371 of International Application No. PCT/US2012/063931, filed Nov. 7, 2012, which claims priority to U.S. Provisional Patent Application No. 61/556,667, filed Nov. 7, 2011 and entitled "Analytical System and Method for Processing Samples." PCT/US2012/063931, filed Nov. 7, 2012, also claims priority to U.S. Provisional Patent Application No. 61/616,994, filed Mar. 28, 2012 and entitled "Analytical System and Method for Processing Samples." PCT/US2012/063931, filed Nov. 7, 2012, further claims priority to U.S. Provisional Patent Application No. 61/680,066, filed Aug. 6, 2012 and entitled "Analytical System and Method for Processing Samples." All of these applications are herein incorporated by reference in their entirety for all purposes.

BACKGROUND

Conventional medical laboratory systems implement a variety of processes for analyzing medical specimens. These systems have become more efficient due to the increasing extent to which laboratory analysis processes have become automated. However, there remain several components of medical laboratory systems that can be automated. Automation can beneficially reduce the time required to analyze a sample, reduce the need for manual operation of the system, and reduce the space required by machinery.

Specimens may need to be transferred between several stations in a laboratory analysis system in order to be identified, prepared for analysis, analyzed, and disposed of or stored. Varying implementations of these laboratory processes present challenges for automation. For example, in some laboratories, specimens are manually transported between standalone stations whereas other laboratories may have a conveyance system to transport specimens between stations. Additionally, some conventional laboratories may consistently process the same types of sample tubes (e.g., as in those from a kit) while others may accommodate tubes having a variety of physical characteristics. Further, there are laboratories that have a preference for a particular manufacturer of an analyzer while others may use a variety of analyzers.

Thus, there is a need for a more efficient system and method for processing patient samples that can accommodate both a process using standalone units and units connected with a conveyance system, a variety of sample tube types, and analyzers from any manufacturer.

Below, background information is provided for specific features of a laboratory system for processing samples.

Conventional recappers typically utilize robots for performing the capping functions. For example, a recapper for push caps utilizes a robot to pick up the push cap from one side of the robot and apply it to a sample tube located on the other side of the robot. In this case, the push caps are provided already separated and pre-aligned in the racks beside the open tubes. In another conventional recapper, a universal push cap may be provided in bulk storage separated and aligned for the transport robot via a screw-conveyor on the bottom of the bulk container. Alternatively, tape sealing is used to cap the tube. This technology uses a heat sensitive lamination tape to seal an open sample tube. However, the conventional recappers are only able to utilize one type of cap for recapping and thus these recappers are unable to accommodate different tubes needing different types of caps.

Conventional tube-in-rack detection typically utilizes image analysis tools on 2-dimensional images acquired by one camera or a plurality of cameras in order to determine objects in the field of view of the cameras. This technology is well known in various fields, including, e.g., the analysis of pathology samples by microscopes. In other fields, this technology may be used to identify objects in moveable loading or unloading means of a system, including, e.g., identifying drawers of a workbench. A series of images can be taken by each camera during the opening and closing of the drawer and stitched together to generate an overview image. Within this overview image, single objects can be detected by image analysis. In the field of laboratory automation systems, it is well known that single objects, such as a cap or closure of a sample tube, located in a holding rack can be identified by employing image analysis algorithms on top views of the hold racks. However, the image analysis algorithms are typically limited to the identification of only the single object and are unable to identify other details of the objects within the image.

Conventional sample tube markers used to identify a sample tube requiring immediate analysis typically include self-adhering labels (e.g., colored labels indicating urgency), "urgent" stickers, or simply a handwritten note indicating urgency on already existing labels. These urgent sample tube markers are inefficient and non-automated, requiring a laboratory technician to apply and/or handwrite the indication of urgency.

Conventional sample volume or sample level detection devices are able to detect the total level of a liquid in a sample container either by (i) an image analysis approach of 2-dimensional images acquired by a camera system, or (ii) an absorption/transmission measurement of different wavelengths in a focused light beam. However, these devices are typically stand-alone devices that are manually operated by the laboratory system.

Conventional robotic arm technology for transporting objects from one position to another may utilize an xyz-robot employing a gripper unit to grip and transport sample tubes or centrifuge adapters. However, the current robotic arm technology is generally limited to gripping either the sample tubes or centrifuge adapter, but not both. Additionally, the current technology cannot perform any additional functions besides the gripping features.

It is well known that a continuous and thus cost-effective use of an object transportation system basically depends on the uptime of such a system. The temporary unavailability of subassemblies in the system due to failure, maintenance, scheduled service, etc. may cause a complete stop of the whole system, and currently there does not exist an efficient way to continue the operation of the system during such an unavailability. Thus, there is a need to minimize the downtime of an object transportation system during the temporary unavailability of one or more subassemblies in the laboratory automation system.

Puck transport systems may use autonomous guided vehicles for transporting an individual sample tube between modules or stations within a laboratory system. Generally, these puck transport systems can detect obstacles that may be blocking the path of the puck so as to avoid or reroute the path of the puck. However, the obstacle detection used in the conventional systems is discontinuous, such that obstacles are detected on a periodic basis. This can lead to an obstacle being undetected during the interim.

Additionally, the intersections at which pucks may cross paths within the puck transport systems can be managed by the puck itself by broadcasting its presence. This broadcast is used by other pucks in the intersection so that the other pucks will refrain from entering the intersection. However, if a puck failed to operate properly, the puck transport system may become jammed.

Furthermore, each processing station may have a unique RFID tag so that the puck can determine which actions to perform while in that processing station. However, the puck is only able to determine which actions to perform as it is entering the processing station and cannot determine these actions any further in advance.

Conventional conveyor transport systems may transport sample tubes within single tube carriers. The conveyor transport systems are capable of diverting the tube carriers from one conveyor to another (e.g., the main conveyor to an auxiliary conveyor). However, the currently used means for diverting the tube carriers are typically not capable of actively diverting the carriers from one conveyor to another.

In other conveyor transport systems, a wheel may be used to transfer a carrier from a conveyor land to a processing station and then back onto the conveyor lane. However, during this process, the wheel may cause the carrier to be rotated so that the barcode on the tube is no longer properly aligned.

Conveyor systems may be operated at low speeds to avoid the potential occurrence of sample carrier impacts. Impacts can occur between sample carriers when a first sample carrier encounters an obstacle and the sample carriers following the first sample carrier collide as they form a queue behind the obstacle. An impact may also occur when a sample carrier encounters a diverting arm on a track. These impacts may cause the contents of a sample tube to splash out from a sample carrier. Impacts may also affect sample quality by causing fluid layers separated by centrifugation to remix.

Conventional aliquotter systems typically handle sample tubes via the main transport system of a laboratory automation system. For example, an aliquotter system may transfer liquid from a primary to a secondary tube, both of which are on the main transport system during the aliquoting process. In such a case, once the secondary sample tube is prepared, a laboratory technician must transfer the secondary tube to the desired analysis module. Because the system is not entirely automated, such a process is slow and inefficient.

In another example, a conventional aliquoting system may perform the aliquoting process for sample tubes that are in line with one another. For example, one or more secondary tubes may be directly behind the primary tube on a conveyance system so that the secondary tubes are blocked by the primary tube. Such a system prevents the secondary tube from leaving the aliquoting system until the aliquoting process is finished for all secondary tubes that need to be filled with the sample in the primary tube. The secondary tubes are unable to move on to the next analysis module until all aliquoting for that sample is complete, thereby delaying the entire sample analysis process.

Centrifuges may use imbalance sensors to determine when a centrifuge is experiencing imbalance (e.g., wobbling of the centrifuge rotor due to varying weights of sample tubes within the centrifuge). Centrifuges typically have a tolerance for a degree of sample volume imbalance. However, if imbalance occurs in excess of a centrifuge's imbalance tolerance, samples may be damaged or destroyed. An imbalance sensor may be used to discontinue the spinning of a centrifuge rotor in the case that the imbalance of a centrifuge exceeds the centrifuge's imbalance tolerance.

Conventional centrifuge imbalance sensors use contact switch based imbalance sensing or optical switch based imbalance sensing to determine when sample volume imbalance exceeds a centrifuge's imbalance tolerance. In contact switch based imbalance sensing, imbalance is indicated when a containment vessel of a centrifuge contacts a contact switch. Contact switches must be mechanically adjusted for the tolerance of a particular centrifuge and may be damaged by impact with the containment vessel in the case of large imbalances. In optical switch based imbalance sensing, a flag attached to a containment vessel breaks an optical beam. Contaminants interrupting the beam can interfere with the functionality of optical switch imbalance sensing. Existing contact switch and optical switch based imbalance sensors are limited to sensing displacement of a containment vessel in one dimension.

Embodiments of the invention address these and other problems, individually and collectively.

BRIEF SUMMARY

Embodiments of the technology relate to systems and methods for efficiently processing patient samples.

One embodiment is directed to a system that is capable of preparing a sample for laboratory analysis. The system includes an output/sorter unit. The output/sorter unit is capable of receiving the sample from at least one of a manager unit, a centrifuge unit, an aliquotter unit, or an analyzer that is capable of analyzing the sample. The manager unit includes an input module capable of receiving the sample and a distribution area capable of distributing the sample to a desired component of the system. The centrifuge unit includes a centrifuge capable of centrifuging a sample. The aliquotter unit is capable of pipetting the sample.

Another embodiment of the invention is directed to a system including a manager unit, a centrifuge unit, and an aliquotter unit. The manager unit includes a distribution area and at least one gripper unit and robotic arm. The manager unit is configured to provide sample containers to and retrieve sample containers from the distribution area of the manager unit. The centrifuge unit is coupled to the manager unit. An aliquotter unit is coupled to the manager unit.

A further embodiment of the invention is directed to a method. The method includes placing a sample container in a distribution area of a manager unit using a gripper unit. The sample container is retrieved from the distribution area of the manager unit using the gripper unit. The sample container is transported within the manager unit or to at least one of a centrifuge unit and an aliquotter unit coupled to the manager unit.

An additional embodiment of the invention is directed to a manager unit. The manager unit includes a plurality of input lanes configured to hold a plurality of samples in sample containers. A short turn-around time (STAT) lane is configured to hold STAT samples in sample containers. An error lane is configured to hold samples in sample containers that are associated with errors.

Another embodiment of the invention is directed to a method. The method includes placing a plurality of sample containers into a plurality of input lanes in a manager unit. A first sample in a first sample container is retrieved from the plurality of input lanes. It is determined whether the first sample is a STAT sample, and the first sample is placed in a STAT lane in the manager unit. An error associated with a second sample in a second sample container is determined, and the sample is places in an error lane in the manager unit.

A further embodiment of the invention is directed to a system having a transport track and an output unit adjacent to the transport track. The output unit includes a plurality of output drawers, a buffer area for receiving sample containers, and a gripper unit that is configured to retrieve a sample container from the transport track and place the sample container in the buffer area.

An additional embodiment of the invention is directed to a method. The method includes retrieving a sample in a sample container from a carrier on a transport track. The transport track is adjacent to an output unit comprising a buffer area and a plurality of drawers. The sample container is placed in the buffer area.

Another embodiment of the invention is directed to a system. The system includes a transport track and an output unit adjacent to the transport track. The output unit includes a plurality of output drawers, a buffer area for receiving sample containers, and a gripper unit. The gripper unit is configured to retrieve a sample container from the transport track and to place the sample container in the buffer area.

A further embodiment of the invention is directed to a method. The method includes retrieving a sample in a sample container from a carrier on a transport track. The transport track is adjacent to an output unit. The output unit includes a buffer area and a plurality of drawers. The sample container is placed in the buffer area.

An additional embodiment of the invention is directed to a system. The system includes a first sample container gripper and a second sample container gripper. The first sample container gripper is configured to transport a sample container from a drawer of an input module to a distribution area. A second sample container gripper is configured to transport a sample container to a centrifuge adapter. The second sample container gripper is further configured to transport the sample container to a conveyance device.

Another embodiment of the invention is directed to a method. The method includes transporting a sample container from a drawer of an input module to a distribution area by a first sample container gripper. If the sample container requires centrifuging, a second sample container gripper transports the sample container to a centrifuge adapter. An adapter shuttle transports the centrifuge adapter to a centrifuge area. A centrifuge adapter gripper transports the centrifuge adapter into a centrifuge. The centrifuge adapter gripper transports the centrifuge adapter gripper from the centrifuge to an adapter shuttle. A third sample container gripper transports the sample containers from the centrifuge adapter to a conveyor track. If the sample container does not require centrifuging, the second sample container gripper transports the sample container to a conveyor device. The sample container is inserted into a sample carrier on the conveyor device by the second sample container gripper.

These and other embodiments of the technology are described in further detail below.

BRIEF DESCRIPTION OF THE DRAWINGS

A further understanding of the nature and advantages of the different embodiments may be realized by reference to the following drawings.

FIG. 3 depicts a diagram of components within an aliquotter module.

FIGS. 4(a)-(e) depict diagrams of configurations of components associated with output/sorter modules.

FIG. 4(f) shows region concept—WML instructions according to an embodiment of the invention.

FIG. 6 depicts a diagram of components within a post-analytical phase of the laboratory automation system.

FIG. 24-27 show block diagrams of an illustrative image analysis device according to embodiments.

FIGS. 28(a)-(c) depict examples of camera units for sample tube or rack detection and analysis.

FIGS. 31(a)-(b) depict top views of an exemplary cap having an urgent sample indicator.

FIGS. 32(a)-(b) depict exemplary color indicators of centrifugation indicators.

FIG. 37 depicts an example of a side view diagram of a processing module having a transport unit.

FIGS. 38(a)-(e) depict diagrams of a sample tube being inserted into a sample tube carrier.

FIG. 53 is a diagram of illustrative ring magnets.

FIG. 59 shows a top plan view of a third aliquotter module according to an embodiment of the invention. The third aliquotter module comprises linear lanes and independently movable carriers.

FIG. 60 depicts a diagram of an exemplary non-contact sample tube characterization sensor system.

FIG. 68 shows an illustrative centrifuge drawer.

FIG. 69 shows an illustrative cable management device for a centrifuge drawer, according to a first embodiment.

FIGS. 76(a)-(b) show an illustrative centrifuge adapter gripper, according to a first embodiment.

FIGS. 79(a)-(c) show an illustrative hook lift-up prevention device.

DETAILED DESCRIPTION

Figure 1:
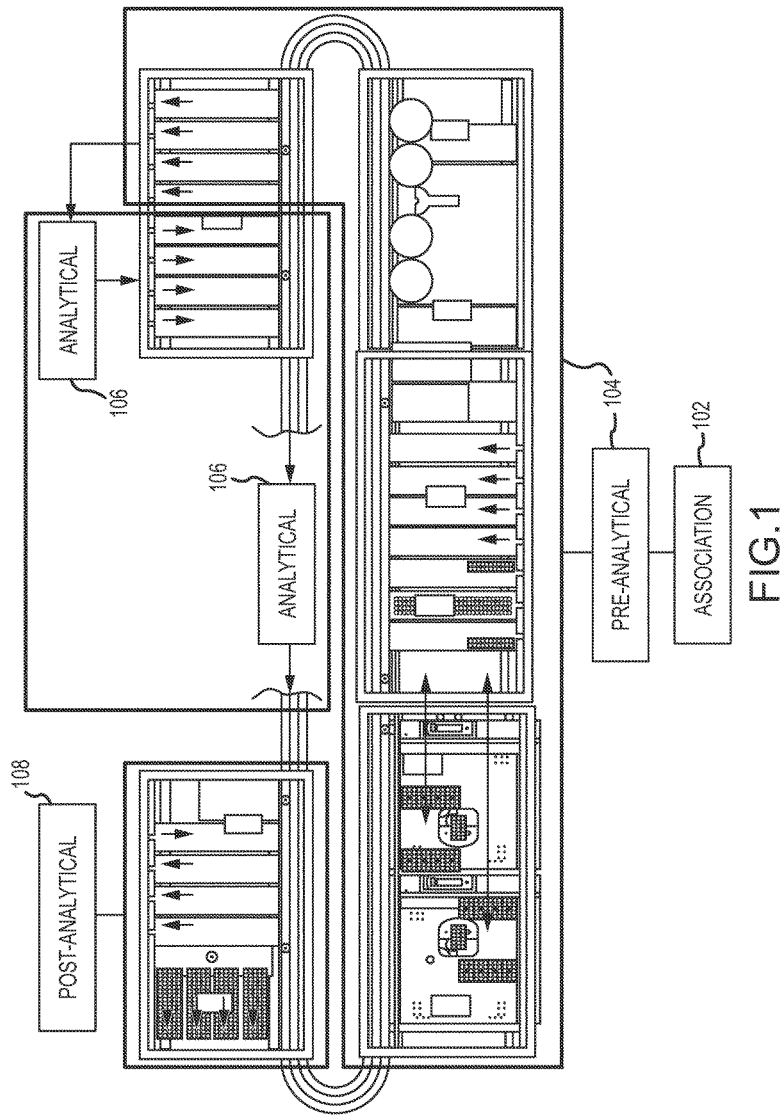
FIG. 1 depicts a diagram of components associated with phases of a laboratory automation system.

Embodiments of the present technology relate to an analytical medical laboratory system and method for processing medical specimens. These embodiments, as will be described in more detail below, are advantageous because they provide, among other advantages, greater speed, accuracy, efficiency, and prevention of contamination. As discussed above, many conventional laboratory systems may have a process that uses standalone units throughout the lab, requiring that specimens be manually transported between each standalone unit, while others may connect some of the units with a conveyance system to move the specimens from unit to unit. Additionally, as discussed above, sample tube sizes and equipment from different manufacturers may be constraints in conventional laboratory systems. Such conventional technology is slow and inaccurate. Embodiments of the present technology provide for a modular laboratory system which is capable of accommodating different laboratory units and transport systems, sample tube sizes, and manufacturers by using more universal components and by grouping functions required by most laboratory systems into five basic functional units: (1) manager, (2) centrifuge, (3), aliquotter, (4) output/sorter, and (5) storage units. These five basic functional units will be described in more detail below. In some instances, the units may be referred to as "modules."

The laboratory system can operate a controlled process using a central controller or scheduler. By keeping the samples under the control of an intelligent scheduler, the system may provide efficient usage of every instrument. The system can maintain a consistent minimal turnaround time and maximize the throughput of the entire system by maintaining control of the process and only delivering samples to instruments when those instruments are ready and available.

In embodiments of the invention, a sample can be contained in a specimen container and processed by a laboratory automation system. A "specimen container," also referred to as a "sample container," "sample tube," and "tube," may have any suitable shape or form. In some embodiments, the specimen container may be in the form of a sample tube. An exemplary specimen container may be a sample tube with a closed bottom end and an open top end. Some sample tubes have an aspect ratio of 3:1 or greater. Specimen containers may be made of any suitable material including plastic, glass, etc. A cap that is structured to cover and attach to the open end of the sample tube body may be used with a sample tube.

In embodiments of the invention, one or more specimen containers may be inserted into a "sample carrier" (also referred to as a "carrier" or a "sample container holder") for transport. A sample carrier may hold the one or more specimen containers in an upright position and provide stability as the carrier is transported along a conveyance system. In some embodiments, a sample carrier may be a puck or a cylindrical receptacle configured to receive a single specimen container. The sample carrier may have vertical slits to allow the contents of a specimen container to be viewed and analyzed. In some cases, the sample carrier may be in the form of a sample tube rack with an array of recesses for receiving specimen containers.

The laboratory system may further utilize one or more robotic gripper units mounted on robotic arms. Each robotic arm unit can have a robotic gripper for gripping sample tubes and may be equipped with one or more means for detecting information about sample tubes. The terms "gripper" and "robotic gripper" are used interchangeably herein. The means for detecting information about a sample tube may include a first imaging device, such as a camera, for identifying a sample tube among a plurality of sample tubes in a rack. The identified sample tube is gripped by the gripper. The means for detecting information about sample tubes may further include a second imaging device to obtain an image of the gripped sample tube. The level of liquid in the sample tube may be determined from the image obtained by the second imaging device or from a transmission measurement using emitter and receiver units coupled to the robotic arm unit. In comparison with prior art systems, which have a camera mounted on a track and thus require all sample tubes to be on the track before the tubes can be identified, the laboratory system described herein can identify a sample tube before it is placed on a conveyer track. As a result, samples that do not need to be transported on the conveyer are not placed on the conveyer merely for the purpose of sample tube identification. Further, urgent samples can have a prioritized placement on the conveyer track.

Use of a plurality of robotic gripper units in the laboratory system can also increase sample processing efficiency. A first gripper, such as an input module gripper, can identify a sample tube and make data measurements as described above. After the first gripper delivers the sample tube to a distribution area, a second gripper, such as a distribution area gripper, can deliver a sample tube to a subsequent module such as a centrifuge module or conveyor. The use of multiple grippers allows an increase in processing efficiency over prior art systems that use only a single gripper to receive, identify, and load all samples on a conveyor track.

I. Overall System

A. Phases of Laboratory System

FIG. 1 depicts one embodiment of a medical laboratory system for processing patient samples. The laboratory system includes components associated with association phase 102, pre-analytical phase 104, analytical phase 106, and post-analytical phase 108.

1. Association Phase

The association phase 102 can be the first phase in the laboratory system. During this phase, various information pertaining to a specimen, such as patient information, requested tests for a specimen, and a unique laboratory identifier (e.g., a barcode), may be associated with a specimen container. In some embodiments, the association phase is handled manually. For example, in some embodiments, a laboratory technician (hereinafter referred to as a "user") can assign a priority to the samples. In a preferred embodiment, a scheduling system is used to determine priority and other information related to how samples are processed. The samples may be loaded into racks or directly onto the system at specific entry points. Although grouping samples into a few basic priority levels (e.g., urgent or high priority, medium priority, low priority, etc.) may be desirable to provide a more consistent turnaround time, it is not necessary. Processing patient samples can be based on any priority defined by the user. However, if a priority is not specified, a priority can be assigned based on factors such as minimizing turnaround time, maximizing throughput, the availability of processes, etc.

2. Pre-Analytical Phase

The pre-analytical phase 104 can include preparing patient samples for analysis. During the pre-analytical phase 104, the patient and test information can be deciphered, the process for analysis can be planned, quality checks may be performed, the sample may be separated into its constituent components (e.g., centrifuged), the sample may be divided into multiple specimen containers (e.g., aliquotted), and/or the sample can be delivered to one or more analyzers and/or racks. The pre-analytical phase 104 can manage the flow of samples to different instruments and different analyzers within the lab system. This process management may permit the system to operate efficiently and with minimal instruments. Additionally, scheduling that occurs during the pre-analytical phase 104 enables efficient processing of samples.

Embodiments of the system can identify the patient samples as quickly as possible and determine the best scheduling of each sample to provide a consistent minimal turnaround time and maximum throughput of the analytical processes. The steps and organization of those steps in the process are designed to avoid accumulation of specimen containers at the input to the system or at other stations of the system. Modules of the laboratory system can operate at a throughput speed that allows processing of samples at the maximum throughput of the upstream processes. However, in some embodiments, at the aliquotter unit, the throughput may be managed by the introduction of samples upstream and by small queues at each aliquoting station.

Figure 2A:
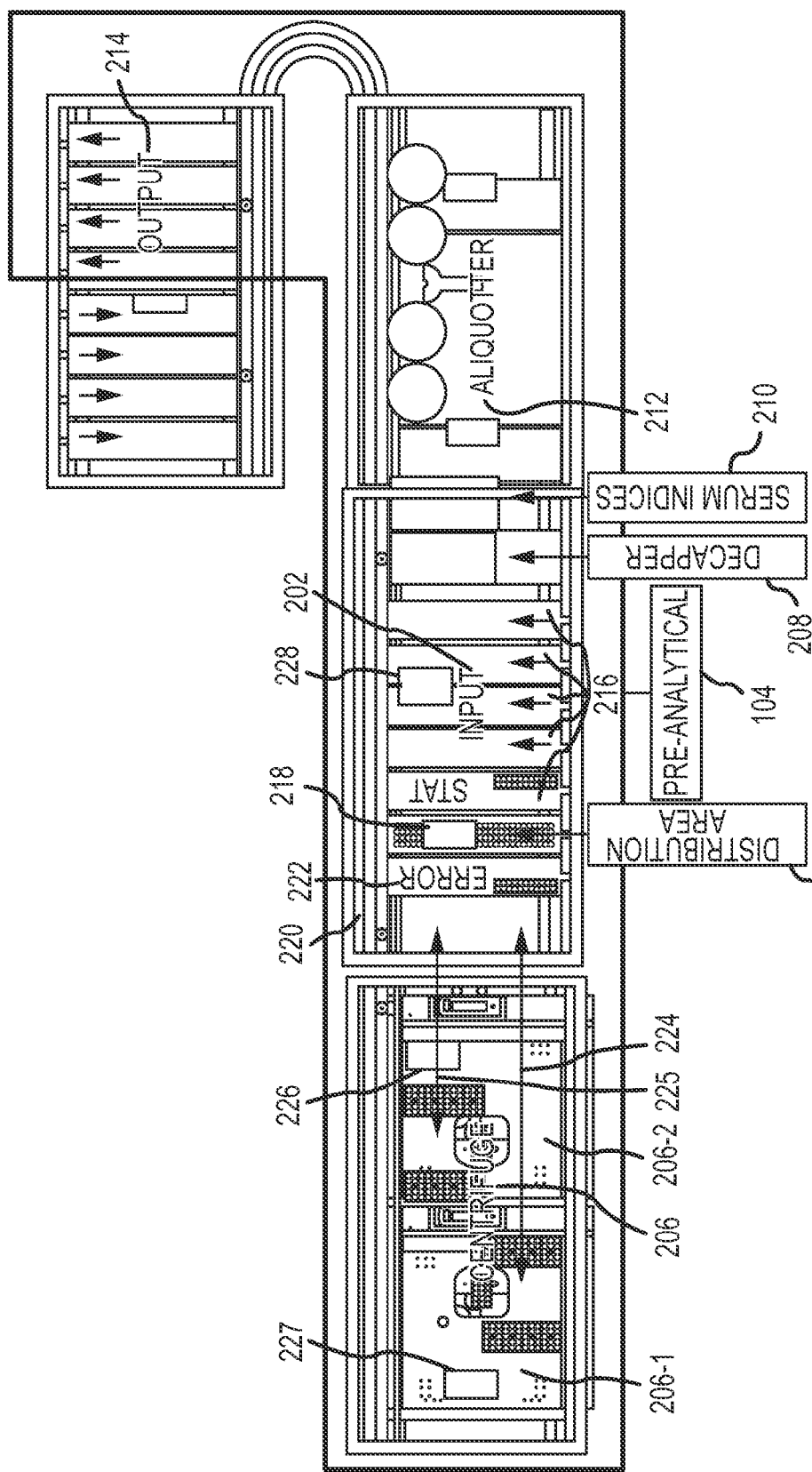
FIG. 2(a) depicts a diagram of components associated with a pre-analytical phase of a laboratory automation system.

FIG. 2(a) is a more detailed depiction of the components associated with the pre-analytical phase 104. The components associated with the pre-analytical phase 104 can include modules such as input module 202, distribution area 204, centrifuge 206, decapper 208, serum indices measurement device 210, aliquotter 212, and output/sorter 214.

(a) Input Module

Figure 2B:
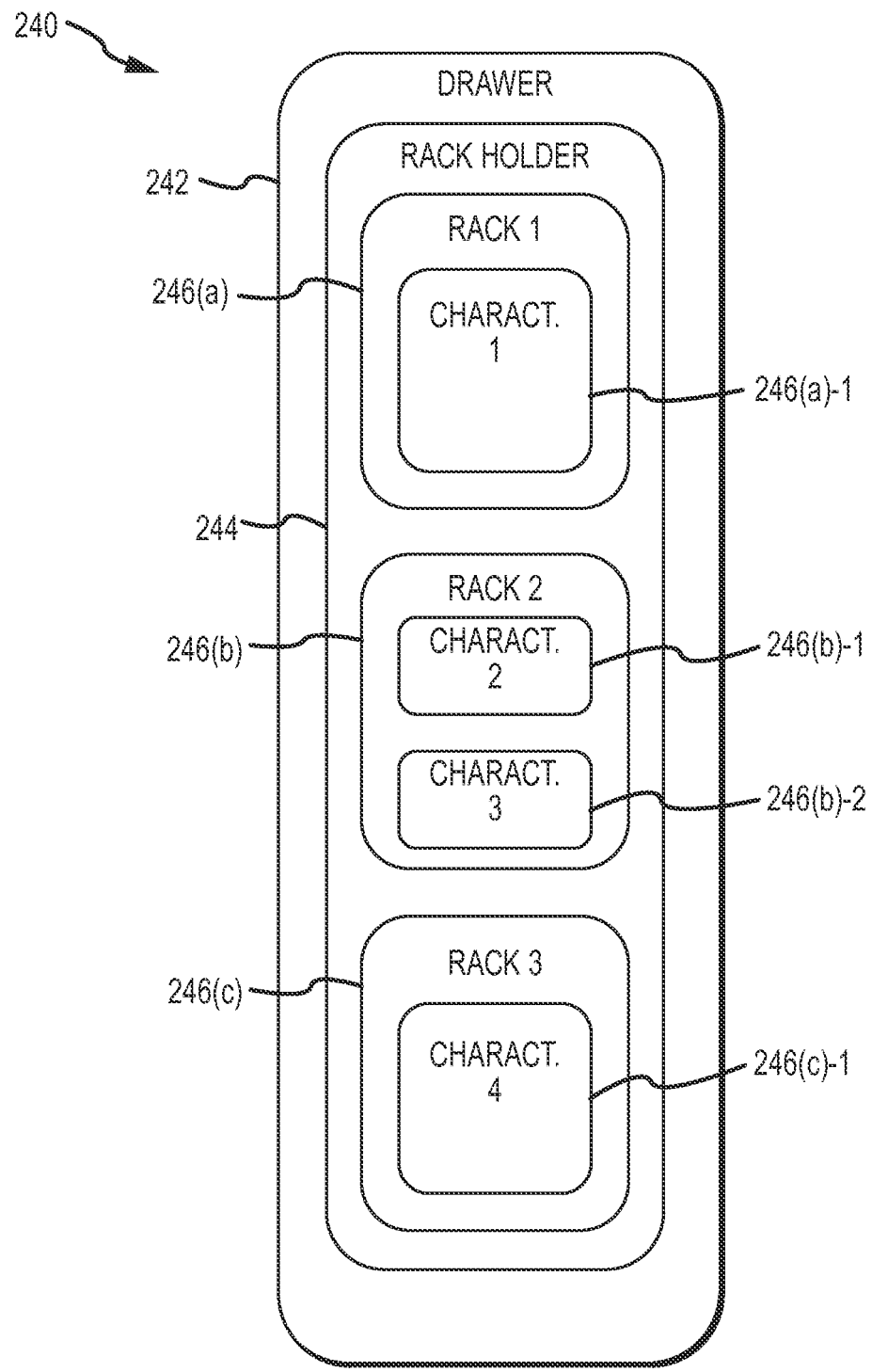
FIG. 2(b) shows region concept—tube characteristics according to an embodiment of the invention.

The input module 202 shown in FIG. 2(*a*) is the point at which a specimen container is introduced to the laboratory system. Racks of tubes and/or individual tubes can be loaded onto one of several lanes 216, which may be manually operated drawers and/or automated devices. In FIG. 2(*a*), five lanes 216 are depicted. However, the lab system can have any number of lanes 216. The lanes 216 can be prioritized according to automated or user-established scheduling. In some embodiments, the highest priority lane (short turnaround time or "STAT") may have a fixed position for accepting a group of individual tubes from the user. Once tubes are loaded in the STAT lane, they become the next tubes processed. Other lanes can be assigned different priority levels in any manner. For example, when the drawers are manually operated, assigning one priority to at least two of the drawers and another priority to at least two other drawers may allow the system to operate continuously on one drawer while the other drawer of the same priority is available to the user.

In some embodiments, while the input module 202 is processing a drawer of samples, the user may be informed that the drawer should not be opened. For example an indicator such as a light on the drawer or a lock on the drawer may be used to warn the user. This may help maintain the process integrity and maximize throughput. When processing of the contents of the first drawer is complete, the drawer may be identified to the user as available, and the system may automatically begin processing another drawer. Additionally, the samples can be transferred to and from the drawers 216 (which may alternatively be referred to as "lanes" in some cases) of the input module 202 using an input module gripper 228.

In some embodiments of the invention, a "region" concept can be used. A "region" can be the basic abstraction for the usage of drawers, rack holders, trays and racks. For example, a region can be a set of tube positions within a rack in one embodiment of the invention. A region can be assigned either tube characteristics (e.g., STAT, sample type, pre-spun, cap type) or a single processing instruction. In embodiments of the invention, a tube characteristic or instruction can be assigned to one or more regions, which allows for a more robust routing scheme.

As shown in FIG. 2(*b*), a region in a drawer assembly 240 including a drawer 242 can be mapped to a set of tubes in racks 246(*a*), 246(*b*), 246(*c*) (held in a rack holder 244 in the drawer 240) with specific tube characteristics 246(*a*)-1, 246(*b*)-1, 246(*b*)-2, 246(*c*)-1. Each region has a set of associated tube characteristics 246(*a*)-1, 246(*b*)-1, 246(*b*)-2, 246(*c*)-1. In some embodiments, the system uses these tube characteristics to calculate an optimized route (discussed in further detail below). A subsystem (e.g., a centrifuge, aliquotter, etc.) uses tube characteristics to calculate the order in which tubes will be processed (e.g. STAT samples before routinely processed samples).

(b) Distribution Area Module

Referring again to FIG. 2(*a*), from the lanes 216 within the input module 202, one or more distribution area grippers 218 may select the highest priority tube and transport it to a fixed matrix called the distribution area 204. The distribution area 204 is capable of distributing a sample container to a designated station of the laboratory automation system. As the input module gripper 228 transfers a specimen to distribution area 204, the gripper 228 can gather information about the specimen. For example, one or more liquid levels of fluid within the specimen container may be measured, e.g., by systems associated with gripper 228. In some embodiments, the sample tube may be photographed, e.g., by systems associated with gripper 228. The information gathered in this manner can be analyzed to determine the tube's manufacturer, diameter, height, cap color, etc. Volumes of the sample's components can be calculated, and an estimate of the total tube weight can be made. This weight can be later used to aid in balancing the centrifuge adapters in the centrifuge module 206, as will be discussed in more detail below.

To protect the distribution area 204 from becoming filled with low priority tubes, a limit can be set on the number of tubes loaded into this area from the low priority input lanes. Moreover, the distribution area 204 may have a reserved area to ensure STAT samples have continuous access to the distribution area 204 from the STAT drawer in the input module 202.

The distribution area 204 can be the holding area which permits the system to access test information associated with the sample tube in the association phase 102 and plan the analysis process for the sample. This enables the system to schedule a sample tube's process with respect to the other sample tubes currently on the system. Scheduling enables the efficient processing of samples based upon priority without overloading any step in the overall system, permitting the optimization of turnaround time and throughput. Furthermore, the sample's schedule can be updated throughout the process as the system's activity or availability changes, providing real time active control of the sample.

Once the schedule is planned by the distribution area module 204, the robotic gripper 218 then selects the sample tube that is the next tube to be transferred to the next module based on the priority of the tubes within the distribution area 204. The selected sample tube is transported from the distribution area 204 to the conveyance system 220, to the centrifuge module 206, or to an output drawer with an error area 222 based on the analysis performed by the distribution area module 204.

If the sample tube is being moved to the centrifuge module 206, the tube can be placed into the appropriate centrifuge adapter based upon the earlier weight estimation to ensure proper balance of the centrifuge rotor. The centrifuge adapter is the component that carries the tubes upon a shuttle from the distribution area 204 to the centrifuge whereupon a robotic gripper transfers the centrifuge adapter with the tubes to a bucket of the centrifuge.

If the distribution area module 204 determines that the sample tube does not require centrifugation, the distribution area robot gripper 218 places the sample into a carrier on the conveyance system 220 with the barcode label properly aligned to the carrier at the direction of the scheduler so as not to overload downstream processes. More details on the conveyance system 220 and the carriers will be discussed below. A carrier can refer to any suitable device, which can be present in a conveyance system and can carry or transport one or more sample containers or tubes. Exemplary carriers may contain recesses that can hold the containers or tubes. If a problem exists with the sample (e.g., the volume is too low, the barcode is unreadable, no test information is downloaded, etc.), the sample tube is moved to the error area 222 and the user is notified of the issue.

(c) Centrifuge Module

The sample tube may be moved from the distribution area 204 of FIG. 2(*a*) to the centrifuge module 206 when the distribution area module 204 determines that the sample requires centrifugation before analysis of the sample. Centrifuge module 206 may include one or more automated centrifuges (e.g., first centrifuge 206-1 and second centrifuge 206-2) and an adapter shuttle for each centrifuge (e.g. first adapter shuttle 224 and second adapter shuttle 225). Centrifuge module 206 may further include one or more robot grippers (e.g. robot gripper 226 and robot gripper 227). In some embodiments, a robot gripper 226 may be a centrifuge tube gripper (e.g., a third sample container gripper) used to remove centrifuged sample tubes from adapters 224, 225 and transport the sample tubes to conveyance system 220. A robot gripper 227 may be a centrifuge adapter gripper used to swap adapters into and out of centrifuges 206-1, 206-2.

When a sample tube is to be transported from the distribution area 204 to the centrifuge module 206, the sample tube can be loaded by the distribution area robot gripper 218 into a centrifuge adapter from the distribution area 204. The adapters may accommodate multiple tube sizes for centrifugation. The adapter may be seated on an adapter shuttle 224, 225 that moves between the distribution area 204 and the centrifuge module 206.

When the sample tubes in the adapters arrive at the centrifuge module 206 from the distribution area 204 via the adapter shuttles 224, 225, the adapters are loaded into an available centrifuge bucket. In a preferred embodiment, each centrifuge can accept multiple adapters, e.g., four adapters. In some embodiments, each adapter can hold a plurality of sample tubes, such as 14 sample tubes.

Of the adapters associated with centrifuges 206-1, 206-2, a subset of the associated adapters (e.g., two adapters) may reside on each adapter shuttle. In some embodiments, the following processes may occur simultaneously: distribution area gripper 218 loads tubes into an adapter, centrifuge tube gripper 226 unloads tubes from another adapter on a first adapter shuttle and moves the unloaded sample tubes to sample carriers on conveyance system 220, centrifuge adapter gripper 227 swaps adapters for a centrifuge (e.g., 206-1), and another centrifuge (e.g., 206-2) spins an adapter set. An adapter shuttle may transfer adapters to a centrifuge when one or more of the following occurs: a centrifuge is available, an adapter filling time is expired (which may depend on the scheduled starting time for a centrifuge), or adapters for unloading are empty.

The configuration of the adapters allows for simplification of delivery of sample containers to and removal of sample containers from the centrifugation buckets. Once loaded into a centrifuge bucket, the adapters can be centrifuged. The centrifuge module 206 may include one or more centrifuges that are refrigerated to maintain the temperature of the sample. The centrifuges may use a swinging centrifuge bucket rotor that produces level sedimentation layers from which analyzers and pipettors can consistently aspirate the maximum volume of fluid.

Once centrifugation is complete, centrifuge adapter gripper 227 can remove the adapters from the centrifugation bucket. The adapter shuttle can then move back to the tube loading/unloading position. With the adapter shuttle at the loading/unloading position, centrifuge tube gripper 226 may remove sample tubes from the adapters and place the tubes in carriers on the conveyance system 220 for transport to the next module. Sample tubes may be removed from adapters and placed in a temporary buffer. For example, when a downstream module is temporarily non-operational or otherwise unavailable, the sample tubes may remain in the temporary buffer. When the downstream module becomes available, the sample may be removed from the buffer and placed on conveyance system 220. If the downstream module will be unavailable for an extended period of time, the sample can be placed on conveyance system 220 to be transported to error area 222.

The timing for loading tubes into an adapter at the distribution module 204, sending the tubes in the adapter to the centrifuge module 206 via the adapter shuttle 224, loading the adapter into a centrifuge bucket, centrifuging the samples, unloading the adapter from the centrifuge bucket, and unloading the tubes from the adapter can be established such that the process is continuous, allowing for the continual centrifugation of samples as they arrive at the centrifuge module 206 from the distribution area 204. As the centrifuge completes a spin cycle, the last tube in the distribution area 204 can be loaded by the distribution area gripper 218 into an adapter, and the shuttle 224 can move the adapter to a centrifuge in the centrifuge module 206. At the same time, an automated door on the centrifuge opens and provides access to a bucket as the rotor indexes into position at the doorway.

In one embodiment, a centrifuge adapter gripper 227 in the centrifuge module 206 can remove an empty adapter from the adapter shuttle and place the empty adapter on a deck of centrifuge module 206. Subsequently, the centrifuge adapter gripper 227 can remove an adapter that is in a centrifuge bucket. The centrifuge adapter gripper 227 can move the adapter that was removed from the centrifuge bucket to the area of adapter shuttle from which the empty adapter was removed. Next, the centrifuge adapter gripper 227 selects an adapter that has been recently loaded with tubes from the distribution area 204 and deposits it into the empty bucket. While the centrifuge rotor indexes to the next bucket, a previously emptied adapter is moved to the open position on the shuttle 224 for loading with tubes from the distribution area 204 when the shuttle 224 returns to the distribution area 204.

After the final adapter is loaded into the centrifuge, the centrifuge door, which may be an automated door may be closed to allow the centrifuge cycle to begin. The empty adapter that was on the centrifuge module deck can be placed on the adapter shuttle. The adapter shuttle may move back to the distribution area 204, and a centrifuge tube gripper 226 begins to unload tubes from the adapters removed from the buckets into carriers on the conveyance system 220. As the tubes are moved from the adapter to the carrier, liquid level detection can be performed with centrifuge tube gripper 226. For example, a liquid level measurement can be performed as described in more detail below. In some embodiments, the heights of the sedimentation layers are measured and the barcode on the sample container is read and/or aligned for the carrier. If insufficient serum or plasma is present in a centrifuged sample container, the sample container may be sent to an error area located in the output module 214.

In an alternative embodiment, a shuttle can have additional space for one or more adapters. For example, the shuttle can have a number of positions for adapters that exceeds the numbers of adapters in an adapter set by one. The additional space may be located on the loading side of the shuttle. Rather than moving an empty adapter to a temporary location such as a centrifuge module deck, as described above, the adapter may be placed at the additional space on the shuttle.

If the scheduling algorithm predicts the overloading of an analyzer with samples from the centrifuge module 206, the centrifuge module gripper 226 can unload the samples and distribute the samples from the adapters to the conveyance system. In some embodiments, the full cycle time of the centrifuges can be greater than or equal to, e.g., 360 seconds. In order to ensure optimal turn-around time and throughput the centrifuges are kept, e.g., 180 seconds out of phase for a 360 seconds centrifugation cycle. In some embodiments, downstream processes do not prevent the unloading of samples from the centrifuge adapters. If all the remaining samples in an adapter are destined for unavailable process (es) and depending upon the unavailable process, sample tubes can either be moved to a buffer in the centrifuge instrument or moved to another buffer area elsewhere in the system.

The centrifuge module 206 may include an automated centrifuge controlled by a centrifuge controller. The automated centrifuge can be loaded with multiple centrifuge adapters or receptacles, each adapter receiving multiple sample tubes. The centrifuge includes a motor coupled to a spindle, a rotor assembly, a controller, a lid, and optionally, a lid drive. The centrifuge controller indexes or stops the spindle at selected positions for automated placement and removal of either tubes, adapters or buckets. The lid has a closed position and an open position, and the lid opens and closes in response to instructions from the centrifuge controller.

Various techniques may be used to balance the weight distribution among adapters that are to be loaded into a centrifuge. In some embodiments, the weight of a tube may be determined based on information stored in a database of tube weights. The weight of sample material contained in a tube may be determined based on a measured liquid level or liquid levels in a sample tube and a known density of the liquid or liquids. In another embodiment, sample tubes may be weighed by input module gripper 228 prior to being loaded into centrifuge adapters.

In another embodiment, specimen weights can be determined by one or more balances, for example, a balance located in the distribution area or a balance of a conveyor track. The balance can measure the combined weight of the sample tube and the sample contained in the tube. This may occur as the sample tubes are carried by a conveyor track. To obtain a weight of the sample, a known weight of the sample tube can be subtracted from the combined weight. The known weight can be stored in a database of known tube weights. The sample weight may be determined using a central controller associated with the laboratory system or by another controller of the system. The controller may be communicatively coupled to the database.

Alternatively, centrifuge module 206 may comprise a scale having sites for receiving and holding a plurality of adapters, and a balance controller for selectively depositing sample tubes in cavities of the adapters while correlating incremental weight changes with the locations of each deposit for equalizing weight in pairs of the adapters.

In some embodiments, before the loaded buckets are placed in the centrifuge, the buckets can be balanced in a balance system. The balance system, which can be an included part of the centrifuge module 206, comprises a scale having sites for receiving and holding a plurality of buckets, and a balance controller for selectively depositing sample tubes in cavities of the buckets while correlating incremental weight changes with the locations of each deposit for equalizing weight in pairs of the buckets. The balance controller can be implemented as a balance program within the central controller. The balance program maintains a database of sample container weights. When a container's weight is combined with the sample's weight, the balance program can determine the optimum adapter cavity in which to place it thereby maintaining a balanced rotor within a tolerance. Sample weights are the product of density estimates and the sample volumes calculated from liquid level measurements and container geometry obtained during the initial pick-up from the input. In some embodiments, balance system may also include a supply of dummy loads in buckets for limiting weight variations between buckets. The dummy loads may be weighted for limiting the weight variations to not greater than, e.g., 10 grams between members of each pair of buckets.

In other embodiments, a scale need not be used. For example, in some embodiments, the weight of a sample container and a sample can be estimated, and the adapters can be automatically loaded to ensure a balanced rotor. In some cases, a picture of a sample tube may be taken, and the liquid level of a sample in the sample tube can be determined. Using information about the sample container (e.g., the sample container weight) and the determined liquid level, the weight of the sample tube with the sample in it can be estimated. In such embodiments, a scale is advantageously not needed. Further dummy loads may also not be needed.

The centrifuge controller may operate to perform a number of functions, such as receiving and storing centrifuge spin profiles including a rotor spindle speed and duration; indexing the rotor's sample stations into an access position, spinning the rotor in accordance with the cycle profile, stopping the rotor with a predetermined sample station at the access position, etc.

If two or more centrifuges are used in the pre-analytical system, the centrifuges may be synchronized and/or kept out of phase. For example, the starting time of a spinning cycle for first centrifuge 206-1 may be scheduled at a different time from a spinning cycle for second centrifuge 206-2. Because centrifuges 206-1 and 206-2 do not start spinning at the same time, high priority sample tubes may be processed quickly. In some embodiments, spin cycles for the centrifuges are scheduled such that at least one centrifuge is available to process a high priority sample tube at any time.

In an exemplary embodiment, the centrifuges may be run synchronized and out of phase on a fixed timetable such that a centrifuge is available at predetermined intervals. For example, a centrifuge cycle may have a six minute duration, which can include the time required to swap adapters out of and into the centrifuge. In a system with two centrifuges, the centrifuge cycles may be out of phase such that one of the centrifuges is available every three minutes. (including swapping (e.g., one of two centrifuges is available every three minutes).

(d) Decapper Module

The decapper module 208 of FIG. 2(a) is capable of decapping the cap from the sample tubes in carriers on the conveyance system 220 before they are analyzed. The decapper system may clamp a sample tube and remove the cap from a sample tube. The decapper module 208 follows the distribution module 204 and the centrifuge module 206. For sample tubes which do not require cap removal (e.g., for instances in which the samples may only require sorting), the carrier on the conveyance system 220 will bypass the decapper module 208. For sample tubes that require cap removal, the decapper module 208 may remove the cap from the sample tube and deposit the cap in a biohazardous waste disposal container below the deck of the decapper module 208. The biohazardous waste disposal container is removable and replaceable to protect the user from biohazardous waste.

(e) Serum Indices Module

The serum indices module 210 of FIG. 2(a) is capable of measuring the serum index of a sample. Typically, this function is performed during the analytical phase 106. However, in some instances, certain laboratories may prefer to address any quality issues prior to delivering the samples to the analyzer. Thus, the serum indices module 210 provides this quality control option for samples that should be tested. For samples that do not require a serum index measurement, the sample may bypass the serum indices module 210.

The serum indices module 210 can be the next module after the decapper module 208 since a serum indices measurement typically requires access to the sample. Similar to the decapper module 208, the serum indices module 210 may have a biohazardous waste disposal container below the deck of this module. The container may be removable and replaceable to protect the user from biohazardous waste.

(f) Aliquotter Module

The aliquotter module 212 of FIG. 2(a) is depicted in greater detail in FIG. 3. The aliquotter module 212 divides the sample in primary sample tubes 304 into multiple secondary sample tubes 306 depending on how many tubes are needed for analysis. This module may contain one or more pipettors 302 for dividing the samples in the primary sample tubes 304 into sample aliquots for secondary sample tubes 306.

As shown, the primary and secondary sample tubes 304, 306 may be on respective rotatable wheels so that they can be removed and/or introduced to the conveyance system 220. The pipettors 302 can be between respective pairs of adjacent rotatable wheels containing the primary and secondary sample tubes 304, 306. As shown, the configuration of the components of the aliquotter module are such that the secondary sample tubes 306 containing sample aliquots can leave the aliquotter module via the conveyance system 220, before the primary sample tubes 304 leave the aliquotter module.

The aliquotter module 212 further facilitates labeling of the secondary sample tubes 306 with a barcode label specifying the patient and test information. The barcode labels are attached to the secondary sample tubes 306 below the deck of the aliquotter module 212 in a device called the Secondary Tube Preparation Unit (STPU). The STPU can produce labeled tubes for one or more pipettors. New secondary sample tubes can be delivered to the aliquotter module 212 in racks and loaded into drawers below the aliquotter module 212. The labels are delivered on a roll and printed below the deck of the aliquotter module 212 prior to attachment to the tubes.

To minimize contamination of patient samples, the pipettors 302 use disposable tips 308. These tips arrive in racks which are loaded into drawers on the deck. The pipettor 302 loads a disposable tip from these racks, aspirates 310 the sample from the primary tube 304 and dispenses 314 the sample into one or more secondary tubes 306 and/or a microtiter plate 312. In one embodiment, the tip may be limited to a particular amount (e.g., 1 milliliter) of the sample. In such a case, dispensing volumes exceeding that particular amount may require multiple aspirations. Once the pipetting is finished for a sample, the tip can be disposed in the waste container 320.

In order to manage the tubes during aspiration 310 and dispensing 314, the primary 304 and secondary 306 tubes are removed from the travel lane of conveyance system 220 and queued on supplementary lanes. Because the aliquotter module 212 may operate at a slower rate than the other modules, the queues minimize the effect of aliquotting on the remainder of the system. Although the queuing process may vary depending upon the conveyance system 220, in this embodiment the carriers with the primary tubes 304 are transferred to a queue wheel. Empty carriers for the secondary tubes 306 are transferred to a separate queue wheel adjacent to the primary tubes 304. The labeled secondary tube 306 is loaded 316 into the empty carrier from below the deck by a lift 318 which rotates around to align with the empty carrier. The STPU transfers the tube to the lift 318 in the correct orientation to ensure the barcode is aligned properly with the carrier. In the case of an aliquotter module 212 having more than one pipettor, the lift 318 rotates the opposite direction to place the tube in the carrier (rotatable wheel).

(g) Output/Sorter Module

Figure 4E:
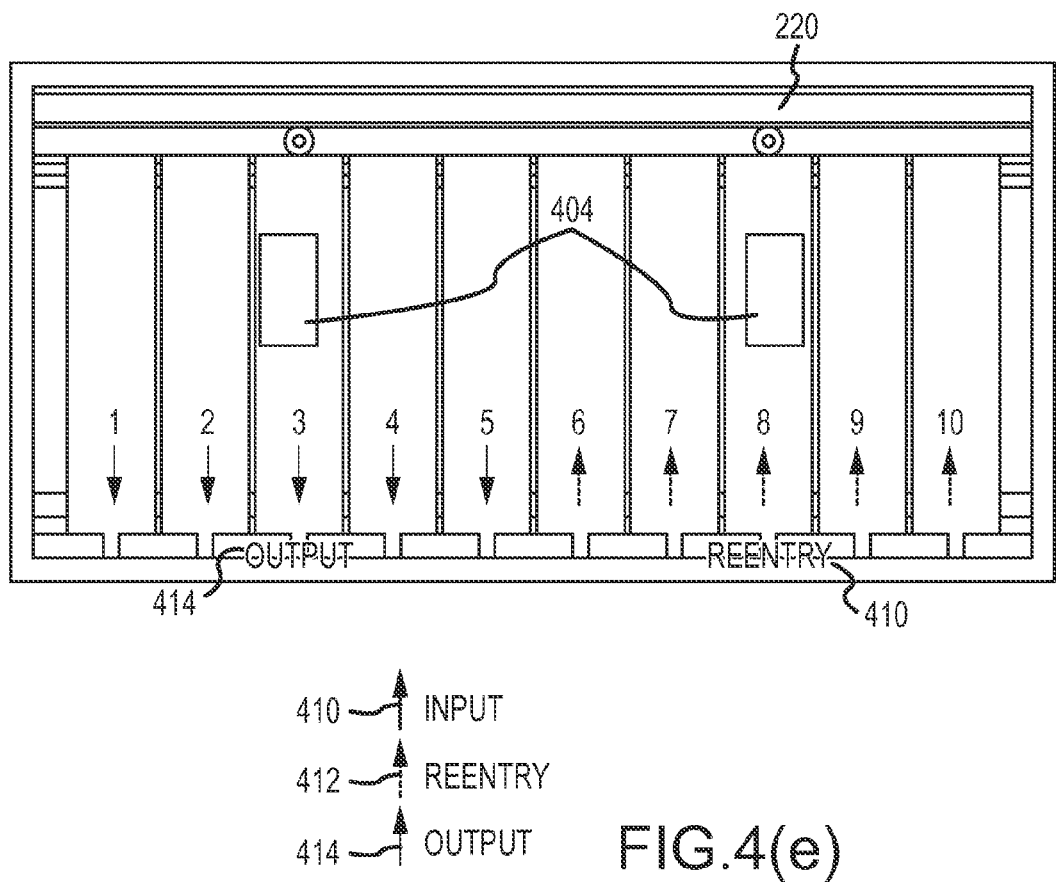

FIGS. 4(a)-(e) depict examples of an output/sorter module 214. The output/sorter module 214 transfers tubes to and/or from racks located in drawers 402 or bays. The racks may be either analyzer racks, standard storage racks, or any rack that meets the Clinical and Laboratory Standards Institute (CLSI) standards. An output/sorter gripper 404 removes the tubes from the carrier and deposits them into the racks. If necessary, the barcode is aligned to the rack as desired. The output/sorter module 214 may have any number of drawers 402 and may have any number of output/sorter grippers 404. The number of output/sorter grippers 404 may depend on how many drawers 402 the output/sorter module 214 contains. That is, more output/sorter grippers 404 may be needed for output/sorter modules 214 having a large number of drawers 402. FIG. 4(a) depicts an example of single gripper output unit 406 that is connected to the conveyance system 220 and a standalone single gripper sorter with input and output 408. FIG. 4(b) depicts an example of a dual gripper sorter with input and output. Depending upon the application, the unit may be connected to the conveyance system 220 or it may operate as a standalone system.

The output/sorter module 214 can function as a component for handling the output of the pre-analytical phase 104 and can also function as a sorter for sorting tubes based on the type of analysis that the samples are to undergo. FIG. 4(c) depicts another embodiment of the output/sorter module 214. The output/sorter module 214 may include drawers for handling the output 414 of the pre-analytical phase 104, drawers for handling tubes that are inputted 410 to the output/sorter module 214 for sorting, and drawers for handling tubes that should be reentered 412 into the analytical phase for further analysis.

The output/sorter module 214 includes areas to load and/or unload racks of tubes. Additionally, some of the drawers on the output/sorter module 214 may be specified as input and some as output. In the sorter mode, the units with a single robotic gripper 404 select a tube from an input drawer, read the barcode, measure the height of the constituent sample components, make a photograph of the tube and analyze the data to record its manufacturer, diameter, height, and cap color. Based upon the information received from the laboratory information system (LIS), the gripper 404 deposits the tube in the correct rack while aligning the barcode as appropriate. If an error condition is identified, the tube is placed into an error rack.

An output/sorter module 214 having a larger number of drawers 402 and more than one output/sorter robotic gripper 404 may attain a higher throughput. A first output/sorter gripper 404 may perform the same functions as described above; however, since the destination is typically a single point on the conveyance system 220, it may not have to wait on information from the LIS. As the tube is conveyed to the extraction point for a second output/sorter gripper, the LIS has time to respond with the appropriate information. The second output/sorter gripper may remove the tube from the carrier and deposit and align the tube in the appropriate rack. Because these units can function as either an input 410 or an output 414, they can be assembled together with the conveyance system 220 to create even larger input and/or output areas. FIG. 4(d) depicts an example of this embodiment of an output/sorter module 214. Units are combined with the conveyance system 220 to permit the creation of a sorter having an input 410 with five drawers and an output 414 with ten drawers.

3. Analytical Phase

Referring again to FIGS. 1 and 2(a), the analytical phase 106 includes performing the actual measurements needed to process a sample and produce results. This phase is typically composed predominantly of one or more analysis instruments or analyzers. The analysis instruments or analyzers can be any analysis instruments or analyzers known in the art. Typically an analyzer may comprise a mechanism for selectively performing one or more types of analyses on a specimen. The analyzer's controller is in communication with the central controller, so that the central controller can instruct the analyzer controller as to what analysis to perform for the specimen. Each analyzer's controller may also communicate analysis results to the memory of the central controller.

For a laboratory system that has the components associated with the pre-analytical 104, analytical 106, and post-analytical 108 phases connected together via a conveyance system 220, the samples may move past the output/sorter module 214 and onto analyzers. When the carrier reaches the destination analyzer for that particular sample, the carrier pulls off the main travel lane and forms a queue upstream of the analyzer's access point to the conveyance system 220. The queue length is minimal because of the planning done by the scheduler while the tube was still in the distribution area 204 and because of the controlled release of tubes by the distribution 204 and centrifuge 206 modules.

If some of the analyzers are connected via the conveyance system 220 and some are not, the samples destined for the unconnected analyzers will exit the system at the output/sorter module 214. However, these samples may need to reenter the connected system for additional processing. The reentry function of the output/sorter module 214 performs this function by inputting 410 the tubes that should reenter the system for analysis. Thus, since the output/sorter module 214 can function as an input 410, another module is not necessary, increasing the efficiency of the system. The location of this function may vary by the user's laboratory layout. In one embodiment, the location of this function may be adjacent to and downstream of the output/sorter 214 in the pre-analytical phase 104. In one embodiment, two separate frames are used to perform these functions, such as the example depicted in FIG. 4(d). In another embodiment, the functions can be combined into a single frame of an output/sorter module 214, as shown in FIG. 4(e). However, any combination of the configurations shown in FIGS. 4(a)-4(e) can be used.

The throughput of the output 414 and input or reentry 410 may be tailored to match the needs of the user. For example, a user with few samples destined for an unconnected analyzer may only need an output/sorter module 214 that has one single output/sorter gripper 404. On the other hand, a user with no connected analyzers and high throughput may prefer a large output area and a separate sorter.

In some embodiments, regions may be assigned to tubes in a rack or drawer. As shown in FIG. 4(f), a region 446(a)-1, 446(b)-1, 446(b)-2, 446(c)-1, 456(a)-1, 456(b)-1, 456(c)-1, 456(c)-2 in a drawer 402, 452 can be mapped to a set of instructions provided by a central controller. An example of an instruction may be to store the samples in a particular rack (e.g., Rack 3) in a storage unit such as a freezer. Racks 406(a), 406(b), 406(c), 456(a), 456(b), 456(c) may be in rack holders 444, 454 in the drawers 402, 452. Each region 446(a)-1, 446(b)-1, 446(b)-2, 446(c)-1, 456(a)-1, 456(b)-1, 456(c)-1, 456(c)-2 containing sample tubes can be associated with one (or more) instruction(s). Any suitable subsystem can be aware of this mapping. A subsystem robot (not shown) can transport a tube to a destination matching the instruction received.

4. Post-Analytical Phase

The final phase of the laboratory process is the post-analytical phase 108. In this phase, the sample is prepared for storage and is stored. Once the sample has completed the testing and analysis required, the sample is capped and placed into storage. This may be either ambient or refrigerated storage depending upon the sample and the laboratory process. Moreover, users with systems having connected analyzers may desire a connected cold storage for some samples and offline ambient storage for others. However, users with unconnected analyzers will likely store all of their samples offline.

Figure 5:
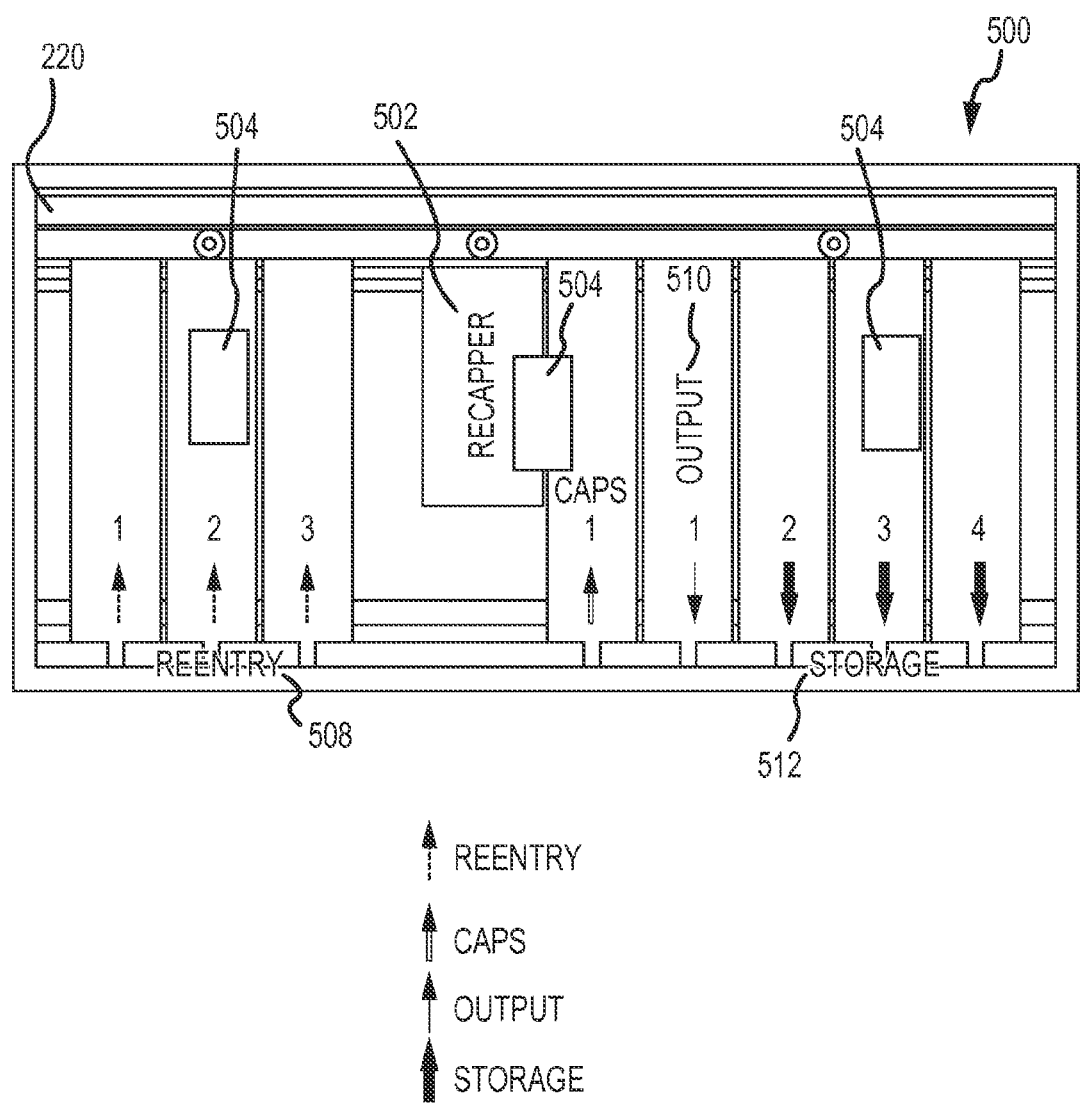
FIG. 5 depicts a diagram of a configuration of a sorter module coupled to a capping device.

The user with unconnected analyzers may use a sorter in combination with a capping device to prepare their samples for storage. FIG. 5 depicts an example of a sorter module 500 coupled to a capping device 502. The sorter module 500 may be similar to the output/sorter modules 214 depicted in FIGS. 4(a)-(e). When a tube completes a test, the user loads the sample on the input or reentry side 508 of the sorter and retrieves the sample on the output side 510. The samples are transferred via the conveyance system 220 using robotic grippers 504 at the reentry side 508, the recapper 502, and the output side 510. The output side 510 of the unit has areas for storage racks 512 and/or racks for tubes requiring additional testing. The samples requiring additional testing are delivered to the subsequent analyzers and subsequently returned to the sorter 500. Because this process is operationally intensive on the sorter unit 500 with multiple passes, this part of the process can be properly sized for the lab throughput to prevent unnecessary backups. Once the samples are capped and placed into a storage rack 512, the racks are removed and stored elsewhere in the lab.

A user with connected analyzers may prefer to have a connected refrigerated storage unit, as shown in FIG. 6. In the example shown in FIG. 6, the sorter 600 performs similar functions to those performed by the sorter 500 in FIG. 5. That is, the sorter 600 may take a sample from the conveyance system 220 using a robotic gripper 604 and recap samples using the recapper 602 and caps from the cap drawer 656. The recapped samples may be either outputted 610 or sent to storage 612 using the robotic gripper 604. In some cases, the sample may be output so that it can be sent to an ambient storage unit or it may be stored in a refrigerated storage unit. Samples can be retrieved automatically from the refrigerated storage unit for any additional testing that may be needed.

A special environmentally controlled storage unit (ECSU) 614 may been designed to store up to any number of tubes (e.g., 15,000 tubes). The unit may contain racks which can hold multiple size tubes with caps that may minimize the space required between tubes. As shown in the example of FIG. 6, four of the storage racks 612 may be arranged on the surface of a rack builder module to permit continuous loading or unloading and access to stored samples for reruns. During low system input, the ECSU 614 may have the ability to retrieve expired samples and dispose of them in a waste container below the deck of the rack builder module.

As samples enter the sorter unit 600, the recapper 602 applies a cap as necessary. The recapper 602 may have access to different types of caps. For example, from a vibratory bowl feeder, the recapper 602 can access a push style cap, and from a drawer, the recapper 602 can access screw style caps which are arranged in racks loaded on a drawer. After the capping process, a robotic gripper 604 removes the tube from its carrier and deposits and aligns the tube into a storage rack 612. The storage rack may be located on an output drawer 610 or on a position destined for the ECSU 614. When the rack is ready for storage, the ECSU 614 retrieves the rack from the deck and loads it into a matrix inside the ECSU 614. The ECSU 614 may be any size and can accommodate any number of tubes.

When requested, the ECSU 614 may have the ability to retrieve tubes for additional testing. It may also be capable of disposing of samples when they reach their expiration date. In one embodiment, this may be done concurrently with archiving but at a lower priority. A biohazardous waste container may be kept below the deck. Tubes entering the waste container may be capped to minimize the contamination through splashing of biohazardous waste.

In some embodiments, the ECSU 614 may not be large enough to archive all of a laboratory's samples prior to their expiration. Thus, periodic emptying of samples may be performed. This is accomplished via large doors on the backside of the ECSU 614. When the doors are open, the racks can be retrieved from the storage matrix. The racks chosen for removal are identified for the user to reduce the possibility of removing the incorrect rack. The racks may be removed individually from the unit and transported on a laboratory cart to an offline storage unit such as a walk-in refrigeration unit.

If a sample is requested from the offline storage unit, the rack can be reloaded onto the ECSU 614 and retrieved by the ECSU 614, or the user can remove the tube and load it onto the input 508. If samples expire while in the offline storage, the racks can be reloaded onto the ECSU 614 and disposed by the ECSU 614, or the user can dispose of the samples manually.

II. Functional Units of Laboratory System

As discussed above, the components of the laboratory system generally described above can be grouped into basic functional units, as many phases and modules may perform functions similar to functions performed in other phases or modules. In one embodiment, components can be grouped in five basic functional units: (1) manager, (2) centrifuge, (3) aliquotter, (4) output/sorter, and (5) storage units. For simplicity, the functional groupings will be discussed with respect to these five functional units. However, any functions can be grouped in any manner. Grouping the functions into general functional units allows for the design of the laboratory system to be somewhat general, flexible, and easily configurable for any user and the user's laboratory needs, so that the design of a highly customizable system for each lab is not necessary. Within each of the functional units, the specific functionality may vary depending on the laboratory's needs. These functional units may enable the design of standard products that, when combined in various ways, may satisfy any laboratory's needs with a minimal number of standard products.

Figure 7A:
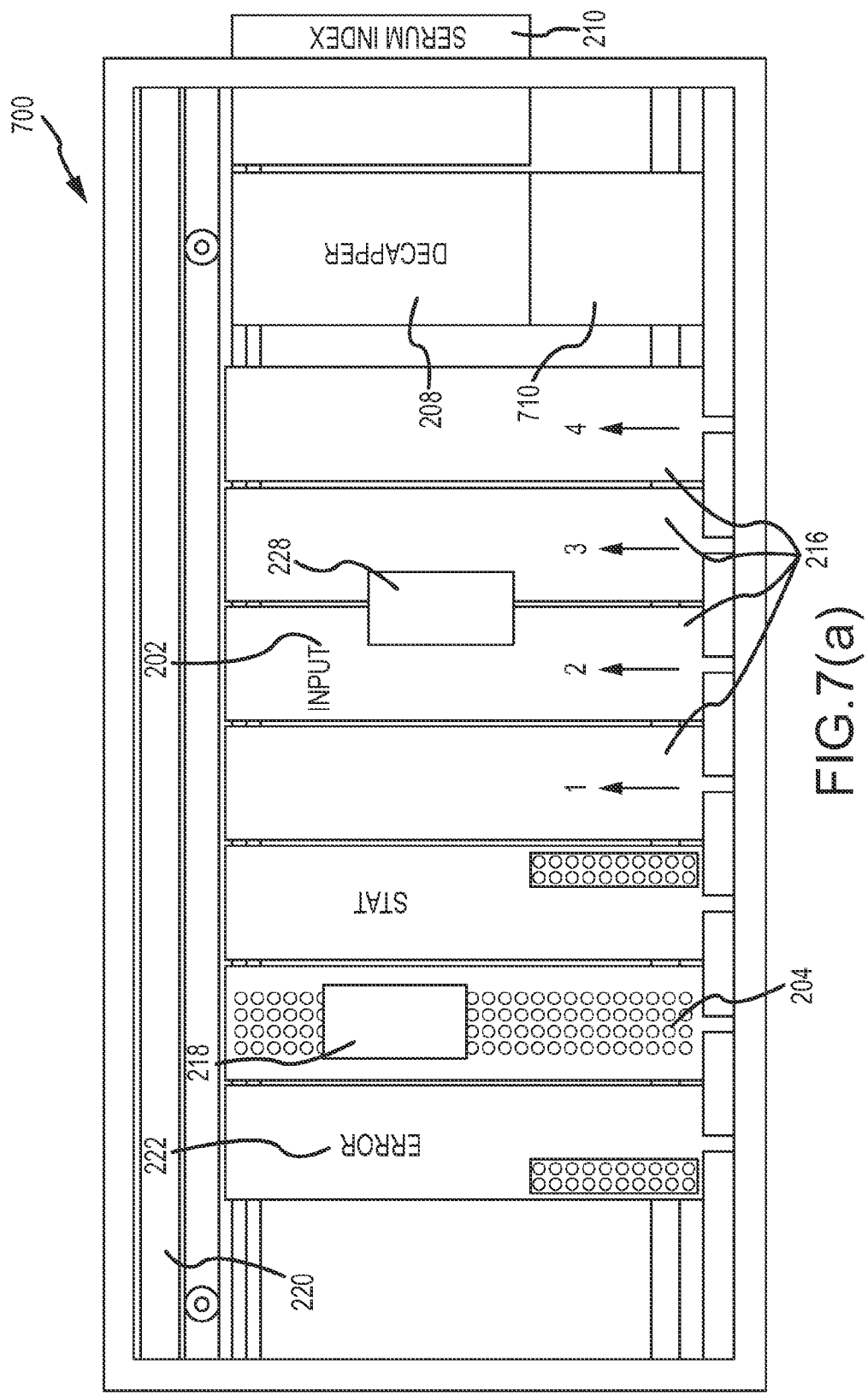
FIG. 7(a) depicts a diagram of components associated with a manager unit.

FIG. 7(a) depicts an example of a manager unit 700. The manager unit 700 depicted in FIG. 7(a) includes the input module 202, the distribution area 204, the decapper 208 with a decapping robot 710, and the device for measuring the serum indices 210 from the pre-analytical phase 104 (see FIG. 2(a) for description). Depending on the needs of the laboratory, any of the modules may be omitted and/or configured within the manager unit 700. For example, based on the laboratory's needs, the area for holding samples 204 while a process routing plan is prepared and/or the device for measuring the serum indices 210 of the sample may be omitted.

Figure 7B:
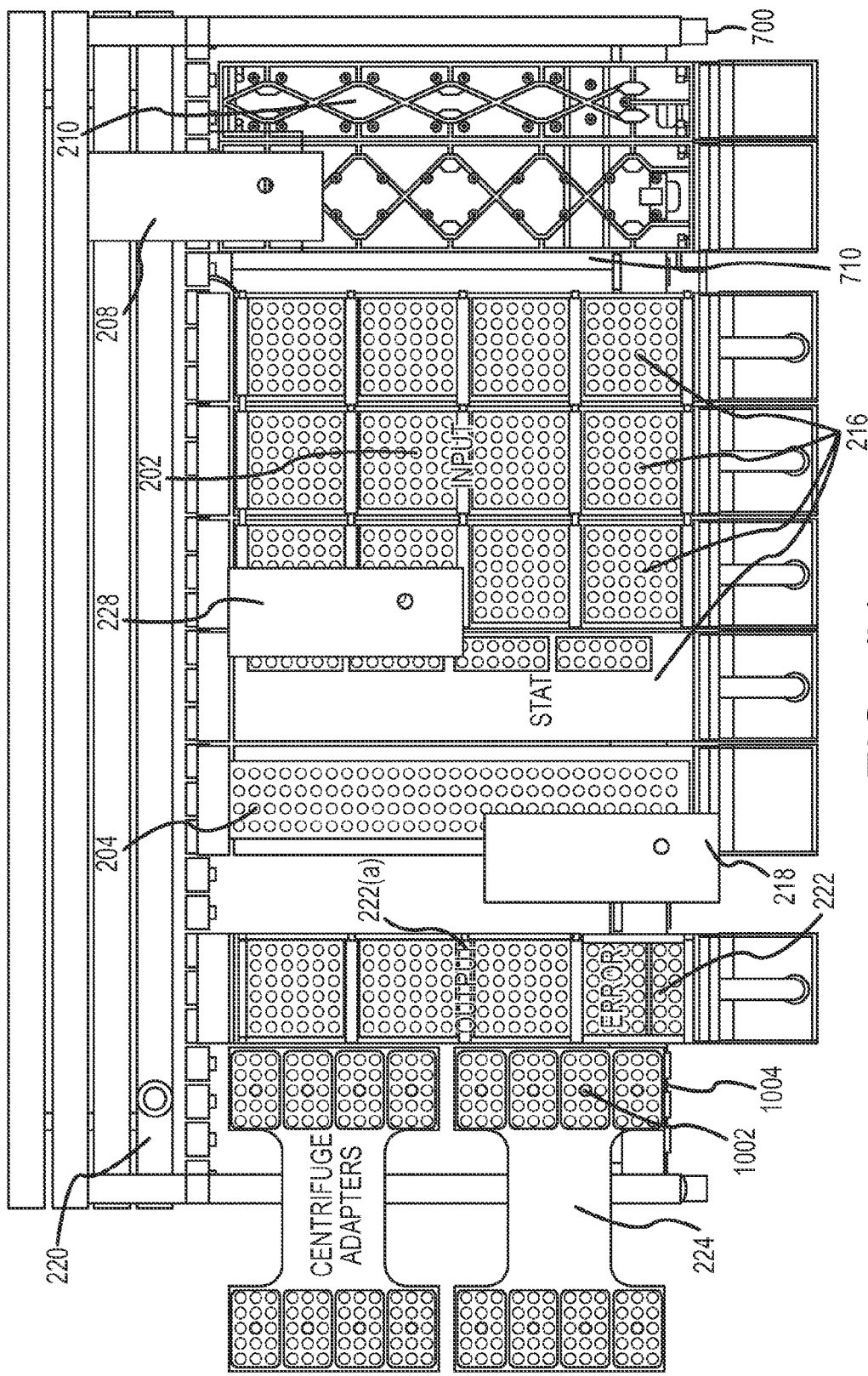
FIG. 7(b) depicts a diagram of components associated with another manager unit embodiment.

FIG. 7(b) shows another manager unit embodiment. In FIGS. 7(a) and 7(b), like numerals designate like elements. FIG. 7(b) specifically shows an error area 222 in an output drawer 222(a). FIG. 7(b) also shows a conveyance system 220, a shuttle 224, a centrifuge adapter 1002, and a centrifuge loading position 1004. These elements are discussed in further detail below.

Figure 8A:
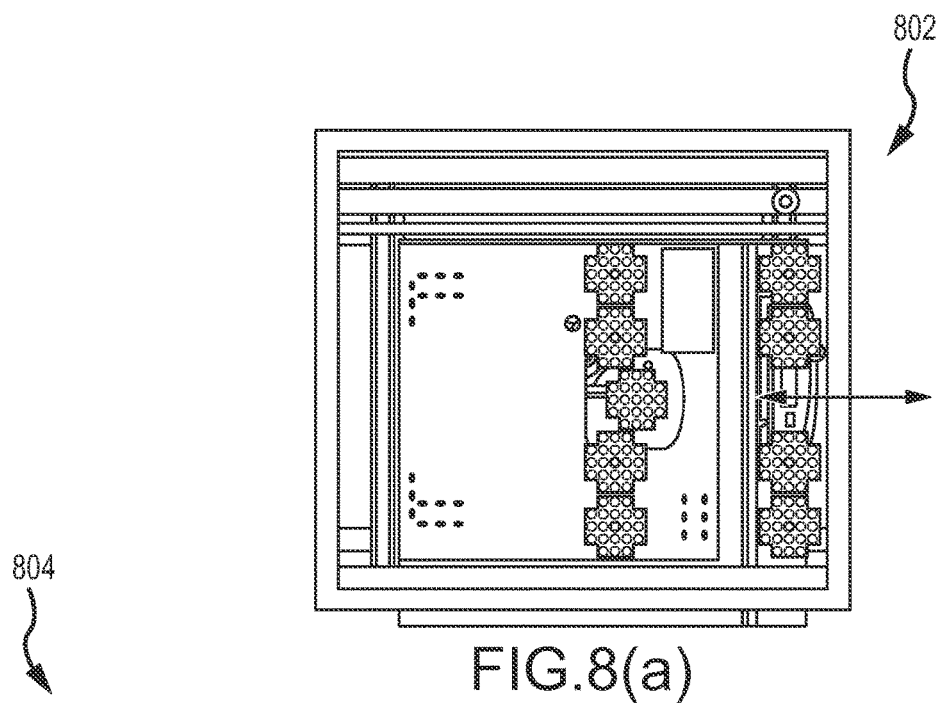
FIGS. 8(a)-(b) depict diagrams of components associated with centrifuge units.
Figure 8B:
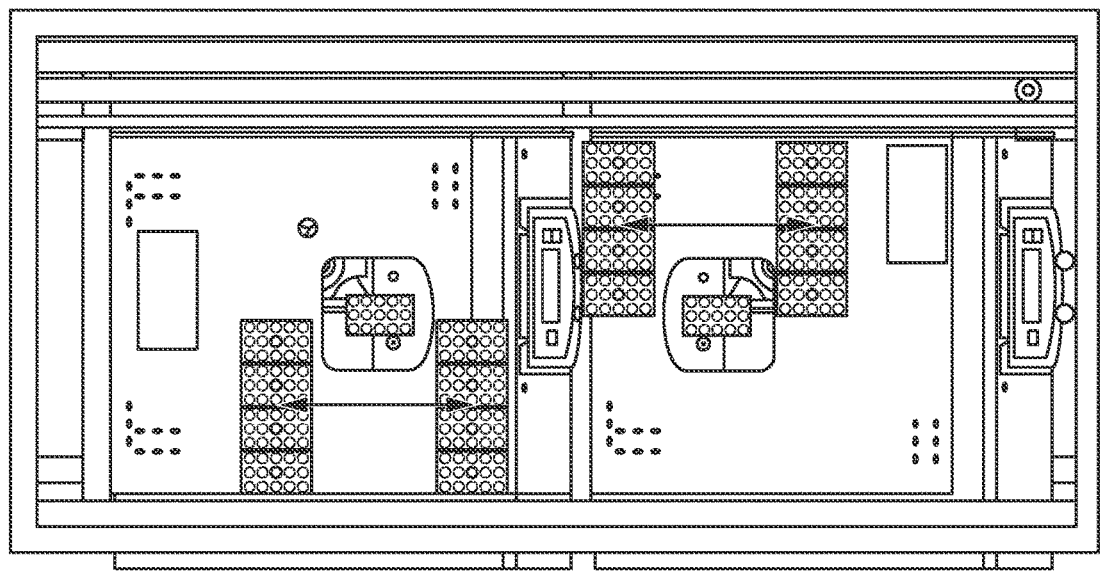

FIG. 8(a) and FIG. 8(b) depict examples of centrifuge units. The centrifuge units include centrifuges that are capable of centrifuging a sample. The centrifuge unit 802 in FIG. 8(a) depicts a single centrifuge unit, while the centrifuge unit 804 in FIG. 8(b) depicts a double centrifuge unit. However, the centrifuge unit may have any number of centrifuges depending on the needs of the laboratory. The centrifuge units may be used as part of the centrifuging module 206 in the pre-analytical phase 104 described in FIG. 2(a).

One example of the aliquotter unit can be found in FIG. 3. An aliquotter unit may be capable of pipetting a sample. FIG. 3 depicts an example of a double aliquotter unit having two pipetting functions. However, any number of pipettes can be included in the aliquotter unit depending on the needs of the laboratory.

Examples of output/sorter units are depicted in FIGS. 4(a)-(e) and FIG. 5. Any output/sorter configuration can be used based on the needs of the laboratory. Typically, the output/sorter unit is capable of receiving a sample from the manager unit, centrifuge unit, aliquotter unit, and/or an analyzer. The output/sorter unit may include areas to load and/or unload racks of tubes and may include any number of robotic grippers for performing any functions necessary for the laboratory.

One example of a storage unit is depicted in FIG. 6. Depending on the needs of the laboratory, the storage unit may be capable of storing a sample and may include a device to install caps on tubes, areas for tubes to be loaded into racks using robotic grippers, and attached storage units.

III. Exemplary Pre-Analytical Phase System

A. Pre-Analytical Phase System Layout

Figure 9:
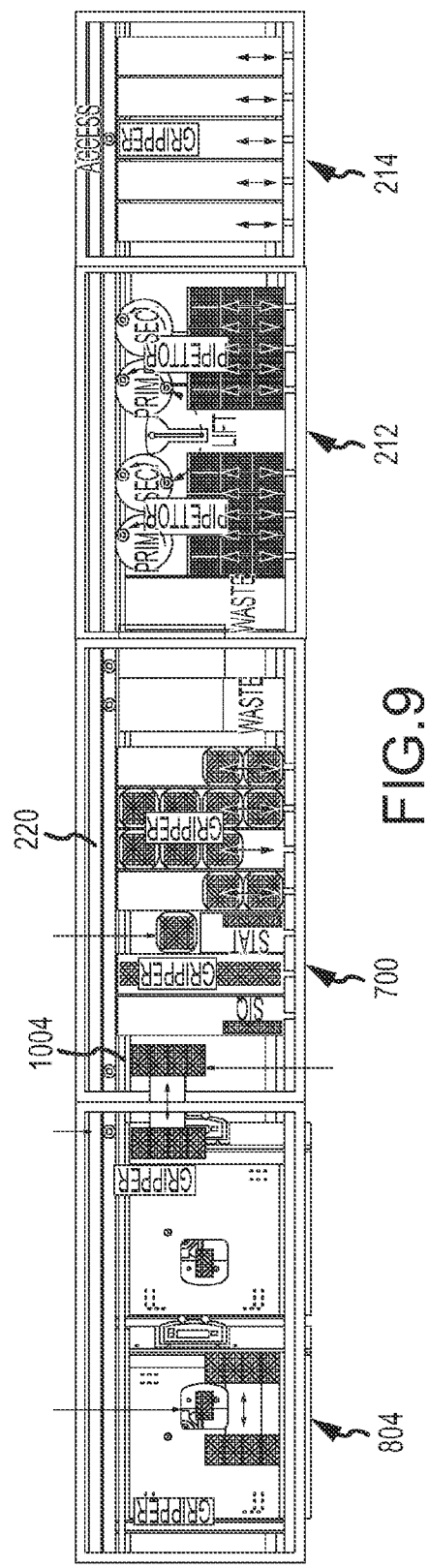
FIG. 9 depicts a diagram of components within a pre-analytical phase of the laboratory automation system.

FIG. 9 depicts a detailed example of the manager unit 700, centrifuge unit 804, the aliquotter unit 212, centrifuge loading position 1004, and the output/sorter unit 214 of the pre-analytical phase 104. Each of these units will be described in more detail below.

Figure 10:
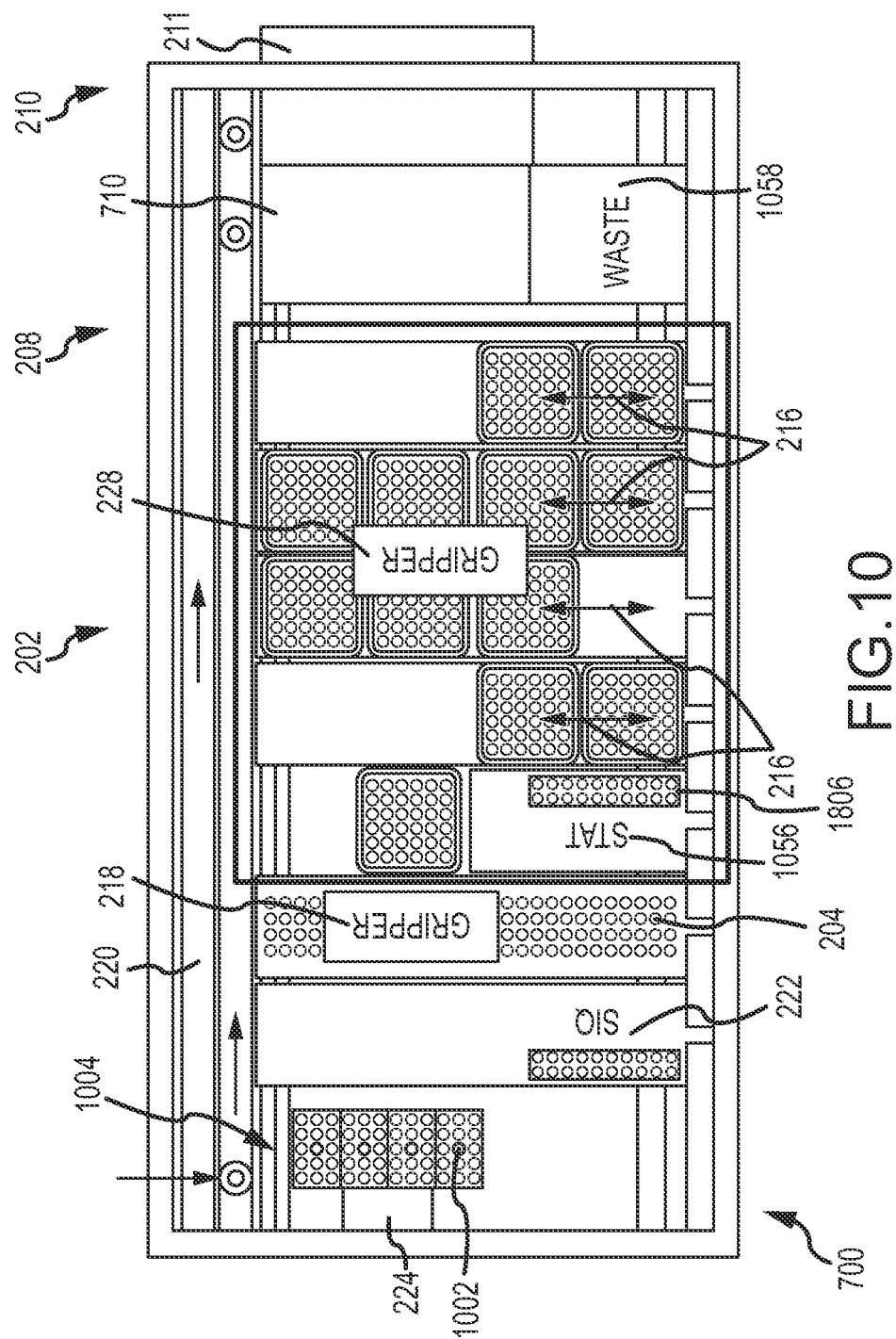
FIG. 10 depicts a diagram of components associated with a manager unit.

FIG. 10 depicts a closer view of the manager unit 700. The manager unit 700 of FIG. 10 includes the input module 202, the distribution area module 204, the decapping module 208 with a decapping robot 710, which were described in more detail in the description of FIG. 2, and the serum indices module 210 with serum indices measurement unit 211. The input module 202 includes input drawers 216, including a STAT drawer 1056 loaded with sample racks 1806, and an input robot 228 that can grip a sample tube, read a barcode, identify the tube by the characteristics, and can detect the sample level within a tube. The distribution area module 204 includes a distribution robot gripper 218 for gripping sample tubes, an error drawer 222, and centrifuge adapters 1002. The centrifuge loading position 1004 is the location for loading the centrifuge adapters 1002 with sample tubes that are to be sent to the centrifuge module 206 via a shuttle 224. The decapper module 208 includes the decapping robot 710 and the waste container 1058.

Figure 11:
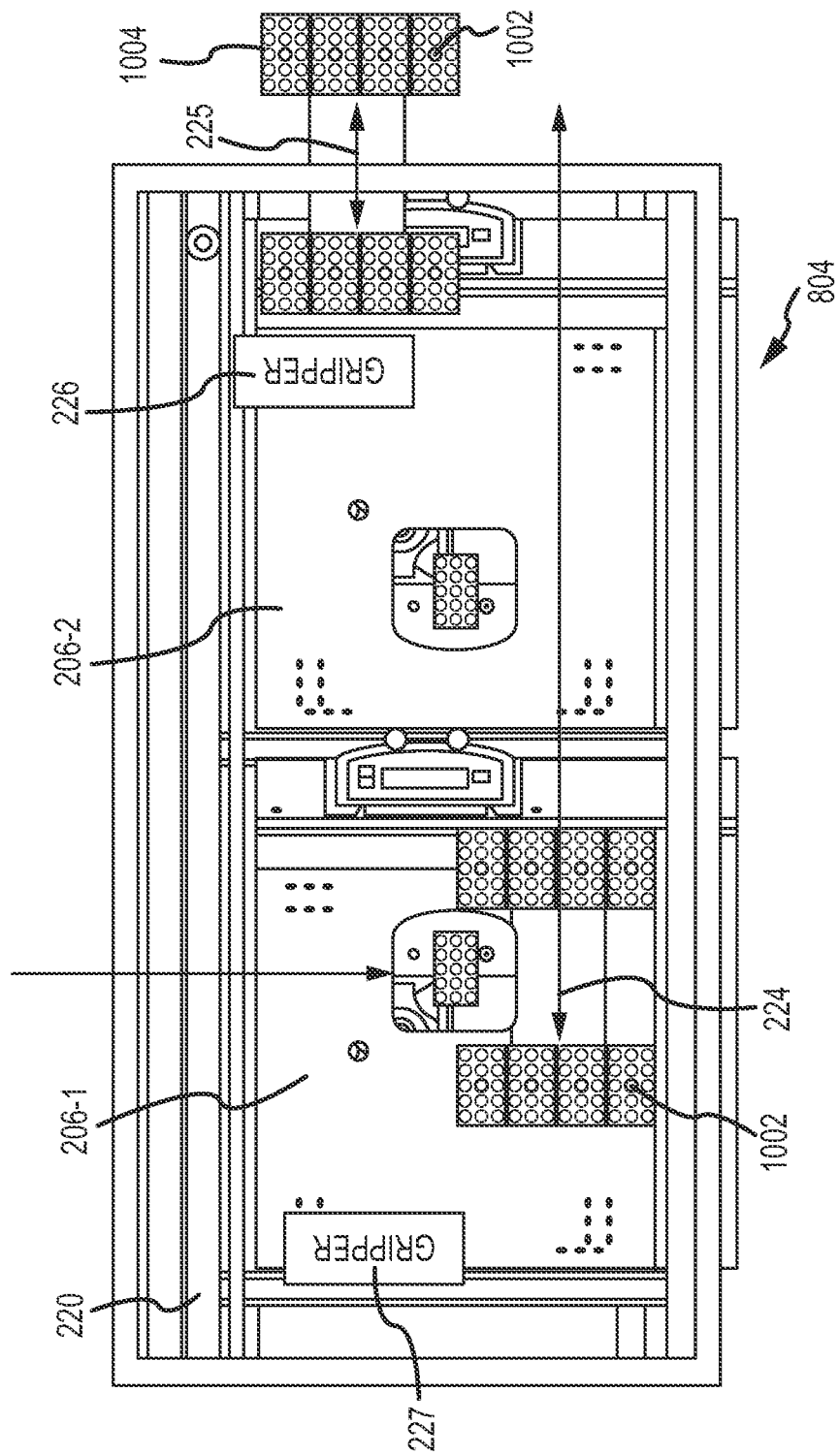
FIG. 11 depicts a diagram of components associated with a double centrifugation unit.

FIG. 11 depicts a closer view of a double centrifuge unit 804, which was described in more detail in the description of FIG. 2(a). The centrifuge unit 804 can include two single centrifuges 206-1 and 206-2, first adapter shuttle 224, and second adapter shuttle 225. Each adapter shuttle can hold centrifuge adapters 1002. Centrifuge unit 804 may further include first robotic gripper 226 and second robotic gripper 227.

Figure 12:
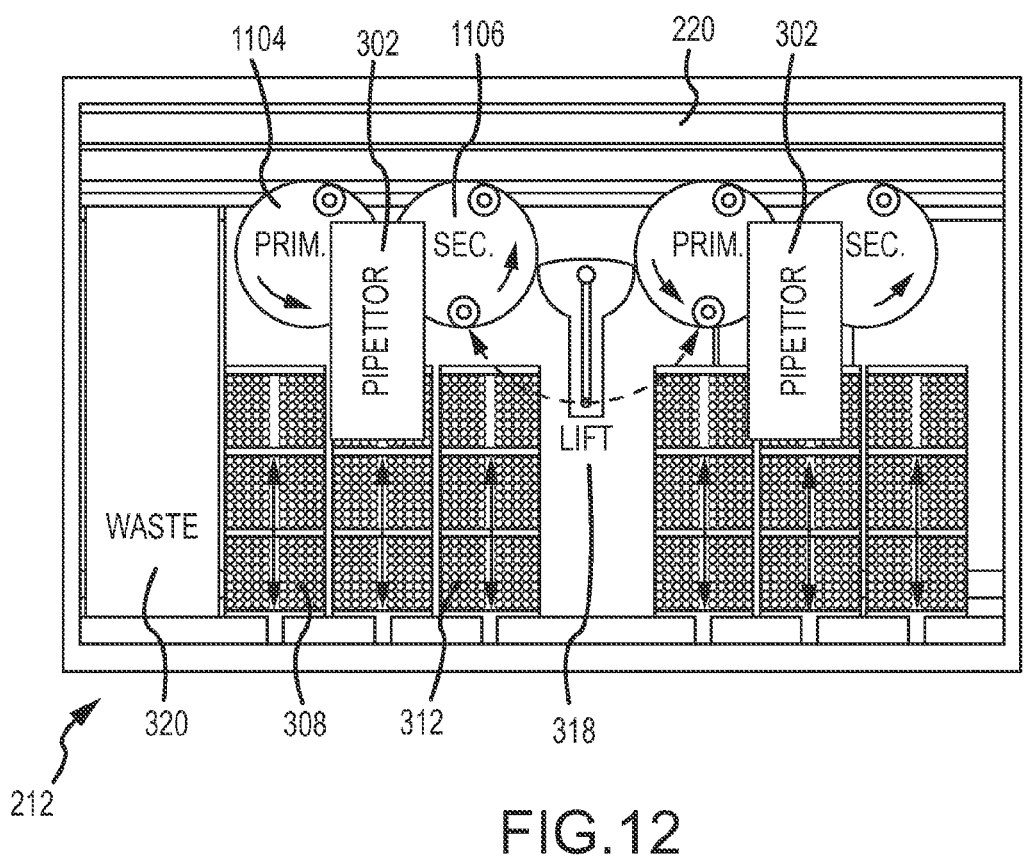
FIG. 12 depicts a diagram of components associated with a double aliquotter unit.

FIG. 12 depicts a closer view of a double aliquotter unit 212, which was described in more detail in the description of FIG. 2(a) and FIG. 3. The aliquotter unit 212 includes a primary tube queue 1104, a secondary tube queue 1106, a secondary tube lift 318 with tube storage and a labeler below the secondary tube lift 318, a waste container 320, a pipette robot 302, tip drawers 308, and microplate drawers 312.

Figure 13A:
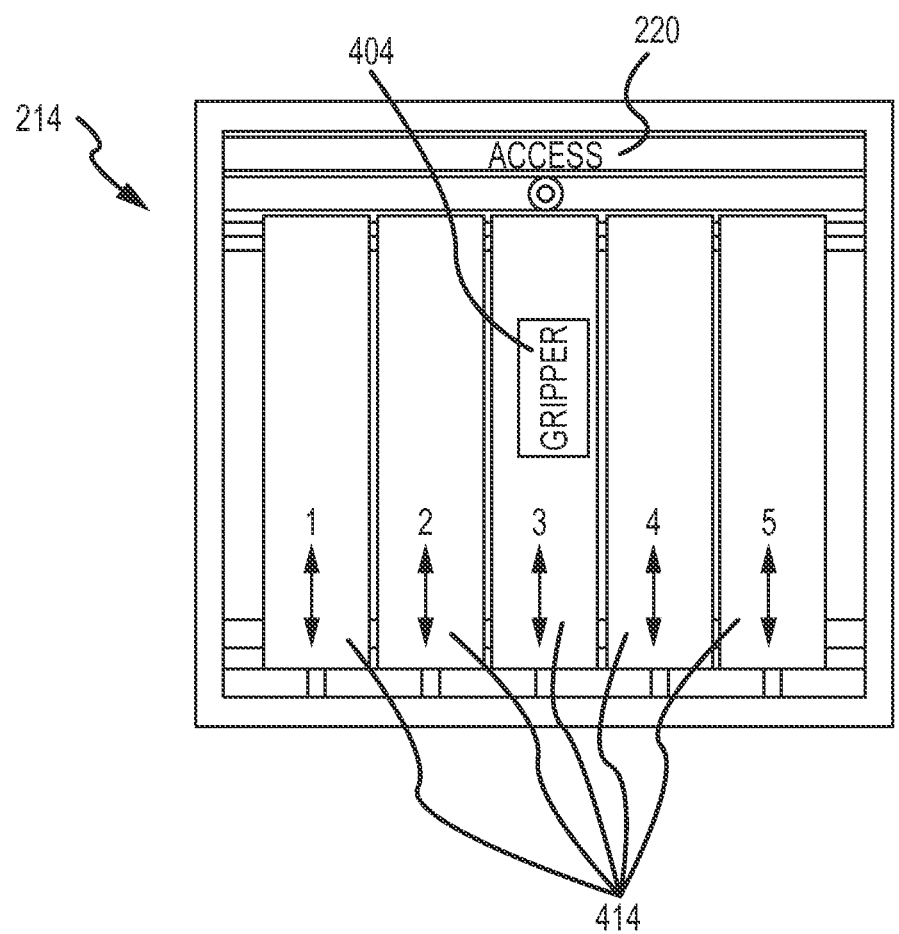
FIGS. 13(a)-(b) depict a diagram of components associated with an output/sorter unit.

FIG. 13(a) depicts a closer view of an output/sorter unit 214 that is capable of recapping sample tubes and outputting, sorting, and/or storing the samples tubes. The output/sorter unit 214 of FIG. 13 includes an output robot 404 and output drawers 414. The components of the output/sorter unit 214 are described in more detail in the description for FIGS. 4(a)-(c) and FIG. 5.

Figure 13B:
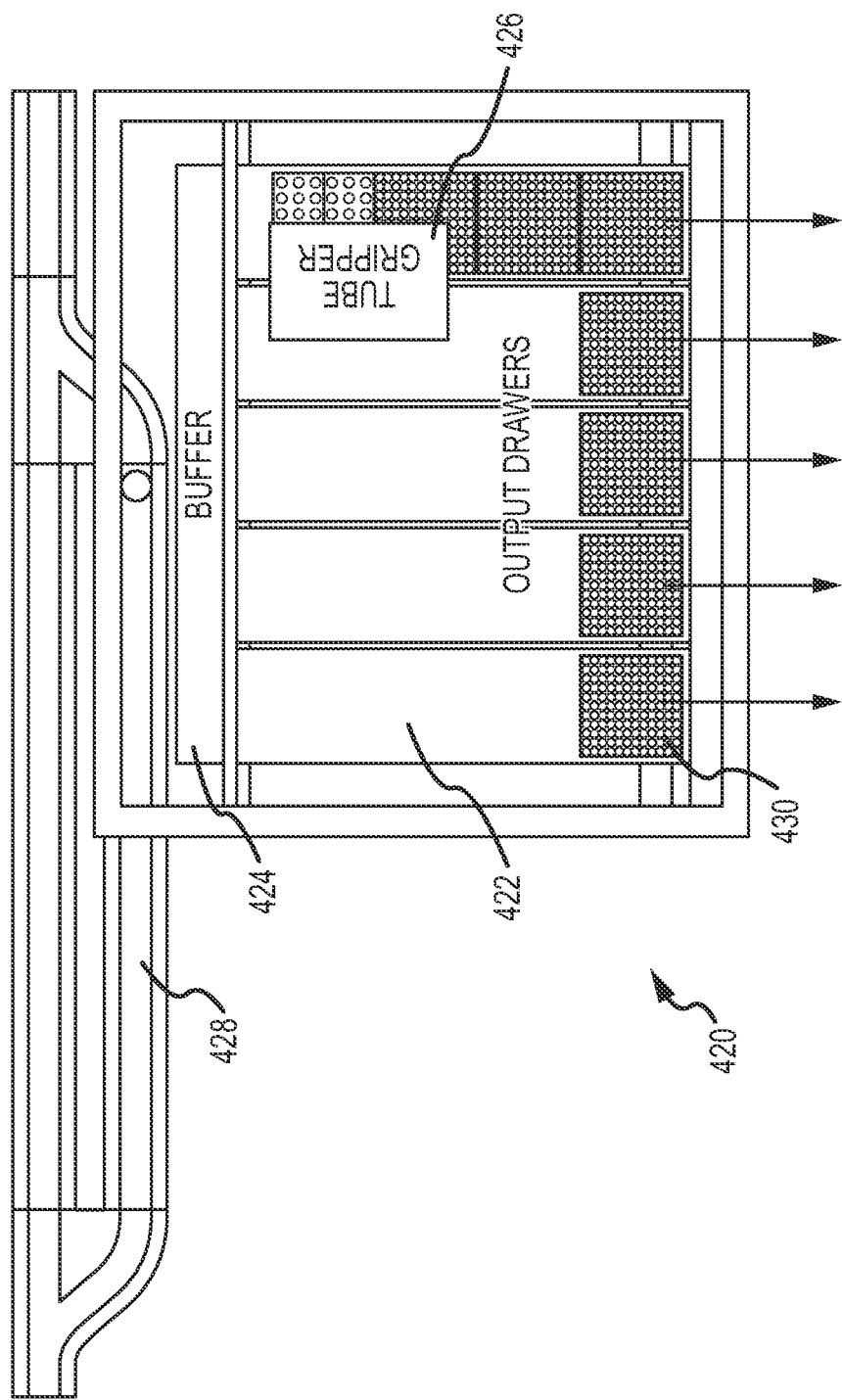

FIG. 13(b) shows a diagram of another output/sorter unit 420 according to an embodiment of the invention. The output/sorter unit 420 comprises a plurality of output drawers and a gripper unit 426 above the output drawers 422. A number of racks 430 with sample containers may be present in the output drawers 422. In embodiments of the invention, the drawers 422 can be divided into regions (as described above with respect to FIG. 4(f)). A region can be a location on a rack and can be a destination of a sample's route.

A buffer area 424 is oriented perpendicular to the orientation of the output drawers 422. The buffer area 424 can be behind the output drawers 422 in an area that is not readily accessible to an operator. The buffer area 424 can be used by the system to store sample that cannot be processed because of a temporary lack of availability of a downstream process (e.g., a downstream analyzer is not available). The buffer 424 may also be used when the output drawers 422 are open and inaccessible to the gripper unit 426 of if a sample container destination is full. In these instances, the samples are moved to the buffer 424 until the output drawers 422 are closed or the destination rack is emptied or replaced.

A track 428 is adjacent to the output/sorter unit, and can provide sample containers (e.g., sample tubes) for the gripper unit 426 to transport. The gripper unit 426 may retrieve sample containers from the track 428 and transfer them to the buffer area 424 if the output drawers 422 are full and/or not available. Once they are available, the gripper unit 426 may transfer the sample containers from the buffer area 424 to the drawers 422.

These embodiments of the invention have advantages, because they allow for a temporary storage area for sample containers in case downstream devices or subsystems are not available.

B. Pre-Analytical Phase System Workflow

As discussed above, the pre-analytical phase may contain seven modules. FIGS. 14(a)-(d) are parts of a flow chart showing an illustrative example of the pre-analytical phase system workflow, which is described with reference to FIGS. 9-12.

1. Input Module Workflow

Figure 14A:
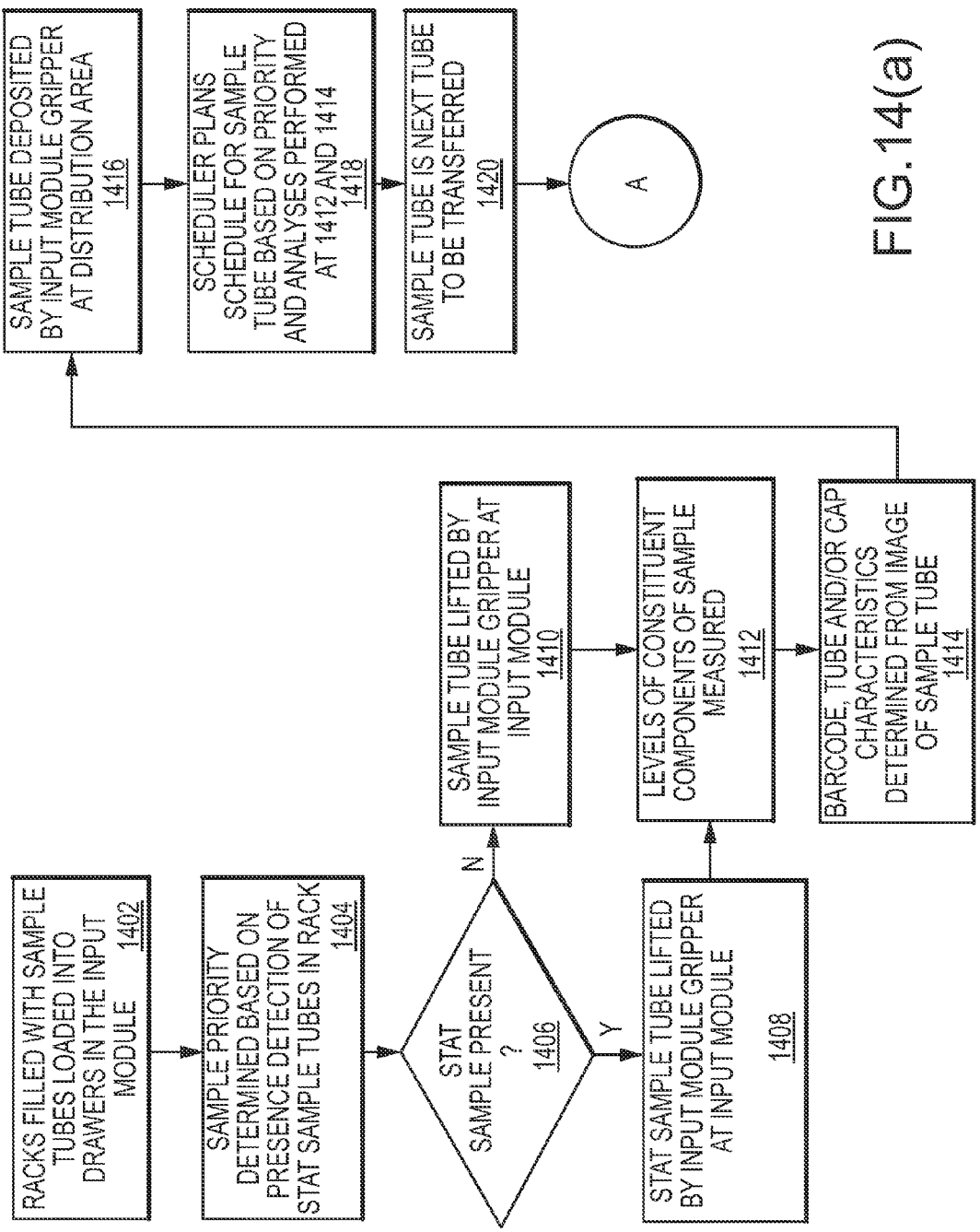
FIGS. 14 (a)-(d) are parts of a flow chart showing an illustrative example of the pre-analytical phase system workflow.

Referring to FIG. 14(a), at the beginning of the pre-analytical phase, the racks 1806 that are filled with sample tubes are loaded into drawers 216 in the input module 202, as indicated at operation 1402. The processing priority for a sample tube may be indicated by placing the sample tube in the STAT drawer 1056 of the input module 202 or by applying a sample tube marker to the sample tube cap, detectable by a tube and rack presence detection unit that will be described in more detail below. The sample priority is determined based on whether a STAT sample tube is located in the rack, as indicated at operation 1404. The pre-analytical phase system then selects sample tubes from the input module 202 based on processing priority, as indicated at operation 1406. If a STAT sample tube is detected, the STAT sample tube will be the first tube to be lifted by an input module gripper 228, as indicated at operation 1408. If no STAT sample tube is detected, a sample tube that is not a STAT sample tube is lifted by input module gripper 228, as indicated at operation 1410. The levels of the constituent components (e.g., gel or packed red blood cells) of the sample in the sample tube are measured, as indicated at operation 1412. The levels of the constituent components of the sample may be measured as the tube is lifted by the input module gripper 228. The liquid level may be determined from a means for inspecting a tube. For example, the liquid level may be determined from a 2-D image captured of the tube contents, as described below. In some embodiments, the liquid level is determined using an absorption and transmission measurement unit, as described below. While the tube is in the input module gripper 228, a 2-D image (e.g., a photograph) is taken of the tube. One or more of the barcode, tube, and cap characteristics are determined by analyzing the image of the tube, as indicated at operation 1414.

In some embodiments, all samples have a priority assigned to them either through information found in the LIS (laboratory information system) or based upon the rack or position in which they reside within the Input. Sample tubes are selected from the input module are in order of priority. If the priority assigned by the LIS and the priority assigned due to the sample's location in the input module do not agree, the sample is assigned the highest priority of the two. Within a priority level, samples are selected by time of entry to the Input (i.e. first in first out, FIFO). Finally within a rack samples are selected in an established order (e.g. left to right and back to front). STAT samples have the highest priority.

At operation 1416 the sample tube is deposited by input module gripper 228 in the distribution area 204. The barcode of the sample tube may be oriented by input module gripper 228 so that it may be later read. Orientation of the barcode may occur before the move, during the move, or after the move of the sample to the distribution area 204.

2. Distribution Area Workflow

While the samples sit in the distribution area 204, several processes for optimizing the functioning of the system may be performed within the distribution area. A scheduler may perform some of these processes. As described above, the scheduler may be a control processor and/or software which schedules each sample tube for processing in order to organize and optimize the flow of sample tubes through the laboratory automation system. In general, the processor may generate a test plan (with a list of processes to be performed on a sample), and then route plans for samples based on the availability of processing units (including analyzers having queues) and schedules each sample located in the distribution buffer based on a single route plans and prioritization for each sample. In some embodiments, the test information and a route plan may be generated by and/or retrieved from a scheduler based on the type of testing needed and the urgency associated with the sample. The scheduler may also take into account and use sample information (e.g., weight, cap color, spun, STAT (short turn-around time), etc.) to develop test information and the route plan. One example of a scheduler can be found in U.S. Pat. No. 6,721,615, which is herein incorporated by reference in its entirety for all purposes.

The scheduler may also determine which sample out of the plurality of samples sitting in the distribution area 204 is the next appropriate sample to begin processing. The appropriate sample may be one that is selected from a list of samples residing in a distribution area. It may be the sample with the highest priority and/or the sample that can be processed using the resources available according to its route plan to maximize throughput and/or TAT (turn around time). If a sample requires centrifugation, the weight of the tube may be calculated based upon the tube and cap characteristics, sample levels, and a density estimate made within the distribution area. In some embodiments, a database accessible to a central processor may store data relating to various types of sample containers. The data may comprise the weight of the containers (without any samples in them) as well as their dimensions (e.g., the inner diameter and height). The database may also store information regarding the densities of various types of samples. The weight of the sample may be determined using the liquid level of the sample in a sample container and the inner dimensions of the sample container. The weight of the sample container (without a sample) can be retrieved from the database to determine the total weight of the sample and the sample container.

Some embodiments of the invention are therefore directed to methods. In one embodiment, the method includes receiving a test plan for a sample in a sample container. The test plan may include a number of processes (e.g., centrifuge, aliquot, etc.) by which the sample is to be processed. The method may also include determining an optimal route for the sample in the sample container through a laboratory automation system, where the route takes into the test plan is created after determining characteristics of the sample or the sample container (e.g., weight, cap color, spun, STAT (short turn-around time). In embodiments of the invention, an optimized route may include two or more specific subsystems (e.g., a specific centrifuge in a plurality of centrifuges), in a specified order, that can process the sample. The sample in the sample container is then processed according to the optimized route. The optimized route may also be determined based on feedback (e.g., whether a subsystem is down, available etc.) provided by the various systems as to the status of those subsystems.

Figure 15:
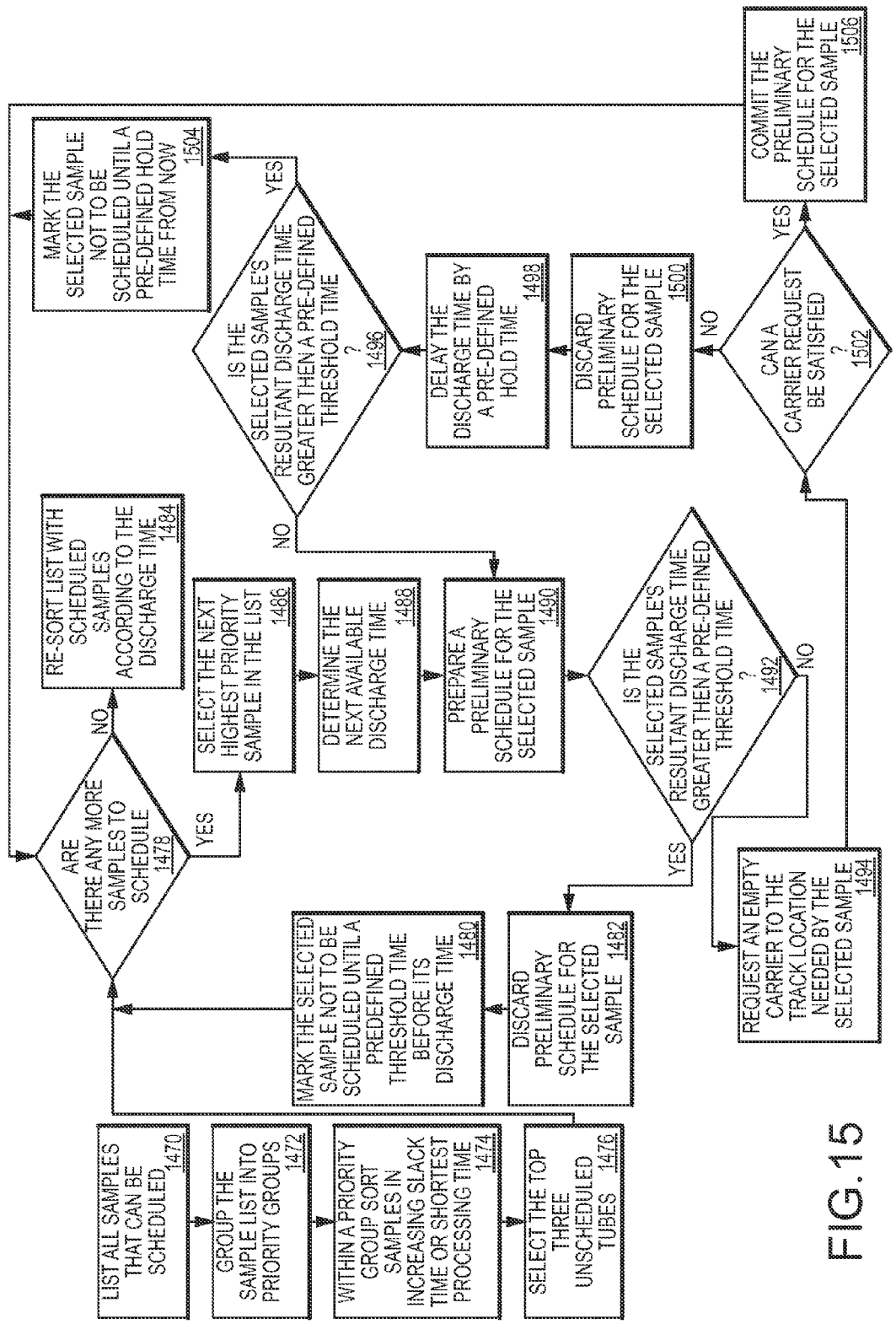
FIG. 15 is a flow chart showing an illustrative process for selecting an appropriate sample.

A process for selecting an appropriate sample can be described with reference to FIG. 15. As shown in the flowchart, the selection of the appropriate sample can be somewhat dynamic in nature and can change based on a number of factors including the availability of various subassemblies within the system as well as the nature of the particular sample to be processed.

In step 1470, a central processor may generate a list of all samples that can be scheduled. A sample can be scheduled if sample related work instructions are available. Then, the sample list is grouped into priority groups (step 1472). For example, a sample list may contain a first STAT sample that has a processing time of 10 minutes, a second STAT sample that has a processing time of 20 minutes, a third non-STAT sample that has a processing time of 15 minutes and a fourth non-STAT sample that has a processing time of 9 minutes. The samples may be grouped into two groups: STAT and non-STAT. Within these groups, the samples are sorted according to increasing slack time (the slack time may alternatively be referred to as an aging time, or the time that the sample has been in the distribution area) or the shortest processing time through the laboratory automation system (step 1474). With reference to the previous example, the samples may be sorted as follows according to the shortest processing time. For the STAT samples, the prioritization would be the first STAT sample and the second STAT sample. For the non-STAT samples, the prioritization would be the fourth non-STAT sample and the third non-STAT sample. The top three unscheduled tubes are then selected (step 1476). For example, in the above-noted example, the selected tubes may comprise the first STAT sample, the second STAT sample, and the fourth non-STAT sample. Although the top three tubes are selected in this example, more or less sample tubes may be selected in other examples.

In step 1478, a determination is then made as to whether there are any more samples to schedule. If not, then the list may be re-sorted with scheduled samples according to discharge time (step 1484). If so, then the next highest priority sample in the list is selected for processing (step 1486). As noted above, a STAT sample always has a higher priority than a non-STAT sample. In the above, example, only the third non-STAT sample is unscheduled.

Then, the next available discharge time is determined (step 1488). The discharge time can be when the sample will be moved out of the distribution area. A preliminary schedule is then determined for the selected sample (step 1490).

Then, a determination is made as to whether the sample's resultant discharge time is greater than a pre-defined threshold time (step 1492). If the determination is positive, then the method proceeds to step 1482. In step 1482, the preliminary schedule is discarded for the selected sample. In step 1480, the selected sample is marked as not to be scheduled until a pre-defined threshold time before its discharge time. The method then proceeds to step 1478.

If the sample's resultant discharge time is not greater than the pre-defined threshold time, then an empty carrier is requested to the track location needed by the selected sample (step 1494). If the carrier request can be satisfied (step 1502), then the system can commit to the preliminary schedule for the selected sample (step 1506), and the method can loop back to step 1478 to determine if there are any more samples to schedule.

If the carrier request cannot be scheduled, then the preliminary schedule for the selected sample is discarded (step 1500). The discharge time may then be delayed by the pre-defined hold time (step 1498). Then, a determination is made as to whether the selected sample's resultant discharge time is greater than a pre-defined threshold time (step 1496). If the determined resultant discharge time is not greater than the pre-defined threshold time, then the method proceeds to step 1490. If the determined resultant discharge time is greater than the predetermined threshold time, then selected sample is marked as not to be scheduled until a pre-defined hold time from the present time (step 1504). The method can then proceed to step 1478.

In some embodiments, a sample is only sent to a track only if the required resources are available. If prioritization is equal for all samples, the first sample in the distribution area 204 is sent to the conveyance system 220 (e.g., track).

Conventional systems may use bypass lanes for buffers (e.g., US 2012179405A1) or queue jumping (e.g., US 2011112683A1) or random access buffers beside the track (e.g., U.S. Pat. No. 7,681,466B2). Embodiments of the invention (e.g., which may use a distribution area, along with the determination of sample container and sample characteristics in real time) have advantages over such conventional systems. Such advantages include reduced hardware (e.g., fewer buffers and queues). Also, embodiments of the invention have better random access to sample containers since they are not constrained by being present in a buffer or queue.

3. Turn-Around Time (TAT)

The LAS (laboratory automation system) objectives can be defined as follows:

TAT: Turn-around time is a sample driven objective. There can be different turnaround time definitions, each with different requirements:

$TAT_{PREANALYTICAL}$: Preanalytical TAT is the portion of the TAT budgeted to the LAS. It starts when a sample is recognized by the LAS (i.e., the time the bar code is read by the LAS during input). The time ends when a sample is routed to an output tray for samples assigned to standalone analyzers or when a sample is routed to the first analyzer in a workflow for samples assigned to connected analyzers.

$TAT_{LABORATORY}$: Laboratory TAT is the time from when a sample is first received in the laboratory to when validated results are available.

The LAS objective can be to satisfy $TAT_{PREANALYTICAL}$ and not $TAT_{LABORATORY}$, since $TAT_{LABORATORY}$ includes processing times that cannot be influenced by the LAS or a Workflow Management Layer (WML).

Samples can have different TAT requirements. In general, a sample with a shorter TAT requirement dictates that the sample has a higher priority in the processing order. Samples originating from the emergency department of a hospital, for example, have the highest priority. These samples are referred to as STATS. Other hospital departments dictate their own TAT requirements. Samples originating from patients in the hospital can have a higher priority over samples that were collected outside of the hospital.

Throughput can be a system driven objective. While each subsystem in the LAS can have its own throughput value, "throughput" can refer to the overall system throughput and can be measured as samples processed per hour. The system throughput can depend on the sample processing instructions from the WML and how these are distributed over time. The statement of a constant system throughput value for a specific period of time (e.g. 1 hour) can require that the distribution of samples with different processing requirements is constant for any time interval within that period. If that assumption does not hold, then the system throughput is a dynamically changing value which could be referred to as "instantaneous throughput." "The throughput" can then be an average value.

Analyzers not only generate the test results that drive the existence of clinical laboratories, but also generate revenue that determines the financial viability of clinical laboratories. Analyzers are also expensive. Normally, the number of analyzers is based on the workload of the laboratory. The scheduler can maximize the utilization of this valuable, finite resource.

In order to reflect the actual tube flow and routing through the hardware, the sites can be linked together based on the LAS hardware's connectivity. In other words, a "site network" can be formed.

4. Satisfying Throughput and TAT Requirements

In embodiments of the inventions, TAT, throughput and utilization objectives can be achieved as follows. Prior to system installation, the user specific sample processing requirement can be analyzed and the system layout can be adapted to meet the user objectives. Further, the distribution area (or buffer) allows for the optimization of the processing sequence of samples.

In embodiments of the invention, when an input robot moves a sample from an input drawer to the distribution buffer, the sample characteristics can be identified. While the sample is waiting in the distribution buffer, the test plan can be received from a WML (workflow management layer) in a management architecture. Further details of the management architecture can be found in U.S. Provisional Patent Application No. 61/723,736, filed on the same day as the present application, which is herein incorporated by reference in its entirety for all purposes. While the sample is waiting in the distribution buffer, the route plan can be received from the WML. Once the route plan is known, the scheduler can include this sample in its scheduling calculations. The scheduler is then able to calculate the sample schedule according to its priority. That means that samples can be processed in a different order than the order in which they were picked up on the input drawer. The same is true for samples on any other random access buffer in the system, e.g. centrifuge output adapters, RBU output buffers, storage.

In addition, the scheduler can make time reservations for each sample using its individual processing times in order to ensure that system resources are utilized but not overutilized.

In some embodiments, the LAS uses queues in front of subsystems where processing time estimates tend to be inaccurate, e.g. analyzers.

The scheduler can always schedule a few samples to wait in the queue, such that the queue will neither starve nor overflow. This can keep the system running at all times, which can optimize throughput as well as analyzer utilization.

To achieve TAT and throughput objectives, it is desirable to keep the time short as a subsystem becomes unavailable.

In some embodiments, the LAS can be designed such that most user interactions can keep the system fully operable. For the remaining few user interactions that interrupt a subsystem, the user can be informed to keep the interaction time short.

The general properties for a scheduler to take into account during the calculations include (1) the satisfaction of Turn-Around-Time (TAT), the maximization of sample throughput, the maximization of analyzer utilization, and the minimization of user interaction.

5. STAT Handling

The scheduler treats STAT samples with the highest priority to meet STAT TAT requirements. This can be ensured as follows. Each sample can have a weight, which is based on the remaining time before the individual sample's TAT requirement (that is based on its priority) is violated. The smaller the remaining time, the larger the weight becomes. With this approach, STAT samples will have a higher weight, because their TAT requirement is stricter. However, if there are lower priority samples that had to wait for a long time in the distribution buffer, their weight will increase and could eventually become larger than a STATS's weight. This aging algorithm ensures that also lower priority samples will eventually be processed. Further, ordering the samples from the distribution is done using heuristics in cooperation with the sample weights. If necessary, STAT samples on random access buffers (such as centrifuge output adapters) can be rescheduled such that they will meet their TAT requirement.

There can be two different aspects in scheduling. These include the detail of planning the timing, and the detail of control over a MCL (middle control layer). The detail of planning the timing depends on the accuracy of the timing model used for the system. To obtain good scheduling results, the planning of the timing can be as detailed as the site network graph. The detail of control over the MCL defines how a PCL (process control layer) is able to enforce the planned timing.

The analysis of different scheduling approaches showed that the detail of control of the PCL over the MCL is an issue to note. One approach is to control the MCL on a very low and detailed level; i.e. the timing of each hardware movement is prescribed by the scheduler. Another approach is to only prescribe the time at which a sample is dispatched into the system and then to leave the further timing up to the MCL. The analysis of the different scheduling approaches showed that the level of control of the PCL over the MCL is limited, because of limited communication bandwidth and limited computational time.

The selected approach is therefore a predictive decentralized scheduler; i.e., the scheduler has full (actual and forecasted) state awareness of the instrument and connected devices, but controls influence at only a few locations, which are generically indicated in the site network. Such locations are random access buffers, e.g., distribution buffer, centrifuge output buffer, and RBU output buffer. Such locations also include any transport location that merges an off-ramp track section with the main track.

At such a location, a sample has to wait until a new route leg was received. That way, the PCL has sufficient control over the system enabling it to manage the system workflow to achieve the best TAT and maximum throughput.

The predictive decentralized scheduler can be characterized as a list scheduling algorithm. The list scheduling algorithm can have the following characteristics. Due to the large computational effort, the scheduler algorithm can be executed cyclically (except if there were no changes in the system state since the last cycle). The algorithm can also have four phases including a wipe out phase, a reactive phase, a predictive phase, and a prevention phase. In the wipe out phase, the algorithm removes all previously made time reservations for samples in buffers (e.g. distribution buffer). In the reactive phase, the reactive phase updates remaining sample time reservations based on system feedback. In the predictive phase, using heuristics, determines the best order and the best time at which samples are put into the system from sample buffers (e.g. distribution buffer) to best satisfy TAT and throughput requirements. The predictive phase also makes time reservations for each individual sample on each element of the site network graph (i.e., track system, sites, etc.). This accounts for sample individual processing instructions. In the prevention phase, the algorithm uses control locations in the site network (other than buffers) to prevent system backups or deadlock situations.

Referring again to the workflow of FIG. 14(a), the scheduler plans a schedule for the sample tube, based on the sample processing priority, the liquid level and barcode, tube, and cap characteristics analysis information, as indicated at operation 1418. At operation 1420, when the sample tube is the next tube to be transferred, a distribution area gripper 218 deposits the sample tube at one of the centrifuge adapter 1002, an error area 222, or at the conveyance system 220.

6. Centrifuge Workflow

Figure 14B:
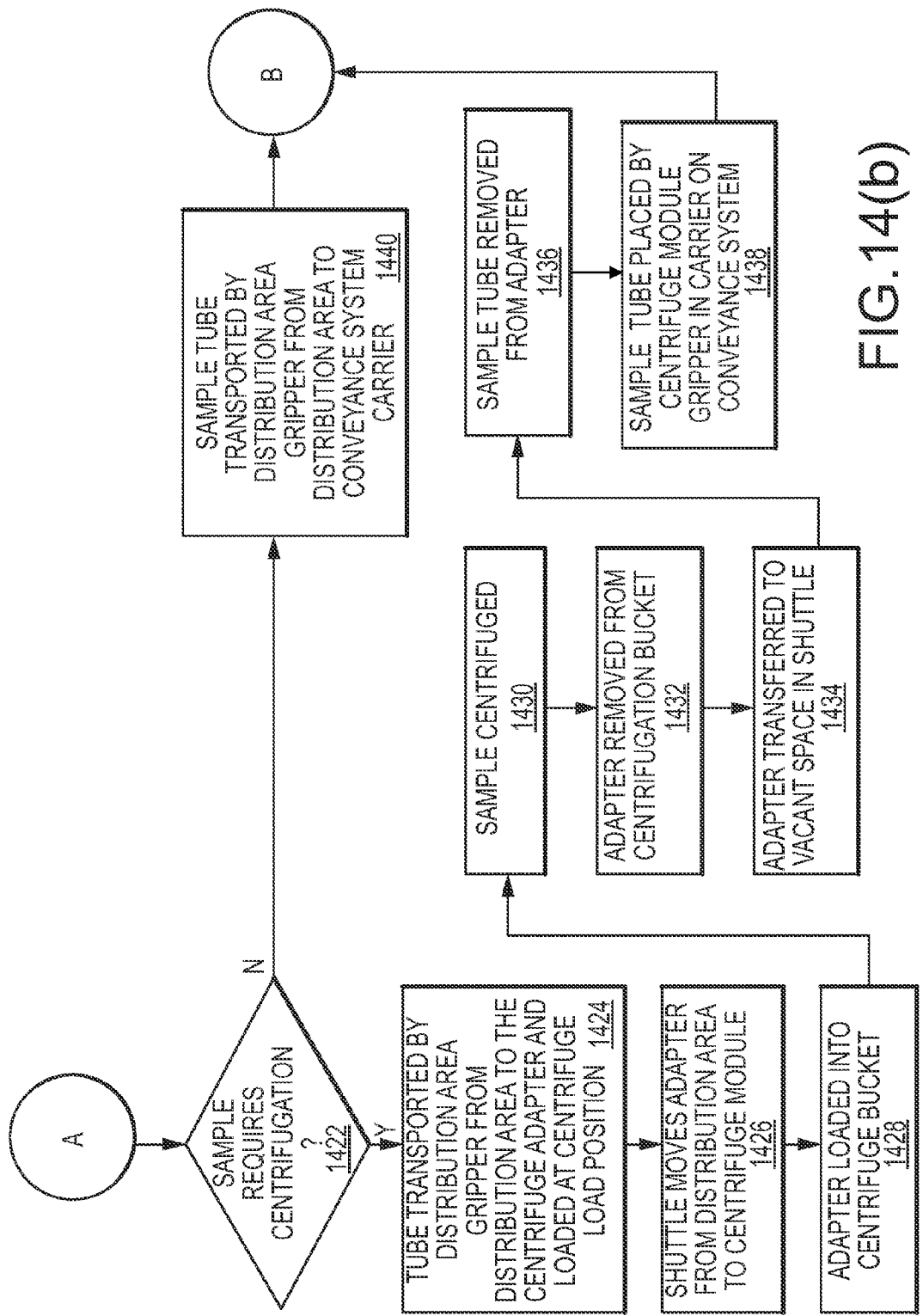
Figure 14C:
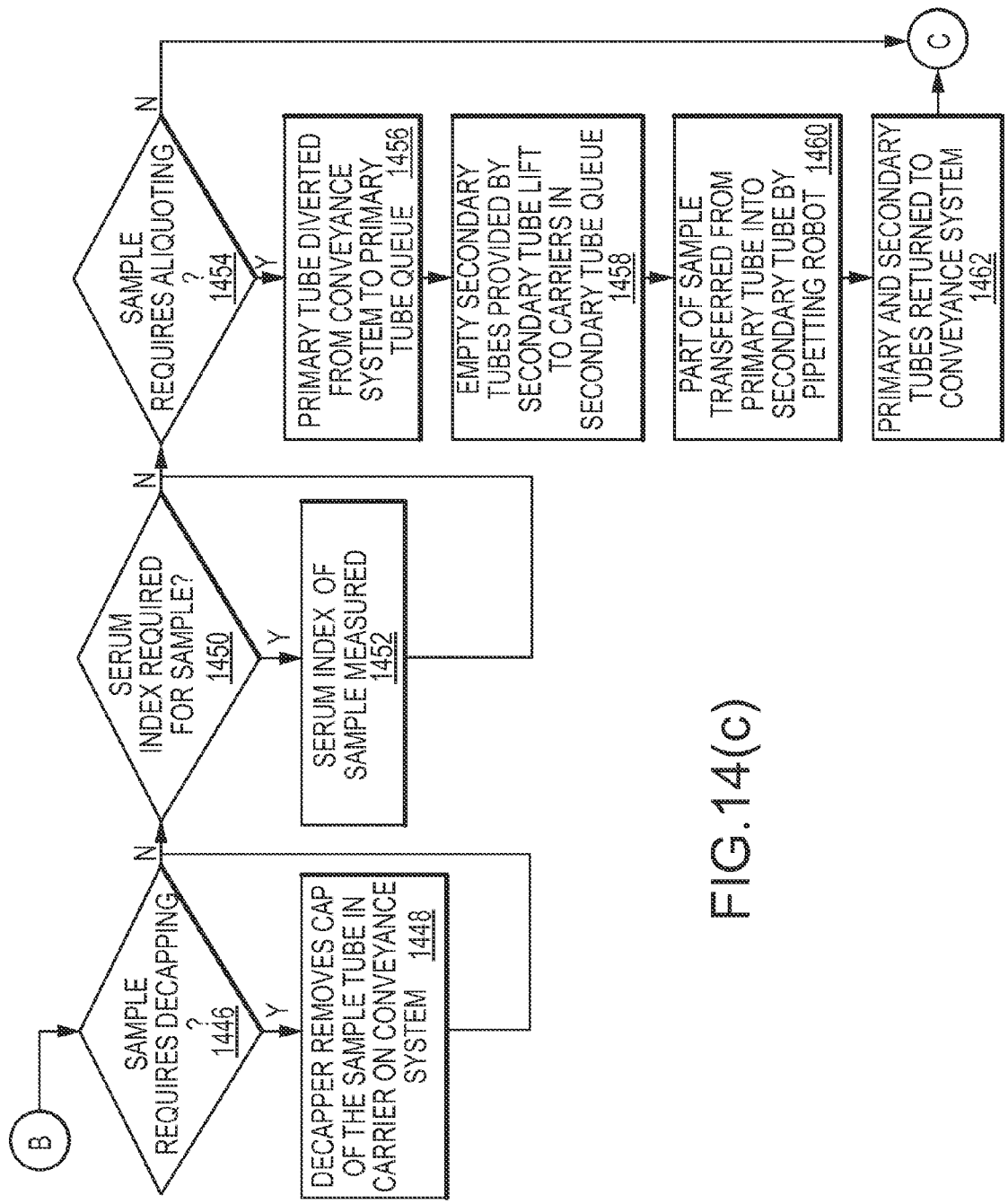
Figure 14D:
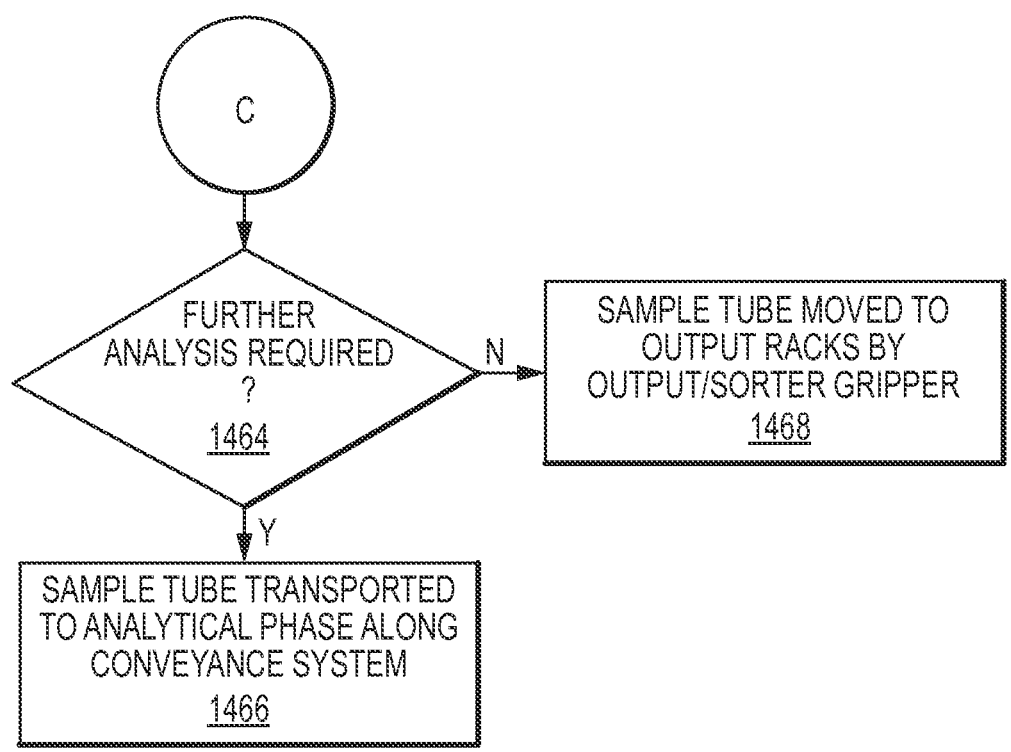

When the scheduler selects a sample for centrifugation, the tube may be loaded by the distribution area gripper 218 into the appropriate centrifuge adapter 1002 at the centrifuge load position 1004 to ensure a balanced centrifuge rotor. At operation 1422, as shown in FIG. 14(b), if the sample is selected for centrifugation, the tube is transported by distribution area gripper 218 from distribution area 204 to the centrifuge adapter 1002, as indicated at operation 1424.

In embodiments of the invention, the sample level of a sample in a sample tube may be determined after taking a picture of the sample tube with a movable assembly comprising a gripper unit and a camera. Other embodiments use an absorption using a transmission measurement device having multiple light sources having wavelengths capable of passing through labels but may or may not be affected by the sample media. After passing through the labels and sample the light is detected with a photoelectric sensor(s). The various sample media can block none, some or all of the light emitting from the LED's. As a result, the sample layer heights can be determined and measured. Further details regarding this embodiment are provided below.

The weight of the sample tube may be calculated by an image analysis device while the sample is being moved. The volume of the sample can be calculated from the layer heights coupled with geometric properties of the tube determined from an analysis of the image captured by the camera in the robot. The weight calculation begins after the image and layer information are obtained. The weight of the sample is calculated from the sample layer volumes and density estimates for the contents which are archived in a system software database. The sample weight is combined with the weight of the sample container which was also previously archived in a system software database. This combined weight is used by the system's software to determine which centrifuge adapter position in which to deposit the sample tube to ensure a balanced centrifuge rotor. The camera can also take a picture of a centrifuge adapter and can determine which locations in the centrifuge adapter can be filled in a manner that allows the centrifuge to be balanced once other centrifuge adapters are filled. For example, centrifuge adapters that will be placed opposite to each other in the centrifuge may each be loaded with a plurality of sample tubes that collectively weigh the same.

Figure 16:
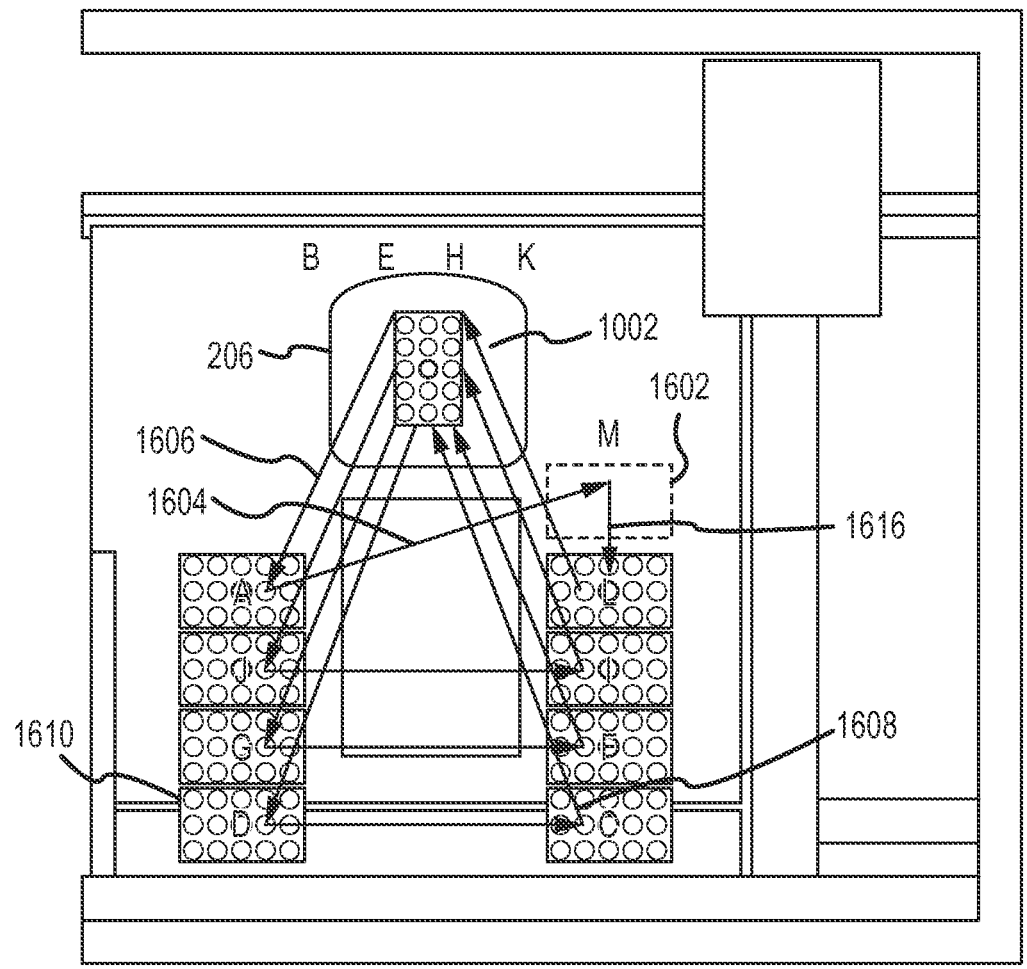
FIG. 16 depicts an illustrative adapter swap sequence for a centrifuge.

As the centrifuge cycle is ending for adapters already loaded into the centrifuge 206-1 or 206-2, the newly loaded centrifuge adapters 1002 are moved to the appropriate centrifuge 206-1 or 206-2. The adapters sit on an adapter shuttle (e.g., 224 or 225) that moves from centrifuge load position 1004, between the manager unit 700 and the centrifuge unit 804, to the appropriate centrifuge 206-1 or 206-2, as indicated at operation 1426. The adapter may be loaded by a robot gripper, such as centrifuge adapter gripper 227, into a centrifuge bucket, as indicated at operation 1428. The sample is centrifuged, as indicated at operation 1430. A previously emptied adapter may be moved from a shuttle (e.g., 224, 225) to a temporary location to create a vacant space in the shuttle. The temporary location may be, e.g., a temporary holding area of a centrifuge area, as shown in FIG. 16 at area M, or a dedicated buffer region. The adapter may be removed from the centrifuge (e.g., removed from a centrifugation bucket), as indicated at operation 1432, and transferred to the vacant space in the shuttle, as indicated at operation 1434. When all adapters have been swapped and the shuttle is moved to the unload position, a sample tube may be removed from the adapter by a robot gripper, such as centrifuge tube gripper 226, as indicated at operation 1436. The sample tube may be placed by centrifuge tube gripper 226 into a carrier on conveyance system 220, as indicated at operation 1438.

Centrifuge adapters 1002 that are loaded with sample tubes may be swapped with the adapters in the centrifuge unit 206-1 or 206-2 by centrifuge adapter gripper 227. The centrifuged adapters can then be removed from the centrifuge unit 206-1 or 206-2 and placed in a vacant space in the shuttle as indicated at 1432. For example, the centrifuged adapters may be placed in specific spots on the shuttle so that when the shuttle returns to the manager unit 700, the tubes can be unloaded by centrifuge tube gripper 226 from the adapters and placed onto the conveyance system 220. The newly loaded adapters 1002 from the manager unit 700 are placed inside the centrifuge 206-1 or 206-2. After the centrifuge adapter has been loaded into the centrifuge rotor, the centrifuge rotor may index to allow loading of a subsequent uncentrifuged centrifuge adapter. An adapter which was previously emptied of its sample tubes may be moved by the centrifuge adapter gripper 227 from an unloading spot on the shuttle to a vacant spot on the shuttle. For example, for a shuttle such as the illustrative shuttle of FIG. 78, a first end of the shuttle 230 may be an unloading spot and a second end 232 of the shuttle may be a vacant spot. Moving the adapter to a vacant spot on the shuttle may occur simultaneously with the indexing of the centrifuge rotor. The empty adapters can then be loaded with new sample tubes in the manager unit 700. The swapping of adapters may continue until all adapters of a centrifuge rotor have been exchanged, allowing the adapter that was placed in a temporary location to be moved to the last empty spot in the shuttle for emptied adapters. Illustrative centrifuge adapter swapping sequences are described further with reference to FIG. 16.

The shuttle may return to its home position where adapters can be loaded with sample tubes by distribution gripper 218 and/or unloaded by centrifuge tube gripper 226. When samples are unloaded from the adapters and transferred to a carrier on the transport by the centrifuge tube gripper, a barcode label on the sample tube may be aligned to the carrier and a liquid level measurement may be made to ensure that the tests required for the sample can be completed. Thus, the centrifuge tube gripper 226 may have a liquid level detection functionality as described with reference to input module gripper 228. If insufficient sample material is present for further processing of the sample, the tube can be processed according to procedures established for insufficient sample material conditions. For example, the sample tube may be processed according to predefined rules which dictate the tests to complete or the sample may be sent to a Sample in Question (SIQ) rack in output module 214.

While adapters are being swapped in the centrifuge unit 804, the scheduler may direct tubes that do not require centrifugation to be moved by the distribution area gripper 218 from the distribution area 204 to the conveyance system 220, bypassing the centrifugation unit 804, as indicated at operation 1440. This can occur anytime the scheduler determines it is best to advance a tube from the distribution area 204 to the conveyance system 220. This depends upon the priorities and processing requirements of samples in the distribution area and downstream processing availability.

While adapters are being swapped in the centrifuge unit 804, the scheduler may direct tubes that do not require centrifugation to be moved by the distribution area gripper 218 from the distribution area 204 to the conveyance system 220, bypassing the centrifugation unit 804, as indicated at operation 1440. This can occur anytime the scheduler determines it is best to advance a tube from the distribution area 204 to the conveyance system 220. This depends upon the priorities and processing requirements of samples in the distribution area and downstream processing availability.

(a) Centrifuge Adapter Swap Sequence

FIG. 16 depicts an illustrative adapter swap sequence for a centrifuge according to a first embodiment. Although a single centrifuge adapter 1002 is shown in centrifuge 206, positions B, E, H and K of centrifuge 206 correspond to four centrifuge buckets that can receive centrifuge adapters 1002. A centrifuge with four centrifuge buckets is shown in FIG. 16. A previously unloaded centrifuge adapter (e.g., centrifuge adapter 1002) is moved by centrifuge adapter gripper 227 from shuttle position A to temporary holding area M (1602), as shown at 1604. An unloaded centrifuge adapter is a centrifuge adapter from which all sample tubes have been removed. Next, a previously centrifuged ("spun") centrifuge adapter is moved by centrifuge adapter gripper 227 from area B of centrifuge 206 to the vacant space on shuttle position A, as indicated at operation 1606. Shuttle positions A, J, G, and D can be collectively referred to as first shuttle position 1610. At operation 1606, the centrifuge adapter 1002 is removed from a centrifuge bucket 502 of centrifuge 206. An adapter 1002 loaded with samples that have not been centrifuged is then moved by centrifuge adapter gripper 227 from shuttle position C to the area B of the centrifuge, as indicated at operation 1608. Shuttle positions L, I, F and C can be collectively referred to as second shuttle position 1612.

Subsequently, a previously emptied centrifuge adapter is moved by centrifuge adapter gripper 227 from shuttle position D to shuttle position C. A previously spun centrifuge adapter is moved by centrifuge adapter gripper 227 from area E of centrifuge 206 to the vacant space on shuttle position D. An adapter loaded with samples that have not been centrifuged is moved by centrifuge adapter gripper 227 from shuttle F to area E of the centrifuge 206.

The sequence continues with a previously emptied centrifuge adapter moved by centrifuge adapter gripper 227 from shuttle position G to shuttle position F. A previously spun centrifuge adapter is moved by centrifuge adapter gripper 227 from area H of centrifuge 206 to the vacant space on shuttle position G. An adapter loaded with samples that have not been centrifuged is moved by centrifuge adapter gripper 227 from shuttle I to the area H of the centrifuge 206.

Next, a previously emptied centrifuge adapter is moved by centrifuge adapter gripper 227 from shuttle position J to shuttle position I. A previously spun centrifuge adapter is moved by centrifuge adapter gripper 227 from area K of centrifuge 206 to the vacant space on shuttle position J. An adapter loaded with samples that have not been centrifuged is moved by centrifuge adapter gripper 227 from shuttle position L to the area K of the centrifuge 206 indicated at K. The adapter that was moved to temporary holding area M is moved to the vacant space in shuttle position L, as indicated at operation 1616.

In this way, spun adapters are swapped out of a centrifuge and unspun adapters are swapped into the centrifuge.

The scheduler determines the order that samples are removed from the adapters and unspun samples are removed from the distribution area. High priority samples (STAT) may be removed first. If a downstream process such as aliquoting in aliquotter unit 212 is unable to handle the flow of samples and the next centrifuge cycle is ready to begin, the samples can be removed from the adapters and placed into a buffer at the back of the centrifuge 206. In some embodiments, the lowest priority samples are removed first to allow more time for the higher priority samples to advance. The scheduler may advance samples from the buffer when downstream processes become available and according to established priorities. If a sample requires another spin cycle, the sample may remain in the adapter to be spun again.

(b) Centrifuge Adapter Loading Sequence

Figure 17:
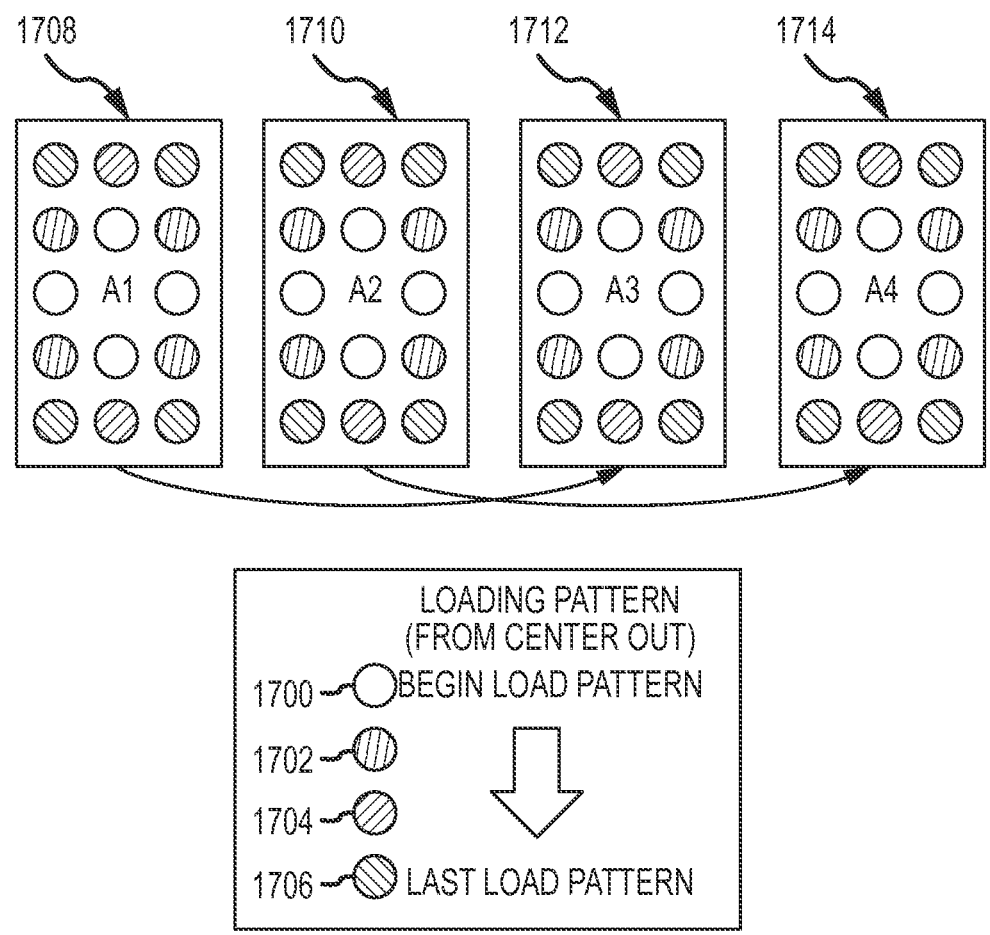
FIG. 17 depicts an illustrative adapter loading sequence for a centrifuge.

FIG. 17 depicts an illustrative adapter loading sequence for a centrifuge. In order to prevent imbalance of the centrifuge rotor, centrifuge adapters 1002 may be loaded in a manner that yields a balanced centrifuge rotor. The weight of each sample tube can be measured and/or estimated from the product of measured sample volume multiplied by a known density for the sample material. In some embodiments, sample tube weights can be determined by one or more balances (e.g., a balance located in the distribution area or a balance of a conveyor track that measures sample tube weights as the sample tubes are carried by a conveyor track).

The centrifuge can be loaded according to the following sequence. A first sample tube with a highest centrifugation priority can be identified by the scheduler in the distribution area 204. Adapter A1 (1708) can be loaded with the first sample tube from distribution area 204 in a position closest to the center position of adapter A1 (1708). A second sample tube with comparable weight to the first sample tube can be selected by the scheduler from distribution area 204 and loaded into a position of A3 (1712) that is the same position occupied by the first sample tube in A1 (1708). A sample tube with the second highest centrifugation priority is identified by the scheduler in distribution area 204 to be the third sample tube. The third sample tube is loaded into a position in adapter A2 (1710) that is closest to the center of A2 (1710). A fourth sample tube with comparable weight to the third sample tube can be selected by the scheduler from distribution area 204 and loaded into a position of A4 (1714) that is the same position occupied by the third sample tube in A2 (1710). The process continues with filling open positions in the adapters A1-A4 (1708-1714) with a first sample tube, a second sample tube, a third sample tube and a fourth sample tube, as described above, to fill the positions indicated in begin load pattern 1700, then the positions indicated in second load pattern 1702, then the positions indicated in third load pattern 1704, and then the positions indicated in last load pattern 1706, until all adapters are filled. In some embodiments, if a centrifuge cycle is nearing completion (e.g., within 30 seconds of completion), the loading of adapters may halt before all adapters are filled and the centrifuge may be loaded with adapters that have not been filled to capacity.

In some embodiments, a sample tube is loaded into an adapter only if its weight is available. The sample tube weight may be determined, for example, based on a liquid level detection performed by input module gripper 228 cross referenced with a table stored in a memory of the LIS. If the weight of a sample tube is not available, centrifugation may not be performed for the sample tube. For example, the sample tube may be placed in an error rack rather than being loaded into an adapter.

In an alternative embodiment, sample tubes may be loaded into adapters according to priority order. The sample tubes may be loaded according to the order described above with reference to FIG. 17. To avoid imbalance, a lower priority sample tube may be loaded in lieu of a higher priority sample tube if the higher priority tube would cause imbalance. For example, if a first (e.g., highest priority) tube is heavy and the second and third tubes (e.g., next in priority order) equal the weight of the first tube, the second and third tubes may be loaded to oppose the force of the first tube.

In some embodiments, a request for immediate centrifugation may be issued by the scheduler, in which case adapters that are not completely filled may be centrifuged. For example, if a loaded sample tube is a STAT tube or if the adapter filling time for a centrifuge is expired, the adapter may be centrifuged immediately.

Figure 18:
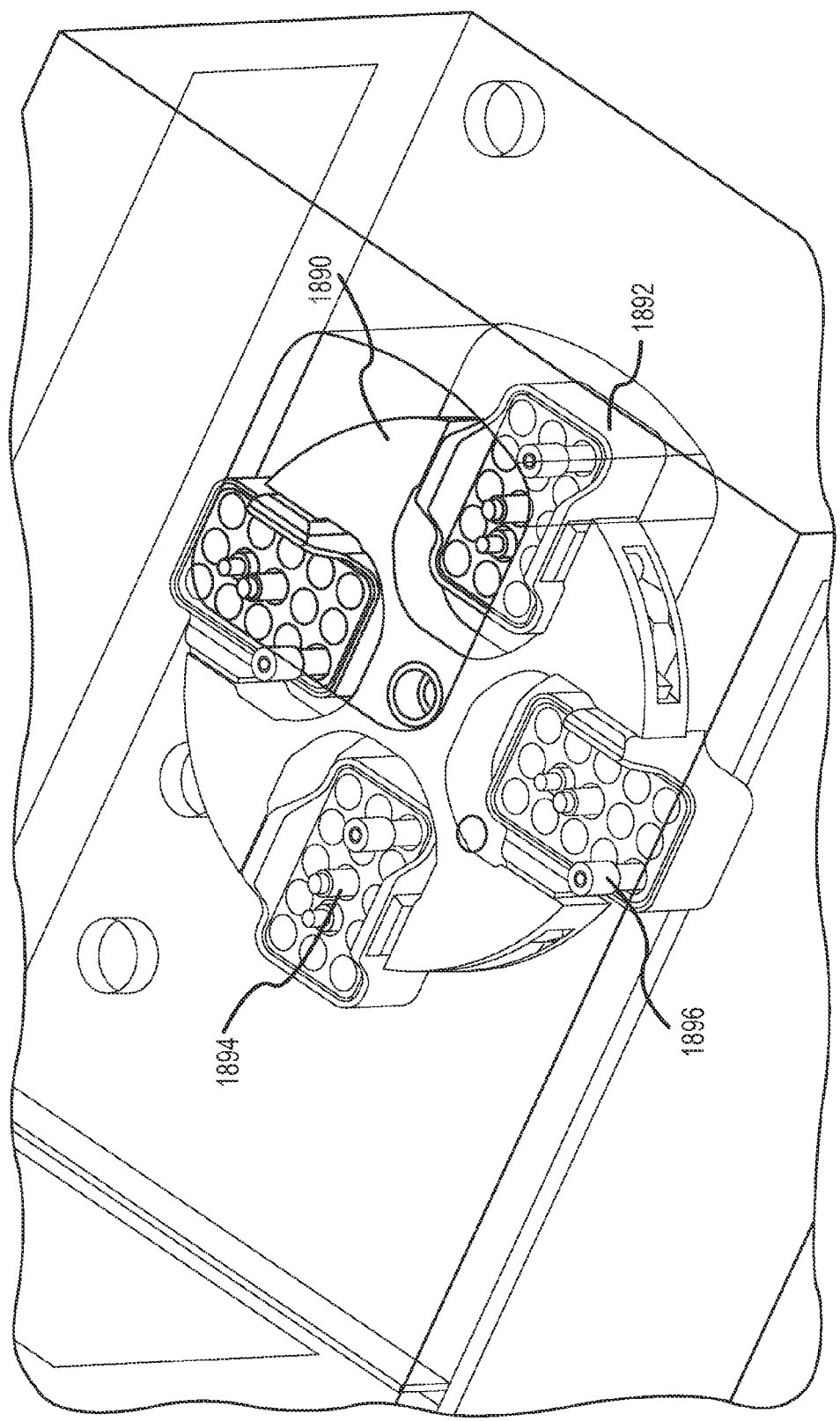
FIG. 18 depicts a centrifuge rotor.

FIG. 18 shows an illustrative centrifuge rotor 1890 configured to receive four centrifuge adapters 1894. Centrifuge adapters 1894 may be loaded into centrifuge buckets 1892 of the centrifuge. Centrifuge adapters are configured to receive one or more sample tubes 1896.

7. Decapping, Serum Index, and Aliquoting

Referring again to FIGS. 14(*a*)-14(*e*), the scheduler determines the appropriate tubes to select from the distribution area 204 and the centrifuge adapters 1002 being unloaded to the conveyance system 220 to ensure the proper flow of samples downstream. The centrifuge adapters can be unloaded to ensure that the next centrifuge cycle can begin on time. This is dependent upon downstream process availability.

When the samples are loaded onto the conveyance system 220, distribution area gripper 218 aligns the barcode of the tube with the carrier used to carry the tube on the conveyance system 220. The carrier orientation is maintained on the conveyance system, simplifying the barcode reading process at downstream processes.

Once the tube is in the carrier on the conveyor system 220, the decapper 710 may remove the cap on the sample tube if the sample requires decapping, as indicated at operations 1446 and 1448. The samples that have been decapped may have their serum indices measured in the serum indices unit 210 if a serum index is required for the sample, as indicated at operations 1450 and 1452.

In certain circumstances, samples may need to be divided into more than one sample tube. These sample tubes may exit the conveyance system 220 of the pre-analytical phase and enter the aliquotter unit 212 at the primary tube queue 1104 if aliquoting is required, as indicated at operations 1454 and 1456. The samples are divided into secondary tubes at the direction of the scheduling system. Before the aliquoting is performed by the pipetting robot 302, empty secondary tubes are provided by the secondary tube lift 318 into carriers in the secondary tube queue 1106, as indicated at operation 1458. Part of the sample is transferred from a primary tube 304 into a secondary tube 306 by pipetting robot 302, as indicated at operation 1460. The primary and new secondary tubes then leave the aliquotter unit 212 and reenter the conveyance system 220, as indicated at operation 1462.

8. Output Workflow

Once any necessary centrifugation, decapping, or aliquoting is performed, and once the sample is ready to be analyzed, the sample tube may continue to the analytical phase along conveyance system 220 if further analysis is required, as indicated at operations 1464 and 1466, or may be moved by an output/sorter gripper 404 to output racks located in the drawers of the output/sorter unit 214, as indicated at operation 1468.

It will be recognized that a plurality of grippers may be used for the functions described as being performed by any single gripper. The functionality described for each gripper may be combined and performed by one or more gripper.

IV. Robotic Arms and Grippers

As discussed above, a robotic arm can be used to move a sample tube or any other object (e.g. a centrifuge adapter) from many different locations within the laboratory system (e.g., input robot 228, distribution robot 218, centrifuge robot 226, decapper robot 710, aliquotter robot 302, output/sorter robot 404, recapper robot 504, secondary tube lift, etc.).

Figure 19:
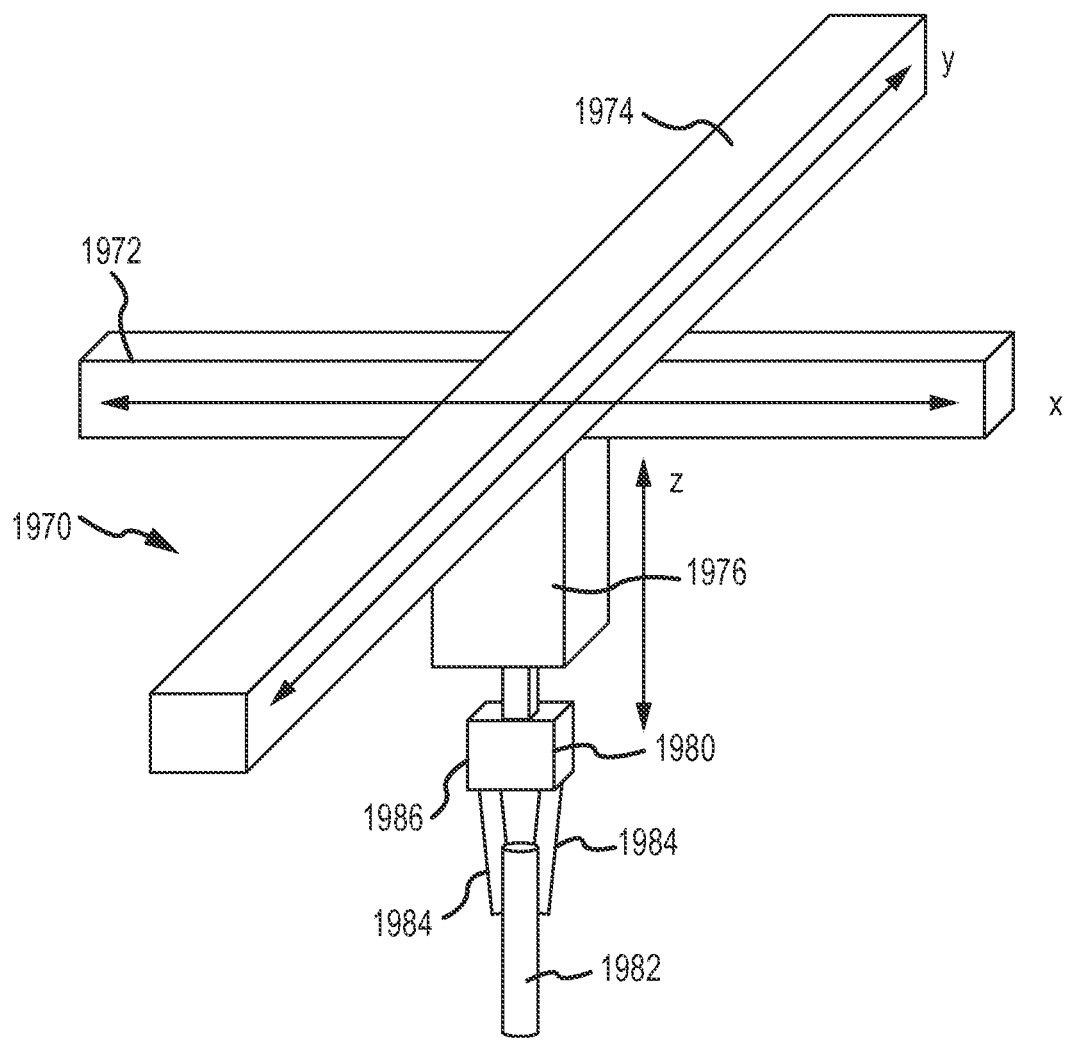
FIG. 19 depicts an example of a Cartesian or gantry robot with three independently moveable directions x-, y-, and z-.

The robotic arm architecture can differ in complexity dependent upon the given task. FIG. 19 depicts an example of a Cartesian or gantry robot 1970 with three independently moveable directions x-, y-, and z-. The x-axis may be defined by an x-axis rail 1972 and the y-axis may be defined by a y-axis rail 1974. The z-axis may be defined by an orientation of a robotic arm 1976 extending in the z-direction. The gantry robot 1970 comprises a robotic arm 1976, and a gripper unit 1980 operatively and physically coupled to the robotic arm 1976. More complex robotic arms may include, for example, the Selective Compliant Assembly Robot Arm (SCARA) or the articulated robotic arm with multiple joint arms. The gripper unit 1980 comprises a gripper housing 1980 and gripper fingers 1984 extending downward from the gripper housing 1986. The gripper fingers 1984 can move inwardly towards each other to grip a sample tube 1982 and outwardly to release a sample tube 1982.

The robotic arm including the gripper unit can be additionally employed for identification and for determination of physical characteristics of the moved object. Therefore, the robotic arm can be equipped with an appropriate identification and determination means (e.g., a camera, a bar code reader, or an absorption and transmission measurement unit). The tube identification, level detection, and tube presence detection units are described in more detail below.

The following description of a tube handling unit, a centrifuge bucket gripper, a tube identification device, a sample level detection device, tube or rack presence detection device, and a combination of these functions in a single robot arm will be discussed in light of the gantry robotic arm depicted in FIG. 19.

A. Tube Handling Units

Figure 20:
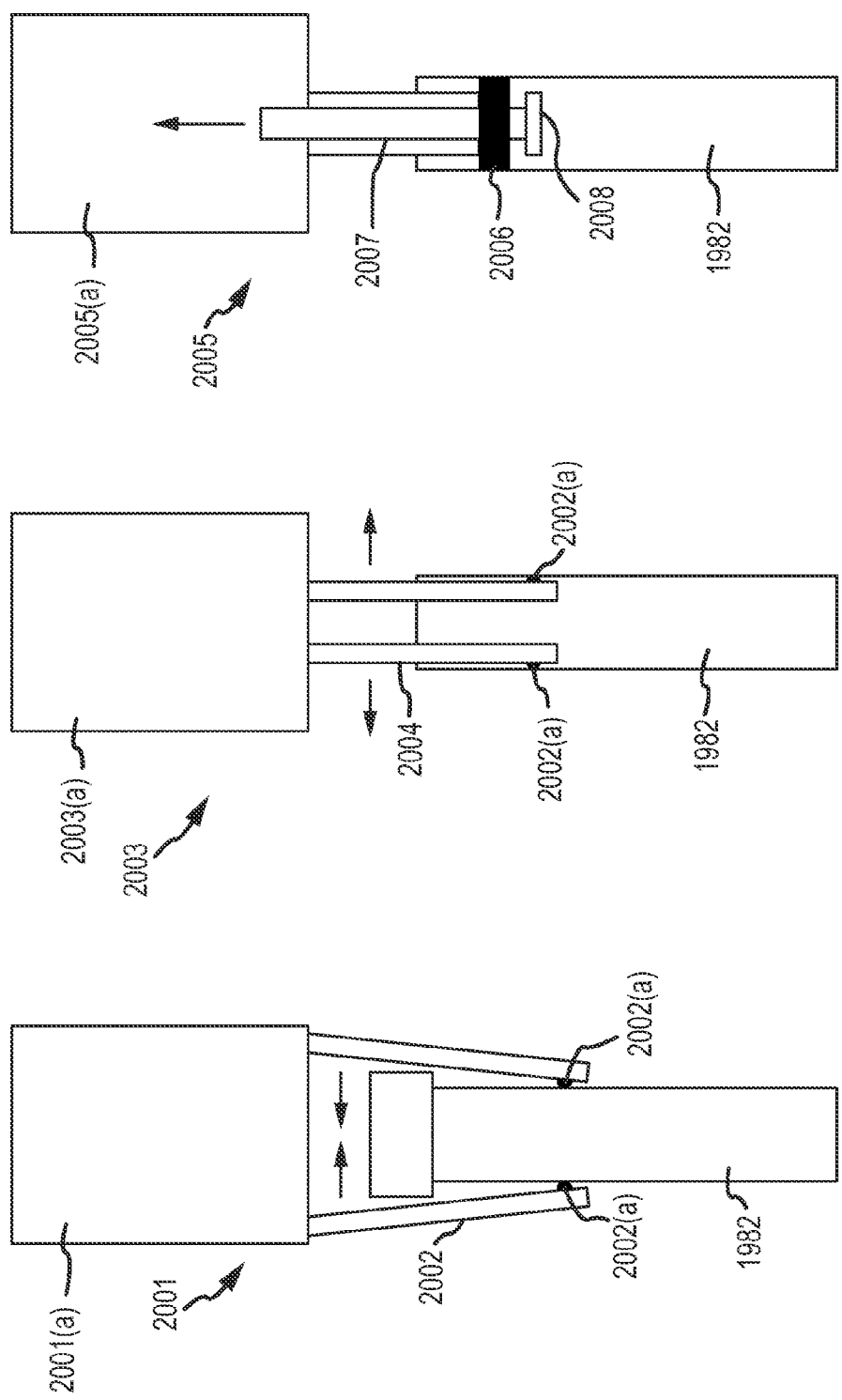
FIGS. 20(a)-(c) depict side-view diagrams of embodiments of gripper units.

The robotic arms according to embodiments of the invention may employ a gripper unit to grip and transport sample tubes to desired locations. FIGS. 20(*a*)-20(*c*) depict several different gripper units to grip and transport sample tubes to desired locations.

FIG. 20(*a*) depicts an example for an outside gripper unit 2001 for sample tubes comprising a gripper housing 2001(*a*) comprising two or more moveable fingers 2002 extending downward and comprising inwardly projecting contact structures 2002(*a*). The inwardly projecting contact structures 2002(*a*) grip a sample tube 1982 by a movement towards the outer wall of the tube 1982.

FIG. 20(*b*) depicts an example for an inside gripper unit 2003 comprising a gripper housing 2003(*a*) comprising two or more fingers 2004 extending downward from the gripper housing 2003(*a*). In this embodiment, the two or more fingers 2004 move outwards toward the inner wall of a sample tube 1982.

Another embodiment of an inside gripper unit 2005 is depicted in FIG. 20(*c*). The gripper unit 2005 employs a flexible ring element 2006 which extends radially from a linear carrier 2007 (which extends downward from the gripper housing 2005(*a*)) to grip an inside surface of a sample tube 1982. The flexible ring element (e.g., silicon o-ring) 2006 is compressed by moving the lower plunger segment 2008 of the linear carrier 2007 upwards.

B. Sample Level Detection

In embodiments of the invention, a camera unit and analysis tool can use the 2-D image captured by the system to determine a sample volume and sample level for the sample in the sample tube.

Figure 21:
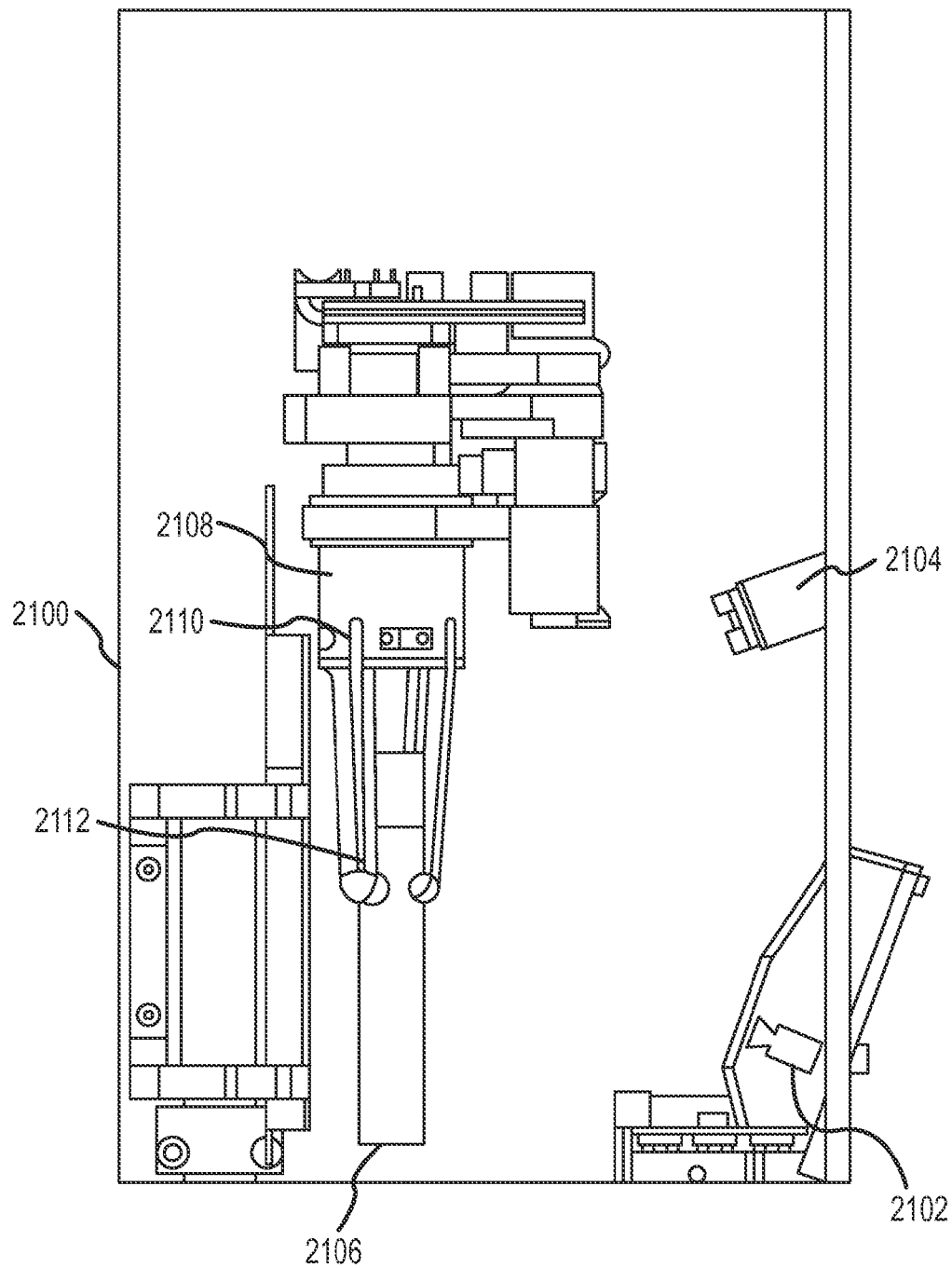
FIG. 21 depicts an exemplary diagram of a camera unit for sample tube detection and analysis.

A sample level detection unit (or assembly) and a sample tube are depicted in FIG. 21. The sample level detection unit includes a chamber 2100. A camera unit 2102 is accommodated in the chamber 2100, which has few and, if possible, no optical reflections. The camera unit 2102 can be aligned with and focused on the sample tube 2106 containing the body fluid. An illumination source 2104 may provide light to the sample tube 2106 so that the camera unit 2102 can take a picture of the sample tube 2106.

The camera unit 2102 can be a still camera, a color image camera, a video camera, a spectral camera or the like. A color image camera, for example a 3CCD video camera, may be used. The settings of the color camera, such as focusing, white balance, diaphragm setting, filling-in, can be permanently preset or adjustable. For example, they can be adjusted with the aid of image evaluation software, as in when the data reported by the image evaluation software to the control software are of reduced quality with reference to store reference data. An algorithm can be used to calculate the sample level and/or volume using known data, such as the type of sample tube used, the type of sample, etc.

As shown in FIG. 21, the camera unit 2102 can be inclined to optimize its view of the sample tube 2106. The sample tube 2106 information can be recorded with comparatively few optical reflections with the aid of this measure.

Arranged above and in the middle relative to the analysis position of the sample tube is a gripper unit 2108 that is controlled by a computer. The gripper unit 2108 grips the sample tube 2106 located in a rack of the input section and lifts it into the analysis position. The gripper unit 2108 can comprise a gripper housing 2110. The gripper unit 2108 can also have a plurality of gripper fingers 2112 which can be used to grip the sample tube 2106.

As an alternative to the liquid level detection device using a camera unit, the liquid level detection may also be accomplished by the use of another type of image acquisition device such as a device that has laser diodes with a defined wavelength and analysis algorithms to evaluate the absorption spectra. A laser diode beam can be focused on sections of the sample tube, and an absorption and transmission measurement of different wavelengths of the focused beam can be measured. The analysis algorithm can then use the measurements to provide the liquid level and volume.

Figure 22:
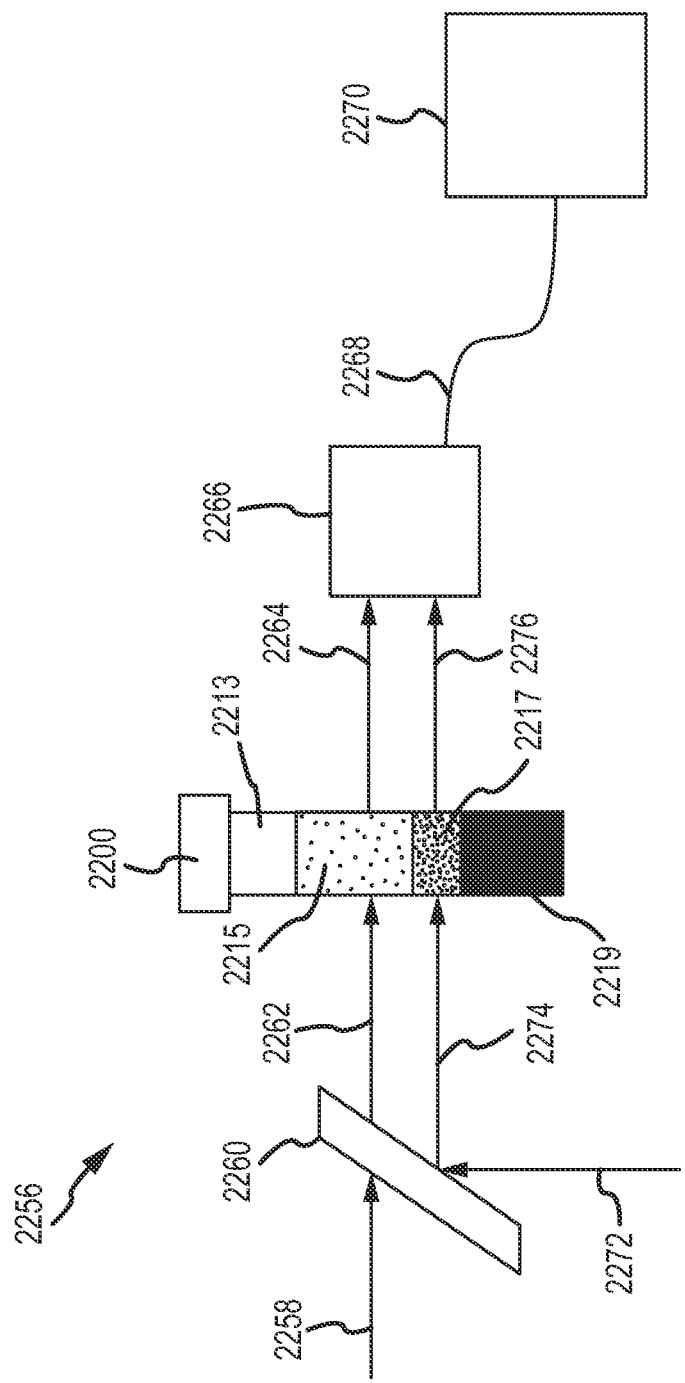
FIG. 22 depicts an example of sample level detection utilizing the analysis of absorption and transmission curves at distinct wavelengths.

FIG. 22 depicts an example of sample level detection utilizing the analysis of absorption and transmission curves at distinct wavelengths. In instances in which blood samples are provided with the sample tube container, the system may additionally be able to detect the distinct levels of serum, plasma, or blood-cake in the total liquid level.

In FIG. 22, a portion of an operable fluid sample interrogation system is depicted generally at 2256. A first source of radiation 2258 (with a second source of radiation 2272 turned off) is arranged to apply a first radiation having a first characteristic wavelength (e.g., 980 nm) to beam combiner 2260, which directs the first emitted radiation 2262 toward a location on the sample tube 2200. The first transmitted radiation 2264 is detected by a detector, such as illustrated photo diode and amplifier arrangement 2266. A signal 2268, corresponding to the intensity of first transmitted radiation 2264 can then be stored and/or manipulated in comparison structure, such as programmable integrated circuit 2270, or a computer. The second source of radiation 2272 (with the first source of radiation 2258 turned off) is arranged to apply a second radiation having a second characteristic wavelength (e.g., 1050 nm) to beam combiner 2260 at a slightly shifted position as the first emitted radiation 2262, which directs the second emitted radiation 2274 parallel to the beam path of first emitted radiation 2262 toward a slightly different location on the sample tube 2200. The second transmitted radiation 2276 is detected by the same detector, such as illustrated photo diode and amplifier arrangement 2266. A signal 2268, corresponding to the intensity of second transmitted radiation 2276 can then be stored and/or manipulated in comparison structure, such as programmable integrated circuit 2270, or a computer.

FIG. 22 further depicts a sample tube that is being measured and analyzed using the wavelength process. As shown, serum 2215 and gel 2217 are mostly transparent to visible light while red blood cells 2219 are substantially opaque. Further, gel 2217 is transparent to infrared light while red blood cells 2219 and serum 2215 are substantially opaque. Accordingly, when the sample tube 2200 has gel 2217 to separate the serum 2215 and red blood cells 2219, it is possible just using infrared light to "see through" different sections. The infrared light reading is strong when the infrared light beam passes through air 2213, drops when the infrared light beam is directed toward the serum, is relatively strong when directed toward the gel 2217, and drops again when directed toward the red blood cells 2219. This analysis performed by the analysis tool allows for the measurement of the sample level/volume of the sample.

The liquid level detection unit can be combined with any of the above-described robotic arms with or without a tube identification unit, and with or without a tube or rack presence detection unit. Further details regarding tube identification units and tube or rack presence detection units can be found in U.S. Provisional Patent Application Nos. 61/556,667, 61/616,994, and 61/680,066.

C. Combination Robot with Gripper, Tube Identification Unit, Tube or Rack Presence Detection Unit and Liquid Level Detection Unit A combination robot with gripper, tube identification unit, tube or rack presence detection unit and liquid level detection unit can be utilized by the laboratory automation system. The combination robot utilizes the features of the gripper robot described above and a camera of the tube identification unit, a camera of the tube or rack presence detection unit and laser diodes for sample level detection described above.

Figure 23:
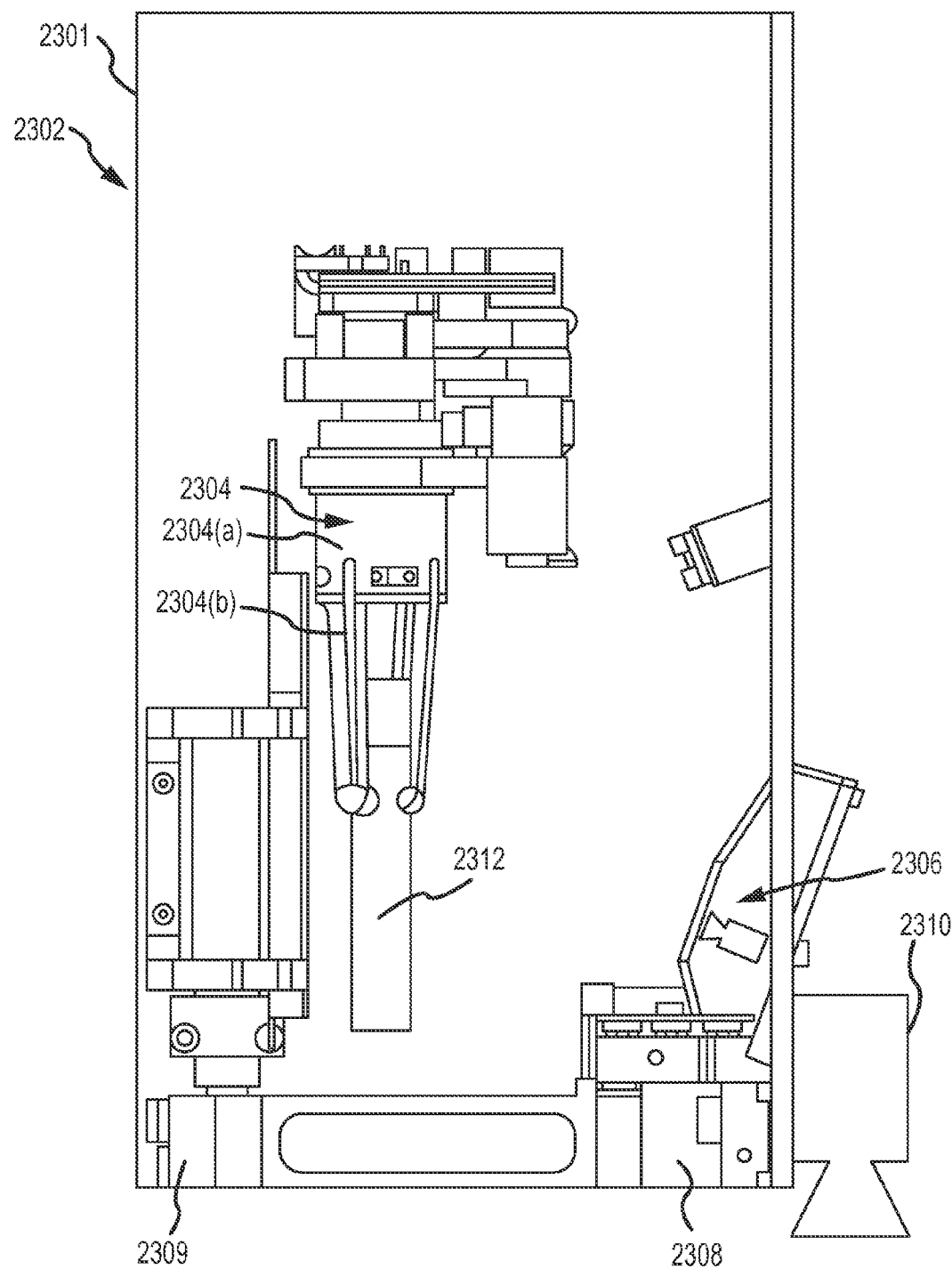
FIG. 23 depicts a diagram of a combination robot.
Figure 24:
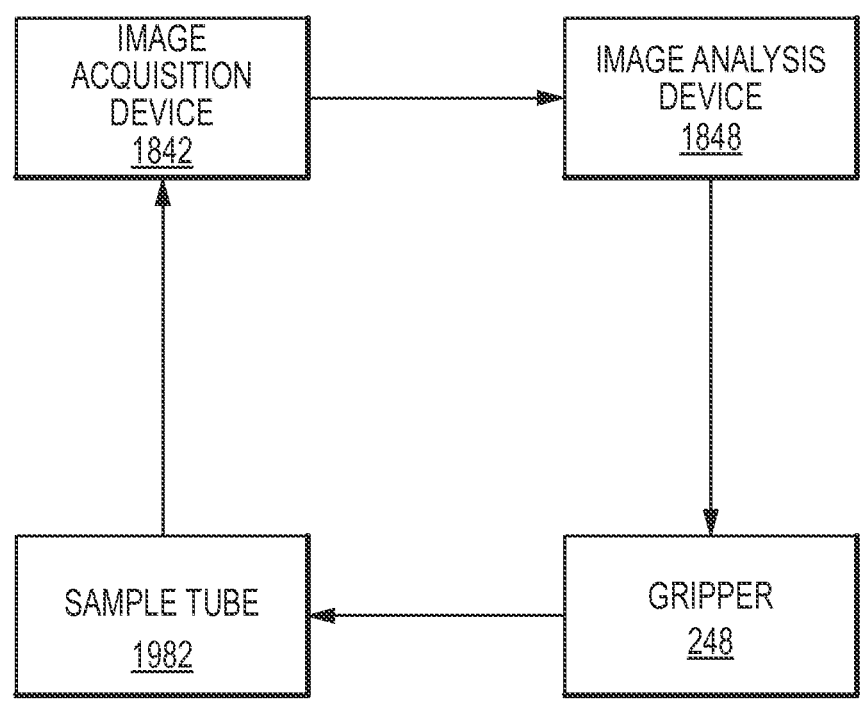

FIG. 23 depicts a schematic drawing of one example of the combination robot (or assembly). The combination robot 2302 can include a robotic gripper 2304 for gripping sample tubes, disposed in a chamber 2301. The robotic gripper 2304 may comprise a gripper housing 2304($a$) with gripper fingers 2304($b$) extending downward and gripping a sample tube 2312. The combination robot 2302 can utilize a camera 2306 for acquiring images to perform tube detection and/or sample level detection. The combination robot 2302 can also utilize an emitter 2308 and a receiver 2309 for performing laser diode sample level/volume detection. The combination robot 2312 can also utilize a tube or rack presence detection camera 2310 for acquiring a series of images during the x-y movement of the gripper to perform tube and rack presence detection and tube and rack identification. Tube and rack presence detection and tube and rack identification systems and methods are described in further detail in U.S. Provisional Patent Application No. 61/556,667, filed Nov. 7, 2011, U.S. Provisional Patent Application No. 61/616,994, filed Mar. 28, 2012, and U.S. Provisional Patent Application No. 61/680,066, filed Aug. 6, 2012, which are herein incorporated by reference in their entirety for all purposes FIG. 24 shows a high-level block diagram of some components in a sample tube and rack identification system according to an embodiment of the invention. FIG. 24 shows an image acquisition device 1842 coupled to an image analysis device 1848. The image analysis device 1848 can also be coupled to a gripper unit 248 and can provide instructions to it. The gripper unit 248 can then secure a specific sample tube.

Suitable image acquisition devices may include cameras, as well as detectors like those described with reference to FIG. 22.

Although the instructions provided by the image analysis device 1848 are provided to a gripper unit 248 in this example, embodiments of the invention are not limited thereto. For example, embodiments of the invention can provide instructions to a central controller in the laboratory automation system to inform other downstream instruments or subsystems that a particular tube has been identified and/or that the sample tube is of a particular weight. For example, once a particular sample tube in a sample rack has been identified, a scheduler in a central controller will know where that particular sample tube is in the system and can plan ahead for any subsequent processing. Thus, the instructions and/or analysis data provided by the image analysis device 1848 may be provided to any suitable downstream instrument or subsystem.

Figure 25:
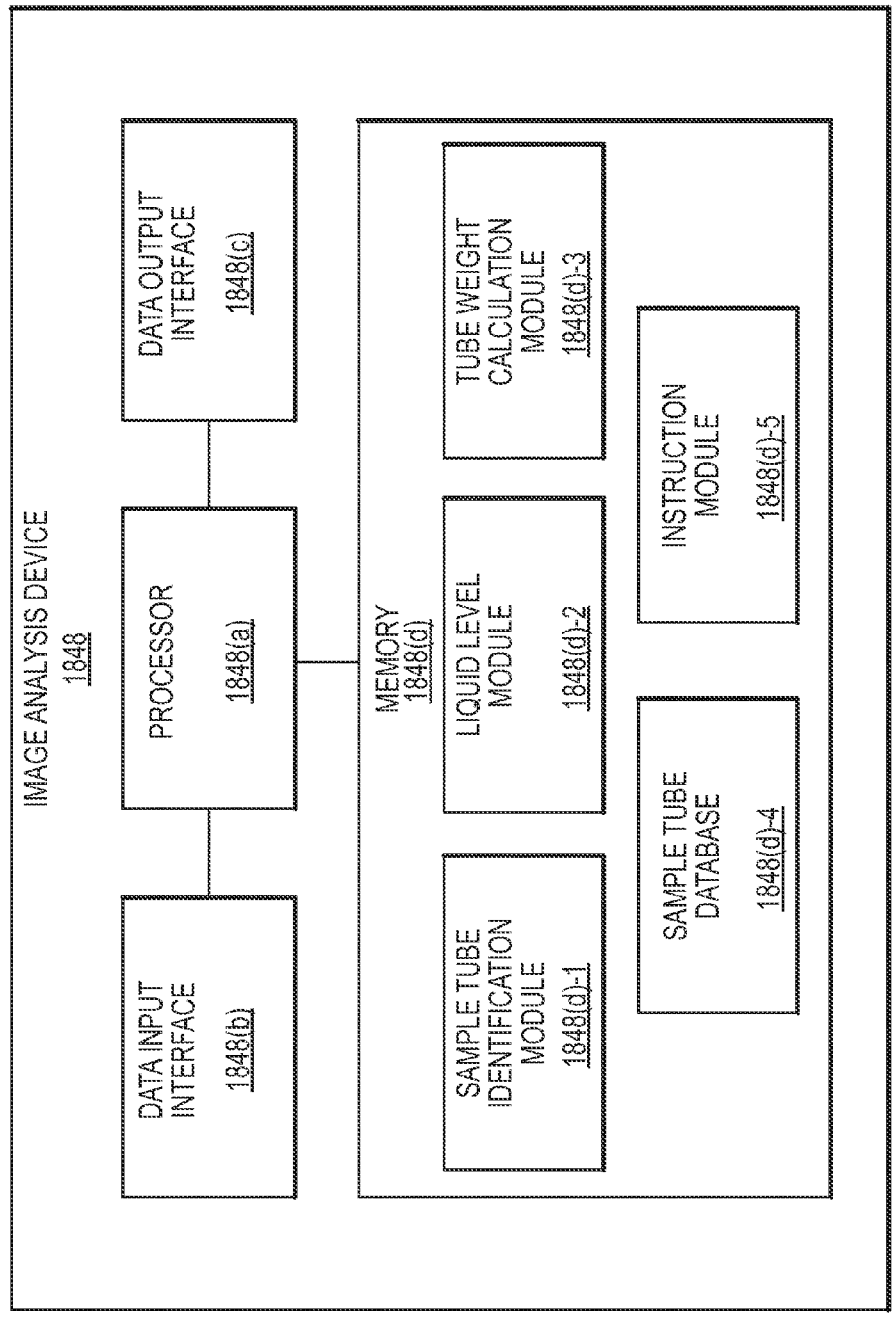

FIG. 25 shows a block diagram of an image analysis device 1848 according to an embodiment of the invention. It may include a data input interface 1848($b$) to receive data from the one or more image acquisition devices (e.g. camera 1842), and a processor 1848($a$) coupled to the input interface 1848($b$). The processor 1848($a$) may also be coupled to a data output interface 1848($c$) which provides data to suitable devices which can manipulate and/or transport a sample tube 1848($c$). The processor 1848($a$) may further be coupled to a memory 1848($d$) which may comprise a sample tube identification module 1848($d$)-1, a liquid level determination module 1848($d$)-2, a tube weight calculation module 1848($d$)-3, a sample tube database 1848($d$)-4, and an instruction module 1848($d$)-5. The sample tube identification module 1848($d$)-1 may comprises computer code, executable by the processor 1848($a$), to determine the identity of a sample tube. A sample tube can be identified, for example, by a barcode on the sample tube, a cap color, a tube shape, etc. The liquid level determination module 1848($d$)-2 may comprise computer code, executable by the processor 1848($a$) to determine a liquid level of a sample in a sample tube. The tube weight calculation module 1848($d$)-3 may comprise computer code, executable by the processor 1848($a$) to calculate the weight of a sample tube. The sample tube database 1848($d$)-4 may information relating to sample tubes. The sample tube instruction module 1808($d$)-5 may comprise code, executable by the processor 1808($a$) to provide instructions to an external device via the data output interface 1808($c$). The instructions that are provided may include instructions to a gripper unit, which cause the gripper unit to transport the sample tube to a particular location or a particular subsystem after identifying the sample tube. Note that any of the previously described software modules may function independently or together. For instance, the sample tube identification module 1848(*d*)-1 may operate with the liquid level module 1848(*d*)-2 and the sample tube weight calculation module 1848(*d*)-3 to identify the particular sample tube and to calculate a weight of the sample tube.

The sample tube database 1848(*d*)-4 may comprise any suitable type of information relating to sample tubes. It may include, for example, sample tube information correlating samples to sample tube characteristics, markers or labels on a sample tube. The sample tube database 1848(*d*)-4 may also include information regarding different types of sample tubes and their corresponding volumes and weights (without a sample in it). This information, along with information about the level of a sample if a tube, can be used to calculate the weight of a sample tube.

In methods according to embodiments of the invention, at least one camera acquires at least one picture of the rack with sample tubes comprising samples. The method further comprises analyzing, by the image analysis device, the at least one picture to identify characteristics of the sample tubes and/or rack. If the sample tubes comprise different samples, then these samples may be in different sample tubes with different characteristics, and the samples may be processed differently, after they have been identified. For example, after receiving instructions from the analysis device, a first sample tube with a first characteristic and a first sample could be sent to a storage unit by a gripper (coupled to a robotic arm) that is capable of moving in three directions (X, Y, and Z), while a second sample tube with a second characteristic and a second sample may be sent to a centrifuge, prior to being analyzed.

The processor 1808(*a*) may comprise any suitable data processor for processing data. For example, the processor may comprise one or more microprocessors that function separately or together to cause various components of the system to operate.

The memory 1808(*d*) may comprise any suitable type of memory device, in any suitable combination. The memory 1808(*d*) may comprise one or more volatile or non-volatile memory devices, which operate using any suitable electrical, magnetic, and/or optical data storage technology.

V. Tube or Rack Presence Detection Unit

The laboratory automated system may use a tube or rack presence detection apparatus for detecting the presence of a sample tube or rack and its characteristics. Analysis tools or an image analysis device can be used to analyze or process one or more images acquired by one or more cameras and determine objects in the field of view of the cameras. The image analysis device can determine the presence and characteristics of each rack and of each sample tube in the rack and identify each sample tube in the rack using the determined characteristics.

The embodiments of the invention that relate to the tube or rack identification systems and methods can be used in any suitable part of the above-described system. For example, they may be used in the above-described input module 202, output module 214, or any other part of the system that uses racks and tubes.

In embodiments of the invention, as noted above, an "image acquisition device" may be used to capture images such as 2-D images of sample containers or sample container holders Examples of image acquisition devices comprise cameras as well as detectors that can detect any suitable type of electromagnetic energy.

In embodiments of the invention, "sample container characteristics" may comprise any suitable characteristics about a sample container. Such characteristics may relate to a physical characteristic of a container such as a tube body and/or tube cap. Examples of sample tube characteristics include cap color, cap shape, labels and markers.

In embodiments of the invention, "sample container holder characteristics" may comprise any suitable characteristics of a sample holder. A sample container holder may include a number of recesses to hold an array of sample containers. Exemplary sample container holders characteristics may comprise any suitable characteristics including at least one of a size, shape, or color, as well as labels and/or markers that are associated with (e.g., on) the sample container holders.

A. Sample Tube or Rack Identification

Figure 26:
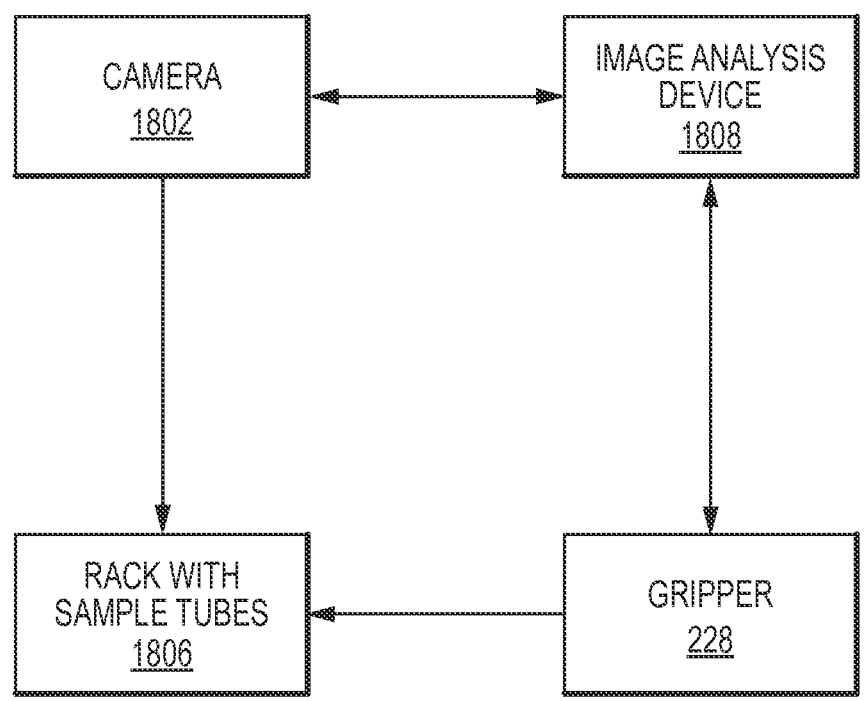

Other embodiments of the invention are directed to sample tube and rack detection. FIG. 26 shows a high-level block diagram of some components in a sample tube and rack identification system according to an embodiment of the invention. FIG. 26 shows a camera 1802 coupled to an image analysis device 1808. The image analysis device 1808 can also be coupled to a gripper 228 and can provide instructions to it. The gripper 228 can then secure a specific sample tube in a rack with sample tubes 1806.

Although the instructions provided by the image analysis device are provided to a gripper 228 in this example, embodiments of the invention are not limited thereto. For example, embodiments of the invention can provide instructions to a central controller in the laboratory automation system to inform other downstream instruments or subsystems that a particular tube and/or rack has been identified. For example, once a particular sample tube in a sample rack has been identified, a scheduler in a central controller will know where that particular sample tube is in the system and can plan ahead for any subsequent processing. Thus, the instructions and/or analysis data provided by the image analysis device 1808 may be provided to any suitable downstream instrument or subsystem.

FIG. 27 shows a block diagram of an image analysis device 1808. It may include a data input interface 1808(*b*) to receive data from the one or more cameras (e.g. camera 1802), and a processor 1808(*a*) coupled to the input interface 1808(*b*). The processor 1808(*a*) may also be coupled to a data output interface 1808(*c*) which provides data to suitable devices which can manipulate and/or transport a sample tube. The central processor 1808(*a*) may further be coupled to a memory 1808(*d*) which may comprise shape determination module 1808(*d*)-1, a color determination module 1808(*d*)-2, a marker and label determination module 1808(*d*)-3, a tube presence detection module 1808(*d*)-4, and an instruction module 1808(*d*)-5. The shape determination module 1808(*d*)-1 may comprises computer code, executable by the processor 1808(*a*), to determine the shape of a sample tube or rack. The color determination module 1808(*d*)-2 may comprise computer code, executable by the processor 1808(*a*) to determine a color of a sample tube cap or rack. The marker and label determination module 1808(*d*)-3 may comprise computer code, executable by the processor 1808(*a*) to determine marker or label associated with a cap, tube body, or rack. The tube presence detection module 1808(*d*)-4 may comprise code, executable by the processor, to determine the absence or presence of a sample tube at a particular rack location within a rack. The sample tube instruction module 1808(*d*)-5 may comprise code, executable by the processor 1808(*a*) to provide instructions to an external device via the data output interface 1808(*c*). The instructions that are provided may include instructions to a gripper unit, which cause the gripper unit to locate and grip a particular sample tube or tubes in one or more racks. Note that any of the previously described software modules may function independently or together. For instance, the shape determination module 1808(*d*)-1 may operate with the color determination module 1808(*d*)-2 to identify both the shape of a particular cap as well as its color, in order to identify the sample tube associated with the cap.

In methods according to embodiments of the invention, at least one camera acquires at least one image of the rack with sample tubes comprising samples. The method further comprises analyzing, by the image analysis device, the at least one image to identify characteristics of the sample tubes and/or rack. If the sample tubes comprise different samples, then these samples may be in different sample tubes with different characteristics, and the samples may be processed differently, after they have been identified. For example, after receiving instructions from the analysis device, a first sample tube with a first characteristic and a first sample could be sent to a storage unit by a gripper (coupled to a robotic arm) that is capable of moving in three directions (X, Y, and Z), while a second sample tube with a second characteristic and a second sample may be sent to a centrifuge, prior to being analyzed.

The processor 1808(*a*) may comprise any suitable data processor for processing data. For example, the processor may comprise one or more microprocessors that function separately or together to cause various components of the system to operate.

The memory 1808(*d*) may comprise any suitable type of memory device, in any suitable combination. The memory 1808(*d*) may comprise one or more volatile or non-volatile memory devices, which operate using any suitable electrical, magnetic, and/or optical data storage technology.

FIG. 28(*a*) shows a system 1800 comprising a camera unit (e.g., 2-D arrays or line scanners) comprising a camera 1802 and illumination elements 1804 (e.g., lights). The camera 1802 acquires a 2-D image for a target object can be used in the laboratory automation system to detect the presence of and identify the target object. The camera 1802 and the illumination elements 1804 may be movable or stationary and may be mounted to a frame (not shown) in a processing module above racks with sample tubes. In this example, the target objects are multiple sample tubes 1806(*a*) being provided in a 6×6 rack 1806(*b*). The 2-D image can then be further processed by image analysis software in the image analysis device and can detect the presence and to derive characteristics of the target object (e.g., sample tubes or racks), such as tube cap indicators, rack markers, circular barcode labels, cap or rack color and shape, etc. The 2-D image can also be analyzed to determine the presence or absence of a sample tube in various sample tube locations in the rack 1806. By analyzing the tube characteristics and by analyzing the presence of the sample tubes in a rack, a gripper or other transport device knows which samples to select for further processing, and also knows whether or not additional samples can be placed in the rack for further processing.

FIG. 28(*b*) depicts another embodiment of a system for sample tube or rack detection and analysis. The camera unit 1808 (e.g., 2-D arrays or line scanners) comprises a plurality of cameras 1810(*a*), 1810(*b*), 1810(*c*) and illumination elements 1812 to acquire one or more 2-D images of the target objects can be used in the laboratory automation system to detect the presence of and identify the target objects. The camera unit 1808 comprising the plurality of cameras 1810(*a*), 1810(*b*), 1810(*c*) is arranged on top of an input unit 202 facing the input area including the target objects. In this example, the target objects comprise sample tubes being provided in racks 1806 provided on a plurality of parallel drawers 216 of the input unit 202. As shown, the plurality of cameras 1810(*a*), 1810(*b*), 1810(*c*) can capture different images 1820(*a*), 1820(*b*), 1820(*c*). Adjacent images 1820(*a*), 1820(*b*) and 1820(*b*), 1820(*c*) can overlap so a larger image can be stitched together if desired.

The 2-D images obtained by the plurality of cameras 1810(*a*), 1810(*b*), 1810(*c*) can then be further processed by image analysis software to detect the presence of and to derive characteristic features of the target objects (e.g., sample tubes and racks), such as tube cap indicators, rack markers, circular barcode labels, cap or rack color and shape, etc. Either a series of images can be acquired by the camera unit 1808 during the movement of the drawers 216, or an overview image of the input area can be made in a closed state for the drawers 216.

FIG. 28(*c*) depicts another embodiment of a camera unit for sample tube or rack detection and analysis. A camera unit 1814 (e.g., 2-D arrays or line scanners) having a camera 1816 and illumination elements 1818 to acquire 2-D images for target objects can be used in the laboratory automation system to detect the presence of and identify the target objects.

The camera unit 1814 is coupled to a lower end of a gripper 228 facing the input area. The gripper 228 comprises a gripper body 228(*a*) and gripper fingers 228(*b*), which can grip a sample tube 1840. The gripper 228 may also be attached to an X-Y gantry 1817 so that the gripper 228 can move in an X, Y, or Z direction. A series of images is acquired by the camera 1816 during the movement of the input gripper 228.

In this example, the target objects are one or more sample tubes being provided in one or more racks 1806 provided on the drawers 216 of the input unit 202. The 2-D image can then be further processed by image analysis software to derive characteristic features of the target object (e.g., sample tubes and racks), such as tube cap indicators, rack markers, circular barcode labels, cap or rack color and shape, etc.

When the camera unit 1814 takes a series of images, the images can be stitched together by the analysis tool to generate an overview image. Within this overview image, single objects can be detected by image analysis performed by the analysis tool. For example, single objects such as markers on the holding racks or a cap or closure of a sample tube located in a holding rack can be detected using image analysis.

The embodiment in FIG. 28(*c*) has advantages. For example, using this embodiment, a image can be taken of a sample tube rack with samples, and the image can be analyzed, and the gripper can be instructed to select the appropriate sample tube from the sample tube rack and/or place a tube in a vacant sample tube location in the rack. The gripper and its robotic arm and process information while it is moving, thereby resulting in a very efficient process.

Figure 29:
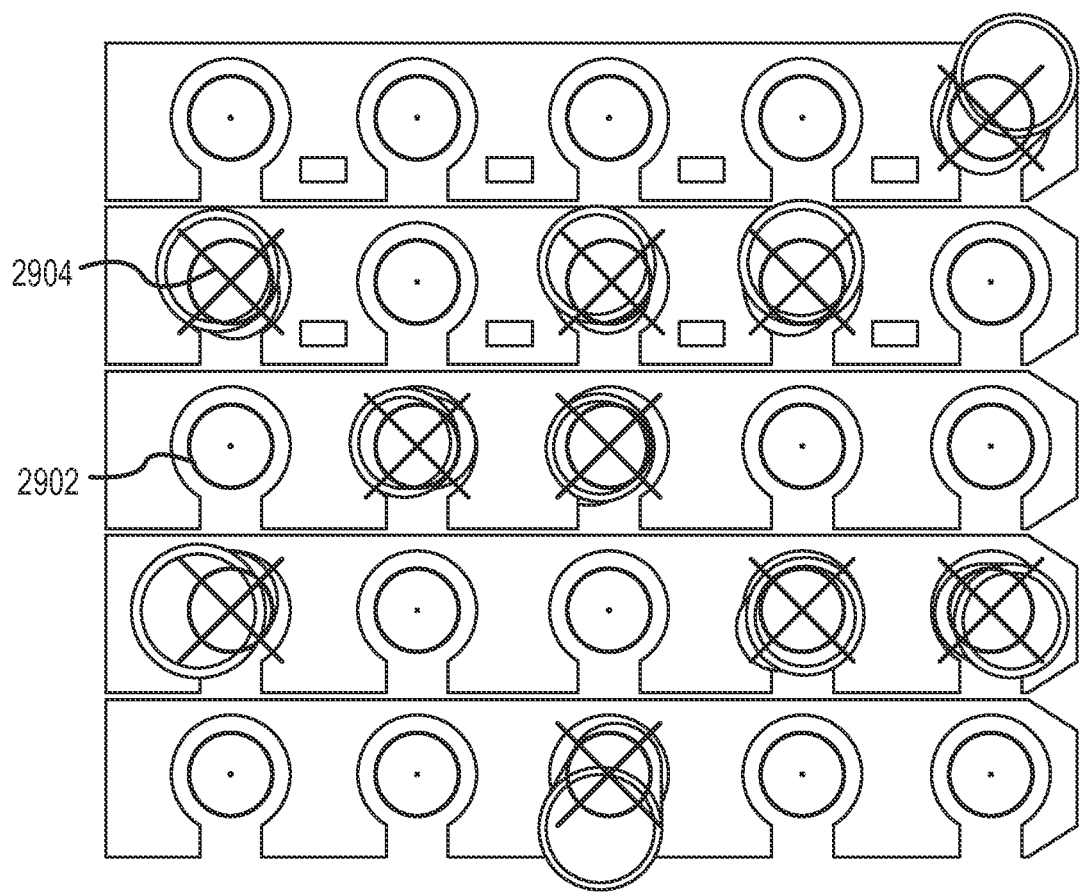
FIG. 29 depicts an example overlay image of an original image and the highlighted analyzed image of the sample tube identification in a sample rack based on a top-view image.

FIG. 29 depicts an example overlay image of an original image and the highlighted analyzed image of the sample tube identification in a sample rack based on a top-view image. Detected potential positions for a sample tube are highlighted with circles 2902, while a detected sample tube is indicated by a cross 2904. Shape recognition software can recognize outlines of potential locations for sample tubes by recognition of particular shapes for the recesses that can receive the sample tubes. In some cases, the recesses in the rack may be colored to assist in the recognition of the empty recesses. Other rack locations with sample tubes cover the empty recesses, and may therefore be considered to be filled with sample tubes. A map of circles and crosses can be formed as shown in FIG. 6, and this can be overlaid on a top plan view image of the rack with the tubes. In some cases, the particular characteristics of the rack and the locations for sample tube placement (e.g., recesses) can be previously mapped and stored in a memory in the system. Thus, embodiments of the invention may determine the presence and/or absence of a sample tube at a particular rack location in a rack.

The analysis tool according to an embodiment of the invention is also capable of deriving details such as cap color, cap shape, markers or labels on the cap for a single sample tube in a holding rack, etc. The derived details may then be used to optimize the subsequent process steps for the laboratory automated system.

B. Sample Tube Marker

1. Urgent Sample Indicator

The laboratory automation system can utilize a sample status indicator device, which can provide an easy way to mark a sample tube as an emergency or urgent tube requiring immediate analysis, without the application of additional material on the sample tube. Currently, sample tubes may be marked with self-adhering labels (e.g., colored labels indicating urgency), "urgent" stickers, of just by using a handwritten note indicating urgency on already existing labels. The urgent sample indicator mechanism of the present technology can indicate urgency or status of the sample without the need to label or handwrite the indication.

The sample status indicator device includes a manually moveable element of the sample tube cap, wherein the moveable element can be moved to at least a first position and a second position. When the moveable element is moved to a first position, a window may display a first status of the sample tube (e.g., normal or non-urgent). When the moveable element is moved to a second position, the window may display a second status of the sample tube (e.g., a mark indicating an urgent status). The indicator or marker can be read by operators as well as by an automated system. The indicator or marker can be a particular color, characters, numbers, icons, etc.

For example, as soon as tubes with different priorities get collected in a multiple-tube rack, the conventional labels may get covered by the rack itself of by neighbor tubes, thus making it difficult to recognize such labels or stickers as an emergency mark for automated processes. In conventional situations, presorting must typically be performed. The urgent sample indicator of the present technology can provide the visual marker on the top of the tube so that the urgent tubes can be recognized immediately by users as well as by an automated process via image processing. This allows the user to mix emergency samples together with lower priority samples in a rack or bag for transport. Undetected emergency samples become unlikely, and additional presorting may not be required.

The indicators in embodiments of the invention can be status indicators. Examples of particular tube statuses include, but are not limited to the particular priority associated with a tube (e.g., urgent, not urgent, STAT, etc.), the particular processing desired for a tube (e.g. centrifuge, aliquot, etc.), etc.

In one embodiment, the markers are not limited to emergency or prioritization marking, and can alternatively allow for several visual predefined marks, such as container content material, additives, reagents, etc., without the need for different parts. The moveable element can be moved (e.g., a first direction or second direction) to a certain position so that the window displays a particular indicator.

In one embodiment, the positions to which the moveable element can be moved may have a mechanical latch function or a limitation device to switch between two or more positions. This prevents the moveable part from being accidentally moved to an incorrect position.

Figure 30:
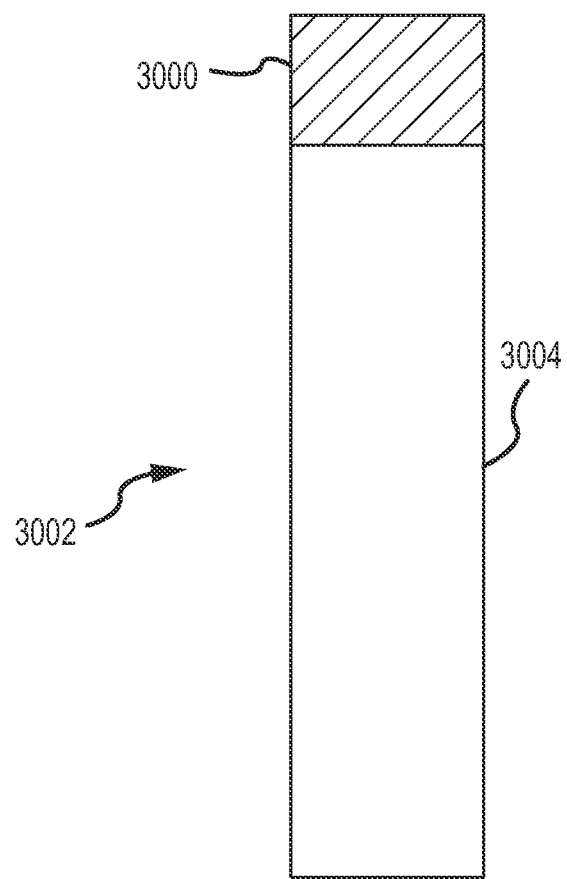
FIG. 30 shows an illustrative sample tube.

FIG. 30 shows a view of a sample tube 3002 comprising a sample tube body 3004 and a cap 3000 on the sample tube body. A sample such as a biological sample can be present in the sample tube 3002. The sample tube body 3004 may comprise a transparent or translucent material comprising plastic or glass. The sample cap 3000 may also comprise a material such as plastic.

FIGS. 31(a)-31(b) depict one example of a cap 3000 having a movable element that expose or not expose an urgent sample indicator.

In FIG. 31(a), the cap 3000 comprises a cylindrical cap body 3000(a) and a movable element 3000(b) at a top region of the cylindrical cap body 3000(a). The movable element 3000(b) may rotate so that a window 3000(b)-1 exposes a non-urgent indicator 3004. The non-urgent indicator 3004 may be a color such as green to indicate that the sample is to be processed in a non-urgent manner. Handles 3000(b)-2 in the form of protrusions may be present in the movable element 3000(b) to allow a human, a gripper or other element to move the movable element 3000(b) change the status of the sample tub. While handles are described in detail, embodiments of the invention can include other types of handling features such as holes.

In FIG. 31(b), the movable element 3000(b) is rotated an emergency or urgent position to expose an urgent sample indicator 3005. The urgent sample indicator 3005 may be red to indicate that the sample tube is to be processed as soon as possible.

While the indicators in FIGS. 31(a) and 31(b) are non-urgent 3004 and urgent 3005, it is understood that the sample tube cap 3000 shown in FIGS. 31(a) and 31(b) could have other types of indicators. For example, the indicators may indicate that a sample is to be processed by a particular machine, by a particular process, in a particular order, etc.

The cap 3000 and its indication of sample tube status can be viewed by the camera units shown in FIGS. 28(a)-28(c) and can be identified, and processed as described above.

2. Centrifugation Indicator

The laboratory automation system can utilize a centrifugation status indicator device, which can indicate whether a sample has been centrifuged. Generally, the majority of sample tubes in a lab require centrifugation since only their serum is used for analysis. When a sample tube sits for long period of time, there is sedimentation of the sample so that the sample appears visually to have been spun. Additionally, it could become less apparent that a pre-spun sample was actually already spun if the sample were shaken (e.g., during transport). If sample tubes that have been sitting for a period of time and pre-spun sample tubes are mixed, a user may not be able to discern which samples tubes were actually already spun. Furthermore, it may be difficult for a user to visually determine the quality of the centrifugation (e.g., whether or not the spin time and force (minutes*g) was sufficient or not).

The centrifugation status indicator device of the present technology provides a way to visualize the centrifugation status of a sample tube. The centrifugation status can be read by users or by a lab automation device independent from the actual appearance of the blood or other sample in the sample tube. The centrifugation indicator prevents user error which could result in incorrect test results. The centrifugation indicator provides a visual mark which changes its appearance during centrifugation according to the centrifugation time and force, but keeps its state under normal tube transport conditions.

The visual marker of the centrifugation indicator may be on the top of the sample tube so that it can be recognized immediately by users as well as by an automated process via image processing. It allows pre-spun samples to be mixed with un-spun samples in a rack and avoids the manual presorting of samples prior to automation entry. In one embodiment, the centrifuge indicator can be part of the sample tube cap for covering the sample tube.

Additionally, the centrifugation quality can be determined automatically and subsequent processes in the laboratory automation system can be controlled according to the result. One embodiment of a centrifugation indicator is shown in FIG. 32(a). The centrifugation indicator depicted includes a small container (which may be in the form of a cap housing) with a transparent top containing a colored gel 3202 (e.g. white) and particles 3204 of a different (e.g., higher) density and with a different color (e.g. blue). Using the example of white gel 3202 and blue particles 3204, the initial appearance of the container may be light blue when the two components are initially mixed, or the appearance may be blue in case the particles are on top of the gel 3206. During centrifugation, the blue particles move to the bottom of the container due to the higher density 3208, and the top appearance changes to white due to the lack of particles 3210. The combination of the chosen materials provides the possibility to gain different appearances according to the applied centrifugation force and time. Additionally, more than one type of particles can be used to get a finer resolution of the applied spin time and force.

In one embodiment, the centrifugation indicator is a transparent cylinder that is pressed onto a pressure sensitive device (e.g., pressure indicating film) which changes its appearance according to the applied centrifugation force. FIG. 32(b) depicts an example of this type of centrifugation indicator. The centrifugation indicator includes the pressure sensitive device 3212 (e.g., foil) in a transparent cylinder 3214, which may comprise a transparent material such as a transparent gel. The transparent cylinder 3214 allows the pressure sensitive device 3212 to be displayed. When the sample is not spun 3216, the pressure sensitive device 3212 may have a transparent appearance. During centrifugation 3218, the pressure sensitive device 3212 on the centrifugation indicator may have an appearance of one particular color. Once the sample tube has been spun 3220, the pressure sensitive device 3212 on the centrifugation indicator may have another appearance of another particular color. One example of a pressure sensitive device 3212 may be Prescale™ film by Fujifilm™.

Figure 33A:
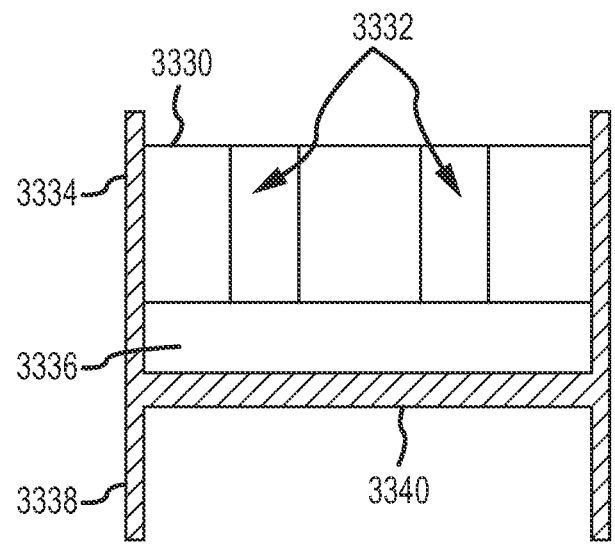
FIGS. 33-34 show a cap with a pressure sensitive device.

FIG. 33(a) shows a side, cross-sectional view of a cap with a pressure sensitive device 3336 in the form of a foil. The cap is shown in a non-centrifuged state. As shown, the cap can include a body with a cylindrical cap thread portion 3338 and a cylindrical cap top portion 3338 separated by a perpendicular circular horizontal portion 3340. A pressure sensitive device 3336 is on the horizontal portion 3340. A plurality of transparent posts 3332 may be on the pressure sensitive device 3336, and the top surfaces of the posts 3332 may be covered with an optically transparent cover 3330 (e.g., made of transparent plastic).

Figure 33B:
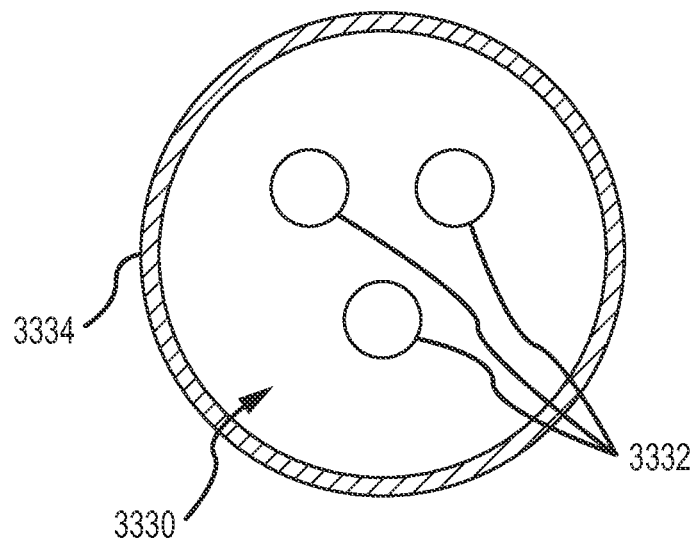

FIG. 33(b) shows a top plan view of the cap in FIG. 33(a). In FIGS. 33(a) and 33(b), like reference numbers designated like elements. As shown, the pressure sensitive device 3336 may be a first color when no pressure is applied to it.

Figure 34A:
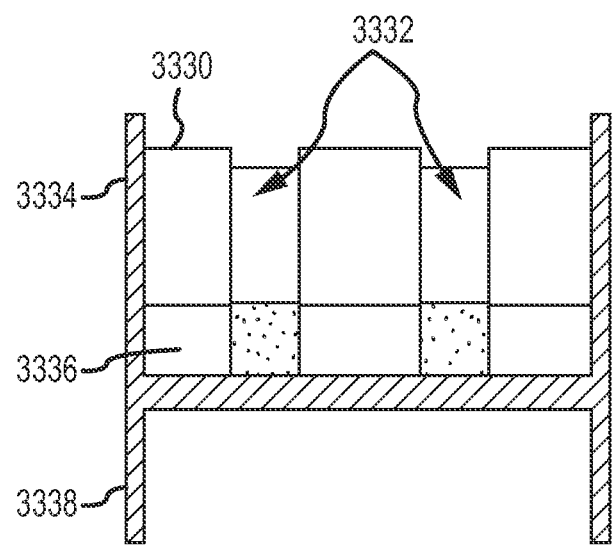
Figure 34B:
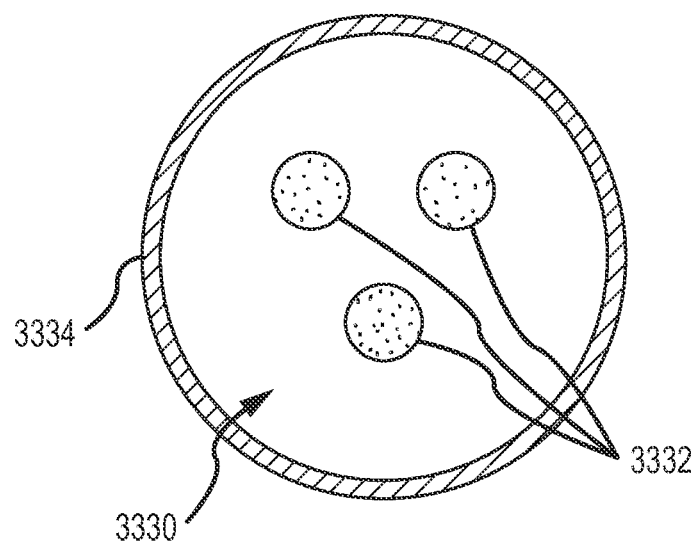

The same cap is shown in FIGS. 34(a) and 34(b). However, this cap is shown after centrifugation. As shown, the posts 3332 applied downward pressure on the pressure sensitive device 3336 causing a color change in the pressure sensitive device 3336 at areas under the posts 3332. When viewed from the top in FIG. 34(b), a distinct pattern of three dots (of a second color) is shown against a background of a different color (e.g., the first color). This pattern can be viewed by a camera looking down on the cap, and an analysis device coupled to the camera can determine that the sample tube with the cap contains a centrifuged sample (as described above with respect to FIGS. 28(a)-28(c).

3. Barcode

The laboratory automation system can utilize a barcode identification device to identify samples. Barcodes may be applied to sample containers. For example, a circular barcode may be applied to the top of a sample tube cap. A circular barcode can provide for an easy and fast way to identify the sample tubes before they get handled by the input gripper for the first time.

VI. Frame and Modularity Concept

A continuous and thus cost-effective use of a transportation system depends on the uptime of the system. For example, the temporary unavailability of subassemblies within the system due to failure, maintenance, scheduled service, etc. may cause a complete stop of the entire system. Thus, in order to avoid or minimize the downtime of such a transportation system, the system may be designed and formed by single independent processing modules connected to a main transport unit that continues working even if one or more modules may not be available.

The present technology uses frames or modules for different components of the laboratory automation system. As discussed above, one embodiment may include a manager unit, a centrifuge unit, an aliquotter unit, an output/sorter unit, and a storage unit. The single processing modules may be independently controlled by local controllers but may stay in continuous communication with a central controller unit for the entire laboratory automation system. This may ensure optimized scheduling of processing steps for single objects and enable the recovery of error conditions in the systems caused by an unexpected unavailability of a single processing module.

The processing modules may represent processing stations designed to conduct processes on the single objects, transported by the main transport unit. The modules may either act directly on the main transport unit or utilize a corresponding processing module transport unit that may direct single objects from the main transport unit through openings between the transport units to the processing station and back to the main transport unit.

Additionally, the processing modules may be received and guided by frames, firmly connected to the main transport unit for transporting a sample. The frames may be part of the main transport unit and may act as support for the main transport unit in case the processing unit is detached from the system.

In order to enable the mechanical attachment and detachment of processing modules to the supporting frame or main transport unit, the processing modules may be moved on casters and guided in or to the frames by means of guiding rails. Additionally, positioning adjustment means may be provided, either in the supporting frames or with the single processing modules. For example, to enable electronic connection for power supply and/or communication between local and central controllers, a plug-in connection may be provided between the processing module and the main transport unit/frame.

Figure 35:
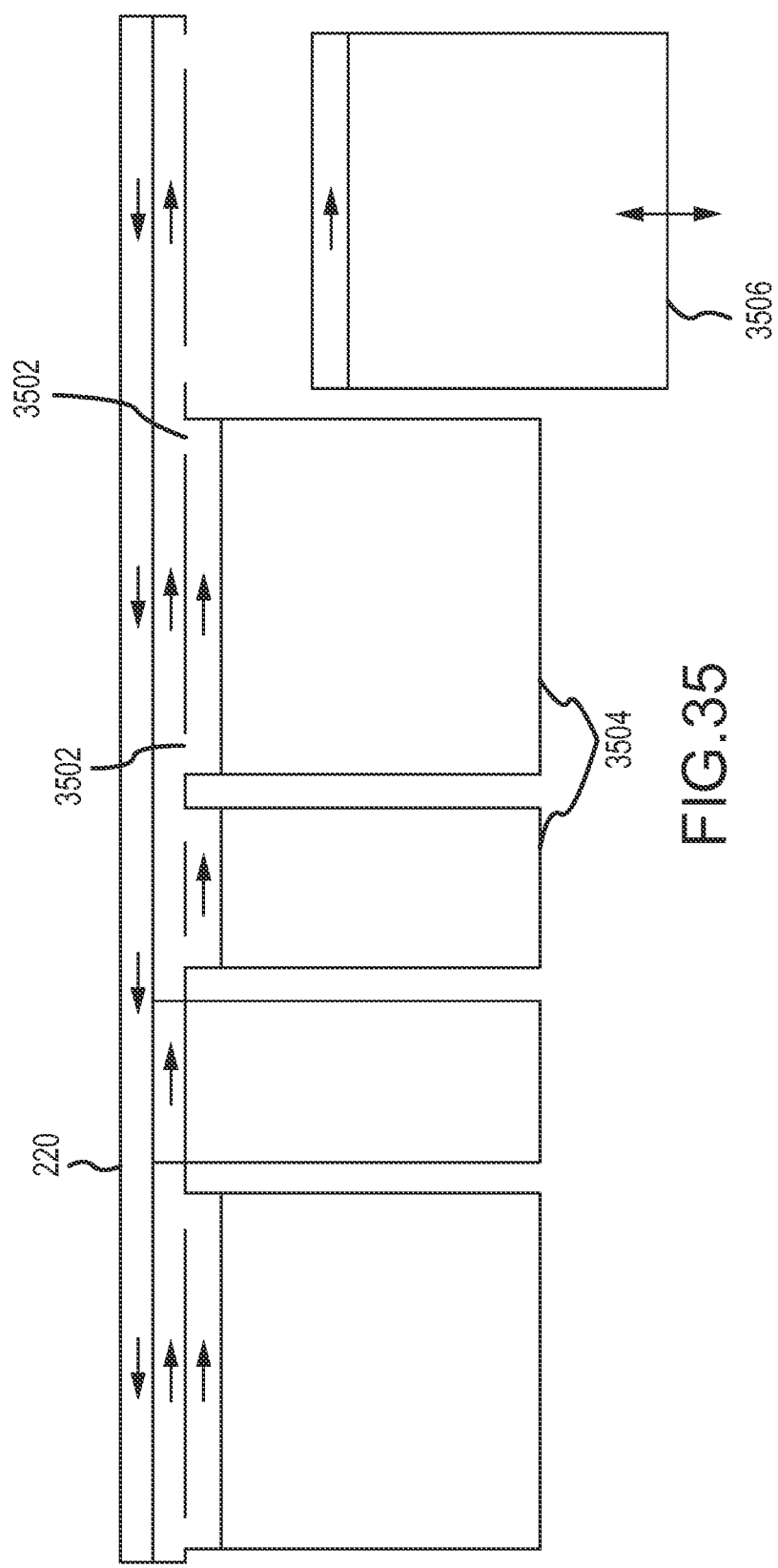
FIG. 35 depicts one example of a top view diagram of an object transportation system showing a main transport system and several processing stations arranged as units or modules.

FIG. 35 depicts one example of a top view of an object transportation system showing a main transport system and several processing stations arranged as units or modules in the laboratory automation system. The processing modules 3504 can electrically and/or communicatively attach to the main transport unit 220 at connection openings between transport units 3502. The modules are movable 3506, allowing a module to either be removed or attached to the main transport unit 220. Any of the previously described modules (e.g., centrifuge module, aliquotter module, etc.) can be used in the embodiments shown in FIG. 35, as well as FIGS. 36-37.

For each processing module, a local controller unit may be provided to monitor the status and functionality of the module. A central controller unit of the laboratory automation system may schedule the transportation of sample tubes to each module based on the availability of the single processing stations' processes that are to be conducted on a single object. Sensor means within the frame or main transport unit may detect the presence or absence of a processing unit.

Figure 36:
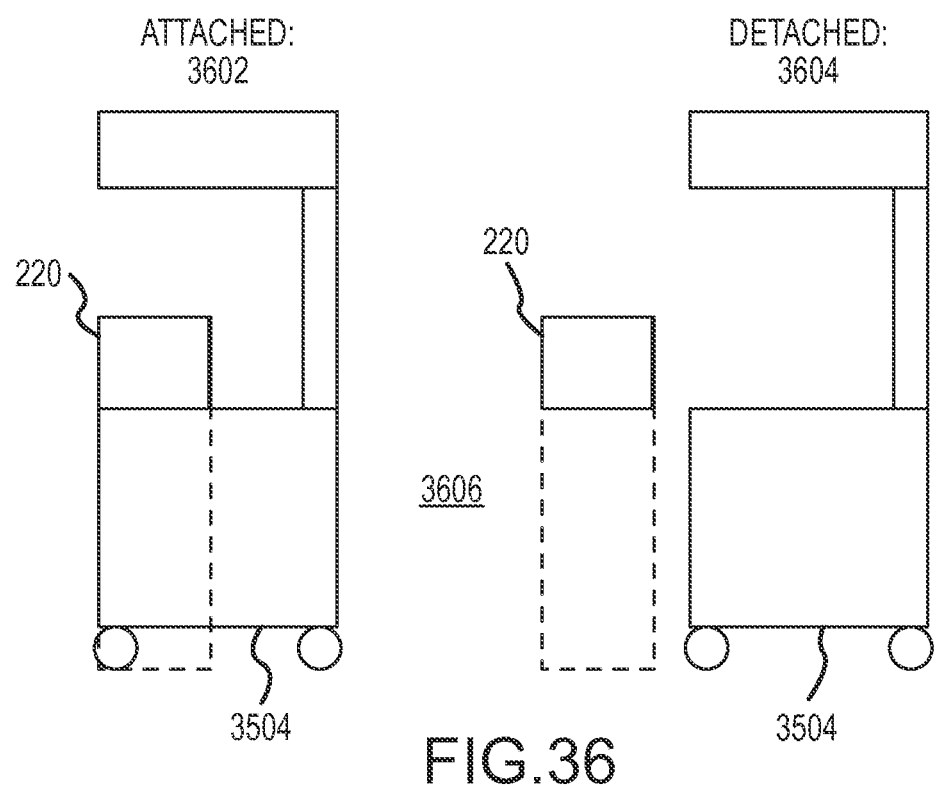
FIG. 36 depicts an example of a side view diagram for processing modules attached and detached to a main transport unit.

FIG. 36 depicts a side view for processing modules 3504 attached 3602 and detached 3604 to the main transport unit 220. When the processing module 3504 is attached 3602, it may be attached via a frame 3606. The processing module 3504 can also be detached 3604 from the frame 3606 when it is not being used in the laboratory automation system. When the processing module 3504 is detached from the object transportation system, the main transport unit remains supported and as part of the frame for the object transportation unit.

FIG. 37 depicts a side view of a processing module with an extra transport unit. The extra transport unit can be attached to and detached from the main transport unit along with the processing module. When the processing module 3504 is attached 3602, the processing module 3504 along with the extra module transport unit 3702 can be attached to the main transport unit 220 via the frame 3606. The processing module 3504 along with the module transport unit 3702 can also be detached 3604 from the frame 3606 and thus the main transport unit 220 when it is not being used by the laboratory automation system. When the processing module 3504 is detached from the main transport unit 220, the main transport unit 220 remains supported and as part of the frame for the object transportation unit, and the module transport unit 2602 gets automatically detached with the processing module 3504.

In the case of a scheduled maintenance or an unexpected failure of a single processing module, the corresponding local controller may be able to send a signal to the main controller and request the approval for detaching the processing module from the system. Furthermore, the user or the central controller may initialize the detachment procedure for a single processing module.

In one embodiment for detaching a processing module, the central controller, on request, may stop scheduling samples to the particular processing unit. At this point, the central controller may reschedule all objects requiring the unavailable processing module to another equivalent processing module if the other equivalent processing module is available. Alternatively, the central controller may instead reschedule all objects requiring the unavailable processing module to an error position.

If the central controller reschedules all objects requiring the unavailable processing module to another equivalent processing module, the central controller may indicate to the user by, e.g., graphical interface, or other similar notification means, to detach the module. In the case of an unexpected failure, the user may be notified that the user should either fix the problem and restart the module or perform user maintenance.

In one embodiment, if the module that is unavailable is a processing module that is critical to the laboratory automation system, the central controller may stop the main transport unit 220 so that the critical processing module can be addressed.

VII. Transportation of Samples

The laboratory automation system may have one or more means of transporting sample tubes from one location within the system to another location. Three types of laboratory transport systems (puck transport system, conveyor transport system, and magnetic transport system) will be described in more detail below.

When a sample tube is carried from one location to another via a particular transport system, the sample tube may be placed in a carrier and then transported. These carriers may also be used for fixed tube positions within the laboratory automation system. Samples tubes may have a variety of tube types and sizes, and the laboratory automation system may need to be able to handle these different sample tube geometries. This may require a carrier that can accept differing tube geometries and fix them adequately within the carrier for automatic processing. Sample carriers used to date typically lack the ability to fix all tube geometries in the carrier adequately and typically block the bottom portion of the sample tube from barcode scanning. The carrier of the present technology may allow for carrying sample tubes of a variety of geometries using a low tube insertion force. A low insertion force may help to preserve the sample quality since less force would result in less shocks/vibrations and therefore less probability that samples would become remixed during the carrier loading. When the carrier is loaded with a sample tube, the sample tube is captured, centered, and held vertically by surfaces parallel to the central axis of the tube by spring loaded inserts, allowing for repeatable locating of the sample tubes with the sample carrier. The carrier design further allows views of the side of the tube so that sample tube identification by barcode scanning is possible. The ability to read a barcode on a tube that has been placed too low with respect to the cap of the tube will save time that might otherwise have been spent having to manually scan the barcode, providing quicker and more consistent turnaround times.

In one embodiment, the sample carrier of the present technology has three jaws that are spring loaded toward the center of the carrier. As shown in FIGS. 38(a)-(e), the tube 3804 is inserted centrally to the jaws 3802, and the spring force is directed toward the center of the tube 3804 and carrier assembly. The low force sample tube insertion is due to the fact that the jaws 3802 rotate back as the tube 3804 is being inserted (FIGS. 38(a), (b), and (c)). The spring force is coupled to the jaws 3802, capturing the tube geometry. As this happens, the tube 3804 is centered and held vertical as the jaws 3802 are spring loaded such that they are forced toward the center of the tube 3804. The interior surface of the jaw 3802 is 'V' shaped to capture the cylindrical side of the sample tube 3804 (FIGS. 38(*d*) and (*e*)). The carrier holds the tube 3804 such that the side of the tube 3804 is visible from top to bottom for scanning the sample identification label with a barcode scanner.

Figure 39:
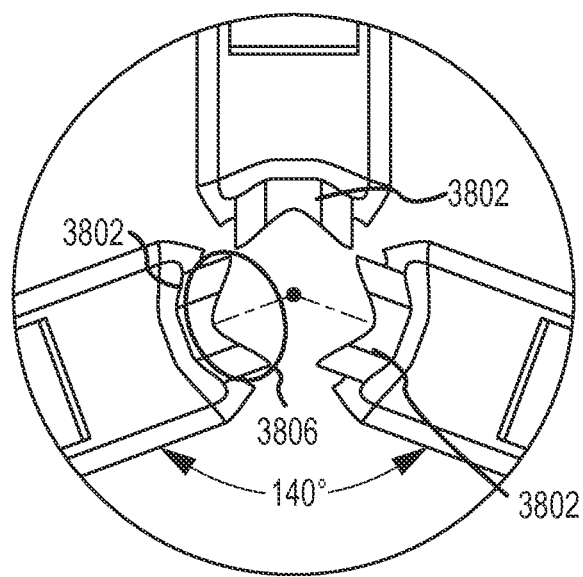
FIG. 39 depicts a top view diagram of jaws of a sample tube carrier.

FIG. 38 depicts one example of the jaws 3802 of the carrier. The orientation of the three jaws 3802 depicted in FIG. 39 provide visibility of the tube's barcode. In the example of FIG. 39, the two lower jaws are placed 140° apart. This may allow better visibility of the barcode than, e.g., three 120° angles. However, any angle can be used. The resulting "side force" on the two lower jaws, in combination with the 'V' shape 3806 of the jaws 3802, helps hold the tube sturdily in place.

A. Puck Transport System

The puck transport system is an autonomous guided vehicle for transporting an individual sample tube. Current chain or belt-driven transportation systems can only control the velocity of the complete track segments. Even if it is possible to have chains with different or even adjustable velocity, it may be difficult to move each individual track with its own velocity. In other words, the puck transport system with the lowest velocity or lowest acceleration/deceleration would dictate the complete segment. The puck transport systems described herein can be further understood with reference to U.S. Provisional Patent Application No. 61/486,126, filed May 13, 2011 and entitled "System and Method Including Laboratory Product Transport Element" and PCT Application No. PCT/US2012/037585. Other automated systems are described in U.S. Non-Provisional patent application Ser. No. 11/555,619 filed Nov. 1, 2006 and entitled "Automated Sample Processing System." All of these applications are incorporated by reference in their entirety for all purposes.

The puck transport system of the present technology provides a transport system that is a self-propelled sample transport unit. The puck transport systems can move samples using the necessary motion parameters and can do so independently from each other. The puck transport systems improve efficiency by maximizing throughput, even with varied statuses for different sample tubes (e.g., normal versus urgent), without the need to sacrifice or risk sample quality of sensitive samples, as each sample can be transported with the maximum velocity. Additionally, the puck transport system may be managed by the central controller or a local intersection controller.

Figure 40:
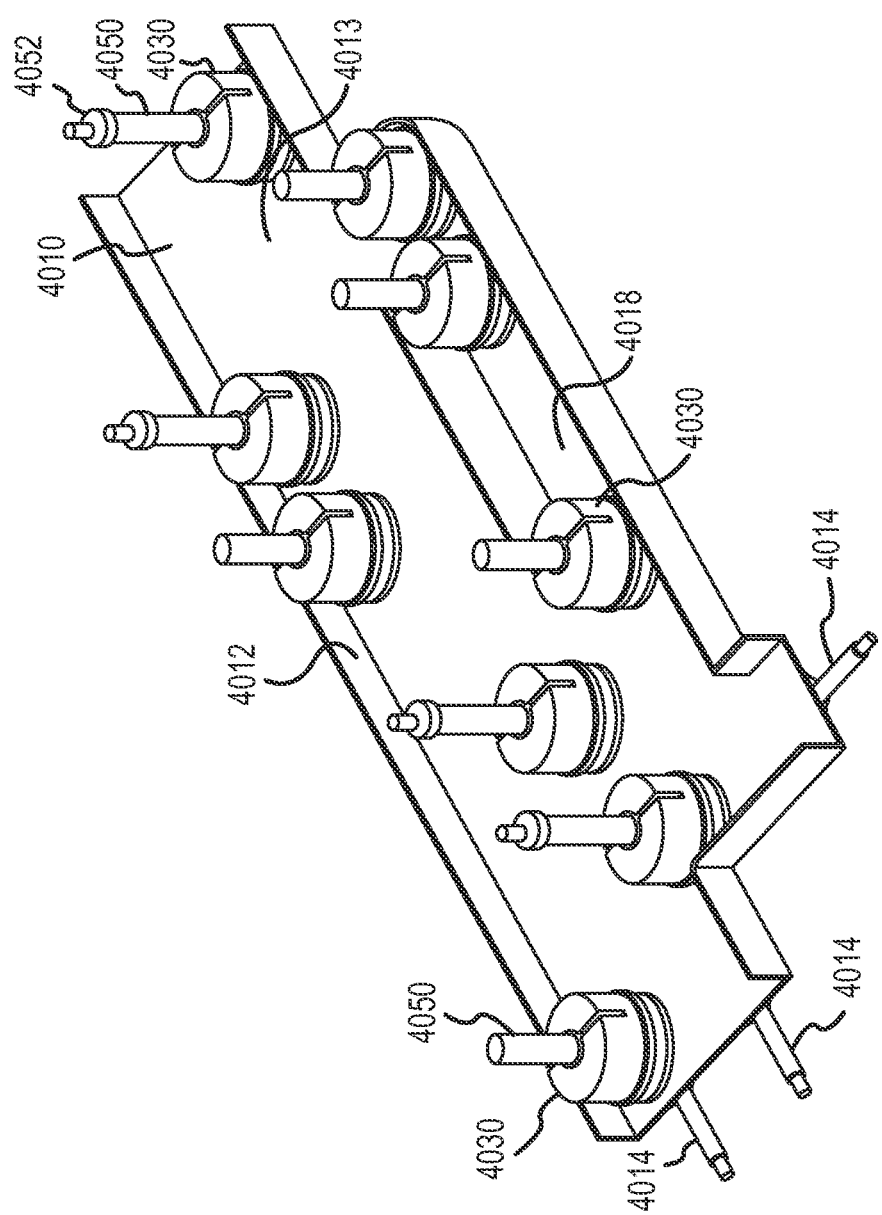
FIG. 40 depicts one example of a perspective partial view of a variant of a transfer path arrangement of a laboratory transport system utilizing the puck transport system.

FIG. 40 shows a perspective partial view of a variant of a transfer path arrangement of a laboratory transport system utilizing the puck transport system. A transfer path 4010, in particular, with side limitation 4012 and a flat horizontal web 4013 are visible. In this example, the side limitation 4012 can be in the form of a raised wall that can at least partially define the transfer path 4010. In this embodiment, there are two raised walls on opposite lateral sides of the flat horizontal web 4013, and the walls and the web 4013 can define the transfer path 4010. Such walls may be of any suitable height depending upon the height of the laboratory product transport element and the sample being carried therein, typically a height of no greater than about 20 mm. Further, the web 4013 can be of any suitable lateral dimensions.

Transfer paths according to embodiments of the technology can also have one or more branches that may lead to other areas. For example, the transfer path 4010 in FIG. 40 can have a lateral branch 4016 that leads to a separation processing station, buffer station, or some other station.

The laboratory transport system can use any suitable numbers or types of devices, which can help guide or move the laboratory product transport elements. As shown in FIG. 40, induction conductors 4014 can be arranged beneath the transfer path 4010. The induction conductors 4014 can be electrically coupled to a high frequency voltage source (not shown), so that they can be supplied with high frequency, in order to generate a high frequency electromagnetic alternating field.

The laboratory product transport elements 4030 that transport sample containers 4050 (e.g. sample tubes) can move on the transfer path 4010. However, the laboratory product transport elements 4030 can be transferred to a processing track 4018 in defined fashion in a row, in order to be able to carry out, for example, optical investigations of the sample material contained in the sample containers 4050.

Electrical conductors 4014 can be provided along the particularly probable paths of the laboratory product transport elements 4030. However, since the laboratory product transport elements 4030 can move independently, they are not bound to the geometry stipulated by the conductors 4014. Their movement is not dependent upon the conductors 4014, as long as the electromagnetic high frequency field generated with conductors 4014 at the location of the laboratory product transport element 4030 is sufficient for corresponding energy transmission or the laboratory product transport element 4030 has energy accumulator 4044 for bridging.

The sample containers 4050 may have any suitable shape or configuration. In some embodiments, the sample containers 4050 may be in the form of tubes. In some cases, covers 4052 may be on the sample containers, while other sample containers do not have a cover on them and are transported open.

Figure 41:
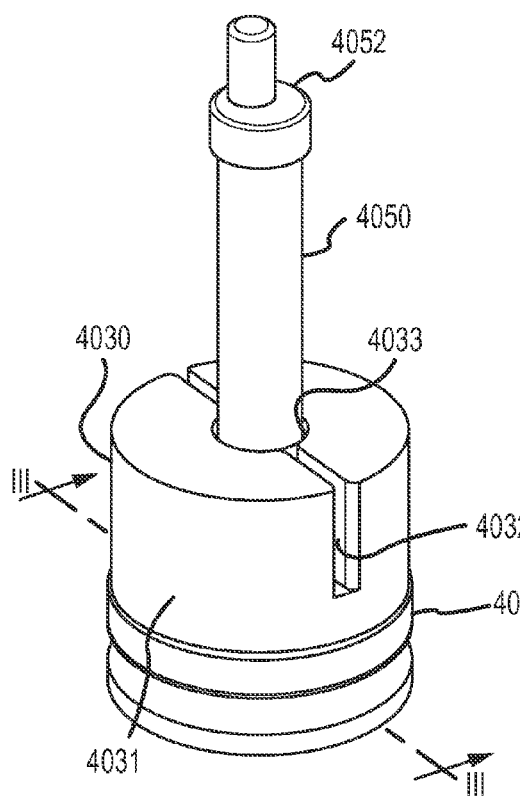
FIG. 41 depicts one example of a side perspective view of a laboratory product transport element.

FIG. 41 shows a side perspective view of a laboratory product transport element 4030 according to an embodiment of the technology. The laboratory product transport element 4030 comprises a laboratory product transport element housing 4031, which may have a cylindrical recess 4033 formed at the top of the housing 4031, which may also be cylindrical. A sample container 4050 with a cover 4052 on it may be received in the cylindrical recess 4033. A slit 4032 may be formed in the side of the housing 4031. The slit 4032 can permit optical investigation of the sample material contained in the sample container 4050, and may be coextensive with the recess 4033. In other embodiments, the slit 4032 need not be coextensive with the recess 4033 and may be formed independent of the recess 4033. Furthermore, in other embodiments, the slit 4032 can be an aperture that is in some other form (e.g., a circle).

In this example, the laboratory product transport element 4030 has a round horizontal cross section and has a rubber strip 4034, which serves as an impact protection against the limitations 4012 of the transfer path 4010 or other laboratory product transport elements 4030.

Figure 42:
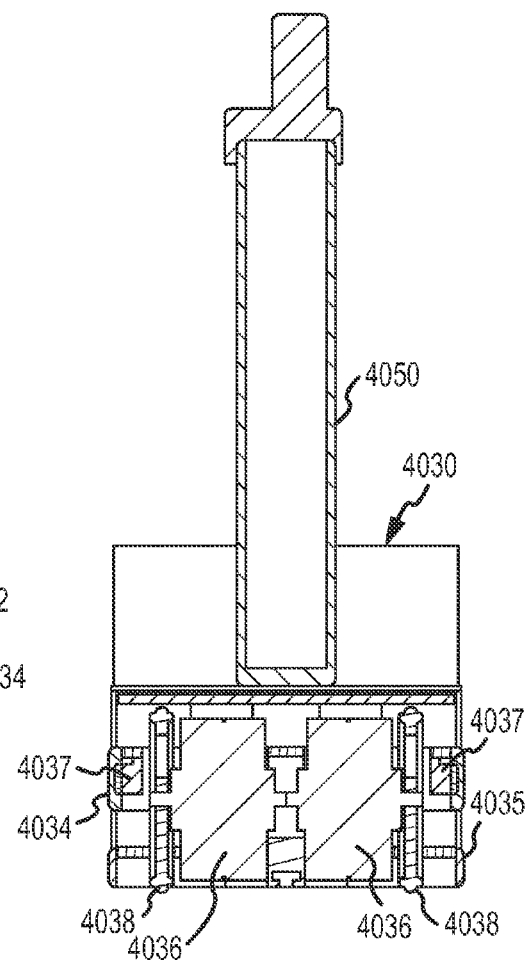
FIG. 42 depicts one example of a side section of a laboratory product transport element.

FIG. 42 shows a side section of the laboratory product transport element 4030 in the viewing direction III shown in FIG. 41. Reference numbers 4036 denote electric motors that drive rubber wheels or rubber-tired wheels 4038. Two opposite wheels 4038 are provided, which are driven individually by one electric motor 4036 each. The wheels 4030 may be examples of movement devices.

A shoulder 4035 is shown in FIG. 42, which can cooperate, for example, in transfer path channels configure more narrowly with optionally present side protrusions of limitations 4012 of transfer path 4010, in order to hold the laboratory product transport element 4030 down, when the sample container 4050 is to be pulled out upward from recess 4033. The use of shoulder 4035 illustrated in FIG. 42 can be described in further detail in the section "Fine Positioning and Lift-Off." In some embodiments, the laboratory product transport element (not shown in the Figures) can have an anchor-like element. The anchor-like element engages in a corresponding mating piece of the transfer path upon entering a processing station, in order to secure the laboratory product transport element during its stay at the processing station.

The laboratory product transport element 4030 may also comprise distance sensors 4037. In FIG. 42, the distance sensors 4037 may include four distance sensors which are arranged behind the rubber strip 4034 at angles relative to each other. One preferred embodiment is to have all of the sensors facing forward and at an angular relationship to each other of between 10° and 30°, a more preferred embodiment of 20°.

Figure 43:
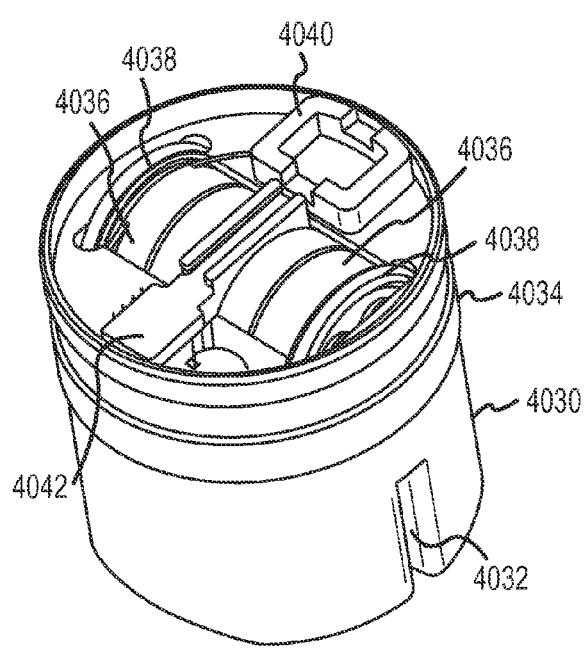
FIG. 43 depicts one example of a bottom perspective view of a laboratory product transport element.

FIG. 43 shows a bottom perspective view of the laboratory product transport element 4030 according to an embodiment of the technology. The induction coil 4040 serves to receive electromagnetic energy from the high frequency fields, which can be generated from electrical conductors 4014 beneath the transfer path.

In some embodiments, it is possible that one or more support wheels are provided, in addition to the driven rubber wheels 4038, so that the laboratory product transport element 4030 rolls on several wheels. However, in other embodiments, no additional wheels are provided, so that the laboratory product transport element, during movement, can lie dragging on one side. This can facilitate curved travel or rotation around its own axis.

In another embodiment of the technology (not shown), the laboratory product transport element 4030 is supported on a ball rotatable in all directions, which is arranged offset to the two driven wheels 4038, in order to avoid dragging on the transfer path. Such a ball can also be used for position detection, as in a computer mouse.

In the embodiment shown in FIG. 43, reference number 4042 denotes a position detector that determines movement of the laboratory product transport element 4030, as in a computer mouse that uses laser light. The traveled surface is then illuminated by an incorporated light source and the reflections taken up with an optical sensor, in order to determine movement of the laboratory product transport element 4030 from them with corresponding image processing algorithms. The position detector 4042 can include a CCD camera and corresponding software, a laser as in a laser mouse, or a ball and sensor as in a ball-type mouse.

Figure 44:
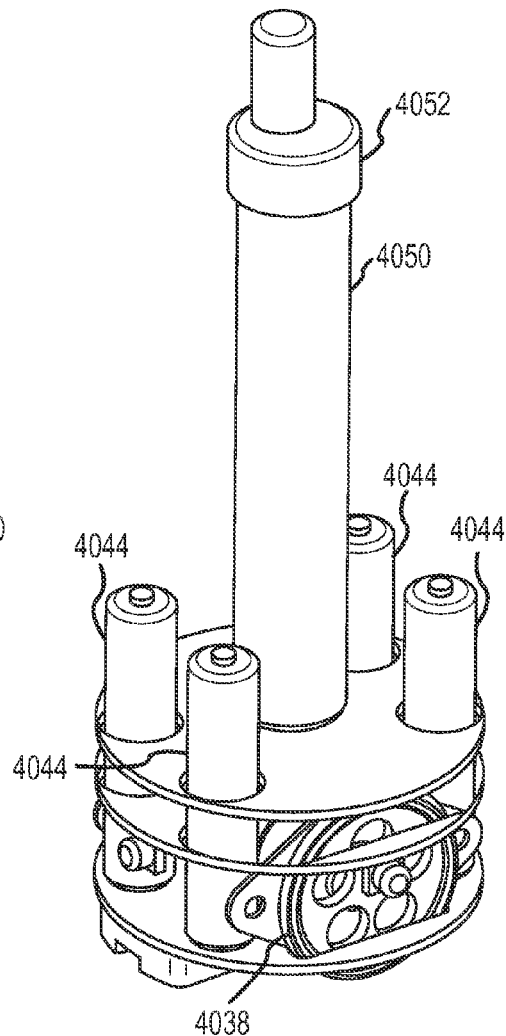
FIG. 44 depicts one example of a laboratory product transport element without external side protection.

FIG. 44 shows the laboratory product transport element 4030 without external side protection. That is, a housing can be removed to show the internal elements of the laboratory product transport element 4030. As shown in FIG. 44, the laboratory product transport element may include batteries 4044. The batteries 4044 can serve to store energy in order to drive of the laboratory product transport element 4030, when the energy generated by the high frequency field of electrical conductors 4014, shown in FIG. 40, and transferred to the induction coil 4040, as seen in FIG. 43, might be too limited. or disabled, to drive the laboratory product transport element 4030. This might be the case, for example, in curves or passing zones.

The laboratory product transport element 4030 also comprises a control unit (not shown), for example, a corresponding microprocessor that receives signals from signal receivers (also not shown). The signal receivers may include infrared light receivers that cooperate with external infrared light transmitters, in order to receive the control signals. Other examples of signal receives may include radio sensors.

Control signals, however, can also be received via the induction coil 4040, as seen in FIG. 43, when corresponding signals are supplied to the electrical conductors 4014, as seen in FIG. 40. Such control signals can be discriminated from the high frequency field that furnishes energy by a corresponding frequency or amplitude modulation.

The laboratory product transport elements 4030 also may optionally have signal transmitters, not shown, in order to produce information and signals. This permits, for example, precise localization of individual selected laboratory product transport elements 4030. The signal transmitters may transmit signals using any suitable frequency and any suitable communications protocol.

Figure 45:
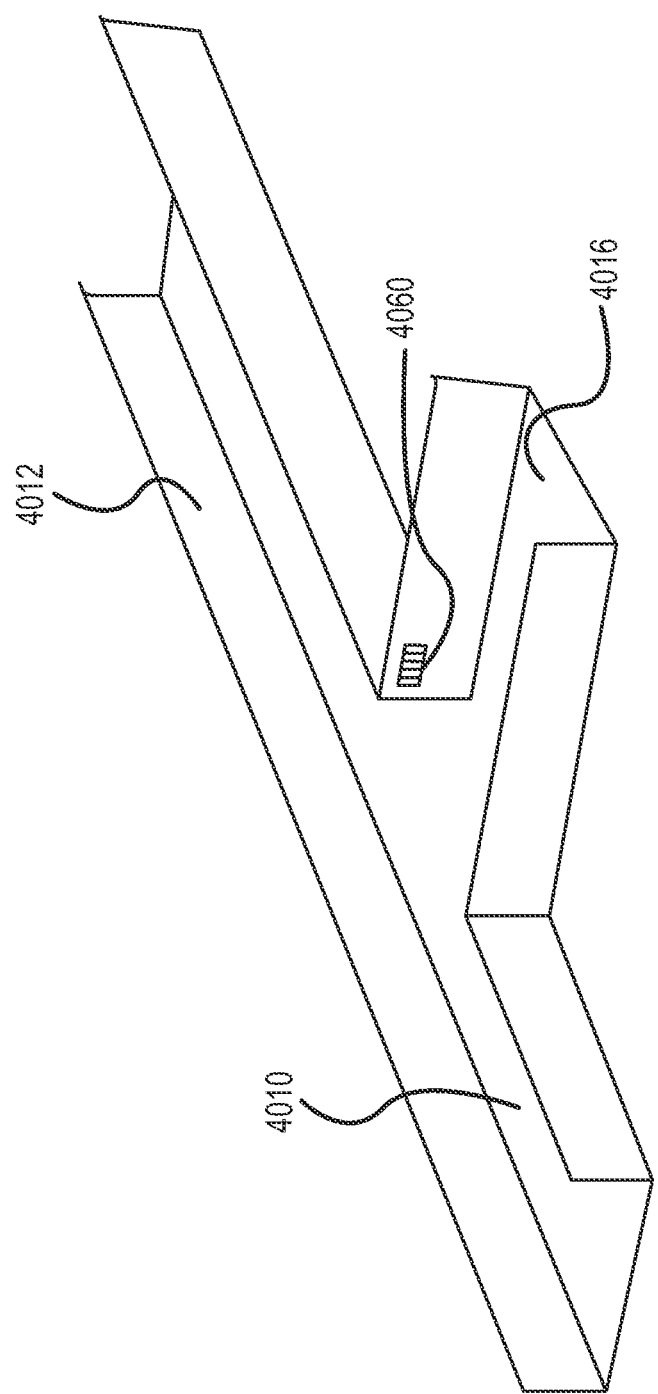
FIG. 45 depicts one example of a cutout of a transfer path.

The laboratory product transport elements 4030 can also have a number of sensors, with which position recognition and fine positioning at processing stations, recognition of the travel path limitation or other laboratory product transport elements, or information exchange is possible. For example, clearly identifiable barcodes can be provided on the transfer path 4010 shown in FIG. 40, either on a side limitation 4012 or a flat horizontal web 4013. The barcodes can be scanned by a laboratory product transport element 4030 with one or more sensors configured as scanners, in order to recognize the precise position of a branch or the precise position of a processing station. An example is shown in FIG. 45 by means of a cutout of a transfer path 4010. A barcode 4060 is situated at a branch 4016, which can be recognized and identified by corresponding scanners of a laboratory product transport element. In this way, the laboratory product transport element obtains information concerning its position. A number of such codes could be provided on the transfer path 4010, which clearly identify the branches, processing tracks, processing stations or the like.

Other possibilities of such orientation features include 2D codes, color marks, reflection films, transponder systems or infrared light transmitters. Suitable sensors capable of sensing such orientation features can be incorporated into the laboratory product transport elements.

The laboratory product transport element 4030 can have a display unit. It can display information as to which path the laboratory product transport element is to take, which laboratory product is being transported, or whether a defect is present. Further, laboratory product transport elements 4030, with signal transmitters and receivers or with display and recording units, can also exchange information with each other either directly via internal communication transmitters, or via a central processor.

In the interior of the laboratory product transport element 4030, a permanent data memory, protected from current failure, can be provided, in which data about the transported laboratory product or data about the path being traveled can be entered.

The diameter of the laboratory product transport element 4030 depicted in the Figures is about 6 cm at a height of about 5.5 cm. The wheels 4038 protrude about 1 mm downward from the laboratory product transport element 4030. The laboratory product transport elements and features thereof may have other suitable dimensions in other embodiments of the technology.

The laboratory product transport element 4030 according to an embodiment of the technology can also have a heating device (not shown). The heating device can keep a sample at a defined temperature during transport or can carry out a defined temperature treatment of the transported sample during the transport. Such a heating device can include, for example, resistance wires which are provided in an appropriate arrangement.

A laboratory transport system according to an embodiment of the technology of the depicted variant can be used, for example, as follows:

Sample containers 4050 are inserted into laboratory product transport elements 4030 at a loading station by using a stationary gripper system or other container transport system. A target is stipulated to the laboratory product transport element via its signal receiver. The geometry of the actual transfer path 4010 can be encoded and entered in a memory of the laboratory product transport element 4030. The control unit of the laboratory product transport element 4030 can identify the stipulated objective by using data about the transfer path geometry entered in the memory and can independently establish an ideal path to this objective. The locations of orientation features, for example, barcode 4060, are also entered in the memory, so that the laboratory product transport element 4030 can orient itself during its travel along a path, and to check its current position or correct it, if necessary.

After a start signal is induced in the laboratory product transport element 4030, the laboratory product transport element 4030 is moved on the pre-defined path established in its memory. If it passes by a barcode 4060, at which a direction change is to be made, the barcode 4060 recorded with the scanner is used as signal by the control unit, in order to make a direction change in the desired direction.

If the laboratory product transport element 4030, for example, reaches a location, at which a direction change is prescribed, one of the drive motors 4036 is stopped or slowed, so that the corresponding wheel 4038 stops or rotates more slowly. In this way, the laboratory product transport element 4030 travels along a curve.

If the laboratory product transport element reaches its destination (e.g., an unloading station) at which a correspondingly programmed laboratory robot is supposed to remove the transported sample container 4050 from the laboratory product transport element 4030, the motors 4036 are stopped. In order to prevent the laboratory product transport element 4030 from being lifted off of the transfer path when the sample container is removed from the recess 33 of the laboratory transport element, the lateral limitations 4012 of the transfer path 4010 may have inward-facing protrusions that cooperate with the shoulder 4035 on the laboratory product transport element 4030. The lateral inward-facing protrusions can prevent the laboratory product transport element 4030 from being lifted upward if there is friction between the sample container and the recess 4033 of the laboratory product transport element 4030.

In some embodiments, the laboratory product transport element 4030 brings the sample container 4050 to a processing or investigation station, in order to conduct a physical, chemical or biological investigation on the sample. In the case of an optical investigation, the laboratory product transport element 4030 reaches a light source on the side with sample container 4050. A light source can illuminate the lower area of the sample container 4050 through the slit 4032 and emitted light from the sample can be detected by a detector arranged opposite it. The detector or electronics associated with the detector can determine the absorption or fluorescence characteristics of the sample. In order for slit 4032 to lie precisely opposite the correspondingly arranged light source, the laboratory product transport element can be aligned accordingly. This can be achieved by driving the rubber wheels 4038 to rotate in opposite directions. Consequently, the laboratory product transport element 4030 rotates around its own axis, until the slit is arranged opposite the corresponding light source for investigation. The slit can also be used to establish the filling level in the sample container 4050 or to read out a barcode optionally provided in the lower area of the sample tube, which contains information about the transported product.

The laboratory product transport element 4030 can also bring the sample container to one or more processing station. Suitable processing stations include the stations described above, such as an aliquoting station, a station for closing or opening of the sample containers, stations for conducting optical investigations, and the like. It should be noted that the laboratory transport system may contain active transport systems which interact with the laboratory transport element 4030 by, for example, the movement of a sample container from the laboratory transport element 4030 onto an active transport system (for example, a conveyor belt) using a gripper device, not shown.

Alternatively or additionally, it is also possible to configure laboratory product transport elements so that they can be controlled by external controls. For this purpose, a control unit can be used, and configured to convert control signals in real time to drive signals used by the electric motors 4036. In this way, it is possible to intervene in the automated laboratory process from the outside and to divert or sort out laboratory product transport elements.

It is also possible to fully stipulate the path of the laboratory product transport element 4030, for example, by a wireless program interface. The corresponding program can be entered in the data memory of the laboratory product transport element 4030. The program data can include information as to at which orientation features (e.g., barcode 4060) provided on the limitation 4012 of transfer path 4010, the laboratory product transport element is supposed use to change its direction. In this way, the complete path of the laboratory product transport element 4030, with the corresponding sample containers 4050, is established and programmed into the laboratory product transport element 4030.

If a laboratory product transport element 4030 is defective or becomes inoperable, it can be removed by a user from the transfer path 4010 and can optionally be replaced with a new laboratory product transport element 4030. If this occurs, the disruption to the system is advantageously short and localized. Further, even if intervention is not possible, the system is not blocked. The other laboratory product transport elements 4030 can move around the inoperable laboratory product transport element. The other laboratory product transport elements can be prompted by corresponding control signals from a central processor, or via programming of the individual laboratory product transport elements 4030 to communicate with other such element 4030. For example, the laboratory product transport elements may have corresponding sensors which can detect the presence of a defective or stationary laboratory product transport element 4030 and via programming of the internal control processor move around it.

When they are on the transport path, the individual laboratory product transport elements 4030 can also communicate with each other via optical signal transmitters and receivers. This communication can occur directly and need not be conducted via a centrally provided communication site of the laboratory transport system. In this way, a laboratory product transport element with a particularly sensitive sample can inform other laboratory product transport elements that it has priority.

The energy needed to move the laboratory product transport element 4030 can be obtained from the electromagnetic field via induction coil 4040, which is generated by a high frequency voltage applied to the electrical conductors 4014. The laboratory product transport element 4030 need not precisely follow the electrical conductors 4014. The interaction only needs to be of sufficient duration so that sufficient energy can be picked up from the electromagnetic field in order to drive the drive motors 4036, which drive wheels 4038. When this is not possible, the laboratory product transport element 4030 can have energy accumulators 4044, which supply power to drive motors 4036 at such locations of the transfer path 4010, in which the electromagnetic field of the electrical conductors 4014 is not sufficient. On straight zones, in which the laboratory product transport element 4030 can move close to the electrical conductors 4014, on the other hand, excess energy from the electromagnetic field can be utilized in order to charge the energy accumulators 4044.

Other embodiments of the technology can have photosensitive elements at the bottom of the laboratory product transport element 4030. The photosensitive elements can be illuminated by light bands arranged on the transfer path. The photosensitive elements can be used to furnish electrical drive power.

It is also possible that the laboratory product transport elements 4030 to obtain their drive power completely from energy accumulators 4044. The energy accumulators 4044 can be charged at corresponding charging stations, which can be at processing stations.

B. Conveyor Transport System

The conveyor transport system is a transport system for single tube carriers, such as puck transport systems, based on conveyor belt technology. The conveyor transport system employs a local module controller for each functioning module of the conveyance system, which increases speed in transport decisions and makes the conveyor belt line more efficient. The functioning modules of the conveyor transport system may include, but are not limited to, motor, diverter, and merger modules. The motor, diverter, and merger modules are integrated into the conveyor belt line for increased efficiency.

Figure 46:
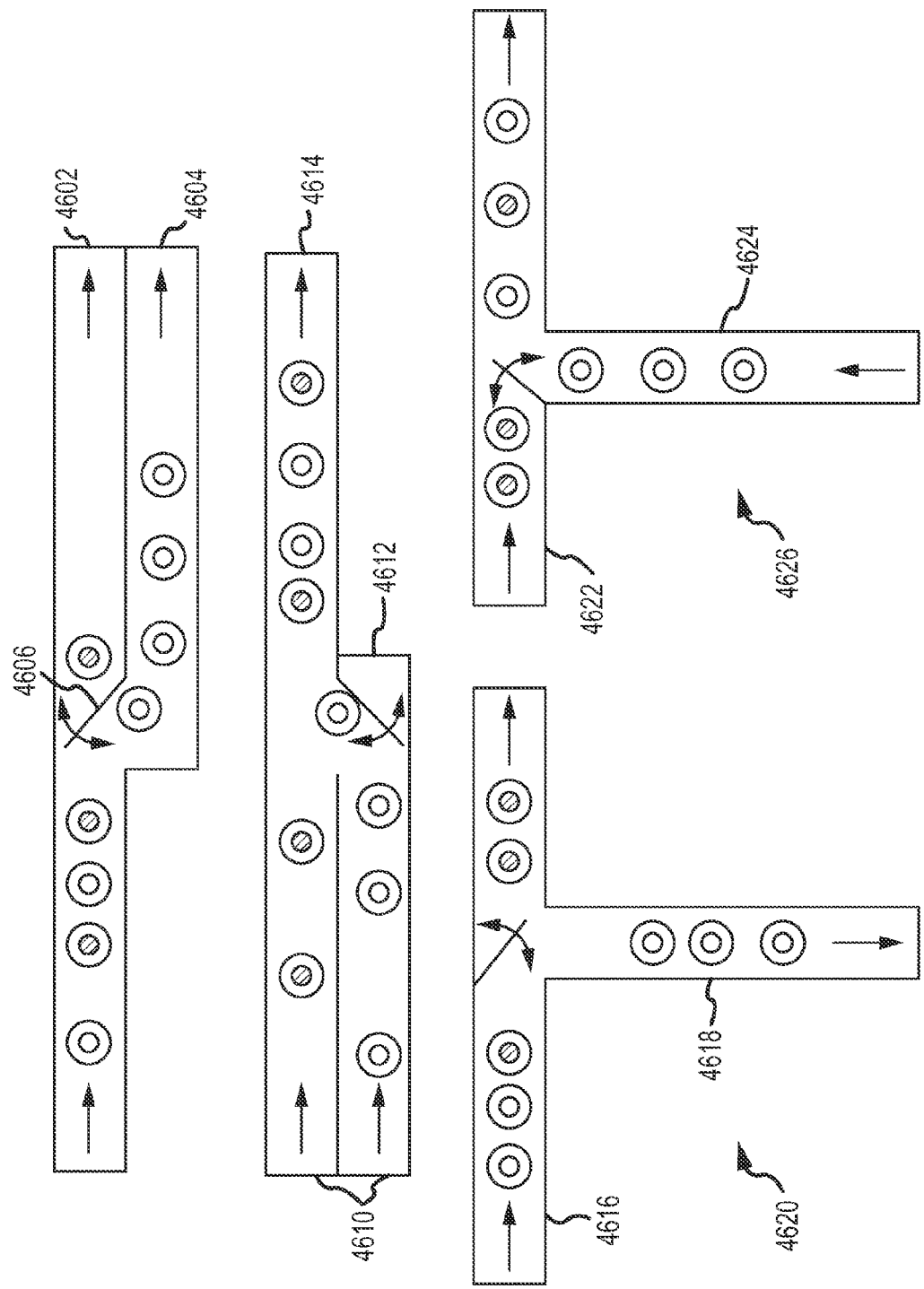
FIG. 46 depicts example diagrams of the diverter and merger functions of the conveyor transport system.

FIG. 46 depicts a few examples of the diverter and merger functions of conveyor transport system. The diverter and merger function may be controlled by a conveyor transport system controller working in communication with the main controller for the laboratory automation system. The conveyor transport system is capable of diverting sample tubes from one line 4602 to an adjacent parallel line 4604. The sample tubes may be diverted when the conveyor transport system controller instructs a diverting arm 4606 to move to a position so that the sample tubes can be diverted to a parallel conveyance line.

As shown in FIG. 46, the conveyor transport system may also merge two conveyance lines that are parallel to each other 4610. This function allows, e.g. sample tubes from second conveyor 4612 to be merged with sample tubes coming down the first conveyor line 4614 by coordinating the timing for tubes coming down each of those lines, ensuring that the tubes from each line do not run into one another and/or become jammed on the line.

The conveyor transport system is also capable of diverting sample tubes coming from a first conveyance line 4616 to a second conveyance line 4618 that is perpendicular to the first conveyance line. As shown in 4620, sample tubes coming down conveyor 4616 can be diverted 90° to conveyor 4618.

As shown in FIG. 46, the conveyor transport system may also be capable of merging samples tubes onto a first conveyance line 4622 from a perpendicular second conveyance line 4624. As shown in 4626, first conveyor 4622 is perpendicular to second conveyor 4624. Sample tubes coming down second conveyor 4624 can be merged onto first conveyor 4622 even if first conveyor 4622 has sample tubes already traveling down the first conveyor line. The merge 900 function coordinates the time for tubes coming down each of those lines, ensuring that the tubes from each line do not run into one another and/or become jammed on the line.

Figure 47:
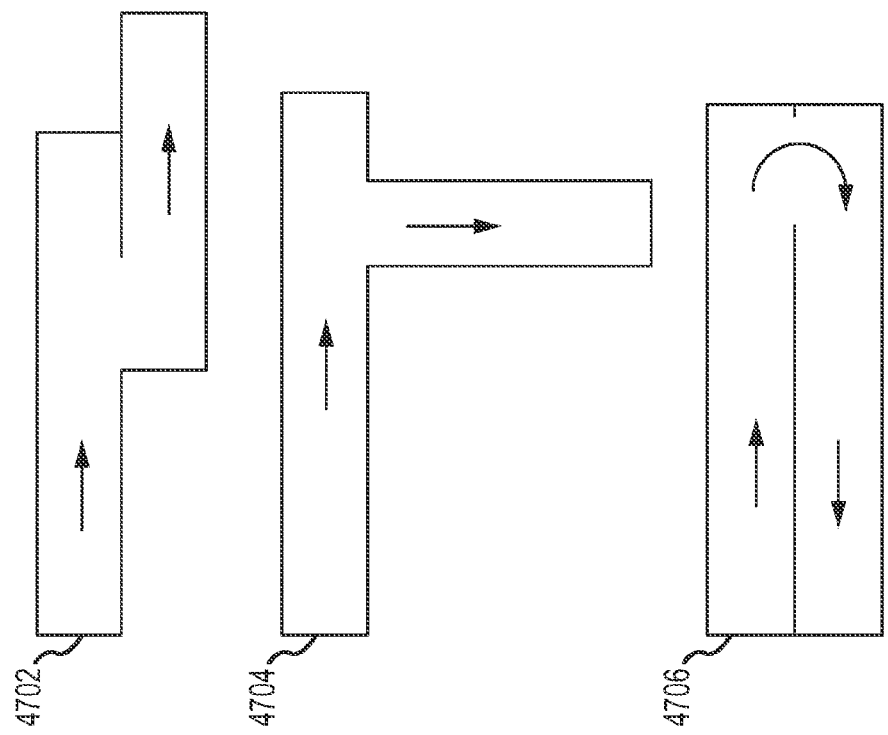
FIG. 47 depicts example diagrams of transfer functions of the conveyor transport system.

FIG. 47 depicts a few examples of transfer functions (parallel, 90°, 180°) provided by the conveyor transport system. The parallel transfer function 4702 allows sample tubes on a first conveyor belt to be transferred to a second conveyor belt that is parallel to the first conveyor belt. The 90° transfer function 4704 allows sample tubes on a first conveyor belt to be transferred to a second conveyor belt that is perpendicular to the first conveyor belt. The 180° transfer function 4706 allows sample tubes on a first conveyor belt to be transferred to a second conveyor belt that is parallel to the first conveyor belt but that is moving in the opposite direction.

Figure 48:
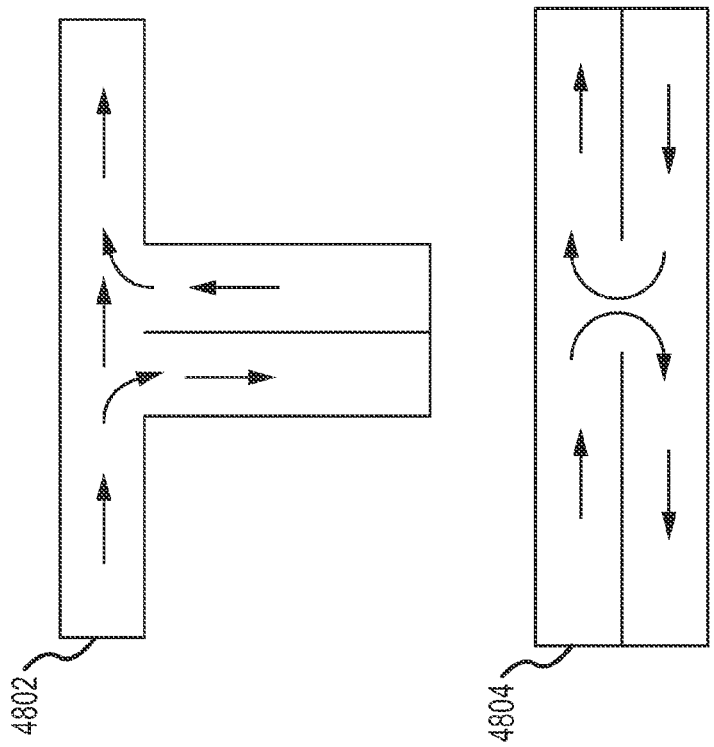
FIG. 48 depicts example diagrams of coupled divert and merge functions of the conveyor transport system.

FIG. 48 depicts a few examples of coupled divert and merge functions. In the example of the divert/merge 900 function 4802, sample tubes from a first conveyor can be diverted 90° to a second conveyor at a particular junction point. Sample tubes from a third conveyor can be diverted onto the first conveyor after that particular junction point. In the example of the divert/merge 1800 function 4804, sample tubes from a first conveyor can be diverted 180° onto a second conveyor and merged with the sample tubes already traveling down the second conveyor Similarly, sample tubes from a second conveyor can be diverted 180° onto a first conveyor and merged with the samples tubes already traveling down the first conveyor.

Figure 49:
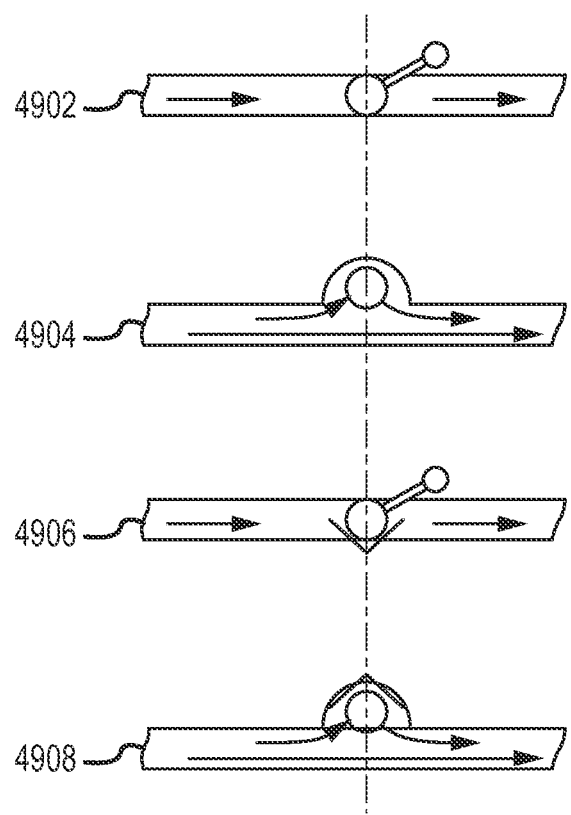
FIG. 49 depicts example diagrams of stop functions and locating functions of the conveyor transport system.

FIG. 49 depicts a few examples of stop functions and locating functions provided by conveyor transport system. The functions include a stop unit 4902, a stop unit off-line 4904, a locating unit 4906, and a locating unit off-line 4908. The stop unit 4902 may be in the form of a bar or other obstruction that prevents a puck (shown by the circle) from traveling down a lane. The stop unit off-line 4904 can be in the form of a semicircle and can receive a puck to allow other pucks to pass by on an adjacent lane. The locating unit may include a V-shaped structure which can receive a puck. A bar or other obstruction can ensure that the puck stays in the V-shaped structure. The V-shaped structure is in the lane and prevents other pucks from passing through the lane. The locating unit off-line 4908 is in the form of a V-shaped structure, but is adjacent to the lane, so that pucks can pass in the lane, even though a puck is present in the V-shaped structure.

As discussed above, the modules (e.g. diverter, merger, motors, etc.) are controlled by a local module controller, as described with reference to the FlexLink® X45E puck handling system described at http://www.flexlink.com/en/offering/conveyor-systems/pallet-and-puck-handling/x45e.jsp and in U.S. patent application Ser. No. 12/725,807, filed Mar. 17, 2010 and in PCT Patent Publication No. WO/2011/028166, filed Aug. 31, 2010. Each local module controller may communicate with a line control via an external field bus. Additionally, each local module controller may have the capability for sensor input (e.g., an RFID reader, IR sensor, etc.). Each local module controller controls a corresponding motor. The local module controllers can cause the motors to perform the functions of the modules. For example, if local module controller controls the diverter function, the local module controller can cause a motor to move a diverter arm to a particular position so that the diverter function can be performed.

C. Magnetic Transport System

The magnetic transport system is a transport system for single tube carriers, such as puck transport systems, based on linear synchronous motor (LSM) technology as described with reference to the MagneMover™ LITE conveyor system described at http://www.magnemotion.com/industrial-automation/magmoverlite.cfm and in U.S. patent application Ser. No. 08/961,632, filed Oct. 31, 1997: U.S. patent application Ser. No. 11/490,516, filed Jul. 19, 2006; and U.S. patent application Ser. No. 11/770,701, filed Jun. 8, 2007. Sample tube carriers can be individually driven by LSMs along a track layout and provided to processing stations and/or modules. The sample tubes in the carriers can travel down the track. Electric coils may be enclosed in the track, and frames on top of the track help guide the carrier along the track.

As described above, carriers such as puck transport systems may have an array of magnets on their bottom. The magnets on the carriers can be used to guide the carriers along the track.

The stop or location functions can be controlled by the LSM. For example, single tube carriers can be stopped by direct control of the LSM. Additionally, the diverter and merger functions of the transport system can be controlled via electromagnetic switches and/or mechanical switches. This allows the processing stations/modules to be located at the main track or at pull-off areas.

Line control software may manage the movement of each single tube by controlling the magnetic force of an electric coil close to the carrier. The carriers can be identified by identifiers such as RFID tags. These identifiers help manage the movement of each carrier.

D. Magnetic Damping for Sample Transportation Systems

Sample transportation systems may be operated at low speeds to avoid the potential occurrence of sample carrier impacts. Impacts can occur between sample carriers when a first sample carrier encounters an obstacle and the sample carriers following the first sample carrier collide as they form a queue behind the obstacle. An impact may also occur when a sample carrier encounters a diverting arm on a track. These impacts may cause the contents of a sample tube to splash out from a sample carrier. Impacts may also affect sample quality by causing fluid layers separated by centrifugation to remix.

Introducing magnets in the sample carriers, such that a magnet of a first sample carrier repels the magnet of an adjacent sample carrier, can prevent the adverse effects that may occur when sample carriers collide with one another. As a result, sample carriers may travel at increased speeds with little to no adverse impact on sample quality.

In some embodiments, one or more magnetic elements may be coupled to a directional gate. A directional gate may be used to move a sample carrier from one track to another track. Existing directional gates can cause a sample carrier to slow down due to friction between the sample carrier and the gate. When a magnet is coupled to a directional gate, the magnet can repel a sample carrier magnet on a sample carrier such that there is no contact between the sample carrier and the directional gate. In this way, the speed at which the sample carriers are able to traverse the directional gates may be increased.

Magnets used in sample carriers and directional gates may be made of any material or device that produces a magnetic field, such as metallic magnets, ceramic magnets, or electromagnets.

Directional gates may be used to guide sample carriers traveling along a conveyor system. For example, a directional gate may be a diverting arm used to divert a sample carrier from one track to an adjacent track. In some embodiments, a directional gate may be operated under the control of one or more processors. For example, a controller of the conveyor transport system may be communicatively coupled to a main controller for the laboratory automation system. The conveyor transport system controller may operate the directional gate in response to commands received from the main controller in order to divert sample carriers to a desired conveyor track or sample carrier destination. FIG. 46 depicts illustrative examples of diverter and merger functions that can be used in a conveyor transport system.

Figure 50:
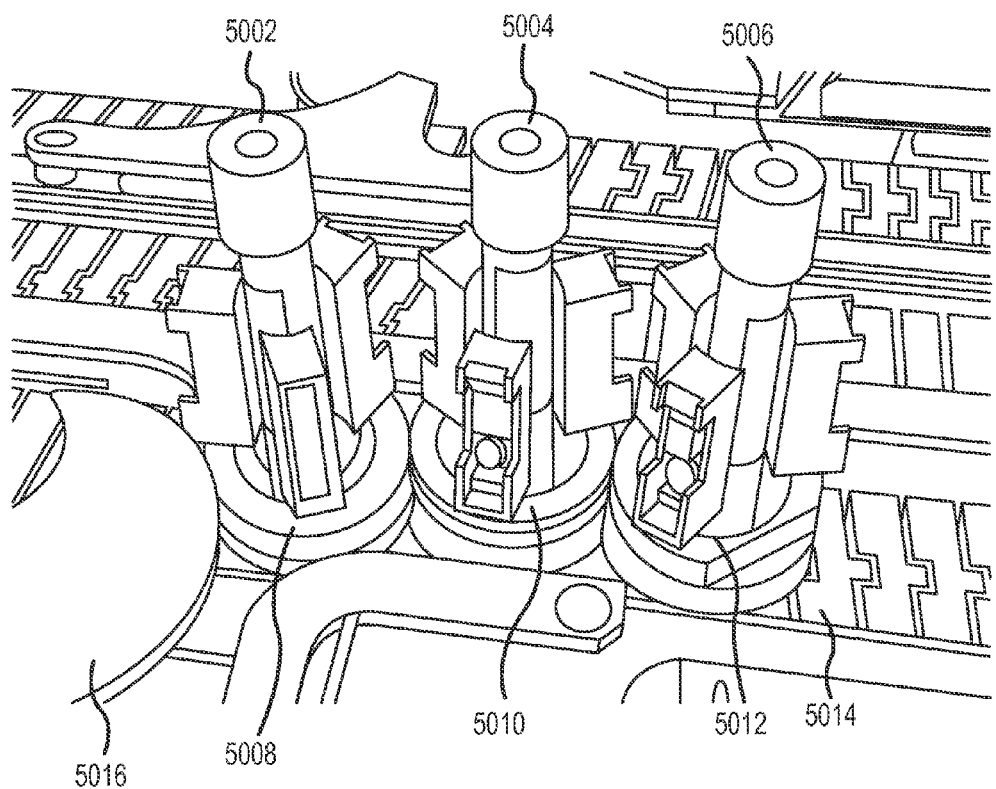
FIG. 50 shows a prior art conveyor transport system in which specimen containers are being transported by sample carriers along a conveyor track.

FIG. 50 shows a prior art conveyor transport system in which specimen containers 5002, 5004, and 5006 are being transported by sample carriers 5008, 5010 and 5012, respectively, along conveyor track 5014. In the illustrative prior art system, sample carrier 5008 has traveled along conveyor track 5014 until the sample carrier encountered obstacle 5016. Sample carrier 5010, which was traveling behind sample carrier 5008, has collided with sample carrier 5008 after sample carrier 5008 was stopped by obstacle 5016. Sample carrier 5012 has likewise collided with sample carrier 5010. Such collisions can cause sample material to splash out of the sample carrier. If the sample material has been separated into layers (e.g., blood separated into its component parts by centrifugation), the collisions can disturb the layers, causing the separated sample material to recombine. The prior art conveyance system must be run at a sufficiently slow rate to prevent spillage and disturbance of the samples.

In various embodiments of an improved specimen transport system that utilizes magnetic damping, magnets are coupled to sample carriers. For example, a ring magnet may be integrated into or otherwise affixed to a sample carrier. When a sample carrier having a ring magnet encounters another sample carrier having a ring magnet, the respective ring magnets repel one other such that the respective sample carriers decelerate. In this way, collisions can be prevented or dampened.

Figure 51:
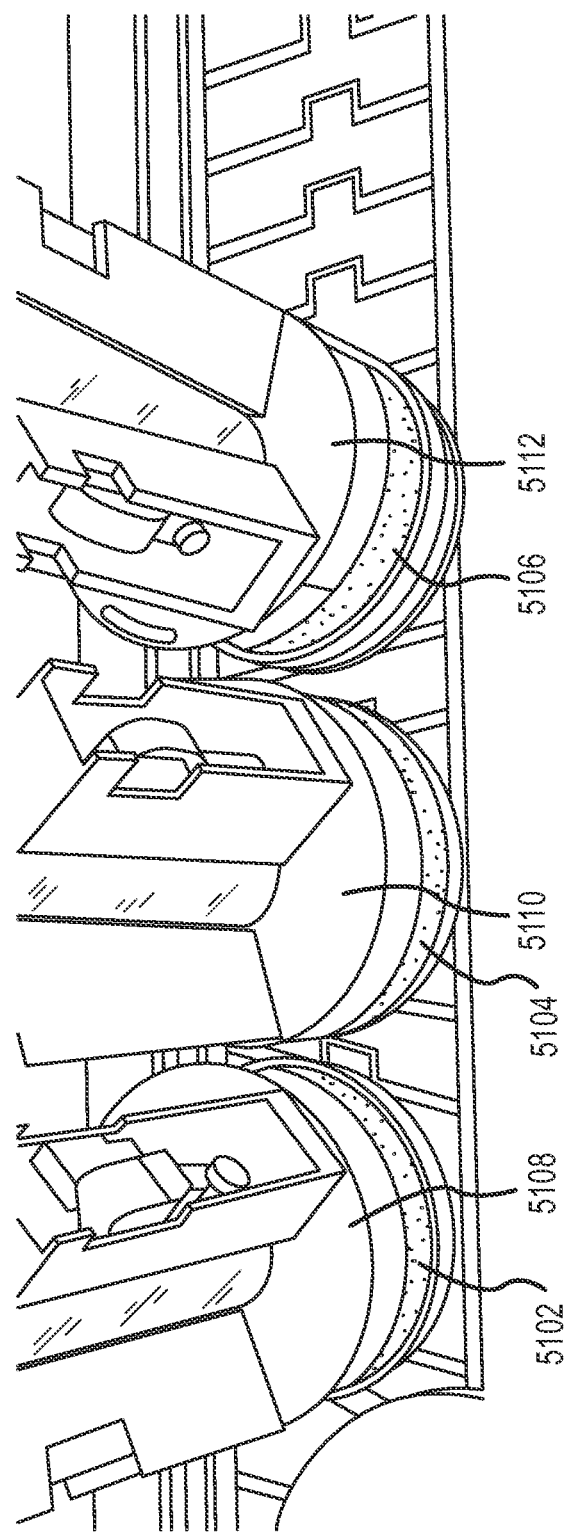
FIG. 51 shows illustrative sample carriers of a specimen transport system with magnetic damping components.

FIG. 51 shows illustrative sample carriers of a specimen transport system with magnetic damping components. First sample carrier magnet 5102, second sample carrier magnet 5104, and third sample carrier magnet 5106, are coupled to first sample carrier 5108, second sample carrier 5110, and third sample carrier 5112, respectively. A specimen container (such as the specimen containers 5002-5006 described with reference to FIG. 50) can be inserted in each sample carrier.

Sample carrier magnets 5102-5106 may be ring-shaped magnets. In some embodiments, the ring magnet may be coupled to the base of the sample carrier (e.g. below the portion of the specimen container that receives the specimen container). The ring magnet may be mounted such that the exterior of the ring magnet is flush with the external surface of the sample carrier. The ring magnet may be radially magnetized such that a first pole of the magnet is the outer surface of the ring and a second pole of the magnet is the inner surface of the ring. Preferably, the pole of the outer surface of each sample carrier ring magnet is matched such that the sample carrier magnets repel one another. Thus, if the outer surface of the first sample carrier magnet is a north pole, the outer surface of the second sample carrier magnet and the third sample carrier magnet are also magnetized such that the outer surface of the ring magnets is a north pole.

In FIG. 51, first sample carrier magnet 5102 repels second sample carrier magnet 5104, causing a space to be maintained between sample carrier 5108 and 5110. Similarly, second sample carrier magnet 5104 repels third sample carrier magnet 5106, causing a space to be maintained between sample carriers 5110 and 5112. In this manner, collisions between adjacent sample carriers are prevented by the repelling effect of the respective magnetic fields of the magnets coupled to the sample carriers.

In some embodiments, a diverting arm magnet is coupled to a diverting arm such that the diverting arm magnet repels the sample carrier magnet of any sample carrier that approaches the diverting arm.

Figure 52:
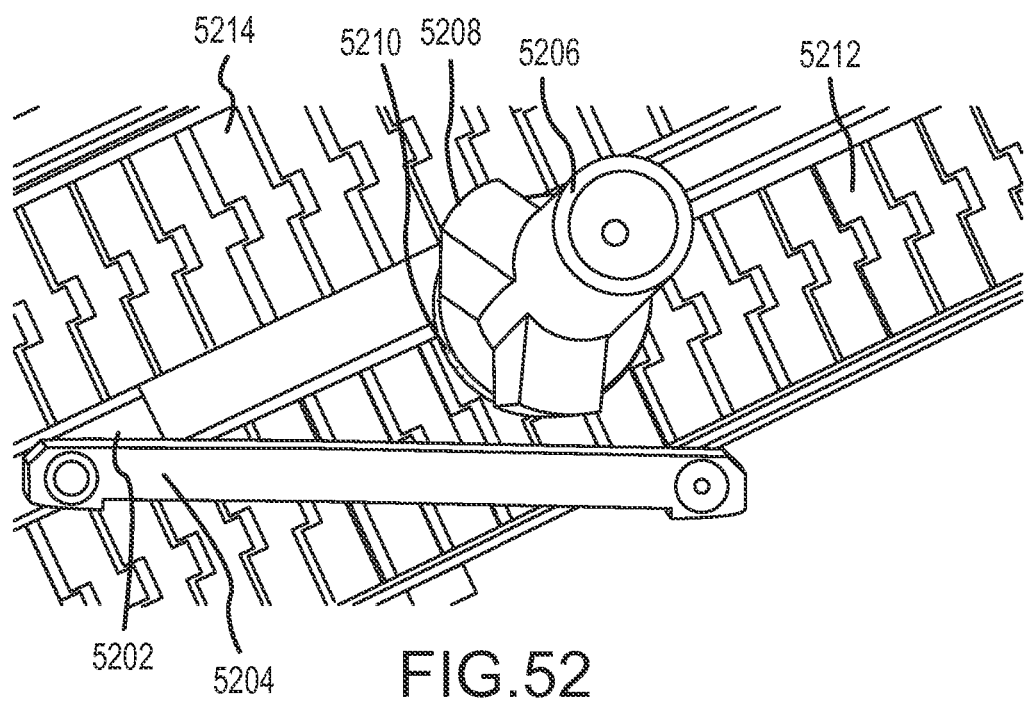
FIG. 52 is a top view of an illustrative diverting arm with a diverting arm magnet

FIG. 52 is a top view of an illustrative diverting arm with a diverting arm magnet. One or more diverting arm magnets 5202 may be coupled to diverting arm 5204. In some embodiments, diverting arm 5204 is fabricated from a material that is magnetized such that it is not necessary to couple a separate magnetic component 5202 to diverting arm 5204. Specimen container 5206 is inserted into sample carrier 5208 having sample carrier magnet 5210. Sample carrier 5208 is transported by first conveyor track 5212 toward diverting arm 5204.

Diverting arm magnet 5202 may be magnetized such that the pole of diverting arm magnet 5202 that faces sample carrier 5208 is the same as the pole of the exterior surface of sample carrier magnet 5210. For example, if diverting arm magnet 5202 has a north pole facing sample carrier magnet 5210, the exterior surface of sample carrier magnet 5210 may be magnetized such that the outer surface of the ring magnet is a north pole. In this manner, when sample carrier 5208 approaches diverting arm 5204, diverting arm magnet 5202 repels sample carrier magnet 5210, such that an impact between diverting arm 5204 and sample carrier 5208 is reduced or avoided. When diverting arm 5204 is in a first position such that diverting arm 5204 extends across first conveyor track 5212, sample container 5208 is urged by first conveyor track 5212 and diverting arm 5204 onto second conveyor track 5214. When diverting arm 5204 is in a second position (not shown) such that diverting arm 5204 does not extend across first conveyor track 5212, sample container 5208 will continue along first conveyor track 5212 undiverted.

FIG. 53 is a diagram of a first ring magnet associated with a first sample carrier (not shown) and a second ring magnet associated with a second sample carrier (not shown). First ring magnet 5302 may be radially magnetized such that a first pole of the magnet is at outer surface 5304 of the ring and a second pole of the magnet is at the inner surface 5306 of the ring. Second ring magnet 5308 may be radially magnetized such that a first pole of the magnet is at outer surface 5310 of the ring and a second pole of the magnet is at the inner surface 5312 of the ring. Because first ring magnet and second ring magnet have the same pole at the outer surface of the rings (such as the north pole, as shown in FIG. 53), the first ring magnet repels the second ring magnet. So long as the force driving the first sample carrier toward the second sample carrier (or vice versa) is less than the force of the magnetic field, the first sample carrier is prevented from coming into contact with the second sample carrier.

The magnetic field of the first ring magnet, the second ring magnet, and/or the diverting arm may be in the range of 150-300 Gauss as measured at a distance of 10 millimeters from the exterior surface of the magnet, such as 200-260 Gauss as measured at a distance of 10 millimeters from the exterior surface of the magnet, e.g., 242 Gauss as measured at a distance of 10 millimeters from the exterior surface of the magnet.

Figure 54:
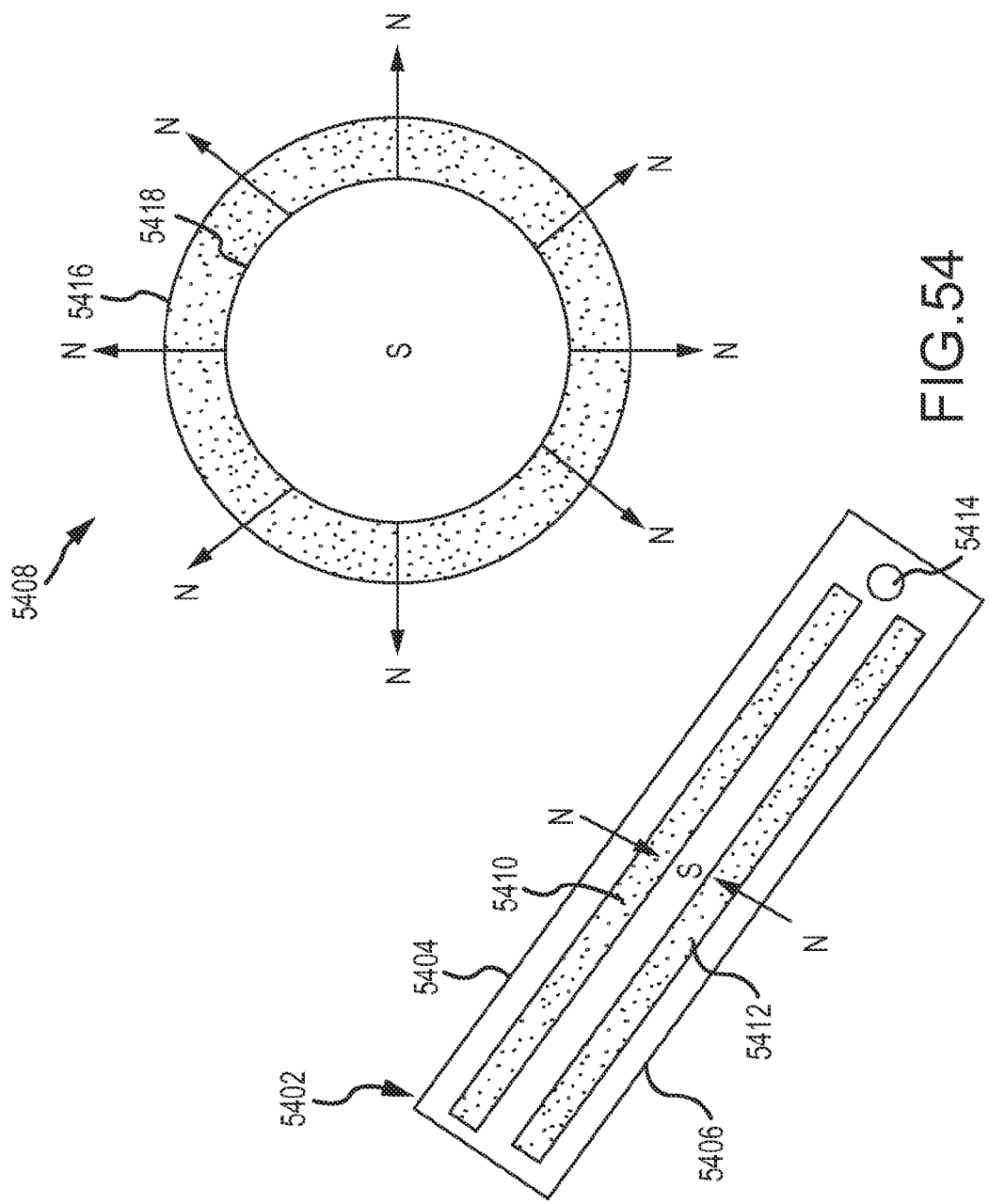
FIG. 54 is a diagram of an illustrative diverting arm magnet.

FIG. 54 is a diagram of one or more diverting arm magnets associated with a diverting arm and a ring magnet associated with a sample carrier. Diverting arm 5402 may be pivotally coupled to the conveyor system such that it pivots about pivot point 5414. Diverting arm 5402 may include one or more magnets, such as first diverting arm magnet 5410 and second diverting arm magnet 5412. Advantageously, in a diverting arm with two magnets, first diverting arm magnet 5410 can repel sample carrier magnets of sample carriers approaching the first face 5404 of the diverting arm and second diverting arm magnet 5412 can repel sample carrier magnets of sample carriers approaching the second face 5406 of the diverting arm. For example, in FIG. 46, sample carriers transported by conveyor track 4622 may approach a first face of diverting arm 4606 and sample carriers transported by conveyor track 4624 may approach a second face of diverting arm 4606.

First diverting arm magnet 5410 and second diverting arm magnet 5412 can be coupled to diverting arm 5402 by a variety of means known in the art. For example, diverting arm magnets 5410, 5412 can be coupled to the surface of diverting arm 5402 with adhesive. In some embodiments, diverting arm magnet 5410 and second diverting arm magnet 5412 can be embedded within diverting arm 5402. In other embodiments, diverting arm magnet 5410 and second diverting arm magnet 5412 can be coupled to a first face and a second face of diverting arm 5402, respectively. The first face of diverting arm 5402 can be a face with which sample carriers come into contact and the second face of diverting arm 5402 can be opposite to the first face.

Preferably, the pole at the exterior surface of diverting arm 5402 that will face the sample carrier is the same as the pole at the exterior surface of sample carrier magnet 5408. For example, if first diverting arm magnet 5410 has a north pole facing sample carrier magnet 5408, as shown in FIG. 54, the outer surface of sample carrier magnet 5408 is preferably magnetized such that the outer surface 5416 of the ring magnet 5408 is a north pole and the inner surface 5418 of the ring magnet 5408 is a south pole. In this manner, when sample carrier 5408 approaches diverting arm 5402, diverting arm magnet 5402 repels sample carrier magnet 5408, such that friction between diverting arm 5402 and sample carrier 5408 is reduced or avoided.

In some embodiments, diverting arm 5402 has a single magnet that may be axially magnetized such that a first pole is at a first surface 5404 of diverting arm 5402 that faces ring magnet 708 and a second pole is at a second surface 5406 of diverting arm 5402.

Because collisions between sample carriers can be prevented or avoided by incorporating magnets into the sample carriers, the sample carriers can be transported at high track speeds with a reduced risk of disturbing the sample. In some embodiments, incorporating sample carrier magnets and diverting arm magnets into a specimen transport system allows specimens to be transported at speeds of 100 mm/s to 200 mm/s, such as 130 mm/s to 170 mm/s, e.g. 150 mm/s.

Figure 55:
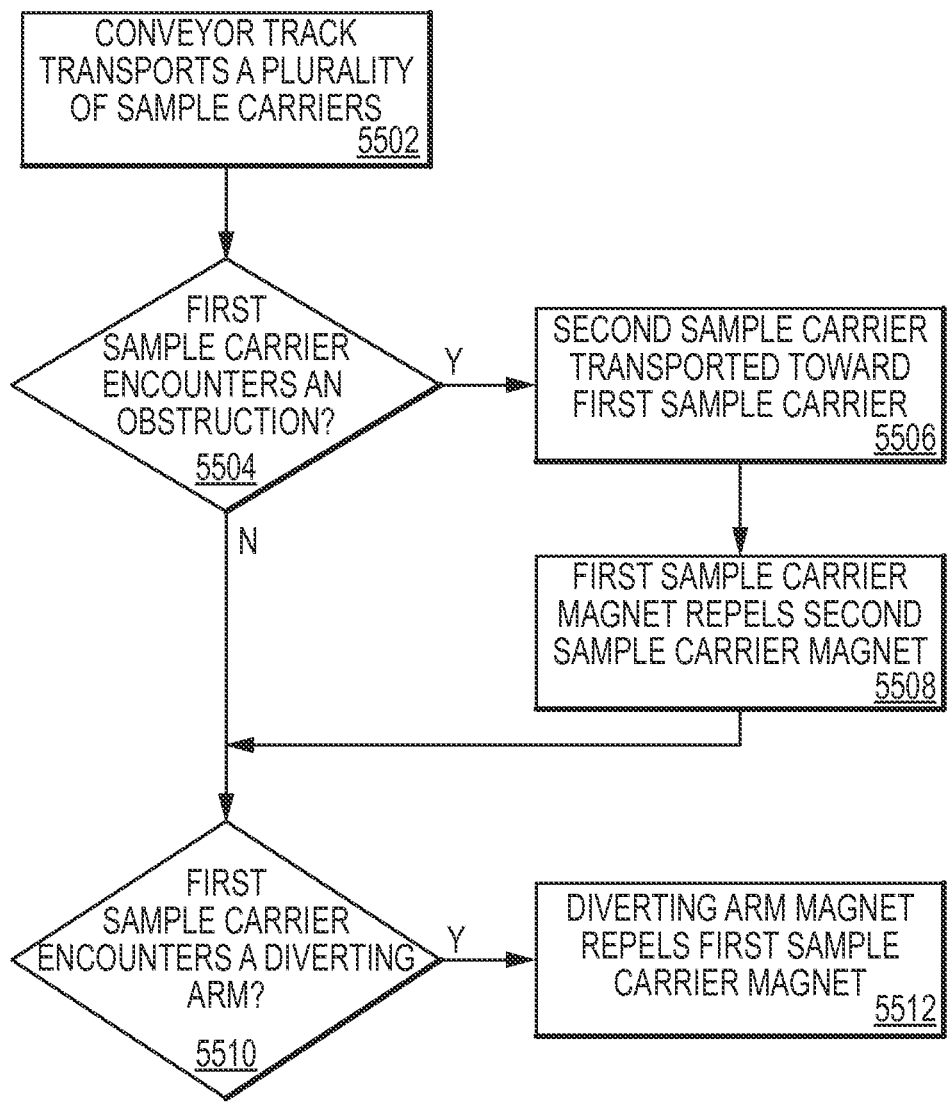
FIG. 55 shows an illustrative flow diagram of magnetic damping in a conveyor transport system.

FIG. 55 shows an illustrative flow diagram of magnetic damping in a conveyor transport system. At operation 5502, a conveyor device such as a conveyor track transports a plurality of sample carriers. If a first sample carrier encounters an obstruction, as indicated at 5504, a second sample carrier is transported toward the first sample carrier, as indicated at operation 5506. The first sample carrier magnet coupled to the first sample carrier repels the second sample carrier magnet coupled to the second sample carrier such that the second sample carrier does not collide with the first sample carrier, as indicated at operation 5508. If a first sample carrier encounters a diverting arm, as indicated at 5510, a diverting arm magnet of the diverting arm repels a first sample carrier magnet of the first sample carrier such that the first sample carrier does not collide with the diverting arm, as indicated at operation 5512.

E. Aliquoting Module for Sample Transportation Systems

As discussed above, the aliquotter module is used in the preparation of sample aliquots from primary into secondary tubes in a laboratory automation system. During the aliquoting process for the preparation of sample aliquots, a primary sample tube containing a fluid sample is provided at an aspiration position. An empty secondary sample tube is provided at a dispensing position. A pipettor, which may be attached to a moveable robotic arm, is used to aspirate an aliquot volume of the fluid sample. The aspirated volume is then transferred to the dispensing position by use of the robotic arm, and the aspirated volume is dispensed in the empty secondary tube. This process can be repeated for additional empty secondary tubes if more sample aliquots are needed.

The aliquotter module of the present technology allows queuing of secondary tubes localized before the primary tubes, relative to the moving direction of the laboratory automation system sample container handling unit. That is, the secondary tubes may leave the aliquotter module as soon as the fluid sample is dispensed in the secondary tube, without having to wait for the aliquoting of that sample to be completed for additional secondary tubes.

The configuration of the aliquotter module is advantageous since the secondary tubes can be released from the dispensing position immediately after the dispensing step and can be directly transferred to the designated target positions in the laboratory automation system, while further aliquots can be produced. Additionally, any number of secondary sample tubes can be consecutively generated from the provided primary tube. This reduces the turn-around-time of a sample in the laboratory automation system and generates a homogenous and optimized load of the transport system and subsequent process steps.

Figure 56:
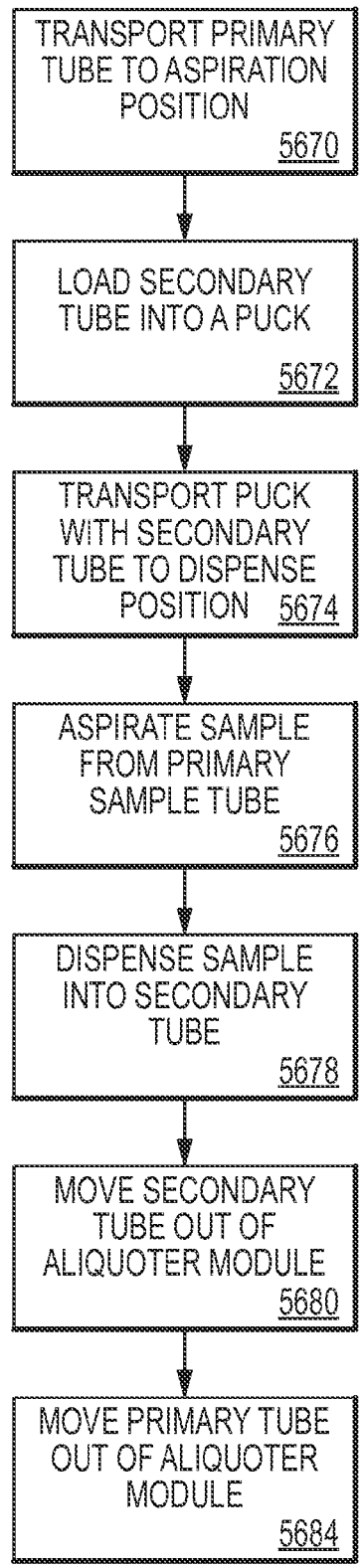
FIG. 56 shows a flowchart for an illustrative method of operating an aliquot module.

FIG. 56 shows a flowchart that can illustrate a method of operating an aliquot module according to an embodiment of the invention. It is understood that embodiments of the invention are not limited to the specific steps shown in FIG. 56 or are limited to any particular step order. Further, a computer readable medium in a computer may comprise code, executable by a processor in the computer to execute any of the steps in FIG. 56 or described in this application.

In step 5670, a primary tube is transported to an aspiration position in the aliquotter module. In some embodiments, the primary tube is transported to the aspiration position in a first puck. The primary tube may be transported to the aspiration position using any suitable transport system including pucks on tracks, magnetic pucks, gripper units, etc.

In step 5672, before or after the primary tube is transported to the aspiration position, a secondary sample tube is loaded into a second puck. The puck with the secondary sample tube is then transported to a dispense position in the aliquotter module (step 5674).

In step 5676, an aliquot volume of a sample in a primary tube located in an aspiration position is aspirated by a pipettor. The aliquot volume of the sample is dispensed in the secondary sample tube located in a dispense position in the aliquotter module (step 5678).

In step 5680, the secondary sample tube in the second puck then leaves the aliquotter module before the primary sample tube leaves the aliquotter module.

Additional sample aliquots may be taken from the primary tube and dispensed into other secondary tubes in a similar manner as in steps 5672 to 5684.

One embodiment of the invention is directed to an aliquotter module comprising a track comprising a plurality of loops comprising a first loop configured to transport a secondary sample container and a second loop configured to transport a primary sample container, and a pipettor configured to aspirate a first aliquot volume of a sample in the primary sample container located in an aspiration position and dispense the first aliquot volume of the sample in the secondary sample container located in a dispensing position. The aliquotter module is configured to cause the secondary sample container to leave the aliquotter module before the primary sample container.

Figure 57:
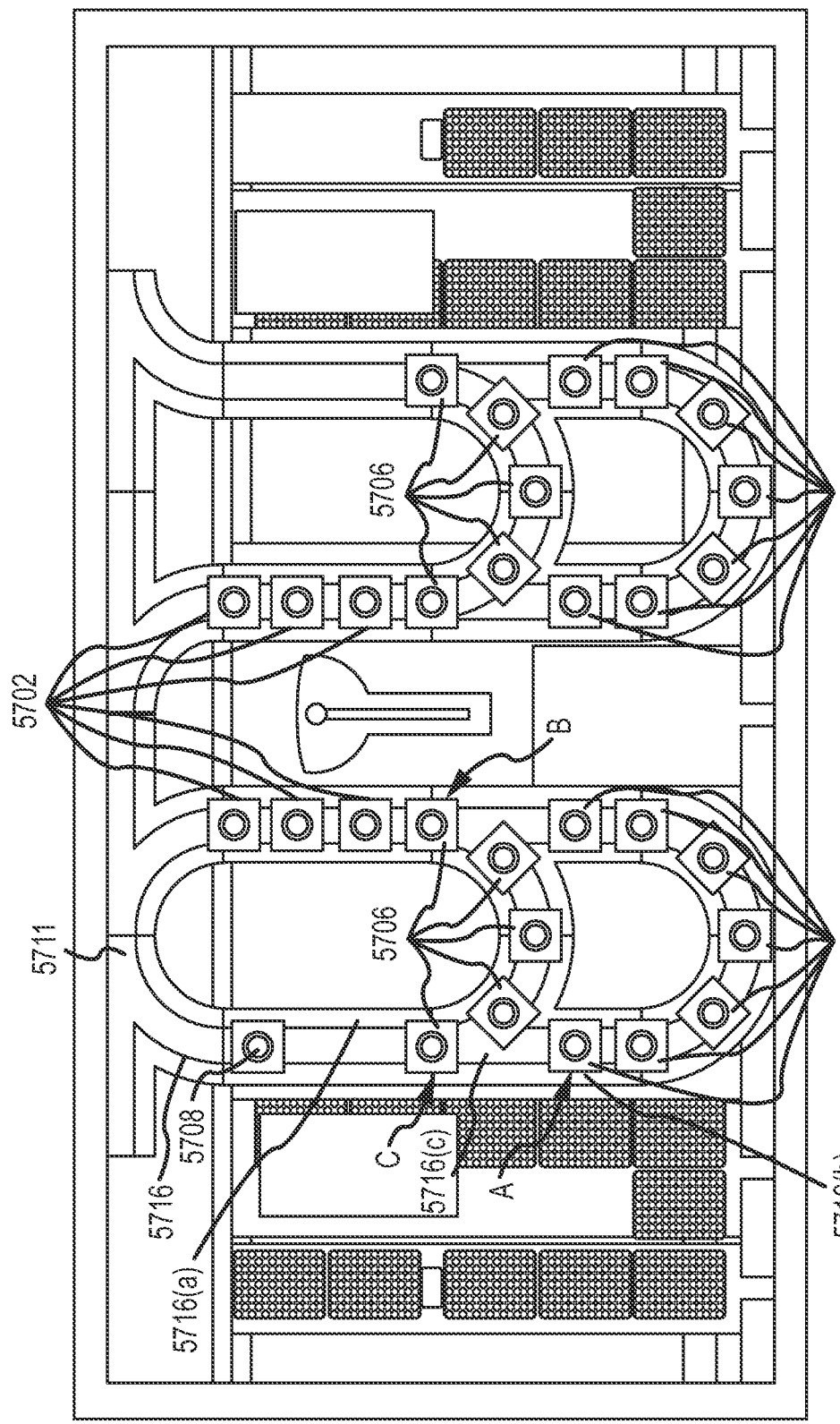
FIG. 57 shows a top plan view of a first aliquotter module according to an embodiment of the invention. The first aliquotter module comprises a number of looped lanes.

In one embodiment, an aliquotter module can utilize a magnetic transport system. FIG. 57 depicts an example of a workflow for an aliquotter module using the magnetic transport system.

The aliquotter module shown on FIG. 57 comprises a track 5716 including a first loop 5716(*a*), a second loop 5716(*b*), and a common track portion 5716(*c*) that is included in both the first and second loops 5716(*a*), 5716(*b*). The track system may comprise magnetic elements that interact with magnetic elements in a number of pucks. The pucks can move at speeds in the range of up to 2 meters per second, which is faster than standard conveyors. Such tracks are commercially available under the tradename Magnemotion™.

FIG. 57 shows a number of pucks in the aliquotter module. They include empty pucks 5702, pucks with primary tubes 5704, and pucks with secondary tubes 5706. A puck with a secondary tube 5708 filled with an appropriate aliquot of a sample from a primary tube is also shown. As shown, the various pucks can travel clockwise around the loops 5716(*a*), 5716(*b*) and may exit the aliquotter module via a linear track 5711. In other embodiments, the pucks could move in a counterclockwise direction.

In an exemplary method of operating the aliquoting module, a primary tube 5704 is identified by the system on the main track for aliquoting and is directed to the aliquotter's aspiration point (A) proximate the second loop 5716(*b*), adjacent to the merge of the loops 5716(*a*), 5716(*b*). The empty pucks 5702 are sent by the system behind the primary tube to the aliquotter's loading point for secondary tubes (B), proximate the loop 5716(*a*). A secondary tube is labeled and loaded into the empty puck 5706 at the aliquotter's loading point for secondary tubes (B) and is directed to the dispensing point (C). The sample is then aspirated from the primary tube 5704 at (A) and dispensed into the secondary tube in the puck 5706 at point (C), proximate to the first loop 5716(*a*). Barcode readers (not shown) at points (A) and (C) verify the correct association by reading barcodes on the sample tube at points (A) and (C). When the secondary tube is complete 5708, it is released to its next destination by entering the linear track 5711 and the next secondary tube moves to the dispensing point (C).

The process can then be completed for any number of additional secondary tubes if the system further routes empty pucks to the aliquotter module. When the last secondary tube is finished, both the last secondary tube and the primary tube are released to their next destinations according to the scheduler, and the trailing secondary and primary tubes are moved to the dispensing (C) and aspiration points (A), respectively. The process can then be completed for the trailing secondary and primary tubes.

The looped track configuration has a number of advantages. They include the ability to continuously and efficiently feed pucks to aspiration and dispense points in an aliquotter module, thereby resulting in faster processing.

Another embodiment of the invention is directed to a system comprising an aliquotter module comprising a first track, a second track, a transport track, a rotatable gateway device proximate the transport track and the first track or the second track, and a pipettor configured to aspirate a first aliquot volume of a sample in the primary sample container located in an aspiration position proximate the first track and dispense the first aliquot volume of the sample in the secondary sample container located in a dispensing position proximate the second track.

Figure 58A:
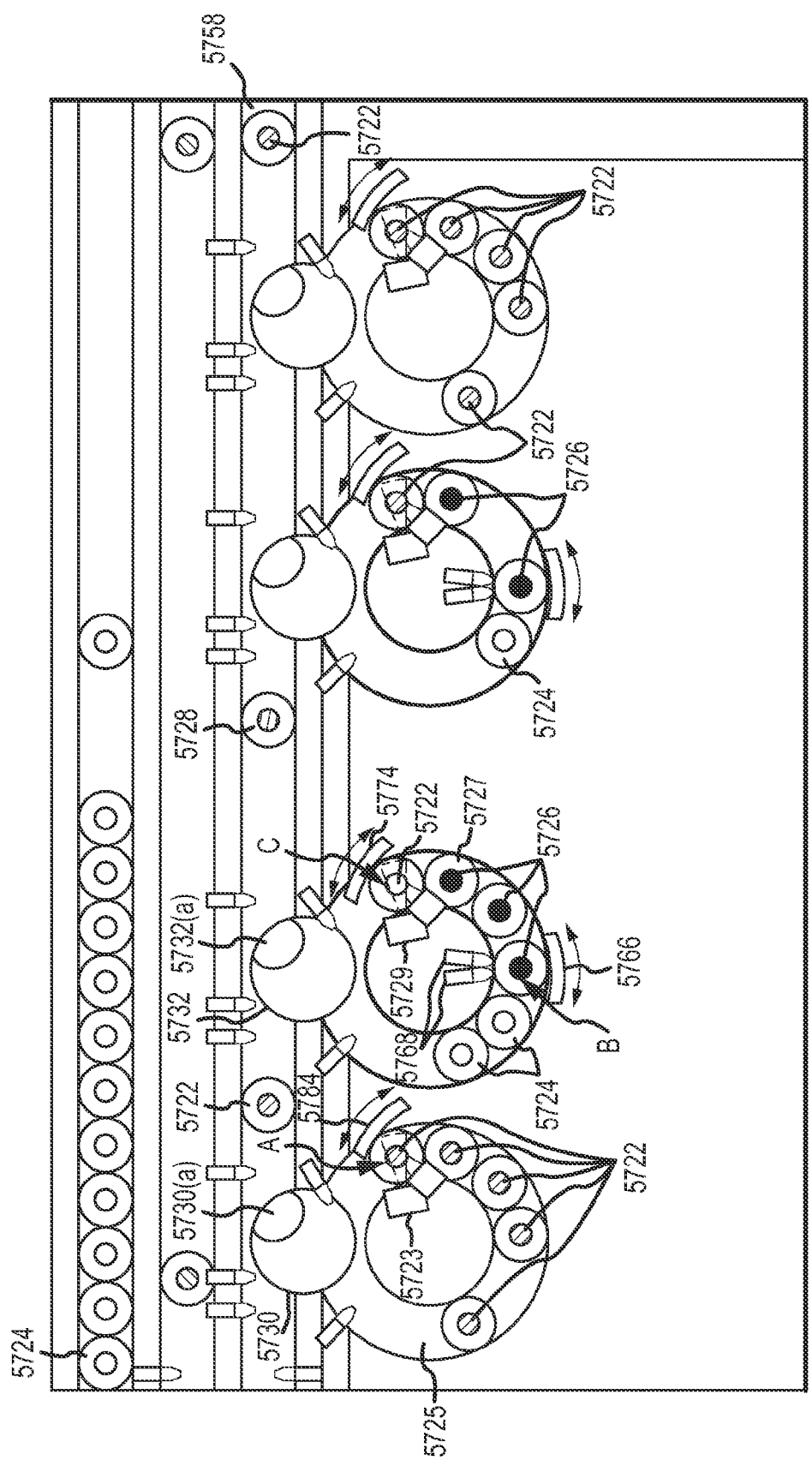
FIG. 58(a) shows a top plan view of a second aliquotter module according to an embodiment of the invention. The second aliquotter module comprises a rotatable gateway device in the form of a disk-like object.

In another embodiment, an aliquotter module is utilized with a conveyor transport system, as described above. FIG. 58 depicts an example of a workflow for an aliquotter module using the conveyor transport system. The aliquotter module comprises a conveyor 5758 which can transport pucks with primary tubes 5722 as well as pucks with secondary tubes with sample aliquots 5728. The system may also comprise a lane or conveyor with empty pucks 5724.

A number of circular tracks may be present in the aliquotter module. Such tracks may comprise a first circular track 5725 for transporting pucks with primary sample tubes and a second circular track 5727 for pucks that are empty 5724, pucks with empty secondary tubes 5726, and pucks with secondary tubes with sample aliquots 5728. Although the tracks 5725 and 5727 are circular in FIG. 58 tracks with any other configuration can be used. In some cases, the tracks can be in the form of endless loops (e.g., circles, ovals, etc.).

In the area of the first circular track 5725, a barcode reader 5723 may be present to read a barcode on a sample tube at an aspiration point (A), adjacent to track 5725. A puck manipulator 5784 may also be present at the aspiration point A to control the movement of a puck at aspiration point (A).

In the area of the second circular track 5727, a first barcode reader 5768 and a puck manipulator 5766 may be present to read a barcode on a secondary tube at a loading point (B) (adjacent to track 5727) for secondary tubes. Also in the area of the second circular track 5727, a second barcode reader 5729 and a second puck manipulator 5774 may be present at a dispensing point (C), adjacent to track 5727. The puck manipulators 5723, 5766, 5774 can be in the form of pivoting angular structures that allow a puck to stop or pass so that an operation can be performed on a sample tube in the puck (e.g., aspiration or dispense, or read a barcode on the sample tube).

The various tracks shown in FIG. 58 may utilize any suitable transport technology including a conveyor system sold under the tradename FlexLink™. The conveyor systems are based on a close-fitting, multiflex plastic chain conveyor that gives a straight, horizontal and vertical running capability.

A first rotatable gateway device 5730 may be adjacent to the linear track 5758 and the first circular track 5725. The first rotatable gateway device 5730 may have a generally crescent shape, so that a concave surface 5730(a) thereof may receive a circular edge of a puck. The first rotatable gateway device 5730 may receive a puck from the linear track 5758 and may direct it to first circular track 5725. The first rotatable gateway device 5730 may also receive a puck from the first circular track 5725 and may direct it to the linear track 5758. The second rotatable gateway device 5732 may also have a concave surface 5732(a) and may operate in a similar manner, allowing pucks to be transitioned from the second circular track 5727 to the linear track 5758, or vice-versa.

The rotatable gateway devices according to embodiments of the invention have a number of advantages. Compared to a gripper, for example, the rotatable gateway devices are less complex and take up less space. Further, the generally crescent shaped rotatable gateway devices can be cooperatively structured with the pucks, so that they temporarily and securely engage the pucks as they are transported from one track to another.

In operation, a primary tube 5722 is identified by the system on the main track 5758 for aliquoting and directed to the aliquotter's aspiration point (A), which may be proximate to the first circular track 5725. The first rotatable gateway device 5730 may receive a puck with a primary tube 5722, rotate, and direct it to the first circular track 5725. Empty pucks 5724 are sent by the system along the main track 5758 behind the puck with the primary tube to the aliquotter's loading point for secondary tubes (B), which may be proximate to the second circular track 5727. An unlimited quantity of empty pucks can be sent for any primary tube. A secondary tube is labeled and loaded into the empty puck 5726 at the aliquotter's loading point for secondary tubes (B) and is directed to the dispensing point (C) proximate to the second circular track 5727. The sample is aspirated from the primary tube at point (A) and dispensed into the secondary tube at point (C). Barcode readers 5723, 5729 at points (A) and (C) verify the correct association. When the aliquoting of the sample into the secondary tube is complete 5728, it is released to its next destination and the next secondary tube moves to the dispensing point (C). The second rotatable gateway device 5732 may receive the puck with the secondary tube with the sample aliquot 5728 from the second circular track 5727 and may transition it to the linear track 5758, by which it leaves the aliquoting unit.

The process can then be completed for any number of additional secondary tubes if the system further routes empty pucks to the aliquotter module. When the last secondary tube is finished, both the last secondary tube and the primary tube are released to their next destinations and the trailing secondary and primary tubes move to the dispensing (C) and aspiration points (A), respectively. The process can then be completed for the trailing secondary and primary tubes.

Figure 58B:
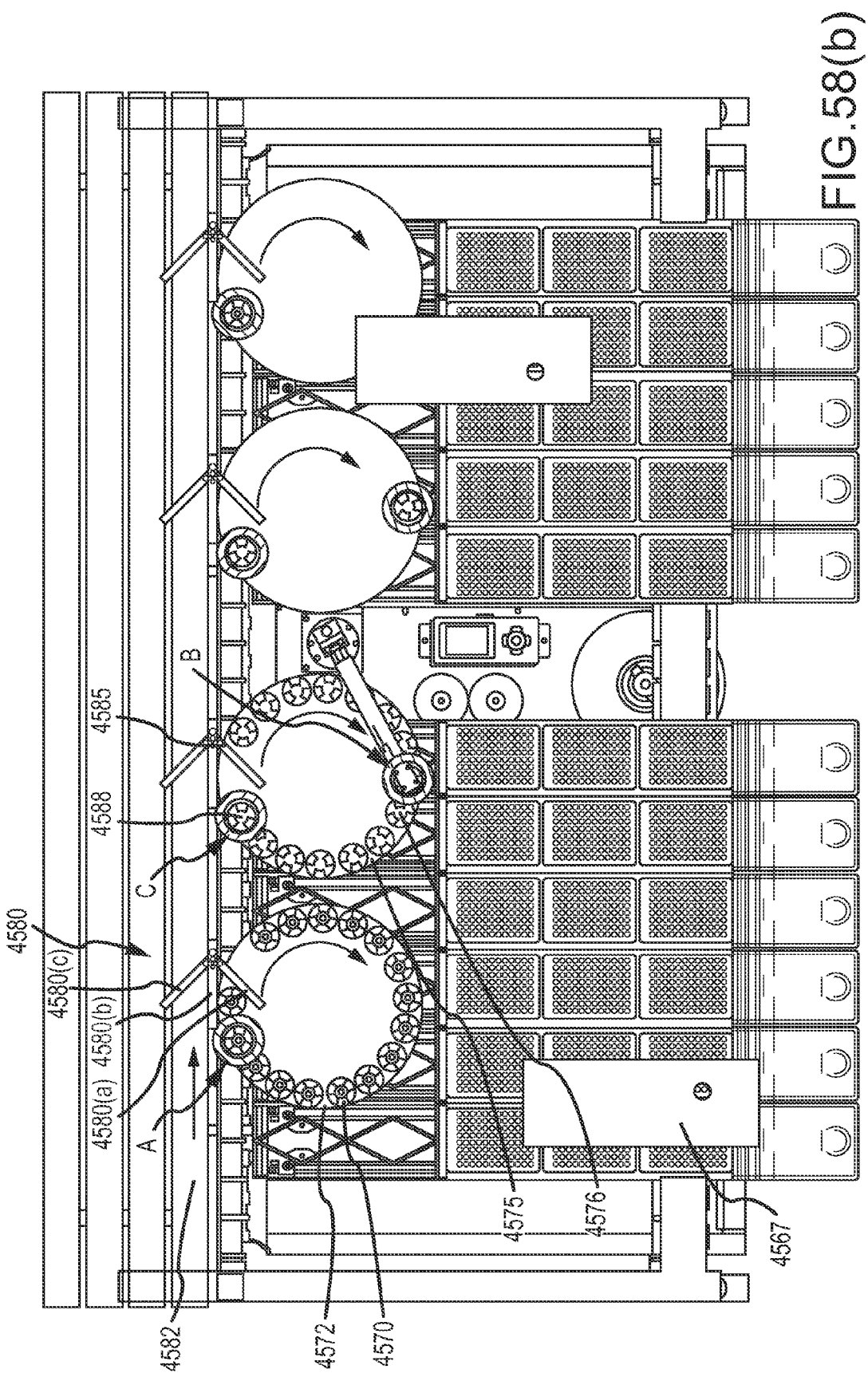
FIG. 58(b) shows a top plan view of a fourth aliquotter module according to an embodiment of the invention. The fourth aliquotter module comprises a rotatable gateway device in the form of a linear bar.

FIG. 58(b) shows another embodiment of the invention. The aliquotter module in FIG. 58(b) comprises linear transport lane 4582. As in the embodiment in FIG. 58(b), the system comprises first and second circular tracks 4572, 4575.

A number of primary sample containers in pucks 4570 may be on the first circular track 4572, and a number of secondary sample containers in pucks 4576 may be on the second circular track 4575. The pucks may move in a clockwise direction around the tracks.

A first rotatable gateway device 4580 in the form of a bar is adjacent to the first circular track 4572, and can direct pucks between the linear transport lane 4582 and the first circular track 4572. The first rotatable gateway device 4580 may include a first position 4580(a), a second position 4580(b), and a third position 4580(c). The first and third positions 4580(a), 4580(c) may be diverting positions. To move puck 4570 from the first circular track 4572 to the linear transport lane 4582, puck 4570 is hold by a puck manipulator (not shown) while the rotatable gateway device 4580 is moved into its first position 4580(*a*). The puck 4570 is released from the puck manipulator and moved by the first circular track 4572 to the linear transport lane 4582, by being diverted by rotatable gateway device 4580 in its first position 4580(*a*). To transfer a puck 4570 from the linear transport lane 4582 to the first circular track 4572, the rotatable gateway device 4580 is moved to its third position 4580(*c*) before a puck 4570 arrives at the diverting position. As soon as the puck 4570 arrives the diverting position the puck 4570 is diverted by rotatable gateway device 4580 in its third position 4580(*c*) from the linear transport lane 4582 to the first circular track 4572. A second rotatable gateway device 4585 is positioned adjacent to the second circular track 4575, and can operate in a similar manner to the first rotatable gateway device 4580.

As in the example shown in FIG. 58(*a*), the system in FIG. 58(*a*) includes a point (A) where aspiration takes place, a point (B) wherein the loading of secondary sample containers into pucks takes place, and a point (C) where the dispensing of a sample aliquot from the primary sample container to the secondary sample container take place. FIG. 58(*b*) also shows a pipettor 4567 which can move between the aspiration point (A) and the dispense point (C).

Another embodiment of the invention is directed to a system comprising an aliquotter module comprising a pipettor configured to aspirate a first aliquot volume of a sample in the primary sample container in a first independently movable puck located in an aspiration position and dispense the first aliquot volume of the sample in the secondary sample container in a second independently movable puck located in a dispensing position. The aliquotter module is configured to cause the secondary sample container to leave the aliquotter module before the primary sample container.

FIG. 59 shows another aliquoting module according to an embodiment of the invention. There are three linear and parallel lanes 5792, 5794, 5796, formed by two parallel walls, which are part of the aliquoting station. A main transport lane 5790 is perpendicular to the three lanes 5792, 5794, 5796. An open region 5798 at the end of the three lanes allows pucks to pass between the three lanes 5792, 5794, 5796, and eventually exit the aliquotter module.

In operation, a primary tube 5742 is identified by the system on the main track for aliquoting and is directed to the aliquotter's aspiration point (A), proximate to track 5794. Empty pucks 5744 are sent by the system behind the primary tube to the aliquotter's loading point for secondary tubes (B), proximate to track 5792. An unlimited quantity can be sent for any primary tube. A secondary tube is labeled and loaded into the empty puck 5746 at the aliquotter's loading point for secondary tubes (B) and directed to the dispensing point (C), proximate to track 5792, at the entrance to the open region 5798. The sample is aspirated from the primary tube at (A) and dispensed into the secondary tube at point (C). Barcode readers at points (A) and (C) verify the correct association. When a secondary tube is complete 5748, it is released to its next destination and the next secondary tube moves to the dispensing point (C).

The process can then be completed for any number of additional secondary tubes if the system further routes empty pucks to the aliquotter module. When the last secondary tube is finished, both the last secondary tube and the primary tube are released to their next destinations and the trailing secondary and primary tubes move to the dispensing (C) and aspiration points (A), respectively. The process can then be completed for the trailing secondary and primary tubes.

The pucks that are used in the embodiment in FIG. 59 can move independently of each other, and may each contain its own processor, memory, and communication interfaces. In some embodiments, the pucks may communicate with a central control system using a wireless communication mechanism. Further details regarding this type of transport system and other suitable transport systems can be found in U.S. Provisional Patent Application Nos. 61/556,667, 61/616,994, 61/486,126, and PCT Application No. PCT/US2012/037585, which are all herein incorporated by reference in their entirety for all purposes. Further details regarding suitable puck transportation system are also provided below. In some cases, the pucks may be generically referred to as "laboratory product transport elements."

The puck transport system is an autonomous guided vehicle for transporting an individual sample tube. Current chain or belt-driven transportation systems can only control the velocity of the complete track segments. Even if it is possible to have chains with different or even adjustable velocity, it may be difficult to move each individual track with its own velocity. In other words, the puck transport system with the lowest velocity or lowest acceleration/deceleration would dictate the complete segment.

The puck transport system of the present technology provides a transport system that is a self-propelled sample transport unit. The puck transport systems can move samples using the necessary motion parameters and can do so independently from each other. The puck transport systems improve efficiency by maximizing throughput, even with varied statuses for different sample tubes (e.g., normal versus urgent), without the need to sacrifice or risk sample quality of sensitive samples, as each sample can be transported with the maximum velocity. Additionally, the puck transport system may be managed by the central controller or a local intersection controller.

VIII. Non-Contact Sample Tube Characterization

Physical characteristics of a specimen container may be determined using one or more sensors that are fixed relative to a specimen transport system. For example, it may be desirable to determine physical characteristics of a specimen container as the specimen container is transported between stations of a laboratory analysis system. A non-contact specimen container characterization system may be capable of determining various physical characteristics of a specimen container with no contact between the sensor devices and the specimen container. In comparison with a specimen container characterization system that picks up a specimen or otherwise requires contact with the specimen container to determine characteristics of the specimen container, a non-contact specimen container characterization system may obtain information about the specimen container in a relatively time-efficient manner, allowing for rapid specimen processing. Additionally, non-contact specimen container characterization system can determine characteristics of a specimen container without disturbing the position of the container. This may be beneficial for systems in which position of specimen containers in a queue is related to the order in which specimen containers are scheduled to be processed.

Physical characteristics such as specimen container diameter and specimen container length may be determined by the non-contact specimen container characterization system.

The color of a cap for a specimen container may also be determined. In some embodiments, liquid level determinations may be performed by a non-contact specimen characterization system.

A specimen container may be transported by a transport system such as a conveyor transport system, a self-propelled puck transport system, a magnetic transport system, or other transport system. A conveyor transport system may include a conveyor, such as a conveyor belt or track, for transporting specimens.

The specimen container may be a sample tube used to contain samples of blood or other fluids for laboratory analysis. One or more specimen containers may be inserted into a sample carrier for transport by a conveyor transport system or other transport system. For example, a sample carrier placed on a conveyor belt may be carried by the movement of the belt.

FIG. 60 is an illustrative top view of a non-contact specimen container characterization system. Sample carrier 6002 is shown on a conveyor 6004. Same carrier 6002 may be configured to hold one or more specimen containers 6012. One or more sensors, such as specimen container diameter sensor 6006, cap color sensor 6008, and specimen container height sensor 6010 are fixed relative to conveyor 6004. For example, sensors 6006-6010 may be coupled to a supporting structure or sidewall of conveyor 6004. Conveyor 6004 may be a conveyor belt, conveyor track, or other surface for transporting specimens. In other embodiments, sensors 6006-6010 may be located in a fixed position and specimen containers are manually transported to the sensors or otherwise become located in the sensor range without a conveyor.

In some embodiments, sensors 6006, 6008 and 6010 are able to determine physical characteristics associated with the specimen container 6002 as the specimen container 6002 is moved by the conveyor belt 6004. In alternative embodiments, conveyor belt 204 is configured to stop when sample tube 6012 is at a position at which sensors 6006, 6008 and 6010 are able to determine physical characteristics of sample tube 6002.

Figure 61:
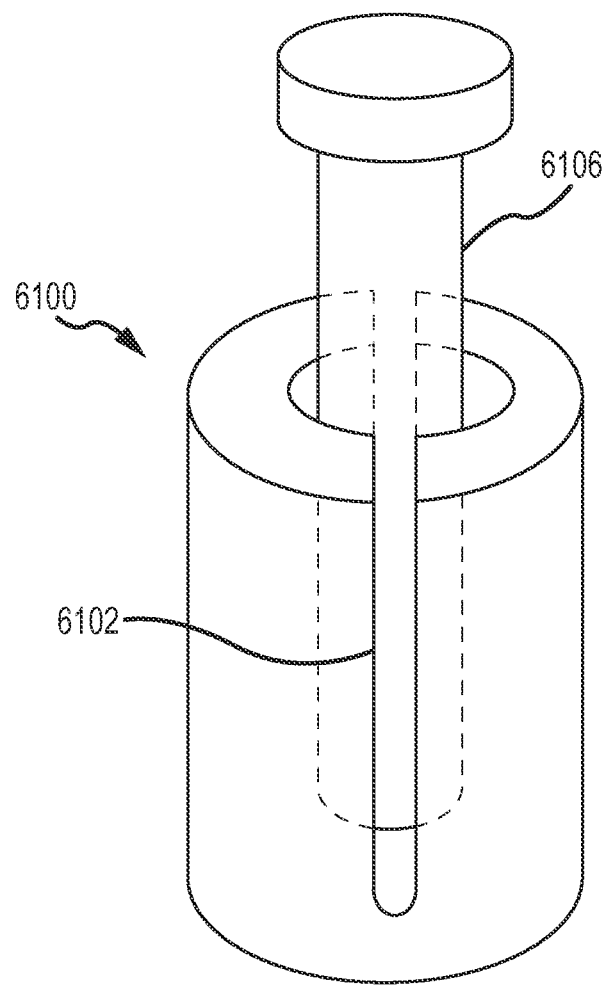
FIG. 61 depicts an illustrative sample carrier.

FIG. 61 shows an illustrative sample carrier with cutouts to allow optical access to the specimen container. A sample carrier 6100 used to transport a specimen container 6106 may have one or more slots 6102 to allow specimen container 6106 to be visible to the non-contact specimen container characterization system. Slots 6102 may have a vertical orientation to allow the length of specimen container 6106 to be determined while the specimen container is held upright within specimen carrier 6100.

Figure 62:
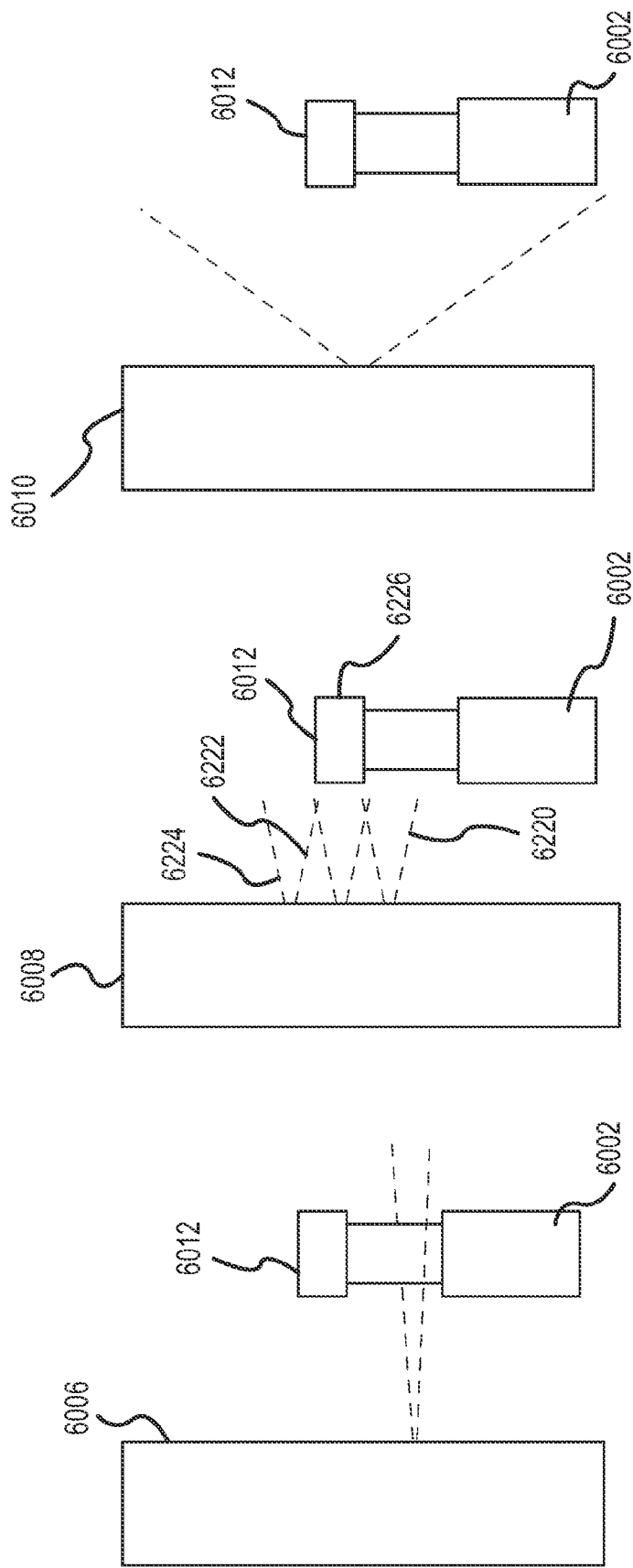
FIGS. 62(a)-(c) depict illustrative side views of sensors of an exemplary non-contact sample tube characterization sensor system.

FIGS. 62(a)-62(c) show illustrative side views of the specimen container sensors depicted in FIG. 60. FIG. 62(a) shows specimen container diameter sensor 6006. Specimen container diameter sensor 6006 can have a light detector that is horizontally oriented (as indicated by the dotted lines originating at diameter sensor 6006). The light detector of diameter sensor 6206 can be a linear optical array having a plurality of photodiodes (i.e., pixels) arranged horizontally. For example, a linear array having 5-1000 pixels, such as 50-300 pixels, e.g., 100 pixels, may be used. In an exemplary embodiment, a TAOS TSL3301-LP linear array can be used. Each photodiode can produce a photocurrent proportional to an amount of light incident on the photodiode. The diameter of specimen container 6012 can be determined based on the output of the linear optical array of diameter sensor 6006. For example, if specimen container 6012 is located between a light source and the linear optical array, a number of photodiodes on which a relatively low amount of light is incident (e.g., a number of photodiodes producing a photocurrent below a threshold level) may correspond to the diameter of the specimen container.

FIG. 62(b) shows specimen container cap color sensor 6008. Specimen container cap color sensor 208 may comprise one or more color sensors for determining a color of a cap on specimen container 6012. The color sensor is configured to sense an area aligned with the cap of specimen container 6012. Multiple cap color sensors 6220, 6222 and 6224 are illustrated by the dotted lines in FIG. 4(b). Specimen container 212 shown in FIG. 4(b) has cap 226 that is aligned with cap color sensor 6222. For a specimen container that is taller than the specimen container 6012 as shown, cap color sensor 6224 may be used. Similarly, for a specimen container that is shorter than the specimen container 6012 as shown, cap color sensor 6220 may be used. A color sensor of cap color sensor 4108 may be TAOS 230D light-to-frequency converter. Alternatively, the color sensor may be a camera such as a CCD camera. The color of cap 6226 may be determined based on the output of the color sensor. A camera may further be used to read a barcode or other label attached to specimen container 6012.

FIG. 62(c) shows a specimen container length sensor 6010. The length sensor 6010 can have a light detector that is vertically oriented (as indicated by the dotted line originating at length sensor 6010). For example, the light detector of length sensor 6010 can be a linear optical array (e.g., a TAOS TSL3301-LP linear array) having a plurality of photodiodes (i.e., pixels) arranged in a linear array similar to the linear optical array described with reference to diameter sensor 206. The length of specimen container 6012 (e.g., from the bottom of the tube to the top of the cap) can be determined based on the output of the linear optical array of length sensor 210. In some embodiments, length sensor 6010 may be used to detect the liquid level of one or more liquid types in specimen container 6012.

In some embodiments, a sensor is used to determine whether specimen container 6012 is in a position at which physical characteristics of specimen container 6012 can be determined. For example, the output of specimen container length sensor 6010 may be used to determine whether specimen container 6012 is in a position at which cap color sensor 6008 can determine the cap color of specimen container 6012.

Figure 63:
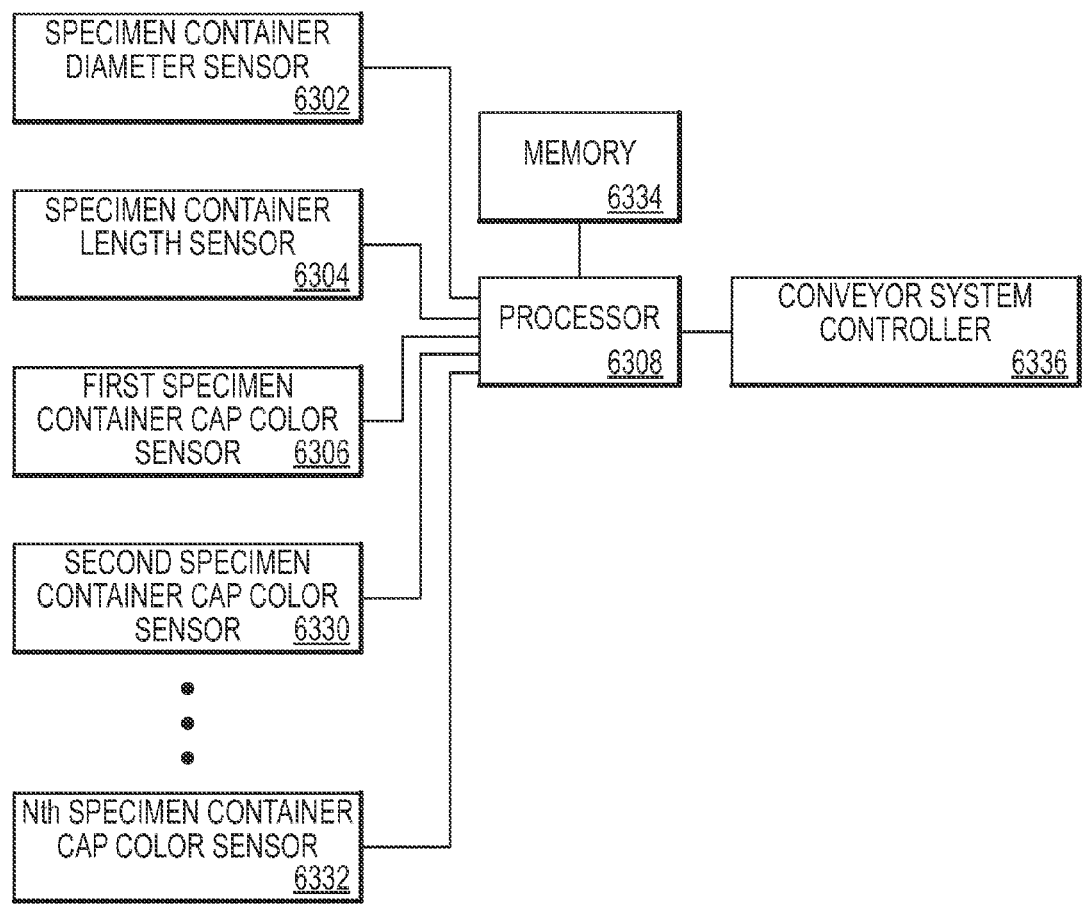
FIG. 63 is an illustrative block diagram for a non-contact specimen container characterization system.

FIG. 63 is an illustrative block diagram for a non-contact specimen container characterization system. Specimen container diameter sensor 6302 (corresponding to diameter sensor 6006 of FIG. 60) and specimen container length sensor 6304 (corresponding to length sensor 6010 of FIG. 60) may be communicatively coupled to processor 6308. Processor 6308 may be a processor of a conveyor control system, a processor of a laboratory automation system, or a processor of another system or computer. One or more cap color sensors, such as a first cap color sensor 506 and second cap color sensor 530 through an Nth cap color sensor 532 (all corresponding to cap color sensor 6008 of FIG. 60), may also be communicatively coupled to the processor. In one embodiment, processor 6308 may receive a signal from specimen container length sensor 6304 indicating the length of specimen container 212. Based on the signal received from specimen container length sensor 6304, processor 6308 may execute instructions to determine which of specimen container cap color sensors 6306, 6330, 6332 to use for sensing the color of cap 6226.

In various embodiments, a conveyor system controller 6336 may be communicatively coupled to processor 6308. Conveyor system controller 6336 may be a processor that generates signals to drive a conveyor motor, such as a conveyor motor associated with a conveyor belt 6004. Alternatively, conveyor system controller 6336 may be a motor associated with a conveyor belt 6004. Processor 6308 may receive a signal from one or more of diameter sensor 6302, length sensor 6304, and/or cap color sensors 6306, 6330, 6332 and processor 6308 may execute instructions to determine when a specimen container 212 is in a position at which its physical characteristics can be determined, based on the received signal or signals. When the specimen container 212 is in a position at which its physical characteristics can be determined, the processor 6308 may generate a signal instructing conveyor system controller 6336 to halt the motion of the conveyor as indicated at 6406. In this manner, a conveyor belt is stopped each time a specimen container 212 is aligned with the characterization sensors.

Instructions executed by the processor 6308 may be stored on processor 6308 or may be stored in a memory 6334 accessible by processor 6308.

Figure 64:
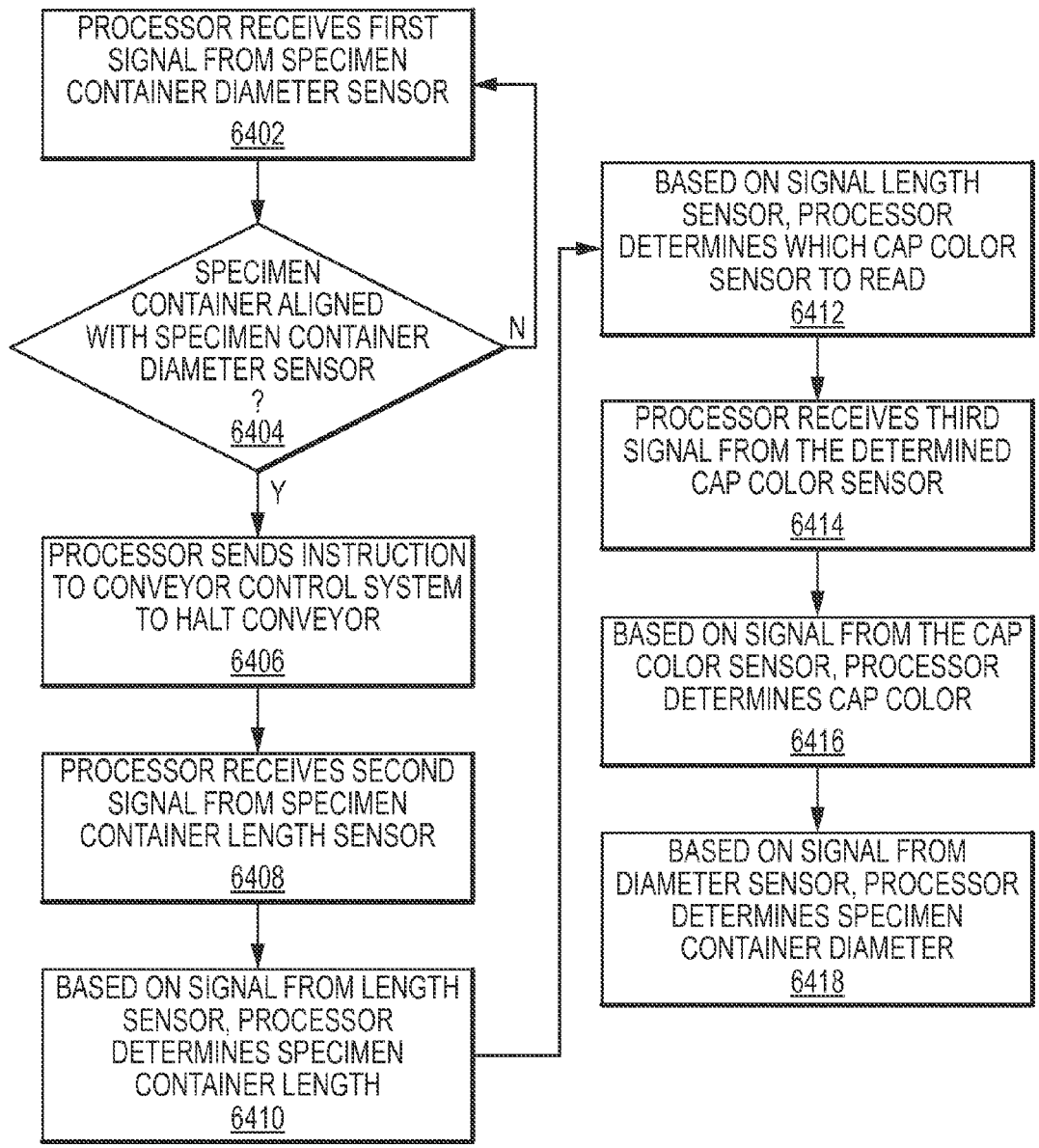
FIG. 64 is a flow diagram for a non-contact specimen container characterization system.

FIG. 64 is a flow diagram for a non-contact specimen container characterization system. At operation 6402, a processor 6308 can receive a first signal from a specimen container diameter sensor 6302. Based on the received signal, the processor 6308 can determine whether a specimen container 6012 is aligned with specimen container diameter sensor such that a diameter can be determined, as indicated at decision diamond 6404. If specimen container 6012 is aligned with diameter sensor 6302, processor 6308 may generate an instruction to halt a conveyor system. For example, processor 6308 may generate an instruction to halt a conveyor system when a signal received from diameter sensor 6302 indicates that a light level has fallen below a threshold level for a predetermined number of photodiodes of a linear optical array. In another example, processor 508 may generate an instruction to halt a conveyor system after a delay starting from when a signal received from diameter sensor 6302 indicates that a light level has fallen below a threshold level for a predetermined number of photodiodes of a linear optical array. In alternative embodiments, processor 6308 can determine a specimen container diameter, specimen container length and cap color without halting the conveyance system. The physical characteristics may be determined after a delay starting at a point in time when diameter sensor 502 or another sensor first detects the presence of a specimen container 6012.

At operation 6408, processor 6308 receives a second signal from specimen container length sensor 504. Based on the second signal, processor 6308 can determine the length of the specimen container 212, as indicated at operation 6410. At operation 6412, processor 6308 can determine which of cap color sensors 6306, 6330, 6332 to use for determining the color of cap 6226. At operation 6414, processor 6308 receives a third signal from the cap color sensor determined at operation 6412. Based on the signal from the cap color sensor determined at operation 6412, processor 6308 can determine the cap color of cap 6226, as indicated at 6416.

In some embodiments, processor 6308 may receive a signal from diameter sensor 6302 after the conveyor has been halted. Based on the signal received from diameter sensor 6302, processor 6308 can determine the diameter of specimen container 6012, as indicated at 6418.

After the physical characteristics of a specimen container have been determined, the specimen container may proceed to a centrifuge module for centrifugation. The physical characteristics of the specimen container can be performed after centrifugation.

IX. Accelerometer Based Centrifuge Imbalance Sensor

A centrifuge may include an imbalance sensor to prevent excessive imbalance of the centrifuge. An accelerometer based imbalance sensor may be used to determine when centrifuge imbalance is occurring in excess of the imbalance tolerance of a centrifuge.

The accelerometer based imbalance sensor may sense acceleration of a centrifuge containment vessel along one, two, or three axes. Sensing along three axes may provide a level of detail about the imbalance occurring in a centrifuge to allow monitoring for early wear of shock mounting structures or other mechanical components of a centrifuge. Determining imbalance based on acceleration (i.e. "g force") may provide a more accurate indication than is available from displacement based sensing techniques.

Figure 65:
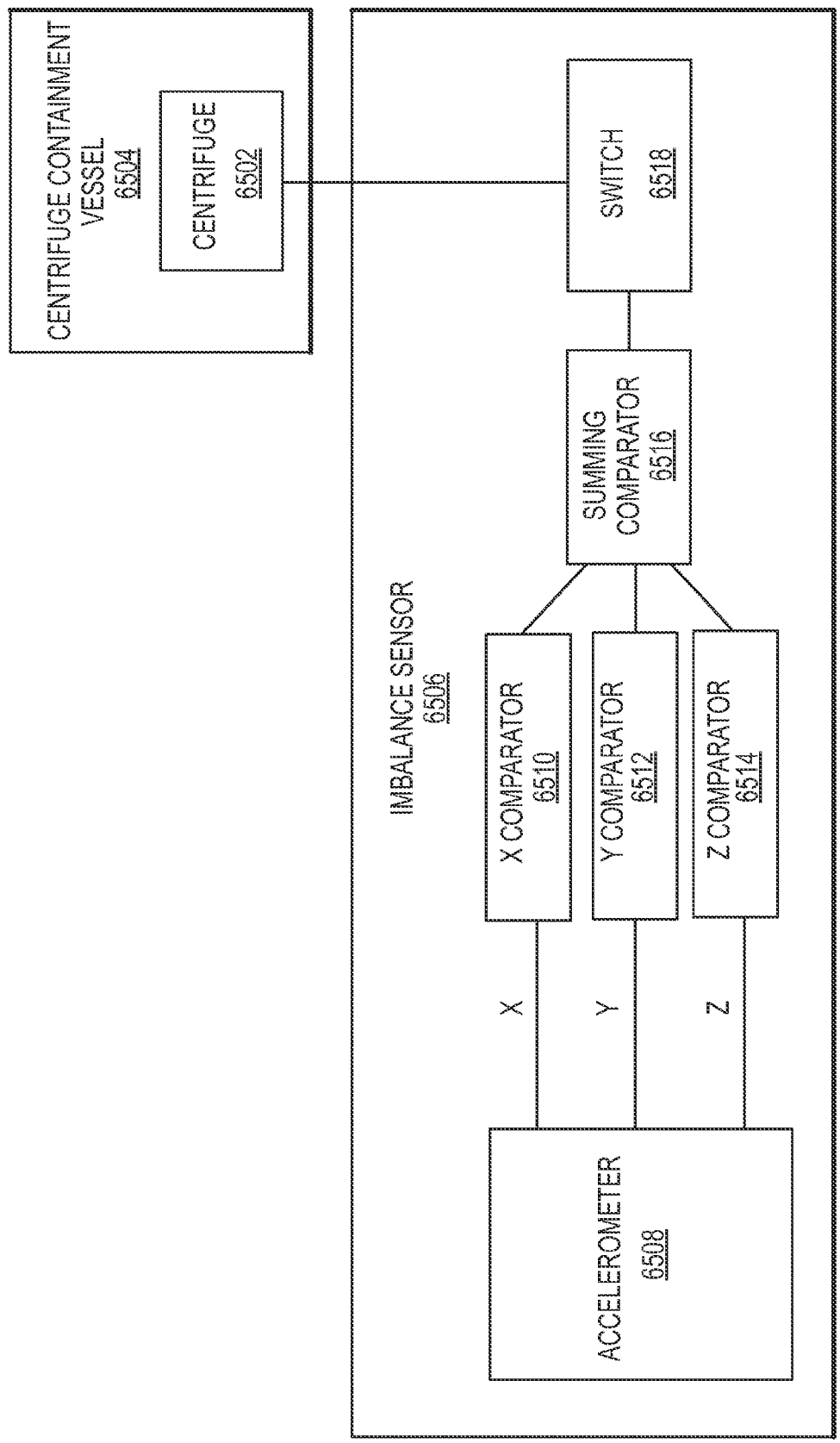
FIG. 65 depicts an illustrative block diagram of an accelerometer based centrifuge imbalance sensor.

An illustrative system diagram of an accelerometer based centrifuge imbalance sensor is depicted in FIG. 65. Centrifuge 6502 may be mounted within centrifuge containment vessel 6504. Accelerometer 6508 of imbalance sensor 6506 may be directly or indirectly mechanically coupled to a component of centrifuge 6502. For example, accelerometer 6508 may be mechanically coupled to centrifuge containment vessel 6504 such that acceleration is transmitted from the surface of centrifuge containment vessel 6504 to accelerometer 6508. In another example, accelerometer 6508 may be mounted on a printed circuit board (PCB) that is mechanically coupled to the centrifuge containment vessel 6504. In other embodiments, accelerometer 6508 may be mounted to another element of centrifuge 6502, such as on or within the centrifuge rotor, shaft, or motor.

Accelerometer 6508 may be a single- or multi-axis device capable of generating a signal corresponding to the acceleration of an object to which the accelerometer is mechanically coupled. The accelerometer may have piezoelectric, piezoresistive, capacitive or other component capable of generating a signal based on acceleration. Accelerometer 6508 may be a micro electro-mechanical systems (MEMS) device, such as the LIS3L02AS4 3-axis solid state linear accelerometer by STMicroelectronics.

Accelerometer 6508 may output voltage values corresponding to the acceleration of centrifuge containment vessel 6504 along three axes, e.g., x, y and z axes. The x axis output voltage of accelerometer 6508 may be compared to a first reference voltage at x-axis comparator 6510. The y axis output voltage of accelerometer 6508 may be compared to a second reference voltage at y-axis comparator 6512. The z axis output voltage of accelerometer 6508 may be compared to a third reference voltage at z-axis comparator 6514. The voltage output of comparators 6510, 6512, and 6514 may be added to obtain a sum voltage. Summing comparator 6516 may compare the sum voltage to a fourth reference voltage. One or more of the first reference voltage, second reference voltage, third reference voltage and fourth reference voltage can be based on the imbalance tolerance of the centrifuge and may be adjustable. For example, a potentiometer may be adjusted to alter a supply voltage, or a value may be adjusted in software or firmware associated with imbalance sensor 6506. The adjustable reference voltage values may allow the imbalance sensor to be adjusted for use with different centrifuges having different imbalance tolerances.

The output of summing comparator 6516 may be provided to switch 6518. Switch 6518 may be, e.g., a field-effect transistor (FET) switch. The output of the switch may be connected to centrifuge 6502 such that rotation of centrifuge 6502 is discontinued when the state of switch 6518 corresponds to an imbalance condition of the centrifuge as indicated by the output of summing comparator 6516. In this manner, when acceleration of centrifuge containment vessel 6504 as measured along one or more of the x-axis, y-axis and z-axis exceeds the imbalance tolerance threshold of centrifuge 6502, rotation of centrifuge 6502 can be discontinued. In some embodiments, an alert may be generated based on the output of comparator 6510, comparator 6512, comparator 6514, comparator 6516, and/or switch 6518. The alert may be a message, light, sound, etc., that may be communicated to a laboratory automation system and/or displayed or emitted by the centrifuge.

One or more of comparators 6510, 6512, 6514, and 6516 may be communicatively coupled to a processor. The processor (not shown) may be a processor associated with centrifuge 6502, a processor of a laboratory automation system, or a processor of another system or computer. Instructions executed by the processor may be stored on the processor or may be stored in a memory (not shown) accessible by the processor. Switch 6518 may be communicatively coupled to a processor. An alert may be generated when the output of one or more of comparators 6510, 6512, 6514, and 6516 exceeds a threshold voltage level. In another embodiment, an alert may be generated when a switch 6518 is switched to a state resulting in centrifuge 6502 shutdown. Such alerts may be transmitted to a laboratory automation system computer such that scheduling of sample processing can be adjusted based on the centrifuge shutdown.

In some embodiments, one or more components of imbalance sensor 6506, such as accelerometer 6508, comparators 6510-6516, switch 6528, and other associated components, may be mounted on a PCB. The PCB may be mounted to centrifuge containment vessel 6504 such that the acceleration of centrifuge containment vessel 6504 is transmitted to accelerometer 6508.

Figure 66A:
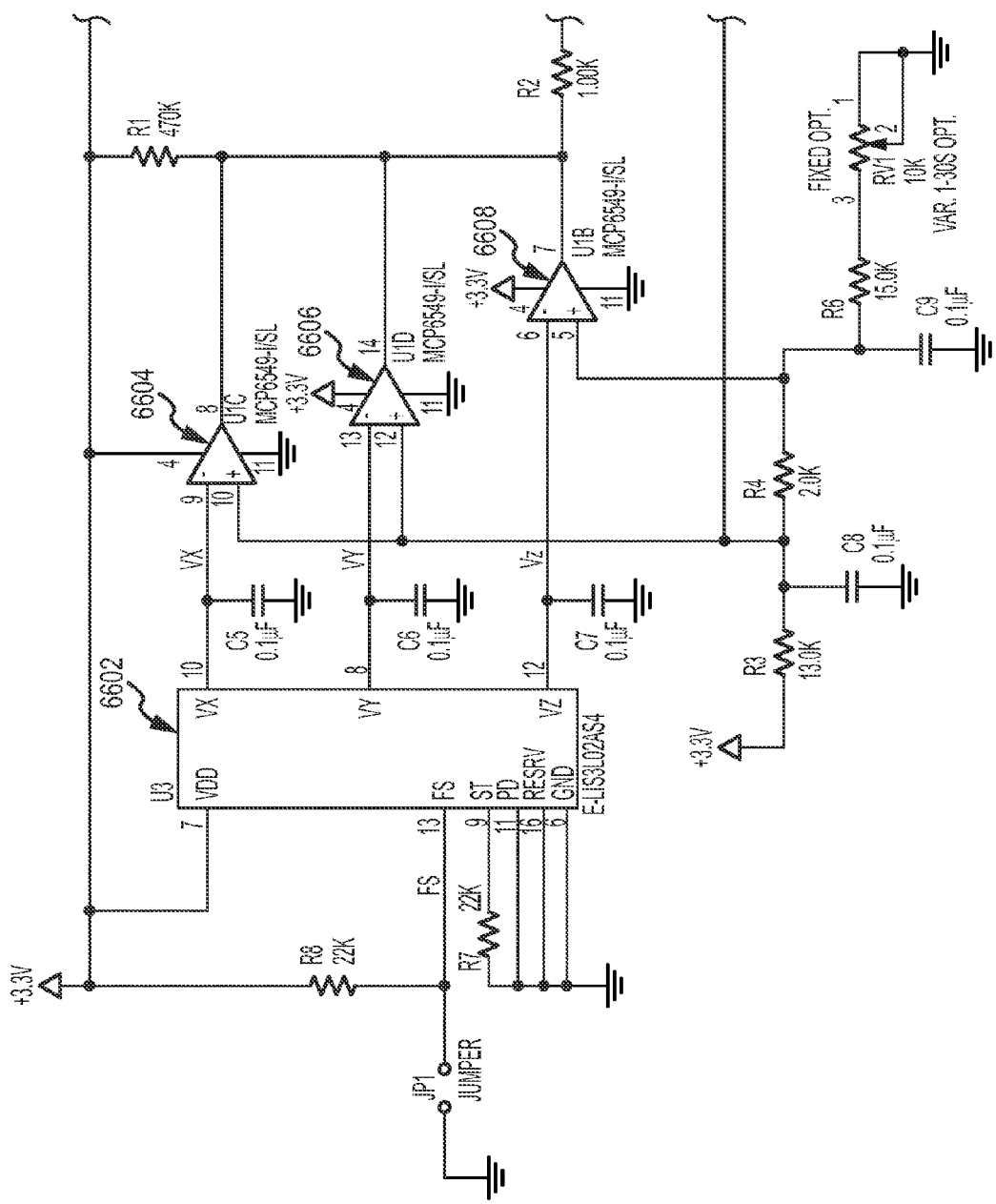
FIGS. 66(a)-(b) depict an illustrative circuit diagram for an accelerometer based centrifuge imbalance sensor.
Figure 66B:
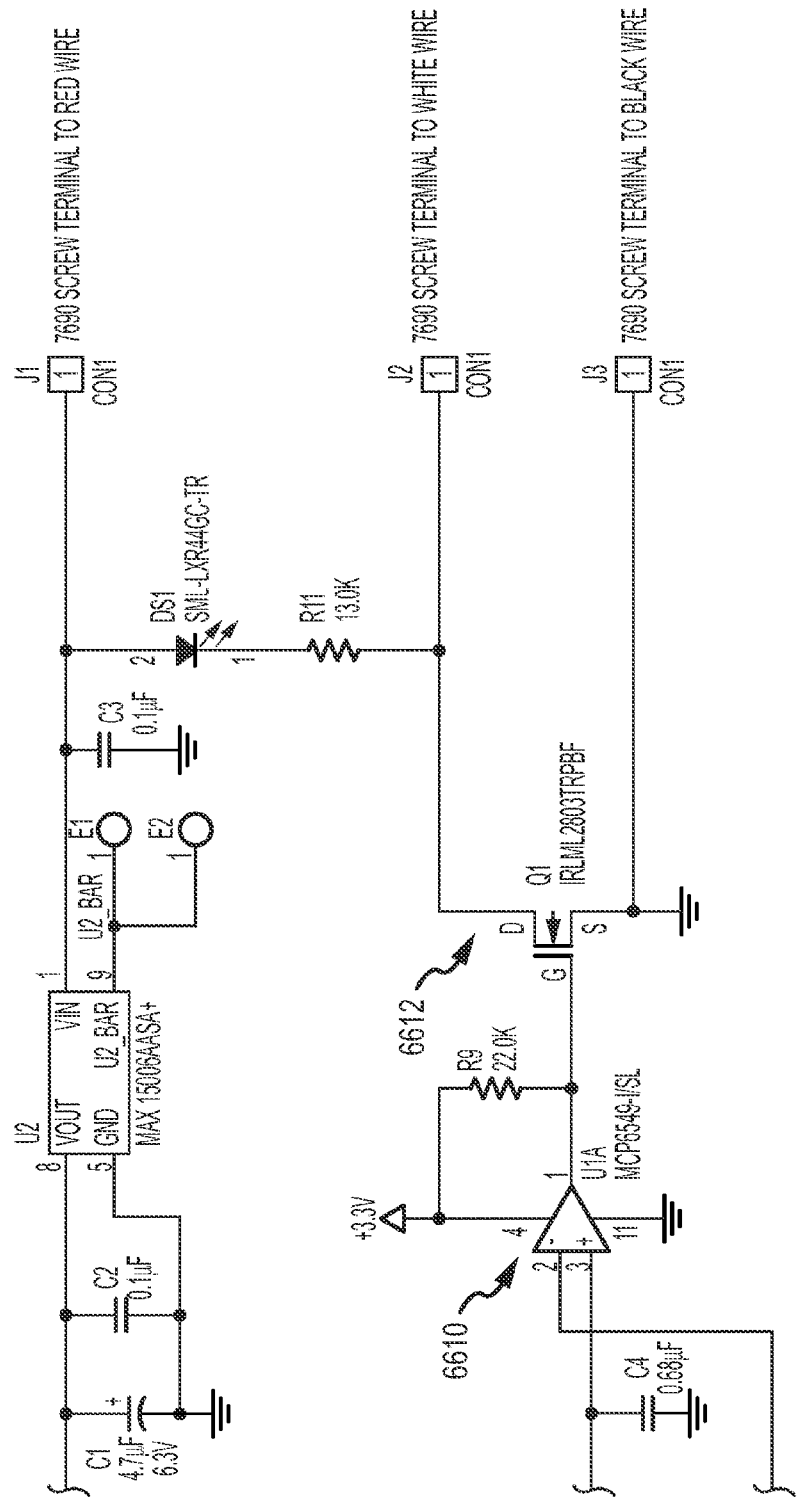

FIGS. 66(*a*)-(*b*) depict an illustrative circuit diagram for an accelerometer based centrifuge imbalance sensor. Accelerometer 6602 (e.g., accelerometer 6508 described with reference to FIG. 65) provides voltage outputs corresponding to acceleration measured along x, y and z axes. The x-axis output is provided to comparator 6604 (e.g., comparator 6510 described with reference to FIG. 65). The y-axis output is provided to comparator 6606 (e.g., comparator 6512 described with reference to FIG. 65). The z-axis output is provided to comparator 6608 (e.g., comparator 6514 described with reference to FIG. 65). The output of comparators 6604, 6606 and 6608 is provided to summing comparator 810 (e.g., comparator 6516 described with reference to FIG. 65). The output of summing comparator 6610 is provided to switch 6612 (e.g., switch 6518 describe with reference to FIG. 65).

In some embodiments, the resistors used to regulate one or more of the first reference voltage, second reference voltage, third reference voltage and fourth reference voltage are replaced with a digital to analog converter that allows setting of reference voltage values with software via a user interface. In this manner, the accelerometer based imbalance sensor is easily adaptable to various centrifuges having different imbalance tolerance levels and to accommodate various sample handling requirements. Alternatively, the resistors used to regulate one or more of the first reference voltage, second reference voltage, third reference voltage and fourth reference voltage are replaced with potentiometers to allow manual adjustment of the resistance values.

Figure 67:
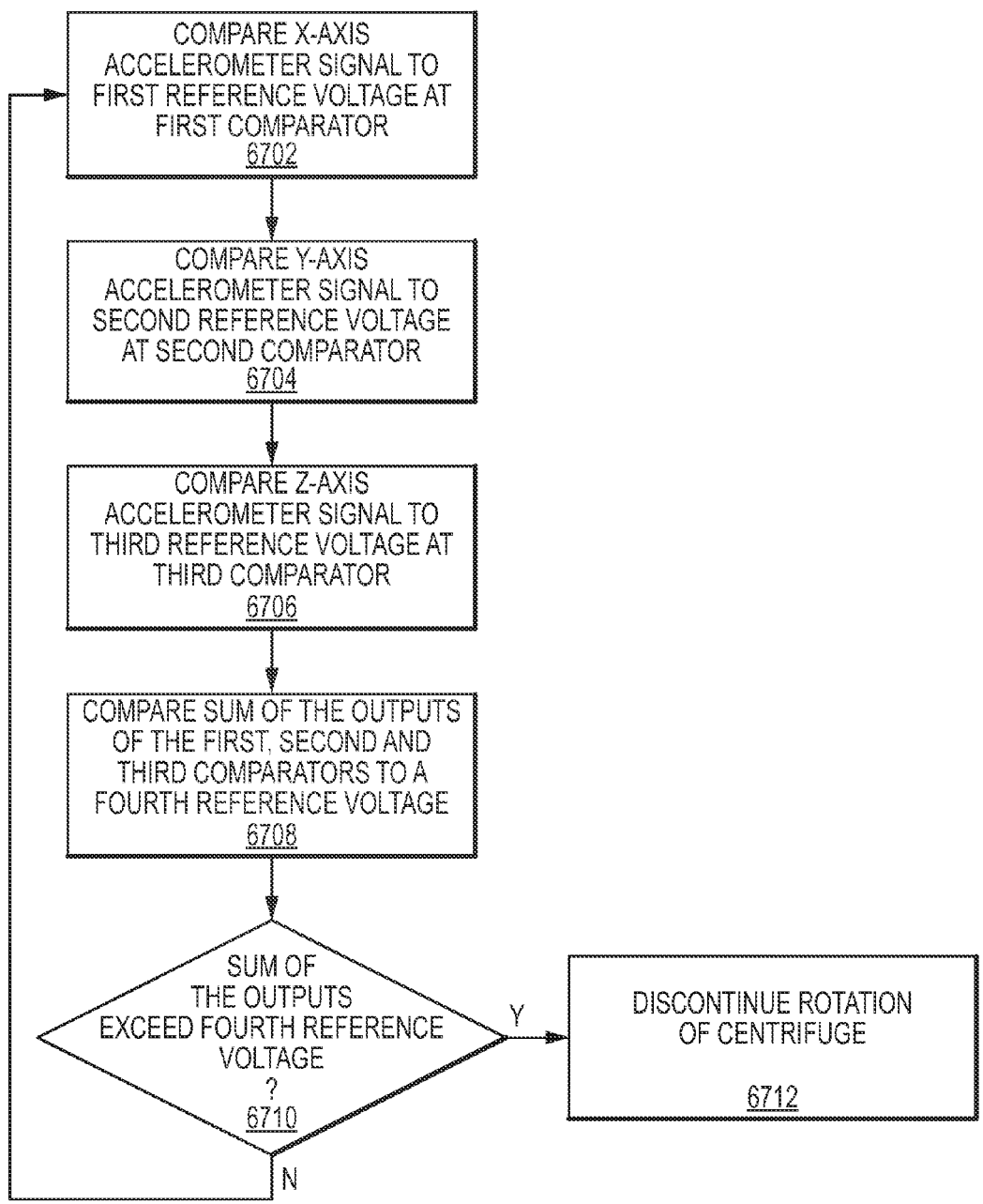
FIG. 67 shows a flow diagram for a centrifuge imbalance sensor.

FIG. 67 shows a flow diagram for a centrifuge imbalance sensor coupled to a centrifuge containment vessel 6504 for a centrifuge 6502. The imbalance sensor can include an accelerometer 6508 capable of measuring acceleration along three axes. At operation 6702, an x-axis accelerometer signal is compared by a first comparator 6510 to a first reference voltage. At operation 6704, a y-axis accelerometer signal is compared by a second comparator 6512 to a second reference voltage. At operation 6706, a z-axis accelerometer signal is compared by a third comparator 6514 to a third reference voltage. The sum of the outputs of the first, second and third comparators are compared by a summing comparator 6516 to a fourth reference voltage, as indicated at operation 6708. The summing comparator 6516 determines whether the sum of the outputs exceeds the first reference voltage, as indicated at decision diamond 6710. If the sum of the outputs exceeds the fourth reference voltage, the operation of centrifuge 6502 can be halted, as indicated at operation 6712. For example, the output of the summing comparator may be coupled to a switch 6518 configured to discontinue the rotation of centrifuge 6502.

X. Centrifuge Drawer

FIGS. 68-75 show various systems associated with a centrifuge drawer 6800. Mounting a centrifuge on a centrifuge drawer can facilitate movement of the centrifuge for service access and can simplify re-installation of a centrifuge. Centrifuge drawer includes a mounting platform 6802 coupled to frame 6804 via telescoping rails 6806. A centrifuge (not shown) may be mounted on mounting platform 6802. Telescoping rails 6806 can be extended to allow the centrifuge to be withdrawn from its installed position. Telescoping rails 6806 may be locking rails such that the centrifuge can be locked in its installed position (retracted position) or locked in a fully extended position in which the centrifuge is extended away from its installed position. In this manner, the centrifuge is prevented from being moved by the drawer while a centrifuge cycle is in progress. In some embodiments, centrifuge drawer 6800 includes alignment pucks 6808 to mechanically hold the position of the centrifuge to frame 6804. Centrifuge drawer 6800 may further comprise two or more wheels 6810 coupled to frame 6804.

The centrifuge typically receives power and communications capability through cables that connect the centrifuge module power source. Centrifuge drawer 6800 may include a feature for managing cables when the drawer is extended and retracted. In some embodiments, centrifuge drawer 6800 comprises an e-chain 6812 as shown in retracted position 6812(*a*) and extended position 6812(*b*) in FIG. 69. Although e-chain 6812 is shown in both retracted and extended positions for illustrative purposes, typically centrifuge drawer 6800 would have a single e-chain 6812 that would move between positions 6812(*a*) and 6812(*b*) as the drawer is operated. E-chain 6812 may contain cables such as power and communication cables. E-chain 6812 may be constructed from a flexible material such as a flexible plastic configured to extend and retract such that cables contained within e-chain 6812 do not interfere with the operation of centrifuge drawer 6800.

Figure 70A:
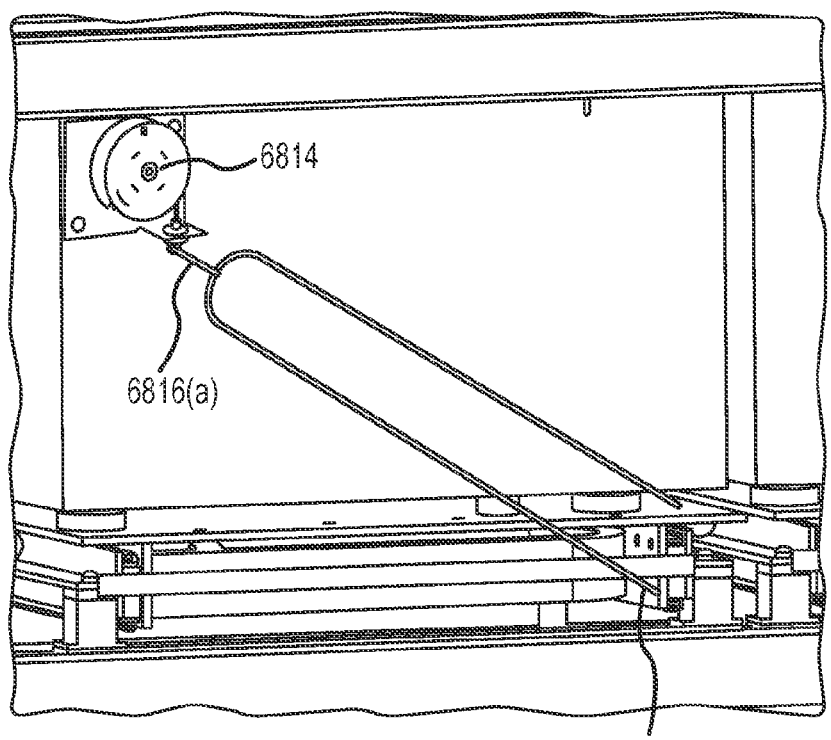
FIGS. 70(a)-(b) show an illustrative cable management device for a centrifuge drawer, according to a second embodiment.
Figure 70B:
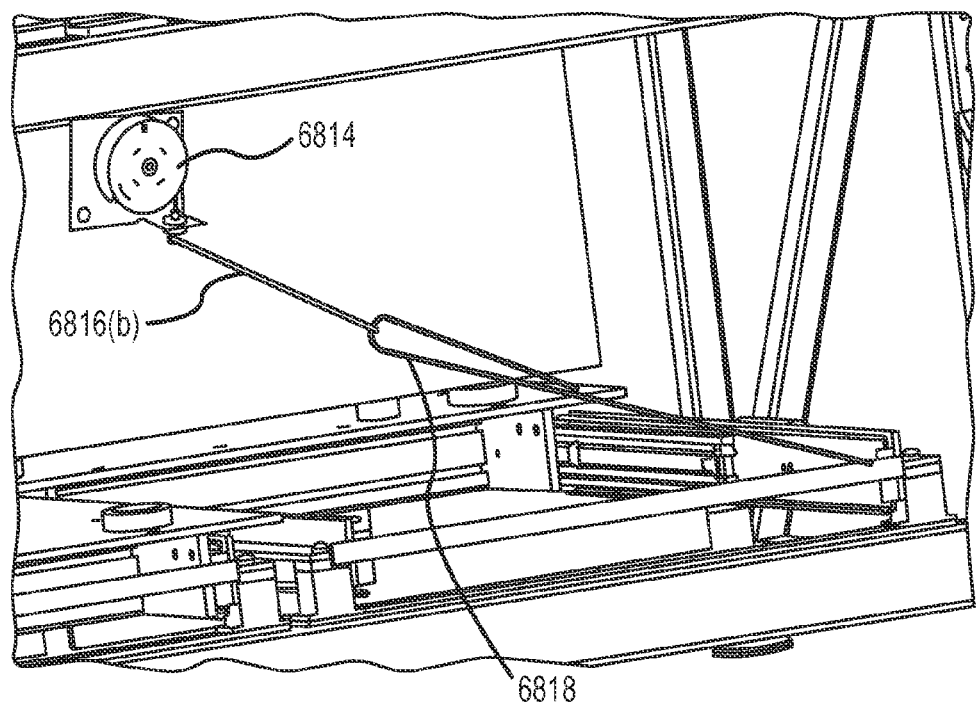

In another embodiment, a cable retractor 6814 can be used to manage cables, as shown in FIGS. 70(*a*)-70(*b*). Cable retractor 6814 may use a spring loaded cable retractor to keep one or more cables 6818 from interfering with the operation of centrifuge drawer 6800. Spring loaded cable retractor is shown in retracted position 6816(*a*) and extended position 6816(*b*).

Figure 71:
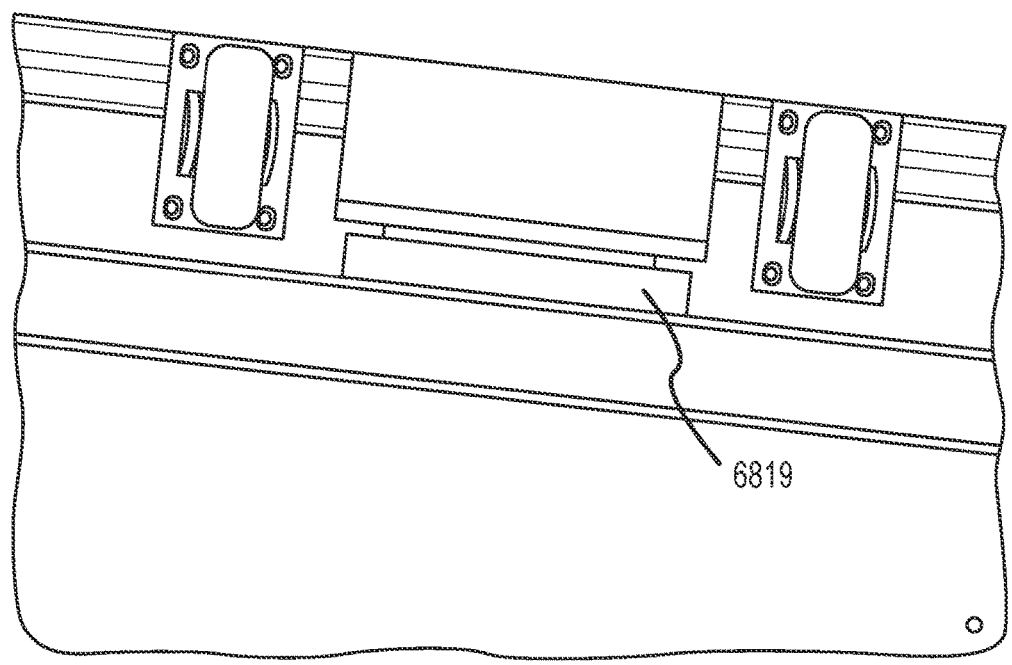
FIG. 71 shows an illustrative magnetic latch for a centrifuge drawer.
Figure 72A:
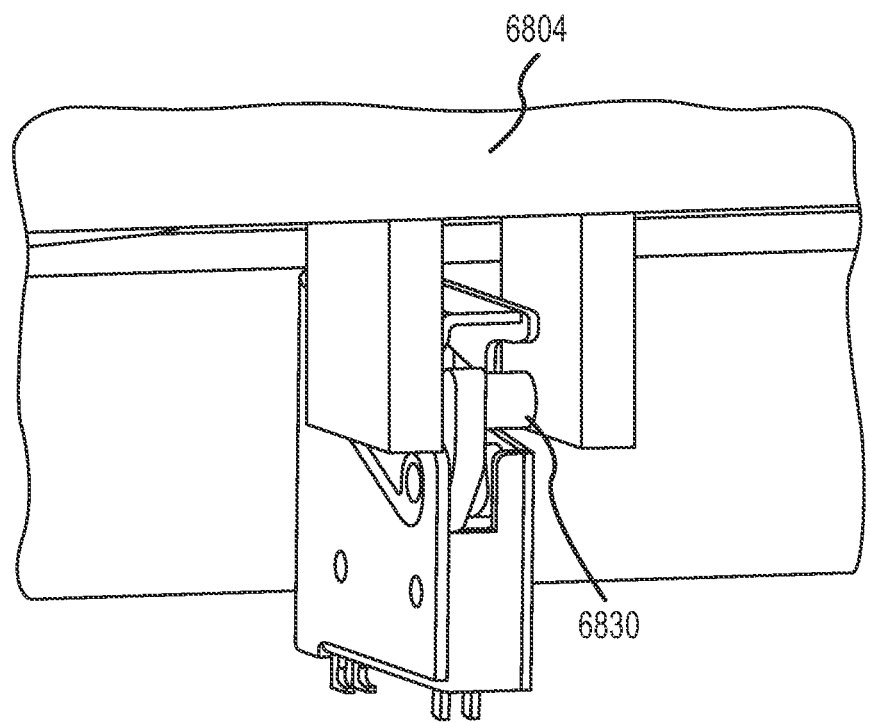
FIGS. 72(a)-(c) show an illustrative mechanical latch for a centrifuge drawer.
Figure 72B:
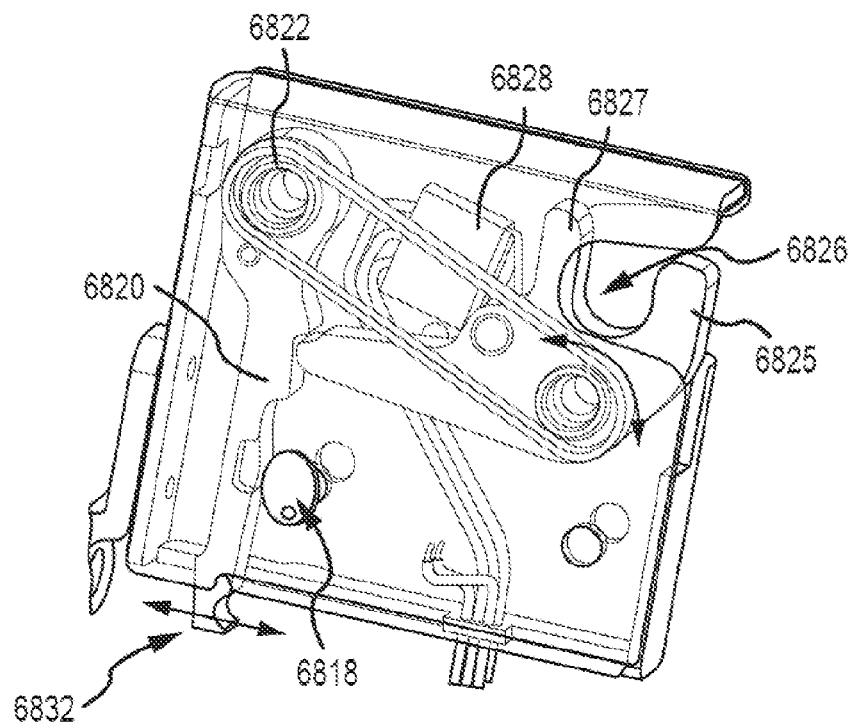
Figure 72C:
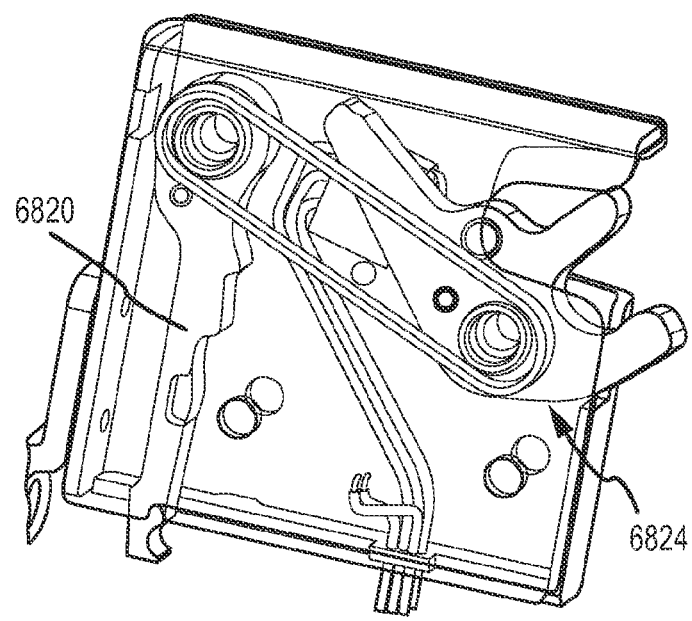
Figure 73:
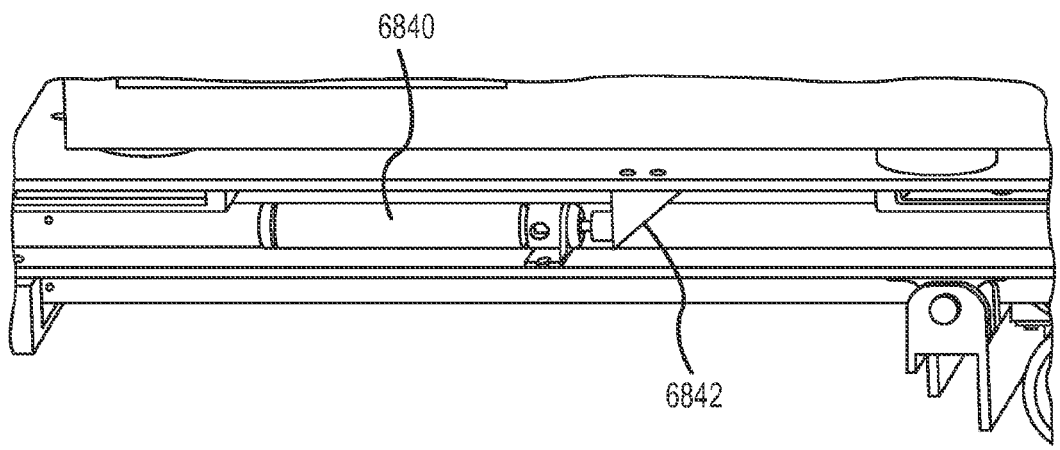
FIG. 73 shows an illustrative compression damper for a centrifuge drawer.

In some embodiments, centrifuge drawer 6800 includes a movement prevention measure. Movement of the drawer while the centrifuge is in operation could cause rotor imbalance and/or collision between the rotor bucket and containment can. Centrifuge drawer 6800 may include a permanent magnet with electric override to hold the centrifuge in place. To extend the drawer, the magnetic force of the permanent magnet is overpowered by application of an electric current to the electromagnet. For example, the electromagnet current may be activated with a polarization to counteract the magnetic field of the permanent magnet. The centrifuge drawer 6800 may include a permanent magnet with electromagnet override latch 6819 as shown in FIG. 71. The permanent magnet latch may be installed between wheels 6810 of centrifuge drawer 6800. The permanent magnet may hold the drawer in a fully retracted state when the drawer is retracted. For example, the electromagnet current may be activated with a polarization to reinforce the magnetic field of the permanent magnet. The force of the permanent magnet may be sufficient to hold centrifuge drawer in place while the centrifuge is not running. In some embodiments, the electromagnet 6819 is engaged to hold the drawer in a fully retracted state when the centrifuge is running.

Centrifuge drawer 6800 may comprise an electric rotary mechanical latch. FIG. 16(a) shows a perspective view of the mechanical latch and FIG. 16(b) shows a cross-sectional view of the mechanical latch. To extend the drawer, an electrical signal is sent from a controller to the latch and, in response, an electric motor rotates cam 6818. The controller may be a latch controller, a centrifuge drawer controller, a centrifuge controller, or another controller. The rotation of cam 6818 causes latch element 6820 to rotate about pivot 6822. Latch element 6820 may be a bar shaped to interface with latch element 6824. Latch element 6820 may also have a cable override element 6832 that will allow the drawer to be extended when power is lost in the event of a power failure. Latch element 6824 may have a first tine 6825 and a second tine 6827. The tines 6825, 6827 can restrain the movement of a striker bolt 6830 when the striker bolt is within opening 6826. Striker bolt 6830 is attached to the drawer frame 6804. The rotation of latch element 6820 around pivot 6822 causes latch element 6824 to be released. A spring (not shown), which may be a torsion spring, such as a weak torsion spring, can cause latch element 6825 to rotate clockwise when latch element 6824 is not restrained by latch element 6820. The operation of drawer 6800 to retract the drawer can also cause latch element 6824 to rotate clockwise. When latch element 6824 has rotated such that opening 6826 is no longer blocked by tine 6825 of the latch element, the striker bolt 6830 is no longer restrained and the drawer can be extended. FIG. 16(c) shows the configuration of latch elements 6820, 6824 when the latch is in an open position such that striker bolt 6830 is no longer restrained.

Latch sensor 6828 may be capable of detecting the position of the drawer. When the drawer is in a retracted position, latch sensor 6828 can send a signal to rotate cam 6818 such that 6820 is returned to the position shown in FIG. 16(b). Counterclockwise rotation of 6825 (e.g., by urging striker bolt 6830 against tine 6827 to return latch element 6824 to the position shown in FIG. 16(b). In this way, the drawer 6800 can be mechanically locked once it is retracted.

In some embodiments, centrifuge drawer 6800 comprises a damping mechanism to mitigate vibration of the frame 6804 when the drawer is being retracted to allow the centrifuge module to continue processing samples. A damping mechanism such as the compression damper 6840 shown in FIG. 73 can be used to couple frame 6804 to platform 6802 via the damper contractor 6842 such that a force exerted to retract the drawer is speed controlled compression damper 6840. The compression damper may be a gas or fluid damper. In some embodiments, the gas damper allows the centrifuge to be retracted freely until a state requiring control is reached.

Figure 74:
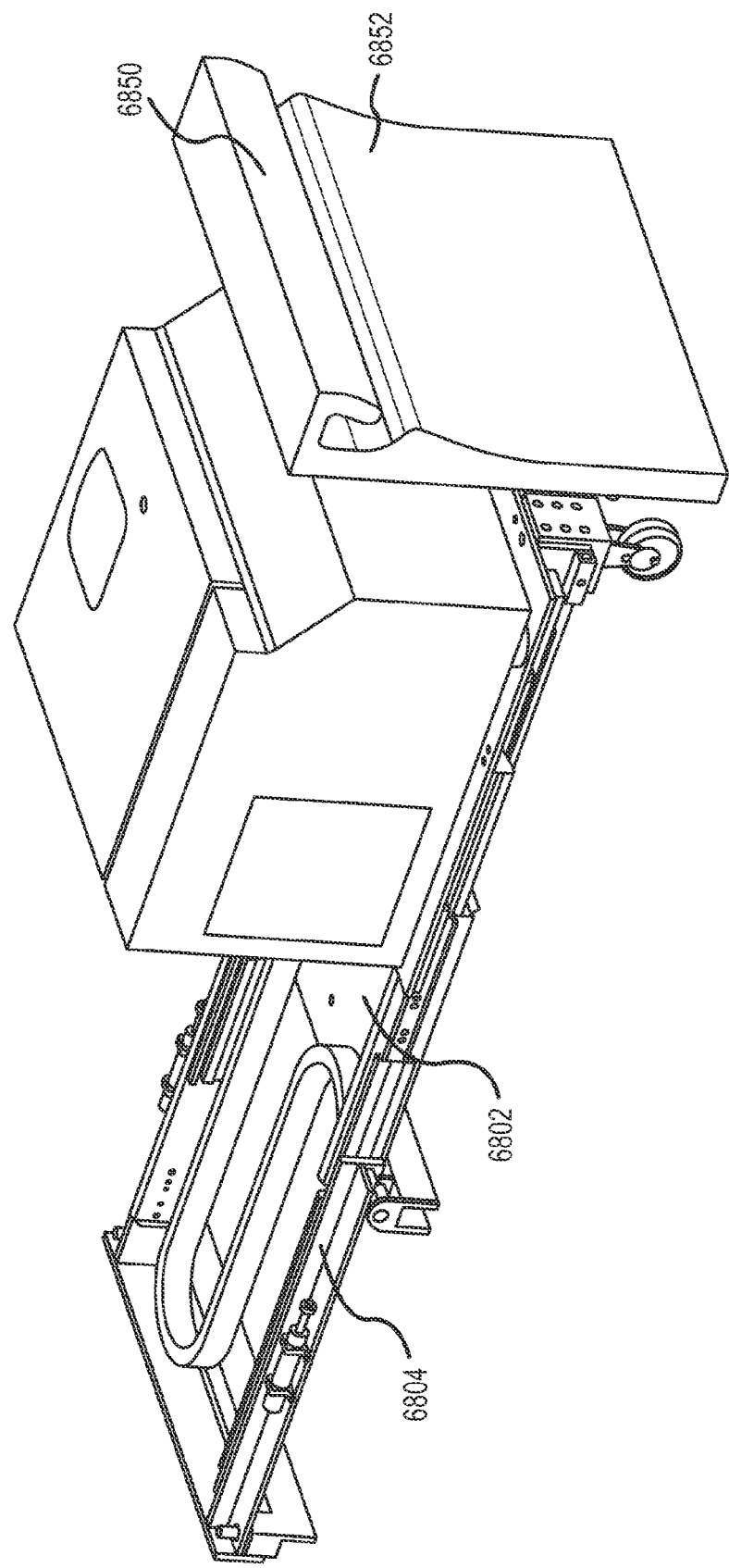
FIG. 74 shows an illustrative cover for a centrifuge drawer.

FIG. 74 shows a cover for a centrifuge drawer. Cover 6850 can be removed from the centrifuge drawer 6800 to allow access to drawer frame 6804 for loading the centrifuge onto the platform 6802. Cover 6850 may include a handle 6852 to provide a user with a gripping point to extend the centrifuge.

Figure 75:
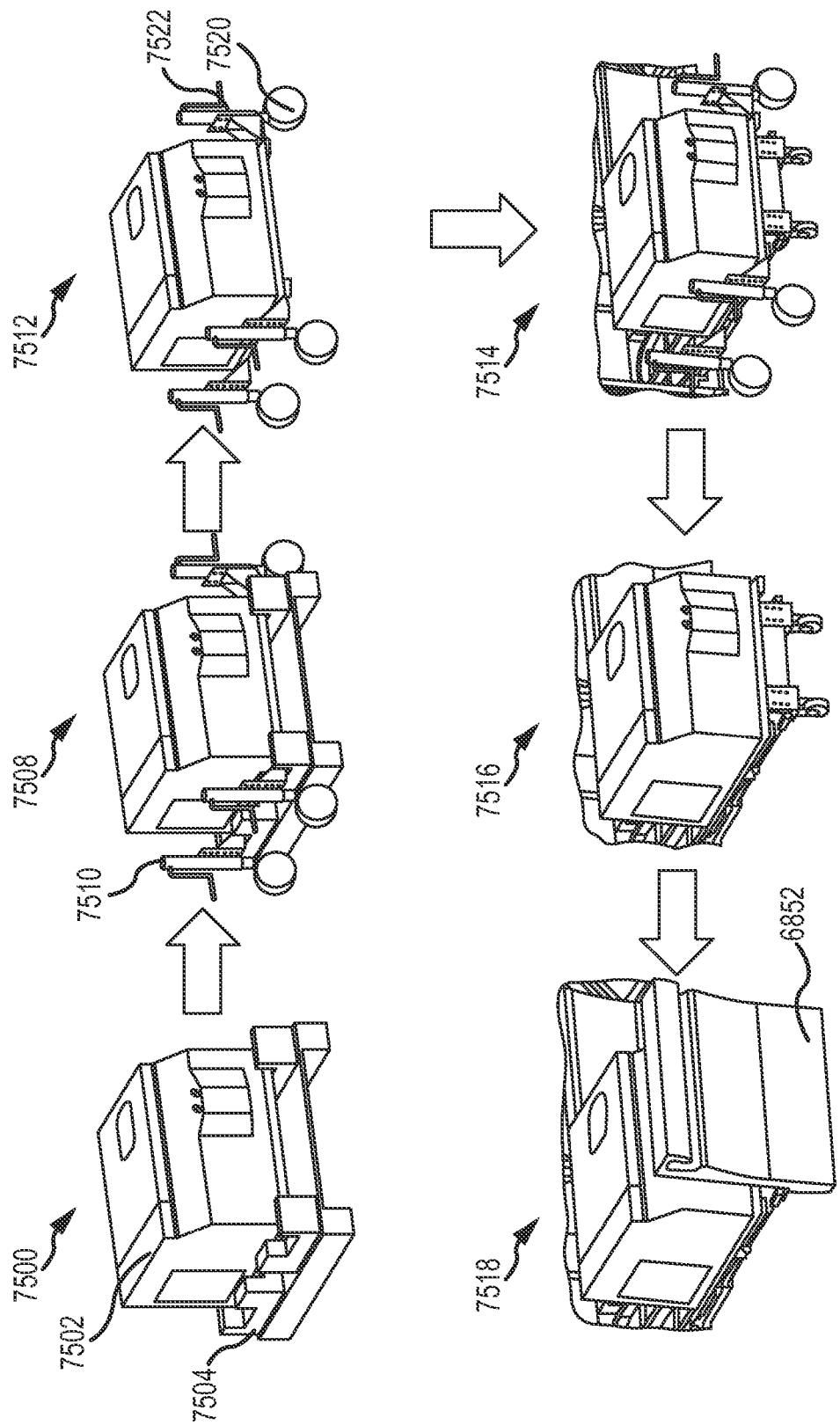
FIG. 75 shows an illustrative workflow for loading a centrifuge onto a centrifuge drawer.

FIG. 75 illustrates a workflow for loading a centrifuge onto drawer 6800. At 7500, centrifuge 7502 is in crate 7504. For example, the centrifuge may have been recently shipped to the laboratory. At 7508, a loading tool 7510 having may be applied to the centrifuge 7502. Loading tool 7510 may have a plurality of wheels 7520 and a plurality of jacks 7522. At 7512, the centrifuge is jacked up by extending the jacks of loading tool 7510. At this point, crate 7504 can be removed. At 7514, centrifuge 7502 can be rolled over drawer 6800 using loading tool 7510. The jacks can be retracted such that the centrifuge 7502 is supported by centrifuge drawer 6800. At 7516, loading tool 7510 is removed. At 7518, cover 6852 can be attached to drawer 6800.

XI. Centrifuge Adapter Gripper

A robotic arm may be capable of picking up and transporting a centrifuge adapter. For example, centrifuge adapters that are loaded with sample tubes ready to be centrifuged may be transported from the distribution area 204 to the centrifuge module 206 via a shuttle 224. The centrifuge adapters are loaded into the centrifuge, after which the samples can be centrifuged.

FIG. 76(a) shows an illustrative gripper element of a centrifuge adapter gripper. Centrifuge adapter gripper 227 (not shown) may comprise a gripper element 7600 coupled to a robotic arm. Gripper element 7600 may be a bolt. The bolt 7600 may be rounded at tip 7602 to allow the bolt 7600 to be inserted into a dedicated hooking element in centrifuge adapter tubular holder 7604. The bolt 7600 may comprise lateral pins 7606 coupled to opposing sides of bolt 7600. When bolt 7600 is rotated to a locked position within tubular holder 7604, the gripper can lift up centrifuge adapter 1002.

FIG. 76(b) shows tubular holder 7604, according to a first embodiment. Tubular holder 7604 may comprise vertical grooves 7608 configured to receive pins 7606 of bolt 7600. Tubular holder 7604 may also comprise horizontal grooves 7610. Each horizontal groove 7610 may connect to a vertical groove 7608. In some embodiments, horizontal groves 7610 may be slots in tubular holder 7604. When bolt 7600 is inserted into tubular holder 7604, gripper pins 7606 may be guided downward by vertical grooves 7608. Gripper 227 may rotate bolt 7600 (e.g., by 90 degrees) such that the pins 7606 follow the horizontal grooves 7610 in tubular holder 7604 until pins 7606 reach the gripping position indicated by notches 7612. In this manner, the gripper can lift and transport centrifuge adapter 1002. To release bolt 7600 from centrifuge adapter tubular holder 7604, the bolt is rotated in the opposite direction.

Figure 77B:
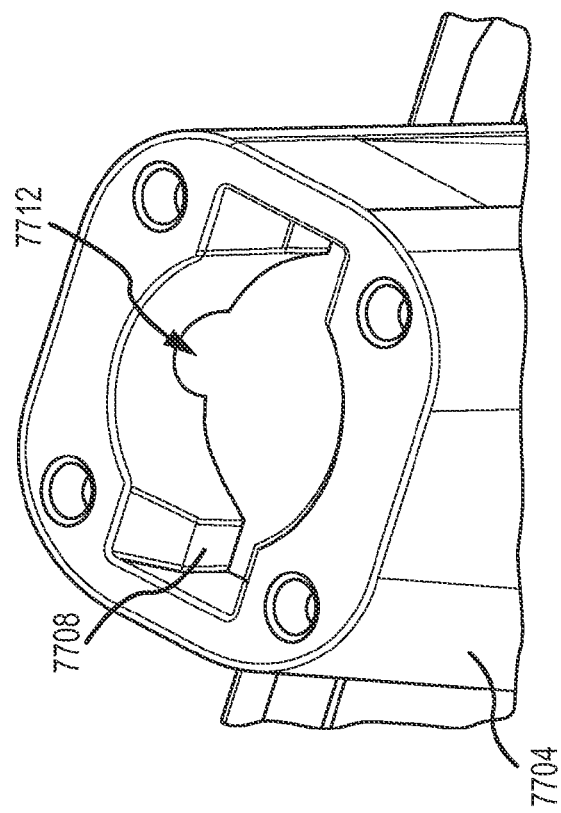
FIGS. 77(a)-(b) show an illustrative centrifuge adapter gripper, according to a first embodiment.
Figure 77A:
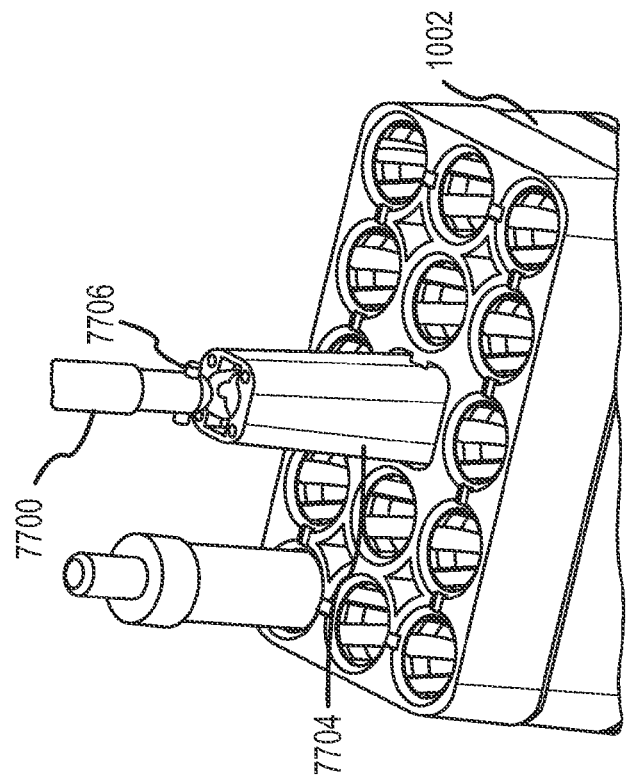

FIGS. 77(a)-(b) show tubular holder 7704, according to a second embodiment. Tubular holder 7704 may have a keyhole opening 7712 configured to match the cross-sectional profile of bolt 7700 with pins 7706. When bolt 7700 is inserted into tubular holder 7704, gripper pins 7606 fit through keyhole opening 7712 and are lowered below a shelf 7708. When the pins 7706 are below shelf 7708, gripper 227 may rotate bolt 7700 (e.g., by 90 degrees) such that the pins 7706 are seated in notch 7712. In this manner, the gripper can lift and transport centrifuge adapter 1002. To release bolt 7700 from centrifuge adapter tubular holder 7704, the bolt is rotated in the opposite direction.

Various measures may be implemented to prevent the centrifuge adapter from swinging during x- and y-axis movement of centrifuge adapter gripper 227. For example, gripper 227 may be operated at the extent of its z-axis range such that the top of the adapter is pressed against the underside of the housing of gripper 227. In this manner, any motion of centrifuge adapter 1002 with respect to gripper may be damped. In some embodiments, one or more springs may be used to prevent vibrations from the gripper housing from causing swinging of the centrifuge adapter.

In some embodiments, a robotic arm may be a combined gripper capable of gripping sample tubes as well as adapters 1002 used in the centrifuge module 206. One or more centrifuge area grippers may perform several functions, including picking up sample tubes at an input area 202, transporting sample tubes to a loading position 1004 for an empty centrifuge bucket, placing sample tubes in a free position of the centrifuge adapter, choosing a completely filled centrifuge adapter, transporting the centrifuge adapter to an available centrifuge, placing the centrifuge adapter in a free position of the centrifuge rotor, choosing a centrifuged adapter, transporting a centrifuged adapter to an unloading position for a centrifuged adapter, picking up centrifuged sample tubes in the centrifuged adapter, etc.

In another embodiment, a single sample tube gripper can be applied to a telescopic robotic arm. The sample tube gripper unit may be moved down into the centrifuge body using the telescopic robotic arm. The sample tube gripper robot may then grip the centrifuge buckets with its standard gripper unit.

In another embodiment, a centrifuge bucket gripper unit can be applied to the telescopic robotic arm in addition to a standard sample tube gripper.

XII. Centrifuge Adapter Lift-Up Prevention

A sticky label or stuck specimen tube may cause a centrifuge adapter 1002 to become airborne when centrifuge tube gripper 226 removes a sample tube from an adapter. Various lift-up prevention devices to prevent adapters 1002 from becoming airborne are described below. Typically, a lift-up prevention device is activated only when sample tubes are being loaded into and unloaded from adapters, allowing the adapters to move freely when adapters are being moved.

Figure 78:
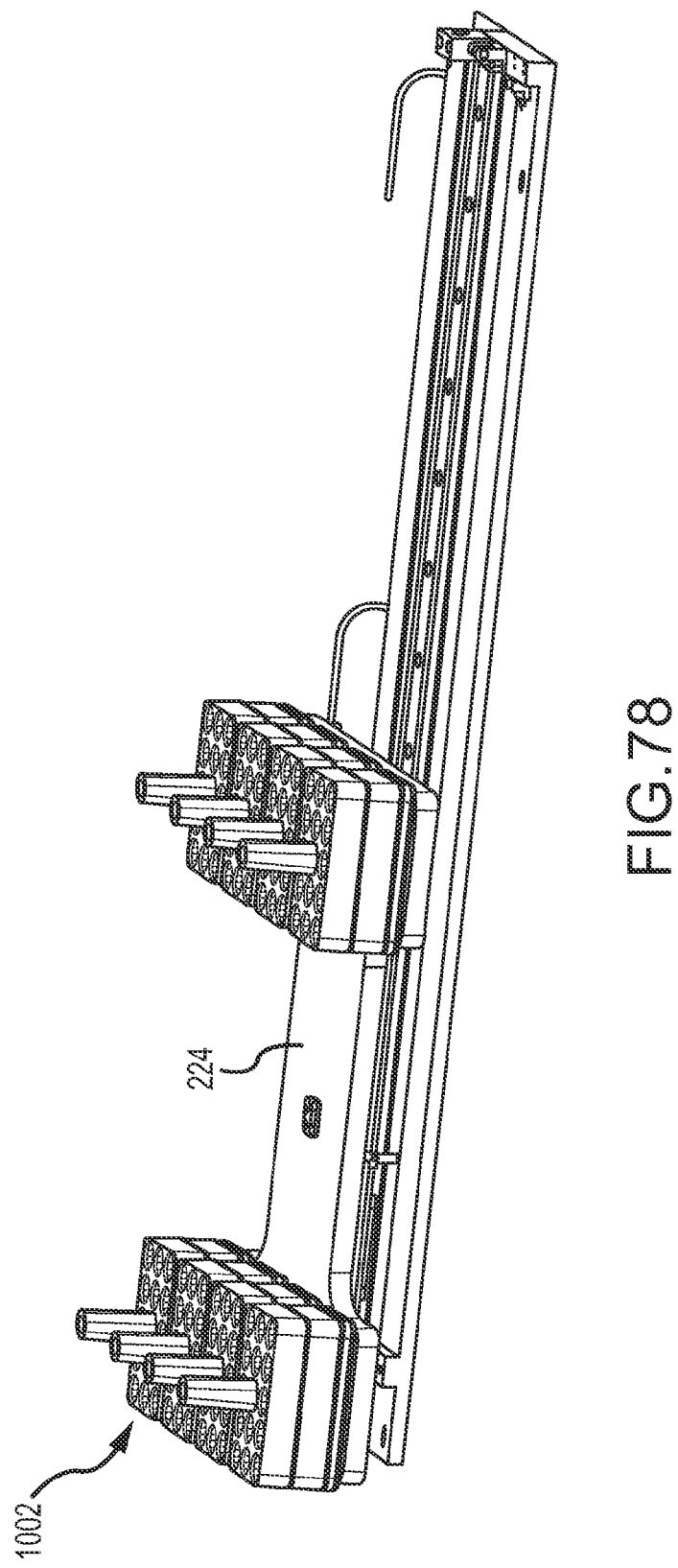
FIG. 78 shows an illustrative shuttle used for transporting centrifuge adapters.

FIG. 78 shows an illustrative shuttle 224 used for transporting centrifuge adapters 1002. The lift-up prevention devices described below can be understood with reference to the shuttle shown in FIGS. 79-80.

FIGS. 79(a)-(c) show an illustrative hook lift-up prevention device. In some embodiments, an adapter has a mechanical locking feature. For example, adapter 1002, shown in FIG. 79(a), may comprise an opening 7902. Shuttle 224, shown in FIG. 79(b), may have hook 7906 configured to be inserted into opening 7902. The hook is configured to be inserted into opening 7902 and to hold adapter 1002 to shuttle 224 when hook 7906 is inserted into opening 7902 of adapter 1002.

When the shuttle is moved to a position at which tubes can be unloaded from an adapter 1002, hook 7906 is inserted through opening 7902 and, subsequently, adapter 1002 is shifted such that hook 7906 overhangs a ledge in opening 7902 to prevent the adapter from lifting off of shuttle 224, as shown in FIG. 79(c). When adapter 1002 is shifted into the adapter swapping position, the hook mechanism may be disengaged.

Figure 80:
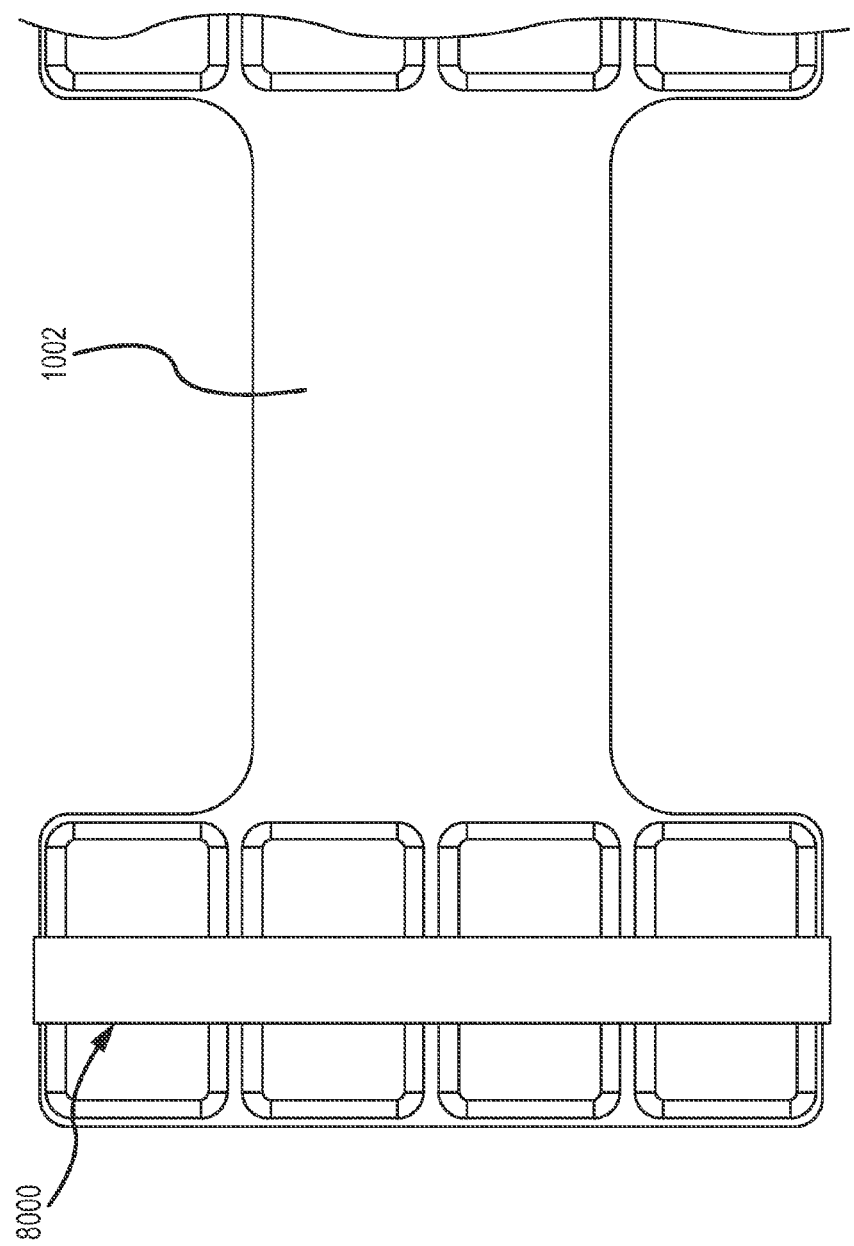
FIG. 80 shows an illustrative magnetic lift-up prevention device.

FIG. 80 shows an illustrative magnetic lift-up prevention device. In some embodiments, a ferromagnetic object, such as metal object 8000 (e.g., a steel bar) may be coupled to adapter 1002. For example, steel bar 8000 may be coupled to underside of adapter 1002 that rests on shuttle 224. When the shuttle is in an unloading position, stationary electromagnet (not shown) under steel bar 8000 may be powered in order to create a magnetic field to attract steel bar 8000 to the stationary electromagnet. The electromagnet may receive power from a power supply coupled to a controller in response to a signal sent to the power supply from the controller. The controller may be a centrifuge adapter shuttle controller or another controller. In this manner, adapter 1002 can be held in place during unloading. When unloading of adapter 1002 is complete, power to the stationary electromagnet can be discontinued to allow adapter 1002 to be moved. The magnetic lift-up prevention approach advantageously requires no mechanical parts and can be quickly activated and de-activated.

XIII. Shelf Arrangements

Apparatuses for automatically treating samples are being increasingly used in laboratories in order to increase the throughput and precision of sample treatment processes. In such apparatuses, the samples to be treated are usually arranged in a sample treatment room and automatically treated by a treatment device arranged in the sample treatment room. The sample treatment process is automatically carried out according to a treatment protocol or according to a command by the user.

However, the arranging of the samples within the sample treatment room before the treatment, or the replacement or removal of the samples from the sample treatment room is carried out manually by the user. Conventional apparatuses for automatically treating samples have not been optimised in view of the manual loading and unloading of the samples by the user. According to an aspect, an apparatus for automatically treating samples arranged on a rack is provided, the apparatus comprising: a sample treatment room; an opening in the sample treatment room; a drawer being movably supported in the apparatus in such a way so as to be displaceable between a closed position and an opened position, the drawer having a drawer face closing the opening when the drawer is in the closed position; a shelf being arranged outside of the sample treatment room substantially directly above the drawer face when the drawer is in the closed position; wherein the drawer includes a rack placing unit, the rack placing unit being arranged within the sample treatment room when the drawer is in the closed position, and wherein the rack placing unit is movable at least partly out of the sample treatment room through the opening when the drawer is displaced from the closed position to the opened position.

Advantageously, the manual arranging of racks with samples into the sample treatment room is optimized, since the user can conveniently place the rack with samples temporarily on the shelf arranged in close proximity directly above the drawer, pull out the drawer and place the rack on the rack placing unit of the pulled out drawer right beneath the shelf and simply push the drawer back to the closed position. The upper surface of the shelf and the opened drawer, particularly the rack placing unit of the opened drawer, are in close proximity. The upper surface of the shelf and the rack placing unit of the opened drawer can both be arranged on the working level of a user. Hence, the loading and unloading of the apparatus is simplified.

Figure 81:
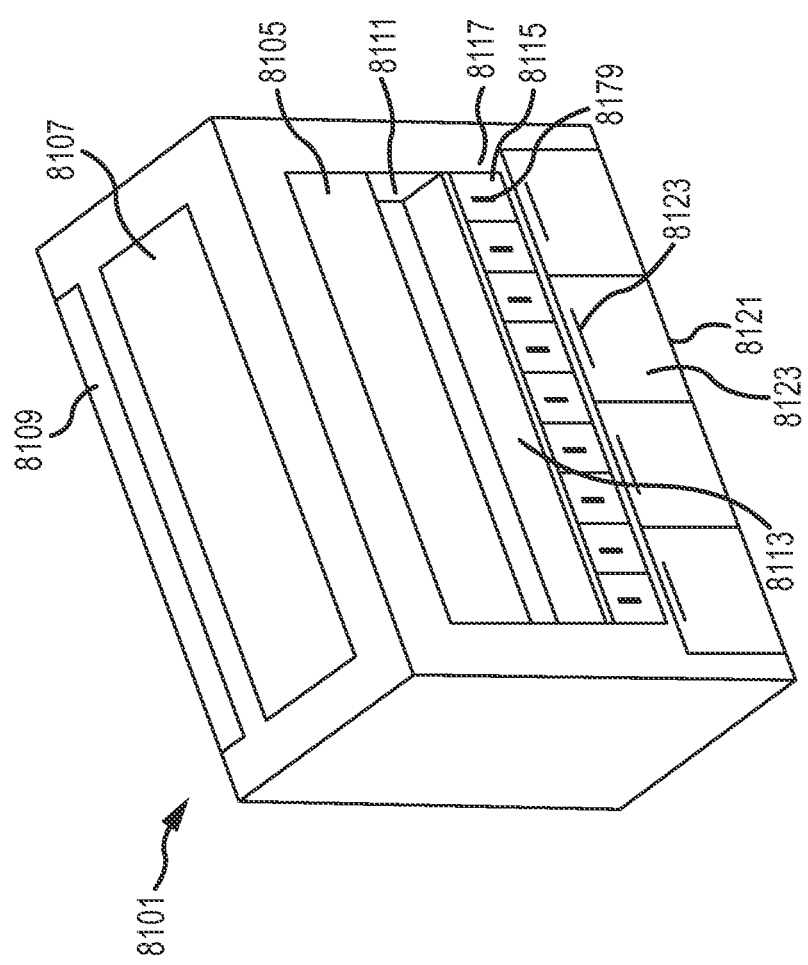
FIGS. 81-83 show an apparatus for automatically treating samples.

FIG. 81 shows an apparatus 8101 for automatically treating samples according to an embodiment of the present invention, the apparatus comprising a housing 8103 with a front cover 8105, a top cover 8107 and a rear cover 8109. The front cover 8105, top cover 8107 and rear cover 8109 can be at least partly transparent to let in ambient light. The front cover 8105 comprises a recessed portion 8111 formed at the lowest portion of the front cover 8105. The recessed portion 8111 provides an area of free space formed within the apparatus 8101.

At the lowest portion of the recessed portion 8111, a shelf 8113 is arranged. The shelf 8113 can be implemented as a separate element which is removably connected to the housing 8103. The shelf 8113 is arranged substantially directly above drawer faces 8115 of drawers 8117. The shelf 8113 is also arranged substantially directly above handles 8119 of the drawer faces 8115. The handles 8119 can be curved handles extending over substantially the entire height of the drawer faces 8115. Optionally, the shelf 8113 can comprise glass material or the shelf 8113 can be made from glass material. The shelf 8113 can also be integrally formed with the front cover 8105.

Optionally, the drawer 8117 of the apparatus 8101 can comprise a drawer face 8115 having a vertical section extending substantially vertically over substantially the entire vertical height of the drawer 8117, and a horizontal section 8115 extending substantially horizontally outward from the apparatus 8101 along the lower surface of the shelf 8113 over substantially the entire depth d of the shelf 8113. At the outward end of the horizontal section 8115 there can be arranged a handle 8119 extending in the vertical plane substantially parallel to the vertical section 8115 of the drawer face 8115. The handle 8119 can extend over substantially the entire width of the drawer face 8115 in the horizontal direction. The handle 8119 can extend 1 cm to 3 cm, in particular 2 cm above the horizontal section 8115 in the vertical direction. The handle 8119 can extend 2 cm to 4 cm, in particular 3 cm below the horizontal section 8115 in the vertical direction. The front face of the handles 19 can have indicators 8147 which can be configured to illuminate when an error has occurred.

In FIG. 81, all drawers 8117 are in the closed position, closing the openings (not shown) of the sample treatment room. The apparatus 8101 comprises nine drawers 8117 arranged parallelly and adjacent in a horizontal direction. In other embodiments, the apparatus 8101 can comprise less drawers or more drawers, for example 1, 2, 3, 4, 5, 6, 7, 8, 10, 11 or 12 drawers. Below the drawers 8117, there are arranged one or more, e.g. three, storage cabinets 8121 having doors 8123 with horizontally arranged handle bars 8125. The storage cabinets 8121 are also arranged parallelly and adjacent in the horizontal direction, and can be used to store consumables and accessories for the apparatus 8101, for example consumables for treating samples in a sample treatment room 8129 of the apparatus 8101.

Figure 82:
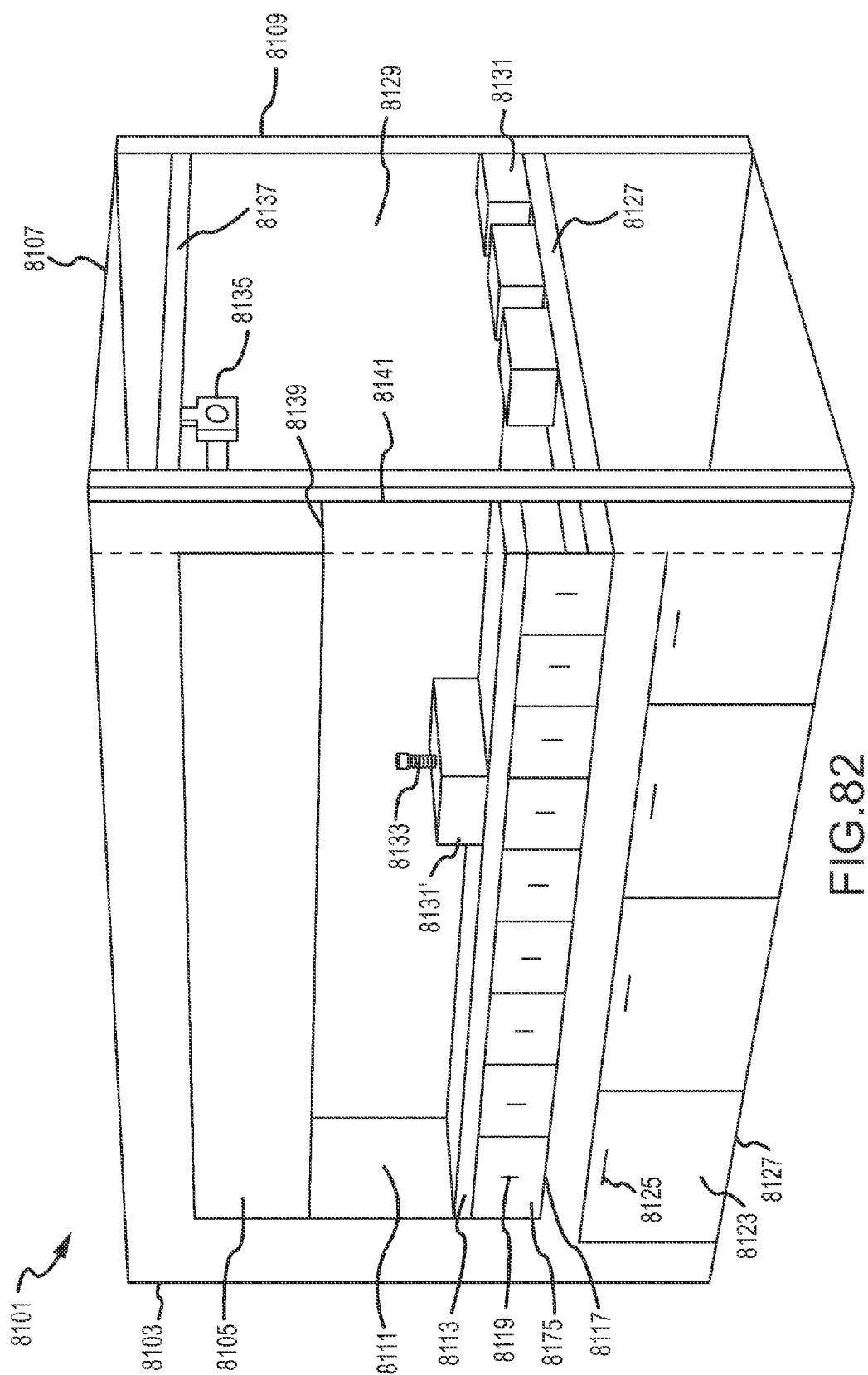

FIG. 82 shows a sectional view of the apparatus 8101 according to the embodiment. With all drawers 8117 in the closed position, all rack placing units 8127 of the drawers 8117 are arranged within the sample treatment room 8129. The rack placing units 8127 can each carry four racks 8131 orderly arranged adjacent to one another. Alternatively, the rack placing units 8127 can be configured to carry more racks or less racks. The rack placing units 8127 are implemented as floors of the drawers 8117. In FIG. 82, no samples are arranged on the racks 8131 which are arranged on the rack placing units 8127 within the sample treatment room 8129. A sample tube 8133 is arranged on a rack 8131' placed on the shelf 8113 outside of the sample treatment room 8129. Arranged within the sample treatment room 8129 is further a sample treatment device 8135 having a sample treatment arm (not shown) movably supported on a frame 8137. The frame 8137 is supported by the ground and carries the weight of the apparatus. The frame can also support the drawers 8117. The drive (not shown) of the sample treatment device 8135 is arranged behind the portion of the housing 8103 above the front cover 8105.

The recessed portion 8111 formed at the lowest portion of the front cover 8105 comprises a substantially horizontal portion 8139 and a substantially vertical portion 8141, wherein the horizontal portion 8139 forms a "roof" over the upper surface of the shelf 8113, and wherein the vertical portion 8141 forms a border between the space above the shelf 8113 and the sample treatment room 8129. The substantially horizontal portion 8139 can be slightly tilted with respect to the horizontal plane. Corners of the recessed portion 8111 can have a smooth curvature, or can be formed having sharp edges.

Figure 83:
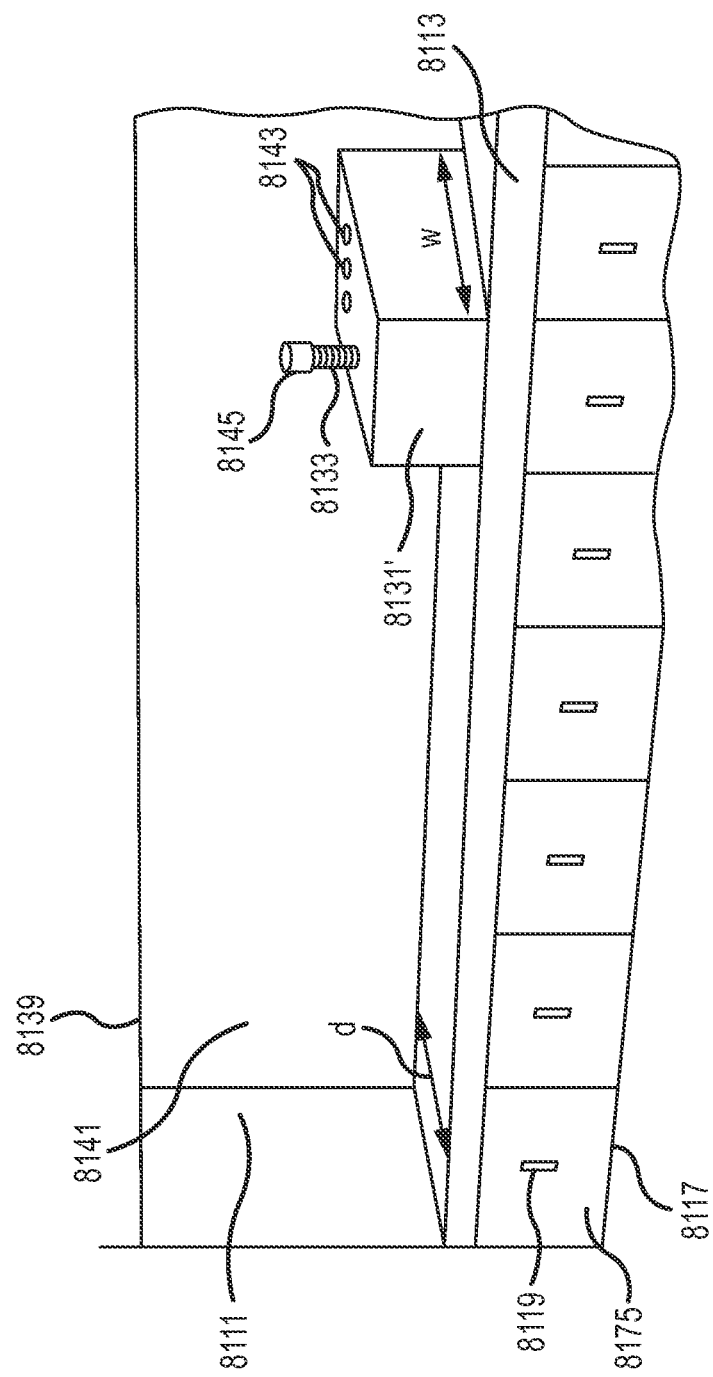

FIG. 83 shows a close-up view of the recessed portion 8111, the shelf 8113 and some of the drawers 8117 of the apparatus 8101 according to the embodiment of the present invention. Also shown in FIG. 83 is the rack 8131' placed on the shelf 8113. The shelf 8113 is in substantially horizontal arrangement. A depth d of the shelf 8113 substantially corresponds to a width w of the rack 8131', wherein d is the depth of the upper side of the shelf 8113. The rack 8131' comprises a plurality of apertures 8143 for holding sample tubes 8133 therein. The sample tubes 8133 can hold samples to be treated, and the sample tubes 8133 are each covered by a cap 8145 for protecting the sample, wherein the cap 8145 can be configured to allow penetration by a pipette of the sample treatment device 8135. The apertures 8143 are formed on the rack 8131' equally spaced from another, in six rows and six columns. Alternatively, the rack 8131' can comprise any other number and/or arrangement of apertures 8143 formed thereon. When the rack 8131' is arranged on a rack placing unit 8127 of a drawer 8117 in the opened position, the rack 8131' can be easily loaded into the sample treatment room 29 of the apparatus 8101 by simply closing the drawer 8117, so that the sample arranged on the rack 8131' can be automatically treated in the sample treatment room 8129 of the apparatus 8101 when the drawer 8117 is in the closed position.

XIV. Computer Apparatus

The various participants and elements described herein with reference to the figures may operate one or more computer apparatuses to facilitate the functions described herein. Any of the elements in the above description, including any servers, processors, or databases, may use any suitable number of subsystems to facilitate the functions described herein, such as, e.g., functions for operating and/or controlling the functional units and modules of the laboratory automation system, transportation systems, the scheduler, the central controller, local controllers, etc.

Figure 84:
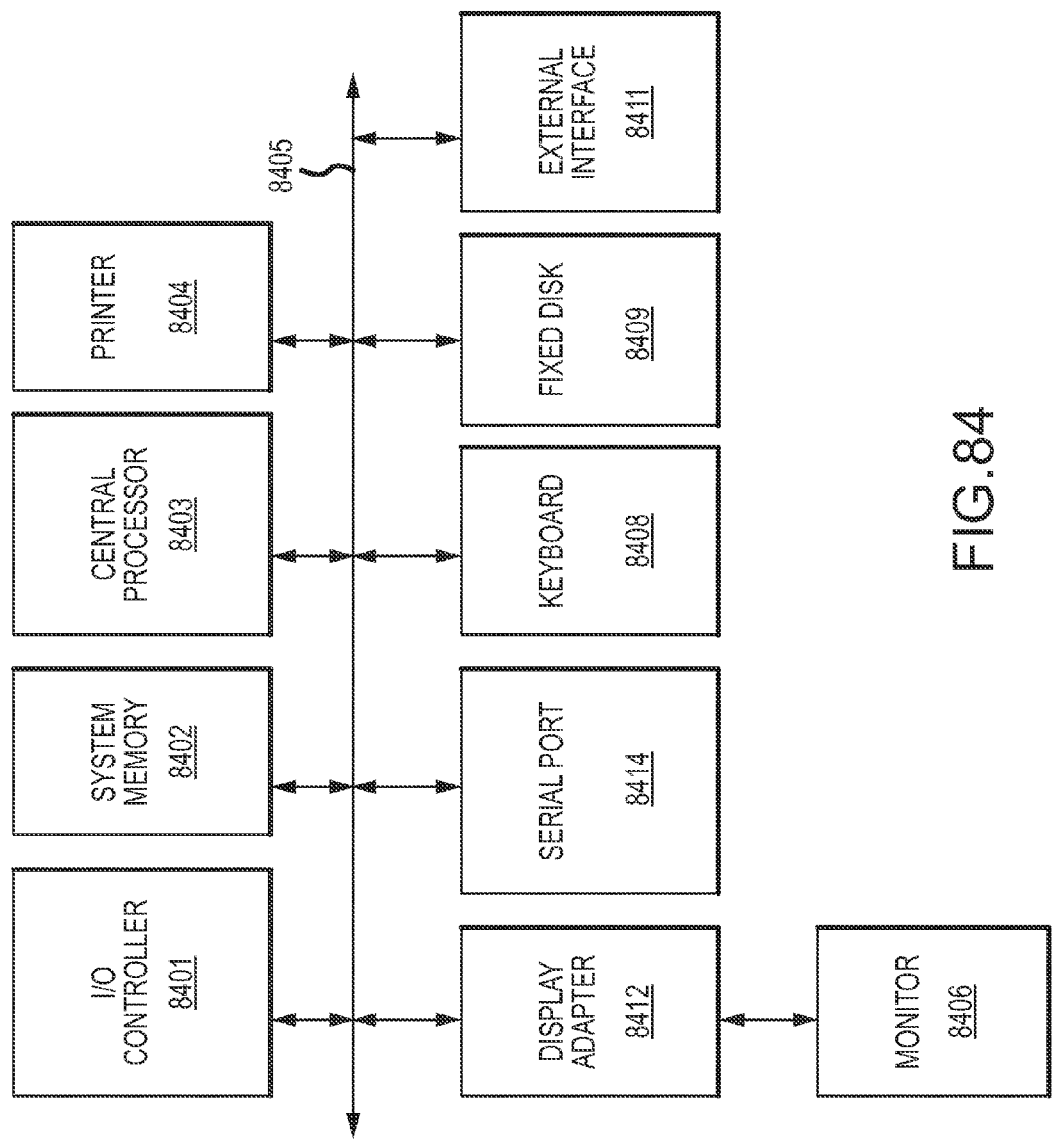
FIG. 84 depicts a block diagram of an exemplary computer apparatus.

Examples of such subsystems or components are shown in FIG. 84. The subsystems shown in FIG. 84 are interconnected via a system bus 8405. Additional subsystems such as a printer 8404, keyboard 8408, fixed disk 8409 (or other memory comprising computer readable media), monitor 8406, which is coupled to display adapter 8412, and others are shown. Peripherals and input/output (I/O) devices, which couple to I/O controller 8401 (which can be a processor or other suitable controller), can be connected to the computer system by any number of means known in the art, such as serial port 8414. For example, serial port 8414 or external interface 8411 can be used to connect the computer apparatus to a wide area network such as the Internet, a mouse input device, or a scanner. The interconnection via system bus allows the central processor 8403 to communicate with each subsystem and to control the execution of instructions from system memory 8402 or the fixed disk 8409, as well as the exchange of information between subsystems. The system memory 8402 and/or the fixed disk 8409 may embody a computer readable medium.

Embodiments of the technology are not limited to the above-described embodiments. Specific details regarding some of the above-described aspects are provided above. The specific details of the specific aspects may be combined in any suitable manner without departing from the spirit and scope of embodiments of the technology. For example, any features of any two or more specific embodiments as described above, can be combined in any suitable manner without departing from the spirit and scope of the invention.

It should be understood that the present technology as described above can be implemented in the form of control logic using computer software (stored in a tangible physical medium) in a modular or integrated manner. Furthermore, the present technology may be implemented in the form and/or combination of any image processing. Based on the disclosure and teachings provided herein, a person of ordinary skill in the art will know and appreciate other ways and/or methods to implement the present technology using hardware and a combination of hardware and software Any of the software components or functions described in this application, may be implemented as software code to be executed by a processor using any suitable computer language such as, for example, Java, C++ or Perl using, for example, conventional or object-oriented techniques. The software code may be stored as a series of instructions, or commands on a computer readable medium, such as a random access memory (RAM), a read only memory (ROM), a magnetic medium such as a hard-drive or a floppy disk, or an optical medium such as a CD-ROM. Any such computer readable medium may reside on or within a single computational apparatus, and may be present on or within different computational apparatuses within a system or network.

The above description is illustrative and is not restrictive. Many variations of the technology will become apparent to those skilled in the art upon review of the disclosure. The scope of the technology should, therefore, be determined not with reference to the above description, but instead should be determined with reference to the pending claims along with their full scope or equivalents.

One or more features from any embodiment may be combined with one or more features of any other embodiment without departing from the scope of the technology.

A recitation of "a", "an" or "the" is intended to mean "one or more" unless specifically indicated to the contrary.

All patents, patent applications, publications, and descriptions mentioned above are herein incorporated by reference in their entirety for all purposes. None is admitted to be prior art.

What is claimed is:

1. A method of handling a sample container within a laboratory automation system, comprising:
    gripping a sample container positioned in an input module for transport from said input module to a distribution area with a first gripper;
    detecting information about the sample container with an instrument associated with the first gripper, which information includes determining a level of one or more liquids of a sample in said sample container and capturing an image of said sample container; and
    transporting with the first gripper the sample container from said input module to said distribution area;
    gripping the sample container positioned in the distribution area with a second gripper;
    transporting with the second gripper the sample container from the distribution area to at least one of a centrifuge adapter, a carrier on a conveyance system, and an error area;
    requesting a sample schedule associated with the sample in the sample container, wherein the sample schedule is requested from a scheduling system based on:
        data obtained by detecting information step, and
        test information associated with the sample; and
    determining, by the scheduling system, a time when the sample container containing the sample should be removed from the distribution area for further processing;
    determining whether an error is associated with the sample;
    when an error is associated with the sample, transporting the sample container to an error area; and
    when no error is associated with the sample, transporting the sample container, based on the obtained sample schedule, via a second gripper, from the distribution area to a subsequent processing module in the laboratory automation system at the time determined by the scheduling system, wherein:
        when the subsequent processing module is a centrifuge unit having a centrifuge rotor, placing the sample container by said second gripper into an adapter of a centrifuge based upon calculated estimate of a total sample container weight for balance of the centrifuge rotor and/or based on a sample priority; and
        when the subsequent processing module is not a centrifuge unit, transporting the sample container, by said second gripper, into a carrier on a conveyance system.

2. The method of claim 1, wherein, during the transporting of the sample container, the level of the one or more liquids of the sample are measured and an image of the sample container is captured.

3. The method of claim 1, wherein, based on the determined level of the one or more liquids, volumes of one or more components of the sample are determined.

4. The method of claim 1, wherein detecting information includes the use of an emitter and a receiver, wherein the emitter and the receiver are used for a measurement to determine one or more liquid levels of the sample.

5. The method of claim 1, further comprising analyzing the captured image to determine at least one of a manufacturer of the sample container, a diameter of the sample container, a height of the sample container, a color of a sample container cap, a shape of the sample container cap, a presence of a marker and a presence of a label.

6. The method of claim 5, further comprising calculating an estimate of a total sample container weight based on:
   the determined level of the one or more liquids of the sample, and
   the analysis of the captured image.

7. The method of claim 1 wherein, if the subsequent processing module is a centrifuge unit:
   transporting, by a shuttle, the centrifuge adapter from the distribution area to the centrifuge unit, and
   transferring, by a third gripper, the centrifuge adapter to a bucket of the centrifuge.

8. A laboratory automation system for handling sample containers, comprising:
   an input module configured to receive sample containers into the laboratory automation system;
   a distribution area, configured as a holding area for the sample containers;
   a first gripper, for gripping the sample container from the input module and transporting a sample container to the distribution area;
   an instrument associated with said first gripper for detecting information about the sample container, wherein the information includes one or more liquid levels of a sample contained in the sample container and an image of the sample container;
   a conveyance system;
   an error area;
   at least one centrifuge adapter;
   a scheduling system for determining a sample schedule associated with the sample, wherein the sample schedule is based at least in part on:
   the information obtained by the instrument for detecting information, and
   test information associated with the sample; and
   a second gripper, configured to transport the sample container from the distribution area to at least one of the centrifuge adapter, a carrier on the conveyance system, and the error area, wherein the second gripper transports the sample container at a time determined using the sample schedule.

9. The laboratory automation system of claim 8, wherein the information detecting instrument is capable of, during the transport of the sample container from the input module to the distribution area:
   determining one or more liquid levels of the sample, and
   capturing at least one image of the sample container.

10. The laboratory automation system of claim 8, wherein:
    the information detecting instrument includes an emitter and a receiver for determining the one or more liquid levels of said sample; and
    the emitter and the receiver are used for a measurement to determine one or more liquid levels of the sample.

11. The laboratory automation system of claim 8, further comprising:
    a centrifuge unit including a centrifuge; and
    a centrifuge adapter shuttle that transports centrifuge adapters between the distribution area and the centrifuge unit.

12. The laboratory automation system of claim 11, further comprising a third gripper that transfers centrifuge adapters to and from a bucket of the centrifuge.

* * * * *